US012729368B2

(12) United States Patent
Amini

(10) Patent No.: US 12,729,368 B2
(45) Date of Patent: Sep. 8, 2026

(54) METHODS AND COMPOSITIONS FOR GENERATING OLIGODENDROCYTE PROGENITOR CELLS

(71) Applicant: Trailhead Biosystems Inc., Cleveland, OH (US)

(72) Inventor: Nooshin Amini, Cleveland, OH (US)

(73) Assignee: Trailhead Biosystems Inc., Cleveland, OH (US)

( * ) Notice: Subject to any disclaimer, the term of this patent is extended or adjusted under 35 U.S.C. 154(b) by 600 days.

(21) Appl. No.: 18/207,363

(22) Filed: Jun. 8, 2023

(65) Prior Publication Data

US 2024/0043798 A1 Feb. 8, 2024

Related U.S. Application Data

(60) Provisional application No. 63/400,222, filed on Aug. 23, 2022, provisional application No. 63/396,073, filed on Aug. 8, 2022.

(51) Int. Cl.
*C12N 5/079* (2010.01)

(52) U.S. Cl.
CPC ...... *C12N 5/0622* (2013.01); *C12N 2501/105* (2013.01); *C12N 2501/115* (2013.01); *C12N 2501/135* (2013.01); *C12N 2501/155* (2013.01); *C12N 2501/16* (2013.01); *C12N 2501/33* (2013.01); *C12N 2501/38* (2013.01); *C12N 2501/385* (2013.01); *C12N 2501/395* (2013.01); *C12N 2501/405* (2013.01); *C12N 2501/41* (2013.01); *C12N 2501/415* (2013.01); *C12N 2501/42* (2013.01); *C12N 2501/48* (2013.01); *C12N 2501/60* (2013.01); *C12N 2501/727* (2013.01); *C12N 2506/08* (2013.01); *C12N 2506/45* (2013.01)

(58) Field of Classification Search
None
See application file for complete search history.

(56) References Cited

U.S. PATENT DOCUMENTS 8,227,247 B2 7/2012 Zhang et al.
8,633,025 B2 1/2014 Vanderhaeghen et al.
10,100,279 B2 10/2018 Nicholas et al.
10,301,592 B2 5/2019 Fossati et al.
10,828,335 B2 11/2020 George et al.
2015/0361393 A1 12/2015 Nicholas et al.
2016/0272940 A1 9/2016 Chung
2017/0183627 A1 6/2017 Fossati et al.
2017/0239373 A1 8/2017 Chen et al.
2017/0292112 A1 10/2017 Chang et al.
2018/0298333 A1 10/2018 Marton et al.
2019/0062700 A1 2/2019 Nicholas et al.
2020/0087622 A1 3/2020 Nair et al.
2020/0399595 A1* 12/2020 Fossati .................... A61P 25/28
2021/0040443 A1 2/2021 Nicholas et al.
2021/0047618 A1 2/2021 Clevers et al.
2022/0177835 A1 6/2022 Studer et al.
2022/0315891 A1 10/2022 Amini
2023/0027059 A1 1/2023 Amini
2023/0332103 A1 10/2023 Amini et al.
2024/0043798 A1 2/2024 Amini
2024/0117303 A1 4/2024 Amini
2024/0158743 A1 5/2024 Amini
2024/0158744 A1 5/2024 Amini

FOREIGN PATENT DOCUMENTS

CN 110042082 A 7/2019
EP 3031908 A1 6/2016
WO 2012/162124 A1 11/2012
WO 2013/163228 A1 10/2013
WO 2016/103269 A1 6/2016
WO 2016/162747 A2 10/2016
WO 2018/208836 A1 11/2018
WO 2020/219696 A1 10/2020
WO 2021/119209 A1 6/2021
WO 2021/224496 A1 11/2021
WO 2023003621 A1 1/2023
WO 2023/010897 A1 2/2023
WO 2023/075913 A1 5/2023

OTHER PUBLICATIONS

García-León, et al. SOX10 Single transcription factor-based fast and efficient generation of oligodendrocytes from human pluripotent stem cells. Stem Cell Reports. 2018; 10(1):655-672. (Year: 2018).*
Algarni, A. et al. "Activation of transglutaminase 2 by nerve growth factor in differentiating neuroblastoma cells: A role in cell survival and neurite outgrowth," European Journal of Pharmacology, vol. 820:113-129. (2018).
Med Chem Express (Akt). 8 pages https://www.medchemexpress.com/Targets/Akt.html?effectName=Activator&page=3 (2024).
Tang, F. et al., "Resveratrol Enhances Neurite Outgrowth and Synaptogenesis Via Sonic Hedgehog Signaling Following Oxygen-Glucose Deprivation/Reoxygenation Injury," Cell Phys Biochem., vol. 43:852-869 (2017).

(Continued)

*Primary Examiner* — Allison M Fox
*Assistant Examiner* — Gina Pronzati
(74) *Attorney, Agent, or Firm* — Clark & Elbing LLP

(57) ABSTRACT

Methods for generating pre-oligodendrocyte progenitor cells (pre-OPCs), oligodendrocyte progenitor cells (OPCs) and pre-myelinating oligodendrocytes (preOLs) from human pluripotent stem cells are provided using chemically-defined culture media that allow for generation of pre-OPCs in as little as three days, SOX10+ OLIG2+ NKX2-2+ OPCs in as little as twelve days and CD9+A2B5+O4+CNPase+ preOLs in as little as eighteen days. Two alternative culture protocols for generating OPCs are provided. Culture media, isolated cell populations and kits are also provided.

26 Claims, 89 Drawing Sheets

(56) References Cited

OTHER PUBLICATIONS

Arenas, E. et al., "How to make a midbrain dopaminergic neuron," Development, vol. 142(11):1918-1936 (2015).
Brodski C. et al., "Crosstalk of Intercellular Signaling Pathways in the Generation of Midbrain Dopaminergic Neurons In Vivo and from Stem Cells," Journal of Developmental Biology, vol. 7(1):p. 3 (2019).
Bukys, M. et al., "High-Dimensional Design-Of-Experiments Extracts Small-Molecule-Only Induction Conditions for Dorsal Pancreatic Endoderm from Pluripotency," Iscience, vol. 23(8):101346: 35 pages (2020).
Cooper, O. et al., "Differentiation of human ES and Parkinson's disease iPS cells into ventral midbrain dopaminergic neurons requires a high activity form of SHH, FGF8a and specific regionalization by retinoic acid," Mol. Cell. Neurosci, vol. 45:258-266 (2010).
Douvaras & Fossati, "Generation and isolation of oligodendrocyte progenitor cells from human pluripotent stem cells," Nature Protocols, vol. 10(8):1143-1154 (2015).
Douvaras, P. et al., "Efficient generation of myelinating oligodendrocytes from primary progressive multiple sclerosis patients by induced pluripotent stem cells," Stem Cell Reports, vol. 3(2):250-259 (2014).
Drummond, N. et al., "Cryopreservation of Human Midbrain Dopaminergic Neural Progenitor Cells Poised for Neuronal Differentiation," Front. Cell. Dev. Biol., vol. 8:578907 (2020).
Fedele, S. et al., "Expansion of human midbrain floor plate progenitors from induced pluripotent stem cells increases dopaminergic neuron differentiation potential," Sci. Reports, vol. 7:6036 (2017).
Ferri, A. et al., "Foxa1 and Foxa2 regulate multiple phases of midbrain dopaminergic neuron development in a dosage-dependent manner," Development, vol. 134:2761-2769 (2007).
Garcia Leon, J-A.et al., "Generation of oligodendrocytes and establishment of an all-human myelinating platform from human pluripotent stem cells," Nature Protocols, vol. 15 (11):3716-3744 (2020).
Garcia-Leon, J. et al., "SOX10 Single Transcription Factor-Based Fast and Efficient Generation of Oligodendrocytes from Human Pluripotent Stem Cells," Stem Cell Reports, vol. 10(2):655-672 (2018).
Gantner, C. et al., "An Optimized Protocol for the Generation of Midbrain Dopamine Neurons under Defined Conditions," Star Protocols, vol. 1(2):100065 (2020).
Hartfield et al., "Physiological characterisation of human iPS-derived dopaminergic neurons," PLoS One, vol. 92: e87388 (2014).
Hu, B-Y. et al., "Differentiation of human oligodendrocytes from pluripotent stem cells," Nature Protocols, vol. 4 (11):1614-1622 (2009).
International Preliminary Report on Patentability, PCT/US2022/014306, dated Oct. 3, 2023, 10 pages.
International Search Report and Written Opinion, PCT/US2022/014306, dated May 16, 2022, 18 pages.
International Search Report and Written Opinion, PCT/US2022/029979, dated Jan. 4, 2023, 17 pages.
International Search Report and Written Opinion, PCT/US2022/041663, dated Dec. 13, 2022, 23 pages.
International Search Report and Written Opinion, PCT/US2023/022819, dated Oct. 23, 2023, 13 pages.
Kim, S. et al., Neural stem cells derived from human midbrain organoids as a stable source for treating Parkinson's disease Midbrain organoid-NSCs (Og-NSC) as a stable source for PD treatment, Progress in Neurobiology, vol. 204 (2021).
Kriks, S. et al., "Dopamine neurons derived from human ES cells efficiently engraft in animal models of Parkinson's disease." Nature, vol. 480(7378):547-51 (2011).
Kriks, S. et al., "Floor plate-derived dopamine neurons from hESCs efficiently engraft in animal models of PD," Nature, vol. 480(7387):547-551 (2011).
Liu, Y et al.,"Directed differentiation of forebrain GABA interneurons from human pluripotent stem cells," Nature Protocols, vol. 8(9):1670-1679 (2013).
Livesey, M et al., "Maturation and electrophysiological properties of human pluripotent stem cell-derived oligodendrocytes," Stem Cells 34(4):1040-1053 (2016).
Maroof, A. et al., "Directed Differentiation and Functional Maturation of Cortical Interneurons from Human Embryonic Stem Cells," Cell Stem Cell, vol. 12(5):559-572 (2013).
Namchaiw, P. et al., "Temporal and partial inhibition of GLI1 in neural stem cells (NSCs) results in the early maturation of NSC derived oligodendrocytes in vitro," Stem Cell Res & Therapy, vol. 10(1):272 (2019).
Nicholas, C. et al., "Functional Maturation of hPSC-Derived Forebrain Interneurons Requires an Extended Timeline and Mimics Human Neural Development," Cell Stem Cell, vol. 12(5):573-586 (2013).
Nolbrant, S. et al., "Generation of high-purity human ventral midbrain dopaminergic progenitors for in vitro maturation and intracerebral transplantation," Nature Protocols, vol. 12(9):1962-1979 (2017).
Piao, J. et al., "Human embryonic stem cell-derived oligodendrocyte progenitors remyelinate the brain and rescue behavioral deficits following radiation," Cell Stem Cell 16(2):198-210 (2015).
Playne R. et al., "Understanding Parkinson's Disease through the Use of Cell Reprogramming," Stem Cells Reviews and Reports, vol. 13(2):151-169 (2017).
Precious, S. et al., "Dopaminergic Progenitors Derived From Epiblast Stem Cells Function Similarly to Primary VM-Derived Progenitors When Transplanted Into a Parkinson's Disease Model," Front. Neurosci., vol. 14:312 (2020).
Qu Q. et al., "High-efficiency motor neuron differentiation from human pluripotent stem cells and the function of Islet-1," NAture Communications, vol. 5 (1): (2014).
Riemens, R. et al., "Directing neuronal cell fatein vitro: Achievements and challenges," Progress in Neurobiology, vol. 168: 42-68 (2018).
Thomson, J.A. et al., "Embryonic stem cell lines derived from human blastocysts," Science, vol. 282(5391):1145-1147 (1998).
Tyler W. A. et al., "Activation of the Mammalian Target of Rapamycin (mTOR) Is Essential for Oligodendrocyte Differentiation," The Journal of Neuroscience, vol. 29(19):6367-6378 (2009).
Urbanek, P et al., Cooperation of Pax2 and Pax5 in midbrain and cerebellum development, Proc. Natl. Acad. Sci., vol. 94(11):5703-5708 (1997).
Vernay, B. et al. "Otx2 regulates subtype specification and neurogenesis in the midbrain," J. Neurosci., vol. 25 (19):4856-4867 (2005).
Walaa F. Alsanie et al., "Human Embryonic Stem Cell-Derived Oligodendrocytes: Protocols and Perspectives," Stem Cells and Development, vol. 22(18):2459-2476 (2013).
Wang, M. et al., "Development and Differentiation of Midbrain Dopaminergic Neuron: From Bench to Bedside ," Cells, vol. 9:1489 (2020).
Wang, S. et al., "Human iPSC-derived oligodendrocyte progenitor cells can myelinate and rescue a mouse model of congenital hypomyelination," Cell Stem Cell, vol. 12(2):252-264 (2013).
Yamashita, T. et al., "Differentiation of oligodendrocyte progenitor cells from dissociated monolayer and feeder-free cultured pluripotent stem cells," PLOS One, vol. 12(2): e0171947: 16 pages (2017).
Yan, C. et al., "Lmx1a and Imx1b function cooperatively to regulate proliferation, specification, and differentiation of midbrain dopaminergic progenitors," J. Neurosci., vol. 31(35):12413-12425 (2011).
Yang, H. et al., "Generation of functional dopaminergic neurons from human spermatogonial stem cells to rescue parkinsonian phenotypes," Stem Cell Res. Therap., vol. 10(1):195 (2019).
Yu, J. et al. "Human induced pluripotent stem cells free of vector and transgene sequences," Science 324 (5928):797-801 (2009).
Feigenson, K. et al., "Canonical Wnt signalling requires the BMP pathway to inhibit oligodendrocyte maturation," ASN Neuro, vol. 3 (3)(art:e00061):147-158 (2011) doi:10.1042/AN20110004.
Goldman, S.A. et al., "How to make an oligodendrocyte,"Development, vol. 142(23):3983-3995 (2015).
Guardiola-Diaz, H. et al., "Erk1/2 MAPK and mTOR Signaling Sequentially Regulates Progression Through Distinct Stages Of Oligodendrocyte Differentiation," Glia., vol. 60(3): 476-486 (2012) doi:10.1002/glia.22281.

(56) References Cited

OTHER PUBLICATIONS

International Preliminary Report on Patentability, PCT/US2022/029979, dated Jan. 18, 2024, 7 pages.
International Search Report and Written Opinion, PCT/US2023/024792, dated May 22, 2024, 11 pages.
Mccaughey-Chapman, A. et al., "Cell reprogramming for oligodendrocytes: A review of protocols and their applications to disease modeling and cell-based remyelination therapies," Journal of Neuroscience Research, vol. 101 (6):1000-1028 (2023).
Kalani, M. Yashar et al, "Wnt-mediated self-renewal of neural stem/progenitor cells," PNAS, vol. 105(44):16970-16975 (2008).
Adams, K. et al. "Intrinsic and extrinsic regulators of oligodendrocyte progenitor proliferation and differentiation," Seminars in Cell and Developmental Biology, vol. 116: 16-24 (2021).
Alvarez-Dolado, M. et al., "Cortical inhibition modified by embryonic neural precursors grafted into the postnatal brain," J. Neurosci., vol. 26(28):7380-7389 (2006).
Baraban, S et al., "Reduction of seizures by transplantation of cortical GABAergic interneuron precursors into Kv1.1 mutant mice," Proc. Natl. Acad. Sci., vol. 106(36):15472-15477 (2009).
Batista-Brito, R. et al., "The cell-intrinsic requirement of Sox6 for cortical interneuron development," Neuron, vol. 63:466-481 (2009).
Comella-Bolla, A. et al., "Human Pluripotent Stem Cell-Derived Neurons Are Functionally Mature In Vitro and Integrate into the Mouse Striatum Following Transplantation," Mol. Neurobiol. vol. 57(6):2766-2798 (2020).
Crompton, L. et al., "Stepwise, non-adherent differentiation of human pluripotent stem cells to generate basal forebrain cholinergic neurons via hedgehog signaling," Stem Cell Res., vol. 11:1206-1221 (2013).
De Angelis, M. et al., "Short-term retinoic acid treatment sustains pluripotency and suppresses differentiation of human induced pluripotent stem cells," Cell Death and Disease, vol. 9(1):1-13. (2018).
Fishell and Rudy, "Mechanisms of inhibition within the telencephalon: "where the wild things are,"" Annu. Rev. Neurosci., vol. 34:535:567 (2011).
Guo, C. et al., "Fezf2 expression identifies a multipotent progenitor for neocortical projection neurons, astrocytes, and oligodendrocytes," Neuron, vol. 80(5):1167-1174. (2013).
Gusel'Nikova et al., "NeuN As a Neuronal Nuclear Antigen and Neuron Differentiation Marker," Acta Naturae, vol. 7:42-47 (2015).
Hansen et al., "Non-epithelial stem cells and cortical interneuron production in the human ganglionic eminences," Nature Neurosci., vol. 16(11):1576-1587 (2013).
Hoch, R. et al., "OTX2 Transcription Factor Controls Regional Patterning within the Medial Ganglionic Eminence (MGE) and Regional Identity of the Septum," Cell Reports, vol. 12(3):482-494 (2015).
Horn and Nicoll, "Somatostatin and parvalbumin inhibitory synapses onto hippocampal pyramidal neurons are regulated by distinct mechanisms," Proc. Natl. Acad. Sci., vol. 115(3):589-594 (2018).
Huebner, L. et al., "FEZF2's Role in Differentiation and Proliferation in Radial Glial Cells During Cortical Development," University of California, Santa Cruz Dissertations Publishing, pp. 1-33 (2020).
Ihnatovych, I. et al., "Timing of Wnt Inhibition Modulates Directed Differentiation of Medial Ganglionic Eminence Progenitors from Human Pluripotent Stem Cells," Stem Cells International, vol. 2018, Article ID 3983090, 11 pages (2018).
Jang, Y. et al., "Retinoic acid-mediated induction of neurons and glial cells from human umbilical cord-derived hematopoietic stem cells," Journal of Neuroscience Research, vol. 75(4): 573-584 (2004).
Kioussi, C. et al., "Pax6 is essential for establishing ventral-dorsal cell boundaries in pituitary gland development," Proc. Natl. Acad. Sci., vol. 96(25):14378-14382 (1999).
Lagutin et al., "Six3 repression of Wnt signaling in the anterior neuroectoderm is essential for vertebrate forebrain development," Genes & Development, vol. 17(3):368-379 (2003).
Le Magueresse and Monyer, "GABAergic interneurons shape the functional maturation of the cortex," Neuron 77(3):388-405 (2013).
Leoni, G. et al., "NG2 cells differentiate into astrocytes in cerebellar slices," Molecular and Cellular Neuroscience, vol. 42(3): 208-218 (2009).
Liu, Y. et al., "Oligodendrocyte and Astrocyte Development in Rodents: An In Situ and Immunohistological Analysis During Embryonic Development," Glia, vol. 40(1): 25-43 (2002).
Lybrand, Z. et al., "Stem cells: A path towards improved epilepsy therapies," Neuropharm., vol. 168:107781 (2020).
Marques, S et al., "Transcriptional Convergence of Oligodendrocyte Lineage Progenitors during Development," Developmental Cell, vol. 46(4): 504-517 (2018).
Mayer, C. et al., "Developmental diversification of cortical inhibitory interneurons," Nature, 555(7697):457-462 (2018).
Nahar, L. et al., "The Role of Parvalbumin Interneurons in Neurotransmitter Balance and Neurological Disease," Front. Psych., vol. 12:679960 (2021).
Nguyen, R. et al., "Parvalbumin and GAD65 interneuron inhibition in the ventral hippocampus induces distinct behavioral deficits relevant to schizophrenia," J. Neurosci., vol. 34(45):14948-14960 (2014).
Pai, E. et al., "Maf and Mafb control mouse pallial interneuron fate and maturation through neuropsychiatric disease gene regulation," Elife, vol. 9:54903 (2020).
Shetty and Upadhya, "GABA-ergic cell therapy for epilepsy: Advances, limitations and challenges," Neurosci. Biobehav. Rev., vol. 62:35-47 (2016).
Shi, Z. et al., "Conversion of Fibroblasts to Parvalbumin Neurons by One Transcription Factor, Ascl1, and the Chemical Compound Forskolin," J. Biol. Chem., vol. 291(26):13560-13570 (2016).
Silberberg, S. et al., "Subpallial Enhancer Transgenic Lines: a Data and Tool Resource to Study Transcriptional Regulation of GABAergic Cell Fate," Neuron, vol. 92(1):59-74 (2016).
Stoykova, A. et al., "Pax6 modulates the dorsoventral patterning of the mammalian telencephalon," J. Neurosci. 20(21):8042-8050 (2000).
Trotter, J. et al., "NG2 cells: Properties, progeny and origin," Brain Research Reviews, vol. 63(1-2): 72-82 (2010).
Wang, Y et al., "DIx5 and DIx6 regulate the development of parvalbumin-expressing cortical interneurons," J. Neurosci., vol. 30(15):5334-5345 (2010).
Wen, W et al., "Mesencephalic Astrocyte-Derived Neurotrophic Factor (MAN F) Regulates Neurite Outgrowth Through the Activation of Akt/mTOR," Front. Mol. Neurosci., vol. 13:1-17 (2020).
Yan, Y. et al., "Efficient and rapid derivation of primitive neural stem cells and generation of brain subtype neurons from human pluripotent stem cells," Stem Cells Transl. Med., vol. 2(11): 862-870 (2013).
Yuan, F. et al., "Efficient generation of region-specific forebrain neurons from human pluripotent stem cells under highly defined condition," Sci Rep., vol. 5:18550 (2015).
Yuan, F. et al., "Induction of human somatostatin and parvalbumin neurons by expressing a single transcription factor LIM homeobox 6," Elife, vol. 7:e37382 (2018).
Zhang et al., "Small Molecules Efficiently Reprogram Human Astroglial Cells into Functional Neurons," Cell Stem Cell, vol. 17: 735-747 (2015).
Zhang et al., "Supplemental Small Molecules Efficiently Reprogram Human Astroglial Cells into Functional Neurons," Cell Stem Cell, vol. 17: 48 pages. (2015).
Zhang, S. et al., "Fezf2 promotes neuronal differentiation through localised activation of Wnt/ß-catenin signalling during forebrain development," Development, vol. 141(24):4794-47805 (2014).
Zhou, J et al., "A Revolution in Reprogramming: Small Molecules," Current Molecular Medicine, vol. 19(2): 77-90 (2019).
International Preliminary Report on Patentability, PCT/US2022/041663, dated Apr. 30, 2024, 14 pages.

* cited by examiner

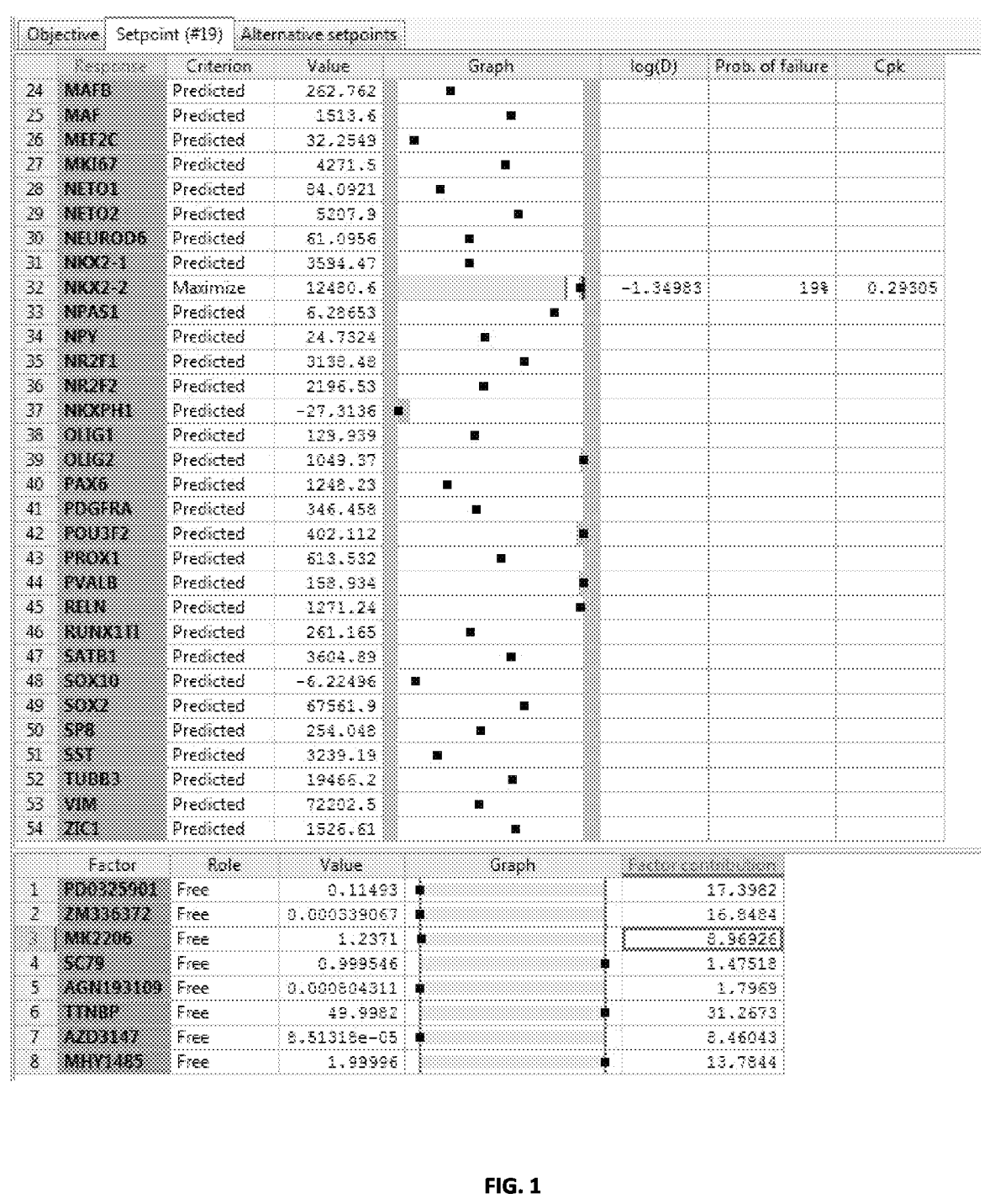

Objective | Setpoint (#19) | Alternative setpoints

| | Response | Criterion | Value | Graph | log(D) | Prob. of failure | Cpk |
|---|---|---|---|---|---|---|---|
| 24 | MAFB | Predicted | 262.762 | | | | |
| 25 | MAF | Predicted | 1513.6 | | | | |
| 26 | MEF2C | Predicted | 32.2549 | | | | |
| 27 | MKI67 | Predicted | 4271.5 | | | | |
| 28 | NETO1 | Predicted | 84.0921 | | | | |
| 29 | NETO2 | Predicted | 5207.9 | | | | |
| 30 | NEUROD6 | Predicted | 61.0956 | | | | |
| 31 | NKX2-1 | Predicted | 3584.47 | | | | |
| 32 | NKX2-2 | Maximize | 12480.6 | | -1.34983 | 19% | 0.29305 |
| 33 | NFASL | Predicted | 6.28653 | | | | |
| 34 | NPY | Predicted | 24.7324 | | | | |
| 35 | NR2F1 | Predicted | 3138.48 | | | | |
| 36 | NR2F2 | Predicted | 2196.53 | | | | |
| 37 | NKXPH1 | Predicted | -27.3136 | | | | |
| 38 | OLIG1 | Predicted | 128.939 | | | | |
| 39 | OLIG2 | Predicted | 1049.37 | | | | |
| 40 | PAX6 | Predicted | 1248.23 | | | | |
| 41 | PDGFRA | Predicted | 346.458 | | | | |
| 42 | POU3F2 | Predicted | 402.112 | | | | |
| 43 | PROX1 | Predicted | 613.532 | | | | |
| 44 | PVALB | Predicted | 158.934 | | | | |
| 45 | RELN | Predicted | 1271.24 | | | | |
| 46 | RUNX1T1 | Predicted | 261.165 | | | | |
| 47 | SATB1 | Predicted | 3604.89 | | | | |
| 48 | SOX10 | Predicted | -6.22496 | | | | |
| 49 | SOX2 | Predicted | 67561.9 | | | | |
| 50 | SP8 | Predicted | 254.048 | | | | |
| 51 | SST | Predicted | 3239.19 | | | | |
| 52 | TUBB3 | Predicted | 19466.2 | | | | |
| 53 | VIM | Predicted | 72202.5 | | | | |
| 54 | ZIC1 | Predicted | 1526.61 | | | | |

| | Factor | Role | Value | Graph | [illegible] |
|---|---|---|---|---|---|
| 1 | PD0325901 | Free | 0.11493 | | 17.3982 |
| 2 | ZM336372 | Free | 0.000339067 | | 16.8484 |
| | MK2206 | Free | 1.2371 | | 8.96926 |
| 4 | SC79 | Free | 0.999546 | | 1.47518 |
| 5 | AGN193109 | Free | 0.000804311 | | 1.7969 |
| 6 | TTNBP | Free | 49.9982 | | 31.2673 |
| 7 | AZD3147 | Free | 8.51318e-05 | | 8.46043 |
| 8 | MHY1485 | Free | 1.99996 | | 13.7844 |

FIG. 1

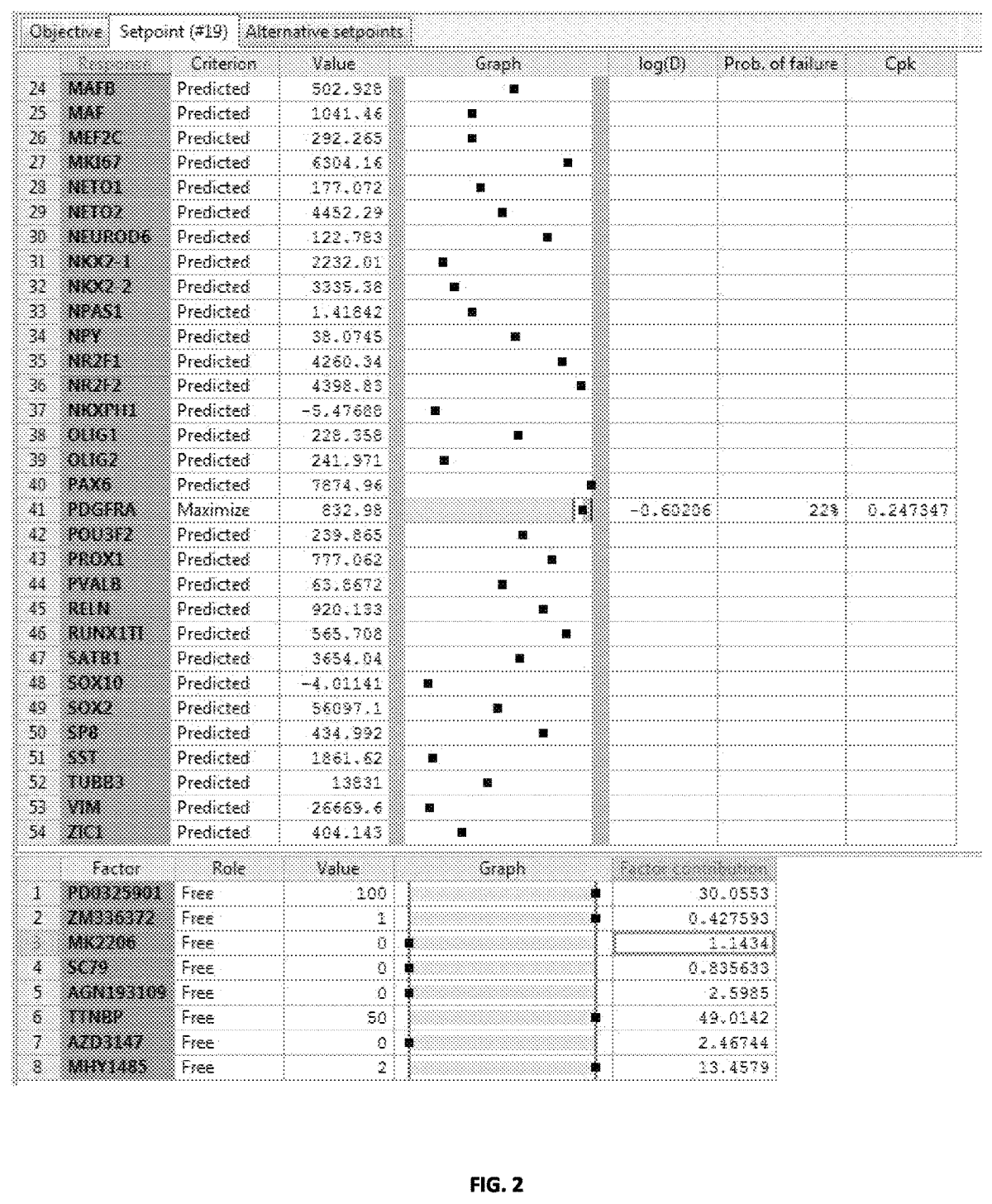

Objective | Setpoint (#19) | Alternative setpoints

| | Response | Criterion | Value | Graph | log(D) | Prob. of failure | Cpk |
|---|---|---|---|---|---|---|---|
| 24 | MAFB | Predicted | 502.928 | | | | |
| 25 | MAF | Predicted | 1041.46 | | | | |
| 26 | MEF2C | Predicted | 292.265 | | | | |
| 27 | MKI67 | Predicted | 6304.16 | | | | |
| 28 | NETO1 | Predicted | 177.072 | | | | |
| 29 | NETO2 | Predicted | 4452.29 | | | | |
| 30 | NEUROD6 | Predicted | 122.783 | | | | |
| 31 | NKX2-1 | Predicted | 2232.01 | | | | |
| 32 | NKX2-2 | Predicted | 3335.38 | | | | |
| 33 | NPAS1 | Predicted | 1.41842 | | | | |
| 34 | NPY | Predicted | 38.0745 | | | | |
| 35 | NR2F1 | Predicted | 4260.34 | | | | |
| 36 | NR2F2 | Predicted | 4398.83 | | | | |
| 37 | NKXPH1 | Predicted | -5.47688 | | | | |
| 38 | OLIG1 | Predicted | 228.358 | | | | |
| 39 | OLIG2 | Predicted | 241.971 | | | | |
| 40 | PAX6 | Predicted | 7674.96 | | | | |
| 41 | PDGFRA | Maximize | 832.98 | | -0.60206 | 22% | 0.247347 |
| 42 | POU3F2 | Predicted | 239.865 | | | | |
| 43 | PROX1 | Predicted | 777.062 | | | | |
| 44 | PVALB | Predicted | 63.8672 | | | | |
| 45 | RELN | Predicted | 920.133 | | | | |
| 46 | RUNX1T1 | Predicted | 565.708 | | | | |
| 47 | SATB1 | Predicted | 3654.04 | | | | |
| 48 | SOX10 | Predicted | -4.01141 | | | | |
| 49 | SOX2 | Predicted | 56097.1 | | | | |
| 50 | SP8 | Predicted | 434.992 | | | | |
| 51 | SST | Predicted | 1861.62 | | | | |
| 52 | TUBB3 | Predicted | 13831 | | | | |
| 53 | VIM | Predicted | 26669.6 | | | | |
| 54 | ZIC1 | Predicted | 404.143 | | | | |

| | Factor | Role | Value | Graph | Factor contribution |
|---|---|---|---|---|---|
| 1 | PD0325901 | Free | 100 | | 30.0553 |
| 2 | ZM336372 | Free | 1 | | 0.427593 |
| 3 | MK2206 | Free | 0 | | 1.1434 |
| 4 | SC79 | Free | 0 | | 0.835633 |
| 5 | AGN193109 | Free | 0 | | 2.5985 |
| 6 | TTNBP | Free | 50 | | 49.0142 |
| 7 | AZD3147 | Free | 0 | | 2.46744 |
| 8 | MHY1485 | Free | 2 | | 13.4579 |

FIG. 2

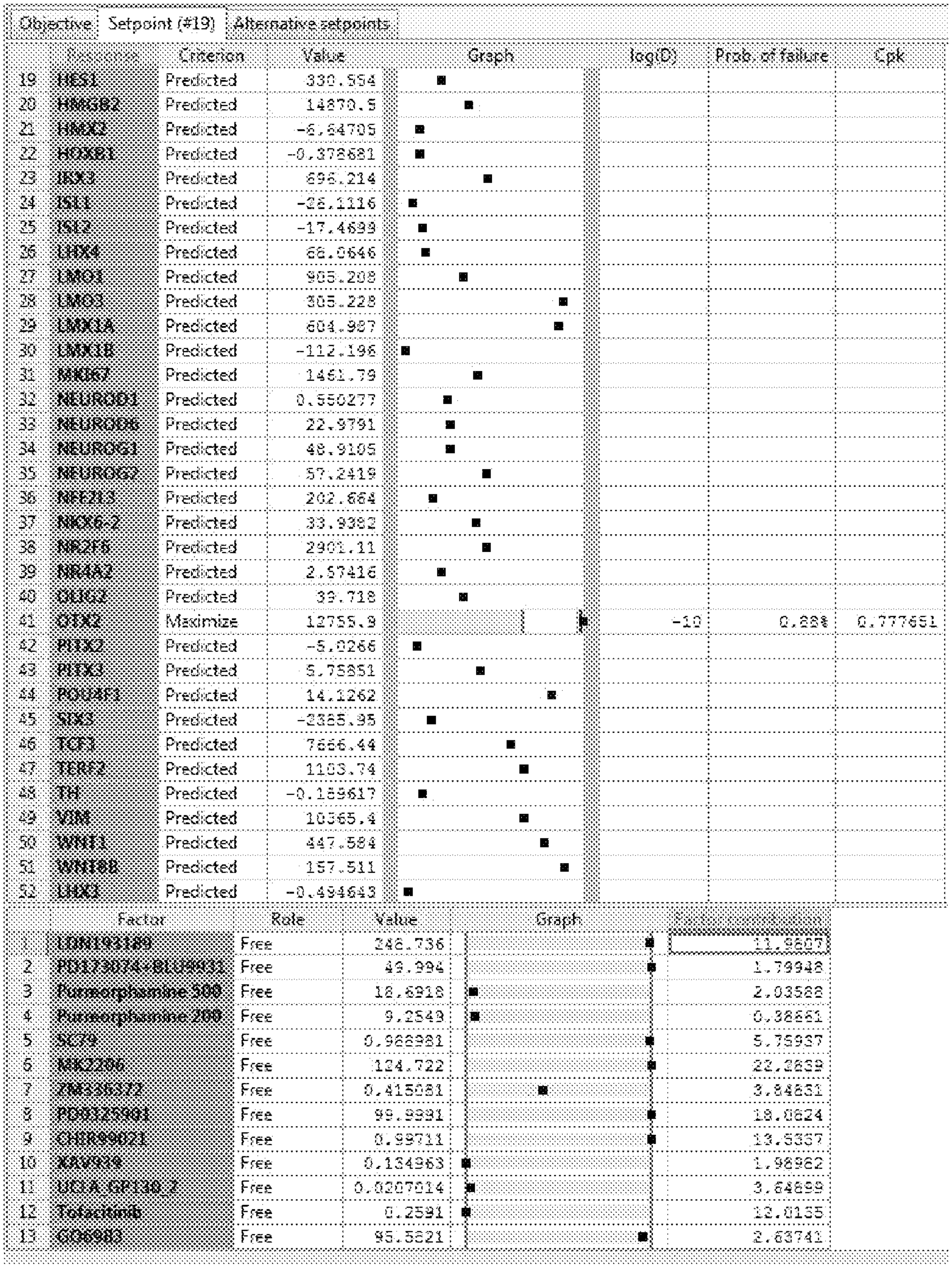

Objective | Setpoint (#19) | Alternative setpoints

| | | Criterion | Value | Graph | log(D) | Prob. of failure | Cpk |
|---|---|---|---|---|---|---|---|
| 19 | HES1 | Predicted | 330.554 | | | | |
| 20 | HMGB2 | Predicted | 14870.5 | | | | |
| 21 | HMX2 | Predicted | -6.64705 | | | | |
| 22 | HOXB1 | Predicted | -0.378681 | | | | |
| 23 | IRX3 | Predicted | 696.214 | | | | |
| 24 | ISL1 | Predicted | -26.1116 | | | | |
| 25 | ISL2 | Predicted | -17.4699 | | | | |
| 26 | LHX4 | Predicted | 66.0646 | | | | |
| 27 | LMO1 | Predicted | 905.208 | | | | |
| 28 | LMO3 | Predicted | 305.228 | | | | |
| 29 | LMX1A | Predicted | 604.987 | | | | |
| 30 | LMX1B | Predicted | -112.196 | | | | |
| 31 | MKI67 | Predicted | 1461.79 | | | | |
| 32 | NEUROD1 | Predicted | 0.550277 | | | | |
| 33 | NEUROD6 | Predicted | 22.9791 | | | | |
| 34 | NEUROG1 | Predicted | 48.9105 | | | | |
| 35 | NEUROG2 | Predicted | 57.2419 | | | | |
| 36 | NFE2L3 | Predicted | 202.664 | | | | |
| 37 | NKX6-2 | Predicted | 33.9382 | | | | |
| 38 | NR2F6 | Predicted | 2901.11 | | | | |
| 39 | NR4A2 | Predicted | 2.57416 | | | | |
| 40 | OLIG2 | Predicted | 39.718 | | | | |
| 41 | OTX2 | Maximize | 12755.9 | | -10 | 0.88% | 0.777651 |
| 42 | PITX2 | Predicted | -5.0266 | | | | |
| 43 | PITX3 | Predicted | 5.75851 | | | | |
| 44 | POU4F1 | Predicted | 14.1262 | | | | |
| 45 | SIX3 | Predicted | -2385.95 | | | | |
| 46 | TCF3 | Predicted | 7666.44 | | | | |
| 47 | TERF2 | Predicted | 1103.74 | | | | |
| 48 | TH | Predicted | -0.189617 | | | | |
| 49 | VIM | Predicted | 10365.4 | | | | |
| 50 | WNT1 | Predicted | 447.584 | | | | |
| 51 | WNT8B | Predicted | 157.511 | | | | |
| 52 | LHX3 | Predicted | -0.494643 | | | | |

| | Factor | Role | Value | Graph | |
|---|---|---|---|---|---|
| 1 | LDN193189 | Free | 246.736 | | 11.9607 |
| 2 | PD173074+BLU9931 | Free | 49.994 | | 1.79948 |
| 3 | Purmorphamine 500 | Free | 18.6918 | | 2.03588 |
| 4 | Purmorphamine 200 | Free | 9.2549 | | 0.38661 |
| 5 | SC79 | Free | 0.966981 | | 5.75937 |
| 6 | MK2206 | Free | 124.722 | | 22.2839 |
| 7 | ZM336372 | Free | 0.415081 | | 3.84851 |
| 8 | PD0325901 | Free | 99.9991 | | 18.0624 |
| 9 | CHIR99021 | Free | 0.99711 | | 13.5357 |
| 10 | XAV939 | Free | 0.134963 | | 1.98962 |
| 11 | UCLA_GP130_2 | Free | 0.0207014 | | 3.64899 |
| 12 | Tofacitinib | Free | 0.2591 | | 12.0135 |
| 13 | GO6983 | Free | 95.5821 | | 2.63741 |

FIG. 4

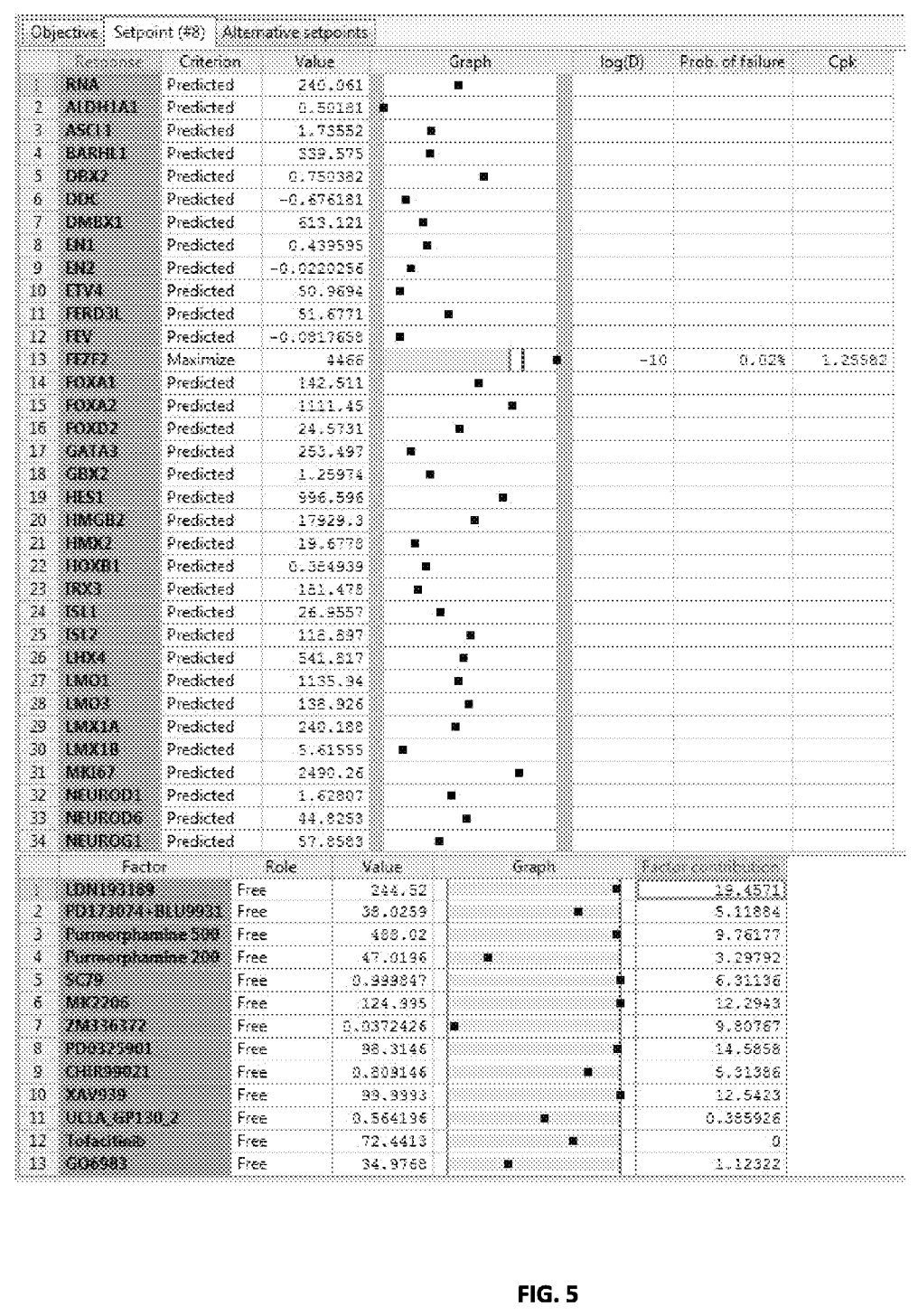

Objective | Setpoint (#8) | Alternative setpoints

| | Response | Criterion | Value | Graph | log(D) | Prob. of failure | Cpk |
|---|---|---|---|---|---|---|---|
| 1 | RNA | Predicted | 240.061 | | | | |
| 2 | ALDH1A1 | Predicted | 0.50181 | | | | |
| 3 | ASCL1 | Predicted | 1.73552 | | | | |
| 4 | BARHL1 | Predicted | 339.575 | | | | |
| 5 | DBX2 | Predicted | 0.750382 | | | | |
| 6 | DDC | Predicted | -0.676181 | | | | |
| 7 | DMBX1 | Predicted | 613.121 | | | | |
| 8 | EN1 | Predicted | 0.439595 | | | | |
| 9 | EN2 | Predicted | -0.0220256 | | | | |
| 10 | ETV4 | Predicted | 50.9694 | | | | |
| 11 | FERD3L | Predicted | 51.6771 | | | | |
| 12 | FEV | Predicted | -0.0817658 | | | | |
| 13 | FEZF2 | Maximize | 4466 | | -10 | 0.02% | 1.25582 |
| 14 | FOXA1 | Predicted | 142.511 | | | | |
| 15 | FOXA2 | Predicted | 1111.45 | | | | |
| 16 | FOXD2 | Predicted | 24.5731 | | | | |
| 17 | GATA3 | Predicted | 253.497 | | | | |
| 18 | GBX2 | Predicted | 1.25974 | | | | |
| 19 | HES1 | Predicted | 996.596 | | | | |
| 20 | HMGB2 | Predicted | 17929.3 | | | | |
| 21 | HMX2 | Predicted | 19.6778 | | | | |
| 22 | HOXB1 | Predicted | 0.384939 | | | | |
| 23 | IRX3 | Predicted | 181.478 | | | | |
| 24 | ISL1 | Predicted | 26.9557 | | | | |
| 25 | ISL2 | Predicted | 118.897 | | | | |
| 26 | LHX4 | Predicted | 541.817 | | | | |
| 27 | LMO1 | Predicted | 1135.94 | | | | |
| 28 | LMO3 | Predicted | 138.926 | | | | |
| 29 | LMX1A | Predicted | 240.188 | | | | |
| 30 | LMX1B | Predicted | 5.61555 | | | | |
| 31 | MKI67 | Predicted | 2490.26 | | | | |
| 32 | NEUROD1 | Predicted | 1.62807 | | | | |
| 33 | NEUROD6 | Predicted | 44.8253 | | | | |
| 34 | NEUROG1 | Predicted | 57.8583 | | | | |

| | Factor | Role | Value | Graph | Factor contribution |
|---|---|---|---|---|---|
| 1 | LDN193189 | Free | 244.52 | | 19.4571 |
| 2 | PD173074+BLU9931 | Free | 38.0259 | | 5.11884 |
| 3 | Purmorphamine 500 | Free | 488.02 | | 9.76177 |
| 4 | Purmorphamine 200 | Free | 47.0196 | | 3.29792 |
| 5 | SC79 | Free | 0.999847 | | 6.31136 |
| 6 | MK2206 | Free | 124.995 | | 12.2943 |
| 7 | ZM336372 | Free | 0.0372426 | | 9.80787 |
| 8 | PD0325901 | Free | 98.3146 | | 14.5858 |
| 9 | CHIR99021 | Free | 0.808146 | | 5.31386 |
| 10 | XAV939 | Free | 99.9993 | | 12.5423 |
| 11 | ULLA_GP130_2 | Free | 0.564196 | | 0.385926 |
| 12 | Tofacitinib | Free | 72.4413 | | 0 |
| 13 | GO6983 | Free | 34.9768 | | 1.12322 |

FIG. 5

Z-score
HOXA1
HOXB1
HOXA3
HOXA2
HOXA4
HOXA5
HOXB4
FOXA2
PHOX2B
PAX6
FEZF2
OTX2
FOXG1
SOX10
OLIG2
OLIG3
PDGFRA
NKX2-2
NANOG
POU5F1
Hindbrain
Fore brain
OPC
SC
hiPSC
Pre-OPC
1.0
0.5
0
-0.5
-1.0

Relative Expression versus iPSC
Pre-OPC
Fold Change
Genes
20
15
10
5
0
-5

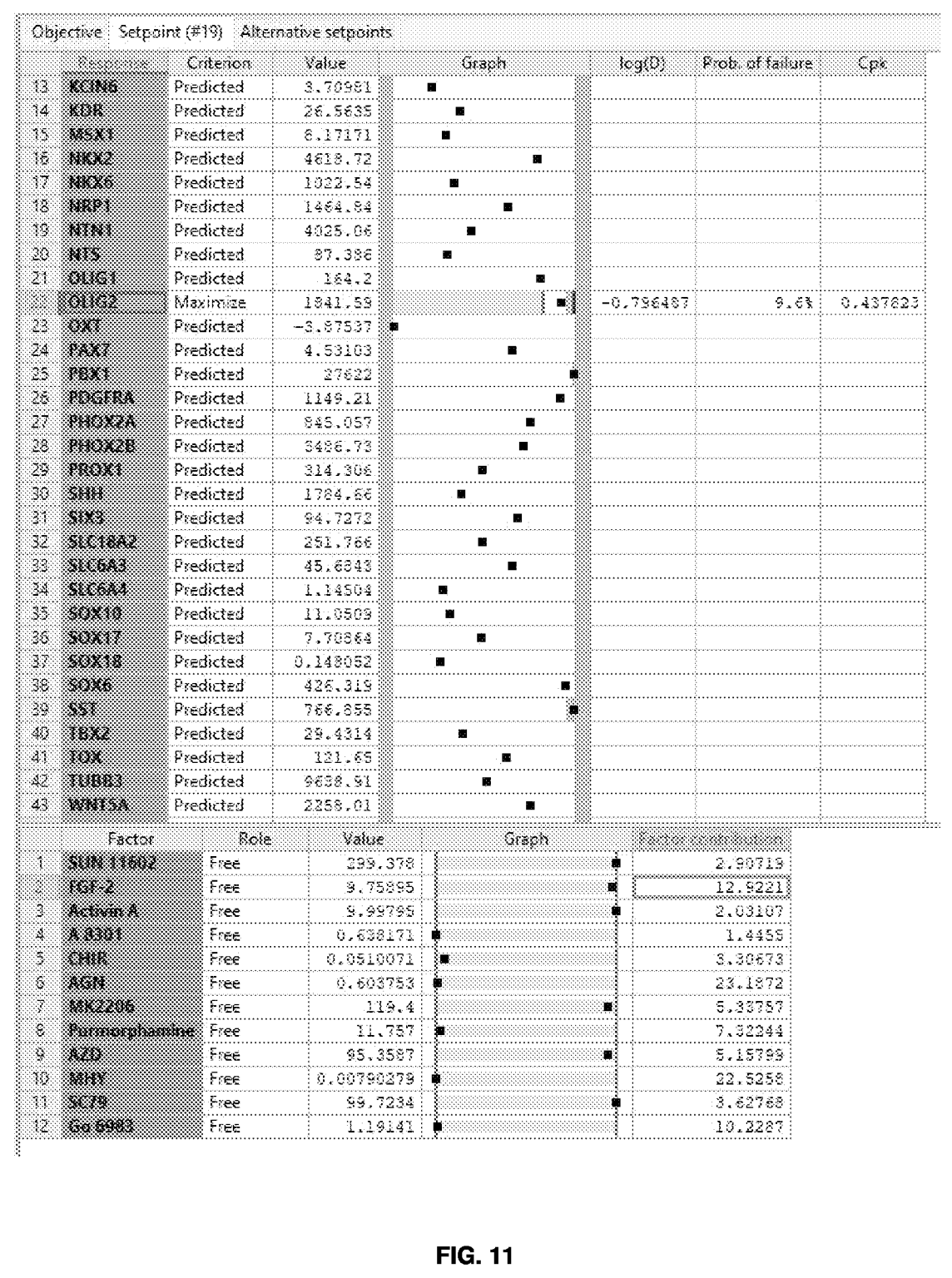

Objective | Setpoint (#19) | Alternative setpoints

| | | Criterion | Value | Graph | log(D) | Prob. of failure | Cpk |
|---|---|---|---|---|---|---|---|
| 13 | KCIN6 | Predicted | 3.70981 | | | | |
| 14 | KDR | Predicted | 26.5635 | | | | |
| 15 | MSX1 | Predicted | 6.17171 | | | | |
| 16 | NKX2 | Predicted | 4618.72 | | | | |
| 17 | NKX6 | Predicted | 1022.54 | | | | |
| 18 | NRP1 | Predicted | 1464.84 | | | | |
| 19 | NTN1 | Predicted | 4025.06 | | | | |
| 20 | NTS | Predicted | 87.386 | | | | |
| 21 | OLIG1 | Predicted | 164.2 | | | | |
| | OLIG2 | Maximize | 1841.59 | | -0.796487 | 9.6% | 0.437623 |
| 23 | OXT | Predicted | -3.87537 | | | | |
| 24 | PAX7 | Predicted | 4.53103 | | | | |
| 25 | PBX1 | Predicted | 27622 | | | | |
| 26 | PDGFRA | Predicted | 1149.21 | | | | |
| 27 | PHOX2A | Predicted | 845.057 | | | | |
| 28 | PHOX2B | Predicted | 3486.73 | | | | |
| 29 | PROX1 | Predicted | 314.306 | | | | |
| 30 | SHH | Predicted | 1784.66 | | | | |
| 31 | SIX3 | Predicted | 94.7272 | | | | |
| 32 | SLC18A2 | Predicted | 251.766 | | | | |
| 33 | SLC6A3 | Predicted | 45.6843 | | | | |
| 34 | SLC6A4 | Predicted | 1.14504 | | | | |
| 35 | SOX10 | Predicted | 11.0509 | | | | |
| 36 | SOX17 | Predicted | 7.70864 | | | | |
| 37 | SOX18 | Predicted | 0.148052 | | | | |
| 38 | SOX6 | Predicted | 426.319 | | | | |
| 39 | SST | Predicted | 766.855 | | | | |
| 40 | TBX2 | Predicted | 29.4314 | | | | |
| 41 | TOX | Predicted | 121.65 | | | | |
| 42 | TUBB3 | Predicted | 9638.91 | | | | |
| 43 | WNT5A | Predicted | 2258.01 | | | | |

| | Factor | Role | Value | Graph | |
|---|---|---|---|---|---|
| 1 | SUN 11602 | Free | 299.378 | | 2.90719 |
| | FGF-2 | Free | 9.75895 | | 12.9221 |
| 3 | Activin A | Free | 9.99795 | | 2.03107 |
| 4 | A 8301 | Free | 0.638171 | | 1.4455 |
| 5 | CHIR | Free | 0.0510071 | | 3.30673 |
| 6 | AGN | Free | 0.603753 | | 23.1872 |
| 7 | MK2206 | Free | 119.4 | | 5.33757 |
| 8 | Purmorphamine | Free | 11.757 | | 7.32244 |
| 9 | AZD | Free | 95.3587 | | 5.15799 |
| 10 | MHY | Free | 0.00790279 | | 22.5258 |
| 11 | SC79 | Free | 99.7234 | | 3.62768 |
| 12 | Go 6983 | Free | 1.19141 | | 10.2287 |

FIG. 11

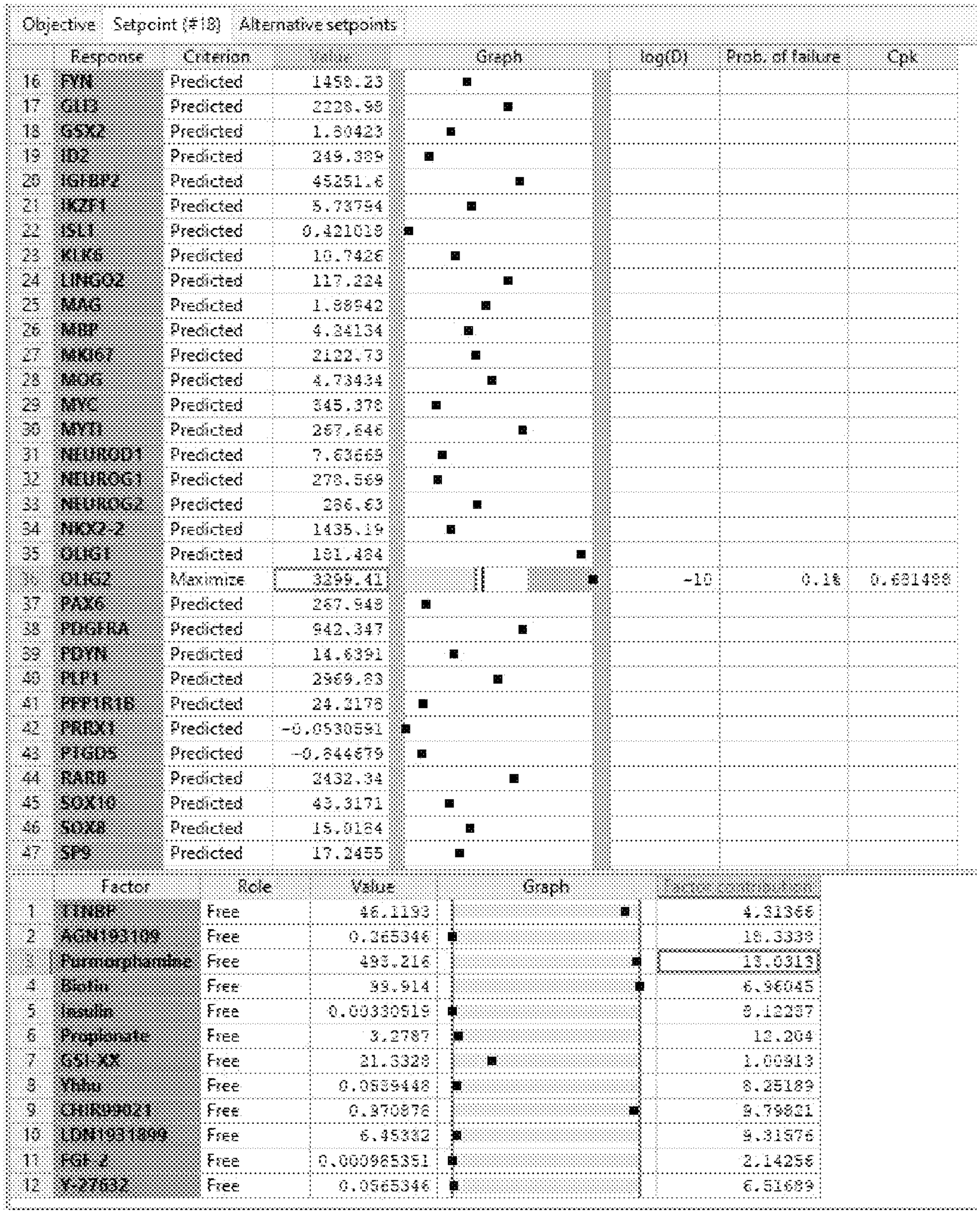
Objective | Setpoint (#18) | Alternative setpoints

| | Response | Criterion | | Graph | log(D) | Prob. of failure | Cpk |
|---|---|---|---|---|---|---|---|
| 16 | FYN | Predicted | 1458.23 | | | | |
| 17 | GLI3 | Predicted | 2228.98 | | | | |
| 18 | GSX2 | Predicted | 1.80423 | | | | |
| 19 | ID2 | Predicted | 249.389 | | | | |
| 20 | IGFBP2 | Predicted | 45251.6 | | | | |
| 21 | IKZF1 | Predicted | 5.73794 | | | | |
| 22 | ISL1 | Predicted | 0.421018 | | | | |
| 23 | KLK6 | Predicted | 10.7426 | | | | |
| 24 | LINGO2 | Predicted | 117.224 | | | | |
| 25 | MAG | Predicted | 1.88942 | | | | |
| 26 | MBP | Predicted | 4.24134 | | | | |
| 27 | MKI67 | Predicted | 2122.73 | | | | |
| 28 | MOG | Predicted | 4.73434 | | | | |
| 29 | MYC | Predicted | 345.378 | | | | |
| 30 | MYT1 | Predicted | 267.646 | | | | |
| 31 | NEUROD1 | Predicted | 7.63669 | | | | |
| 32 | NEUROG1 | Predicted | 278.569 | | | | |
| 33 | NEUROG2 | Predicted | 286.63 | | | | |
| 34 | NKX2-2 | Predicted | 1435.19 | | | | |
| 35 | OLIG1 | Predicted | 181.484 | | | | |
| | OLIG2 | Maximize | 3299.41 | | -10 | 0.1% | 0.681488 |
| 37 | PAX6 | Predicted | 267.948 | | | | |
| 38 | PDGFRA | Predicted | 942.347 | | | | |
| 39 | PDYN | Predicted | 14.6391 | | | | |
| 40 | PLP1 | Predicted | 2969.83 | | | | |
| 41 | PPP1R1B | Predicted | 24.2178 | | | | |
| 42 | PRRX1 | Predicted | -0.0530591 | | | | |
| 43 | PTGDS | Predicted | -0.644679 | | | | |
| 44 | RARB | Predicted | 2432.34 | | | | |
| 45 | SOX10 | Predicted | 43.3171 | | | | |
| 46 | SOX8 | Predicted | 15.0184 | | | | |
| 47 | SP9 | Predicted | 17.2455 | | | | |

| | Factor | Role | Value | Graph | |
|---|---|---|---|---|---|
| 1 | TTNBP | Free | 46.1193 | | 4.31366 |
| 2 | AGN193109 | Free | 0.265346 | | 18.3338 |
| | Purmorphamine | Free | 493.216 | | 13.0313 |
| 4 | Biotin | Free | 38.914 | | 6.96045 |
| 5 | Insulin | Free | 0.00330519 | | 8.12237 |
| 6 | Propionate | Free | 3.2787 | | 12.204 |
| 7 | GSI-XX | Free | 21.3328 | | 1.00913 |
| 8 | Yhhu | Free | 0.0539448 | | 8.25189 |
| 9 | CHIR99021 | Free | 0.370878 | | 9.79821 |
| 10 | LDN193189 | Free | 6.45332 | | 9.31576 |
| 11 | FGF-2 | Free | 0.000985351 | | 2.14256 |
| 12 | Y-27632 | Free | 0.0565346 | | 6.51689 |

FIG. 13

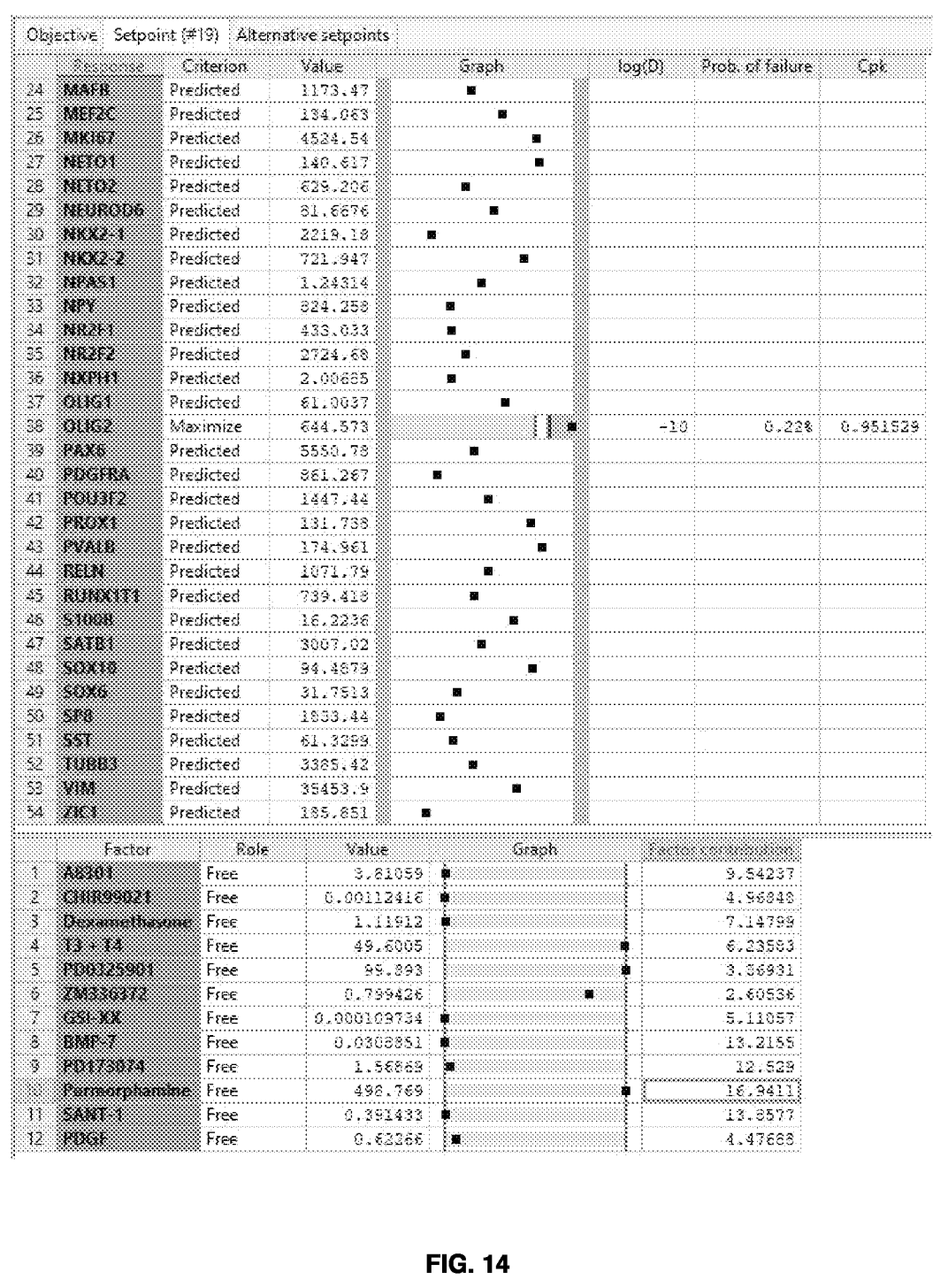

Objective | Setpoint (#19) | Alternative setpoints

| | Response | Criterion | Value | Graph | log(D) | Prob. of failure | Cpk |
|---|---|---|---|---|---|---|---|
| 24 | MAFB | Predicted | 1173.47 | | | | |
| 25 | MEF2C | Predicted | 134.063 | | | | |
| 26 | MKI67 | Predicted | 4524.54 | | | | |
| 27 | NETO1 | Predicted | 140.617 | | | | |
| 28 | NETO2 | Predicted | 629.206 | | | | |
| 29 | NEUROD6 | Predicted | 81.6676 | | | | |
| 30 | NKX2-1 | Predicted | 2219.18 | | | | |
| 31 | NKX2-2 | Predicted | 721.947 | | | | |
| 32 | NPAS1 | Predicted | 1.24314 | | | | |
| 33 | NPY | Predicted | 324.258 | | | | |
| 34 | NR2F1 | Predicted | 433.033 | | | | |
| 35 | NR2F2 | Predicted | 2724.68 | | | | |
| 36 | NXPH1 | Predicted | 2.00685 | | | | |
| 37 | OLIG1 | Predicted | 61.0037 | | | | |
| 38 | OLIG2 | Maximize | 644.573 | | -10 | 0.22% | 0.951529 |
| 39 | PAX6 | Predicted | 5550.78 | | | | |
| 40 | PDGFRA | Predicted | 861.267 | | | | |
| 41 | POU3F2 | Predicted | 1447.44 | | | | |
| 42 | PROX1 | Predicted | 131.738 | | | | |
| 43 | PVALB | Predicted | 174.961 | | | | |
| 44 | RELN | Predicted | 1071.79 | | | | |
| 45 | RUNX1T1 | Predicted | 739.418 | | | | |
| 46 | S100B | Predicted | 16.2236 | | | | |
| 47 | SATB1 | Predicted | 3007.02 | | | | |
| 48 | SOX10 | Predicted | 94.4879 | | | | |
| 49 | SOX6 | Predicted | 31.7513 | | | | |
| 50 | SP8 | Predicted | 1833.44 | | | | |
| 51 | SST | Predicted | 61.3299 | | | | |
| 52 | TUBB3 | Predicted | 3385.42 | | | | |
| 53 | VIM | Predicted | 35453.9 | | | | |
| 54 | ZIC1 | Predicted | 185.851 | | | | |

| | Factor | Role | Value | Graph | |
|---|---|---|---|---|---|
| 1 | A8301 | Free | 3.81059 | | 9.54237 |
| 2 | CHIR99021 | Free | 0.00112416 | | 4.96848 |
| 3 | Dexamethasone | Free | 1.11912 | | 7.14799 |
| 4 | T3 + T4 | Free | 49.6005 | | 6.23583 |
| 5 | PD0325901 | Free | 99.893 | | 3.36931 |
| 6 | ZM336372 | Free | 0.799426 | | 2.60536 |
| 7 | GSI-XX | Free | 0.000109734 | | 5.11057 |
| 8 | BMP-7 | Free | 0.0308851 | | 13.2155 |
| 9 | PD173074 | Free | 1.56869 | | 12.529 |
| | Purmorphamine | Free | 498.769 | | 16.9411 |
| 11 | SANT-1 | Free | 0.391433 | | 13.8577 |
| 12 | PDGF | Free | 0.62366 | | 4.47668 |

FIG. 14

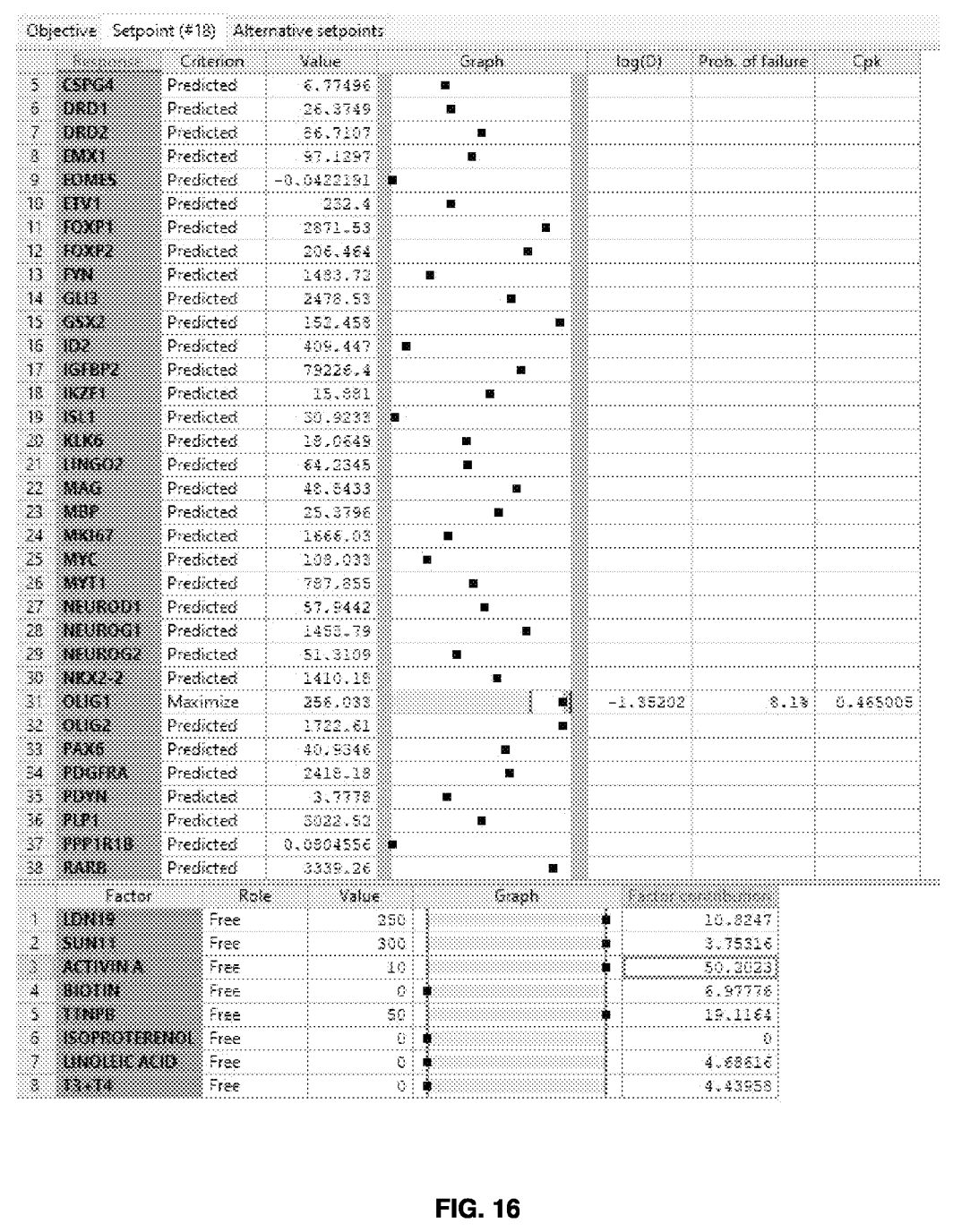

Objective Setpoint (#18) Alternative setpoints

| | | Criterion | Value | Graph | log(D) | Prob. of failure | Cpk |
|---|---|---|---|---|---|---|---|
| 5 | CSPG4 | Predicted | 6.77496 | | | | |
| 6 | DRD1 | Predicted | 26.3749 | | | | |
| 7 | DRD2 | Predicted | 86.7107 | | | | |
| 8 | EMX1 | Predicted | 97.1297 | | | | |
| 9 | EOMES | Predicted | -0.0422191 | | | | |
| 10 | ETV1 | Predicted | 232.4 | | | | |
| 11 | FOXP1 | Predicted | 2871.53 | | | | |
| 12 | FOXP2 | Predicted | 206.464 | | | | |
| 13 | FYN | Predicted | 1483.72 | | | | |
| 14 | GLI3 | Predicted | 2478.53 | | | | |
| 15 | GSX2 | Predicted | 152.458 | | | | |
| 16 | ID2 | Predicted | 409.447 | | | | |
| 17 | IGFBP2 | Predicted | 79226.4 | | | | |
| 18 | IKZF1 | Predicted | 15.881 | | | | |
| 19 | ISL1 | Predicted | 30.9233 | | | | |
| 20 | KLK6 | Predicted | 18.0649 | | | | |
| 21 | LINGO2 | Predicted | 64.2345 | | | | |
| 22 | MAG | Predicted | 48.8433 | | | | |
| 23 | MBP | Predicted | 25.3796 | | | | |
| 24 | MKI67 | Predicted | 1666.03 | | | | |
| 25 | MYC | Predicted | 108.033 | | | | |
| 26 | MYT1 | Predicted | 787.855 | | | | |
| 27 | NEUROD1 | Predicted | 57.9442 | | | | |
| 28 | NEUROG1 | Predicted | 1453.79 | | | | |
| 29 | NEUROG2 | Predicted | 51.3109 | | | | |
| 30 | NKX2-2 | Predicted | 1410.18 | | | | |
| 31 | OLIG1 | Maximize | 256.033 | | -1.35202 | 8.1% | 0.465005 |
| 32 | OLIG2 | Predicted | 1722.61 | | | | |
| 33 | PAX6 | Predicted | 40.9346 | | | | |
| 34 | PDGFRA | Predicted | 2418.18 | | | | |
| 35 | PDYN | Predicted | 3.7778 | | | | |
| 36 | PLP1 | Predicted | 3022.92 | | | | |
| 37 | PPP1R1B | Predicted | 0.0804556 | | | | |
| 38 | RARB | Predicted | 3339.26 | | | | |

| | Factor | Role | Value | Graph | |
|---|---|---|---|---|---|
| 1 | LDN19 | Free | 250 | | 10.8247 |
| 2 | SUN11 | Free | 300 | | 3.75316 |
| 3 | ACTIVIN A | Free | 10 | | 50.2023 |
| 4 | BIOTIN | Free | 0 | | 6.97776 |
| 5 | TTNPB | Free | 50 | | 19.1164 |
| 6 | ISOPROTERENOL | Free | 0 | | 0 |
| 7 | LINOLEIC ACID | Free | 0 | | 4.68616 |
| 8 | T3+T4 | Free | 0 | | 4.43958 |

FIG. 16

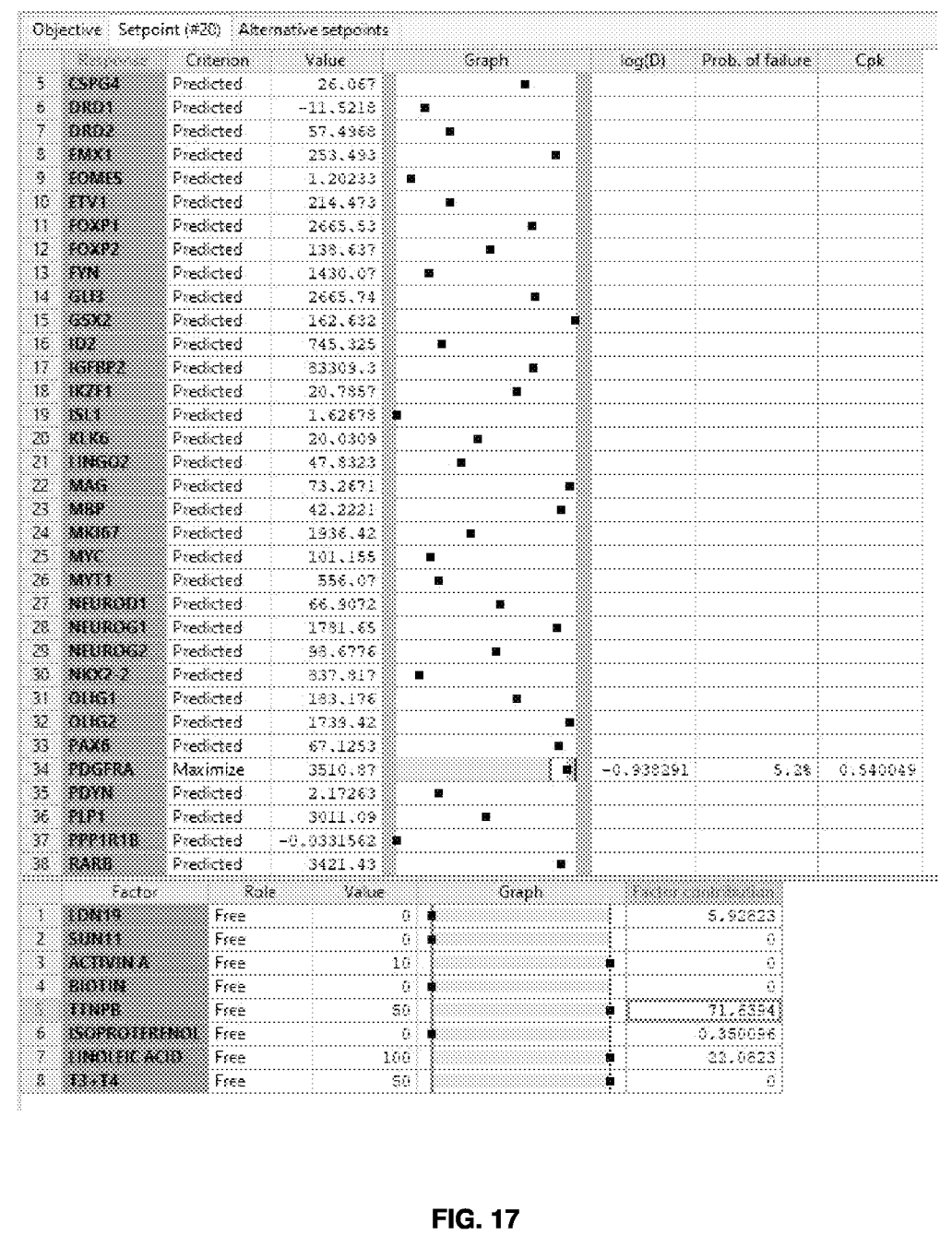

Objective | Setpoint (#20) | Alternative setpoints

| | Response | Criterion | Value | Graph | log(D) | Prob. of failure | Cpk |
|---|---|---|---|---|---|---|---|
| 5 | CSPG4 | Predicted | 26.067 | | | | |
| 6 | DRD1 | Predicted | -11.5218 | | | | |
| 7 | DRD2 | Predicted | 57.4968 | | | | |
| 8 | EMX1 | Predicted | 253.493 | | | | |
| 9 | EOMES | Predicted | 1.20233 | | | | |
| 10 | ETV1 | Predicted | 214.473 | | | | |
| 11 | FOXP1 | Predicted | 2665.53 | | | | |
| 12 | FOXP2 | Predicted | 138.637 | | | | |
| 13 | FYN | Predicted | 1430.07 | | | | |
| 14 | GLI3 | Predicted | 2665.74 | | | | |
| 15 | GSX2 | Predicted | 162.632 | | | | |
| 16 | ID2 | Predicted | 745.325 | | | | |
| 17 | IGFBP2 | Predicted | 83309.3 | | | | |
| 18 | IKZF1 | Predicted | 20.7857 | | | | |
| 19 | ISL1 | Predicted | 1.62678 | | | | |
| 20 | KLK6 | Predicted | 20.0309 | | | | |
| 21 | LINGO2 | Predicted | 47.8323 | | | | |
| 22 | MAG | Predicted | 73.2671 | | | | |
| 23 | MBP | Predicted | 42.2221 | | | | |
| 24 | MKI67 | Predicted | 1936.42 | | | | |
| 25 | MYC | Predicted | 101.155 | | | | |
| 26 | MYT1 | Predicted | 556.07 | | | | |
| 27 | NEUROD1 | Predicted | 66.9072 | | | | |
| 28 | NEUROG1 | Predicted | 1781.65 | | | | |
| 29 | NEUROG2 | Predicted | 98.6776 | | | | |
| 30 | NKX2-2 | Predicted | 837.817 | | | | |
| 31 | OLIG1 | Predicted | 183.176 | | | | |
| 32 | OLIG2 | Predicted | 1739.42 | | | | |
| 33 | PAX6 | Predicted | 67.1253 | | | | |
| 34 | PDGFRA | Maximize | 3510.87 | | -0.938291 | 5.2% | 0.540049 |
| 35 | PDYN | Predicted | 2.17263 | | | | |
| 36 | PLP1 | Predicted | 3011.09 | | | | |
| 37 | PPP1R1B | Predicted | -0.0331562 | | | | |
| 38 | RARB | Predicted | 3421.43 | | | | |

| | Factor | Role | Value | Graph | Factor contribution |
|---|---|---|---|---|---|
| 1 | LDN19 | Free | 0 | | 5.93623 |
| 2 | SUN11 | Free | 0 | | 0 |
| 3 | ACTIVIN A | Free | 10 | | 0 |
| 4 | BIOTIN | Free | 0 | | 0 |
| | TTNPB | Free | 50 | | 71.6394 |
| 6 | ISOPROTERENOL | Free | 0 | | 0.350096 |
| 7 | LINOLEIC ACID | Free | 100 | | 33.0623 |
| 8 | T3+T4 | Free | 50 | | 0 |

FIG. 17

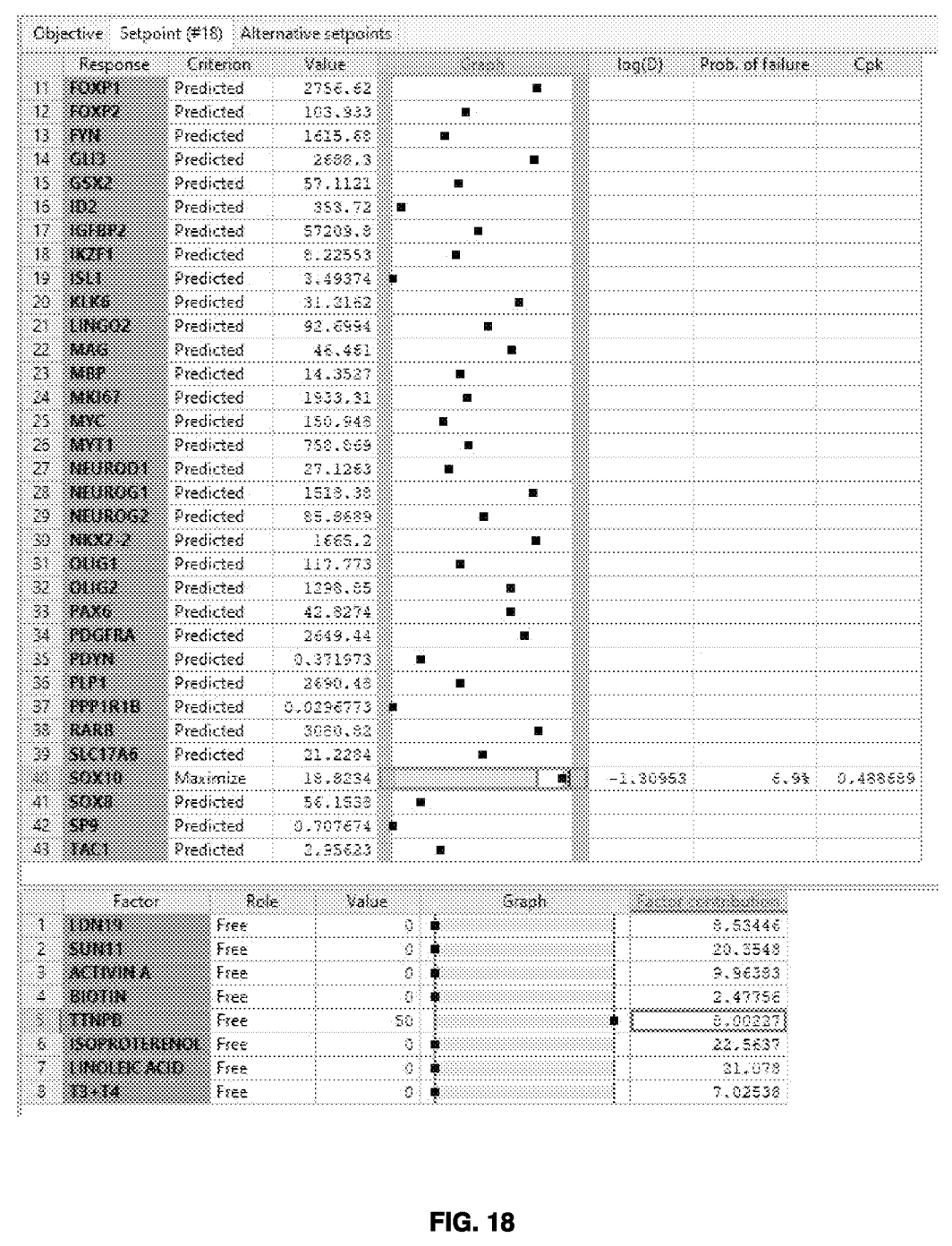

Objective | Setpoint (#18) | Alternative setpoints

| | Response | Criterion | Value | Graph | log(D) | Prob. of failure | Cpk |
|---|---|---|---|---|---|---|---|
| 11 | FOXP1 | Predicted | 2756.62 | | | | |
| 12 | FOXP2 | Predicted | 103.933 | | | | |
| 13 | FYN | Predicted | 1615.68 | | | | |
| 14 | GLI3 | Predicted | 2688.3 | | | | |
| 15 | GSX2 | Predicted | 57.1121 | | | | |
| 16 | ID2 | Predicted | 353.72 | | | | |
| 17 | IGFBP2 | Predicted | 57209.8 | | | | |
| 18 | IKZF1 | Predicted | 8.22553 | | | | |
| 19 | ISL1 | Predicted | 3.49374 | | | | |
| 20 | KLK6 | Predicted | 31.3162 | | | | |
| 21 | LINGO2 | Predicted | 92.6994 | | | | |
| 22 | MAG | Predicted | 46.461 | | | | |
| 23 | MBP | Predicted | 14.3527 | | | | |
| 24 | MKI67 | Predicted | 1933.31 | | | | |
| 25 | MYC | Predicted | 150.948 | | | | |
| 26 | MYT1 | Predicted | 758.869 | | | | |
| 27 | NEUROD1 | Predicted | 27.1263 | | | | |
| 28 | NEUROG1 | Predicted | 1518.38 | | | | |
| 29 | NEUROG2 | Predicted | 85.8689 | | | | |
| 30 | NKX2-2 | Predicted | 1665.2 | | | | |
| 31 | OLIG1 | Predicted | 117.773 | | | | |
| 32 | OLIG2 | Predicted | 1298.85 | | | | |
| 33 | PAX6 | Predicted | 42.8274 | | | | |
| 34 | PDGFRA | Predicted | 2649.44 | | | | |
| 35 | PDYN | Predicted | 0.371973 | | | | |
| 36 | PLP1 | Predicted | 2690.48 | | | | |
| 37 | PPP1R1B | Predicted | 0.0296773 | | | | |
| 38 | RARB | Predicted | 3080.82 | | | | |
| 39 | SLC17A6 | Predicted | 21.2294 | | | | |
| 40 | SOX10 | Maximize | 18.8234 | | -1.30953 | 6.9% | 0.488689 |
| 41 | SOX8 | Predicted | 56.1538 | | | | |
| 42 | SP9 | Predicted | 0.707674 | | | | |
| 43 | TAC1 | Predicted | 2.95623 | | | | |

| | Factor | Role | Value | Graph | Factor contribution |
|---|---|---|---|---|---|
| 1 | LDN19 | Free | 0 | | 8.53446 |
| 2 | SUN11 | Free | 0 | | 20.3548 |
| 3 | ACTIVIN A | Free | 0 | | 9.96383 |
| 4 | BIOTIN | Free | 0 | | 2.47756 |
| 5 | TTNPB | Free | 50 | | 8.00227 |
| 6 | ISOPROTERENOL | Free | 0 | | 22.5637 |
| 7 | LINOLEIC ACID | Free | 0 | | 21.078 |
| 8 | T3+T4 | Free | 0 | | 7.02538 |

FIG. 18

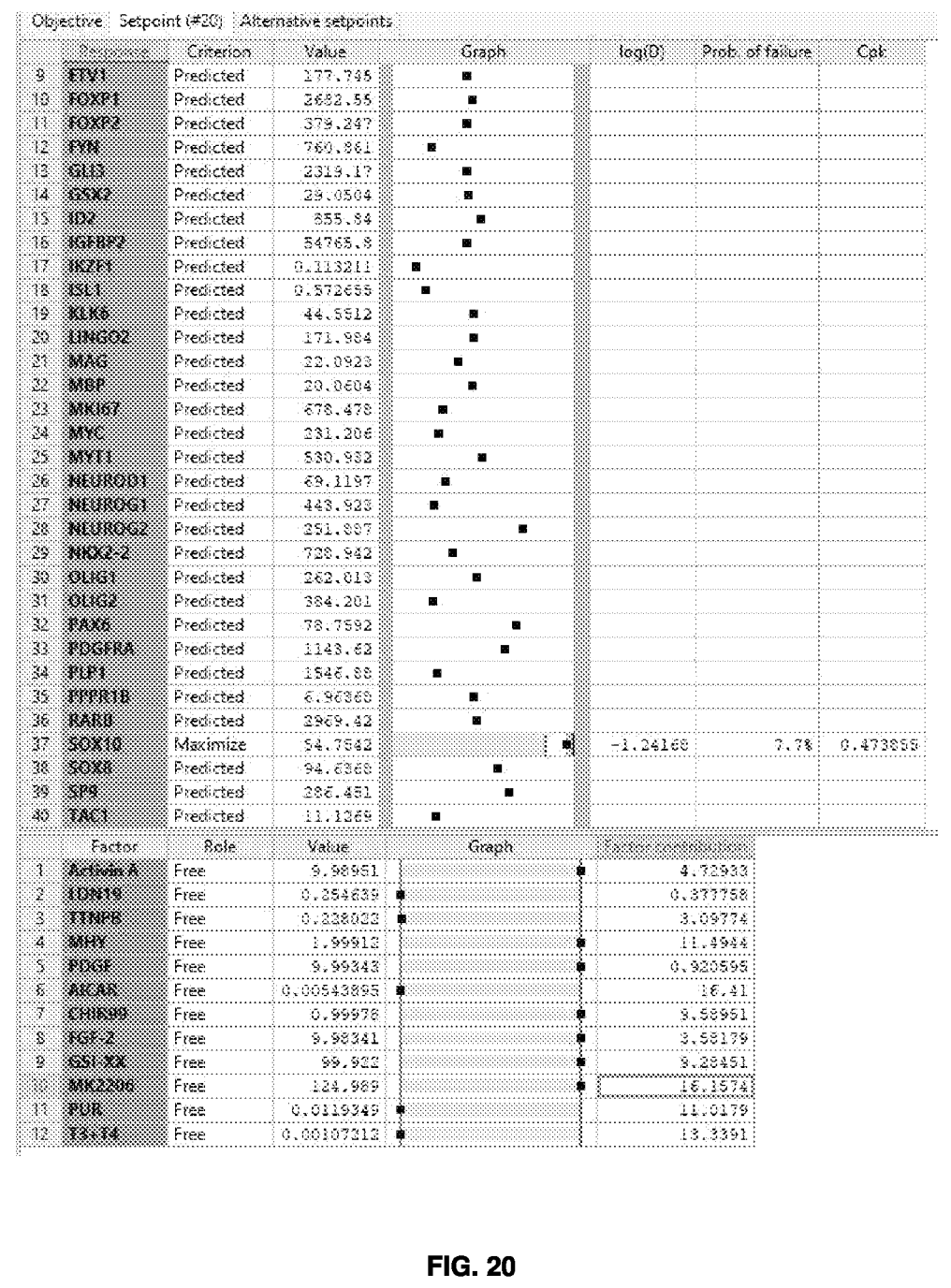

Objective | Setpoint (#20) | Alternative setpoints

| | Response | Criterion | Value | Graph | log(D) | Prob. of failure | Cpk |
|---|---|---|---|---|---|---|---|
| 9 | ETV1 | Predicted | 177.745 | | | | |
| 10 | FOXP1 | Predicted | 2682.55 | | | | |
| 11 | FOXP2 | Predicted | 379.247 | | | | |
| 12 | FYN | Predicted | 760.861 | | | | |
| 13 | GLI3 | Predicted | 2319.17 | | | | |
| 14 | GSX2 | Predicted | 29.0504 | | | | |
| 15 | ID2 | Predicted | 855.84 | | | | |
| 16 | IGFBP2 | Predicted | 54765.8 | | | | |
| 17 | IKZF1 | Predicted | 0.113211 | | | | |
| 18 | ISL1 | Predicted | 0.572655 | | | | |
| 19 | KLK6 | Predicted | 44.5512 | | | | |
| 20 | LINGO2 | Predicted | 171.984 | | | | |
| 21 | MAG | Predicted | 22.0923 | | | | |
| 22 | MBP | Predicted | 20.0604 | | | | |
| 23 | MKI67 | Predicted | 678.478 | | | | |
| 24 | MYC | Predicted | 231.206 | | | | |
| 25 | MYT1 | Predicted | 530.932 | | | | |
| 26 | NEUROD1 | Predicted | 69.1197 | | | | |
| 27 | NEUROG1 | Predicted | 443.923 | | | | |
| 28 | NEUROG2 | Predicted | 251.887 | | | | |
| 29 | NKX2-2 | Predicted | 729.942 | | | | |
| 30 | OLIG1 | Predicted | 262.013 | | | | |
| 31 | OLIG2 | Predicted | 384.201 | | | | |
| 32 | PAX6 | Predicted | 78.7592 | | | | |
| 33 | PDGFRA | Predicted | 1143.62 | | | | |
| 34 | PLP1 | Predicted | 1546.88 | | | | |
| 35 | PPFR1B | Predicted | 6.96368 | | | | |
| 36 | RARB | Predicted | 2969.42 | | | | |
| 37 | SOX10 | Maximize | 54.7542 | | -1.24168 | 7.7% | 0.473855 |
| 38 | SOX8 | Predicted | 94.6368 | | | | |
| 39 | SP9 | Predicted | 286.451 | | | | |
| 40 | TAC1 | Predicted | 11.1269 | | | | |

| | Factor | Role | Value | Graph | [illegible] |
|---|---|---|---|---|---|
| 1 | Activin A | Free | 9.98951 | | 4.72933 |
| 2 | IDN19 | Free | 0.254639 | | 0.377758 |
| 3 | TTNPB | Free | 0.228033 | | 3.09774 |
| 4 | MHY | Free | 1.99913 | | 11.4944 |
| 5 | PDGF | Free | 9.99343 | | 0.920595 |
| 6 | AICAR | Free | 0.00543895 | | 16.41 |
| 7 | CHIR99 | Free | 0.99978 | | 9.58951 |
| 8 | FGF-2 | Free | 9.98341 | | 3.58179 |
| 9 | GSI-XX | Free | 99.922 | | 9.28451 |
| 10 | MK2206 | Free | 124.989 | | 16.1574 |
| 11 | PUR | Free | 0.0119349 | | 11.0179 |
| 12 | T3+T4 | Free | 0.00107313 | | 13.3391 |

FIG. 20

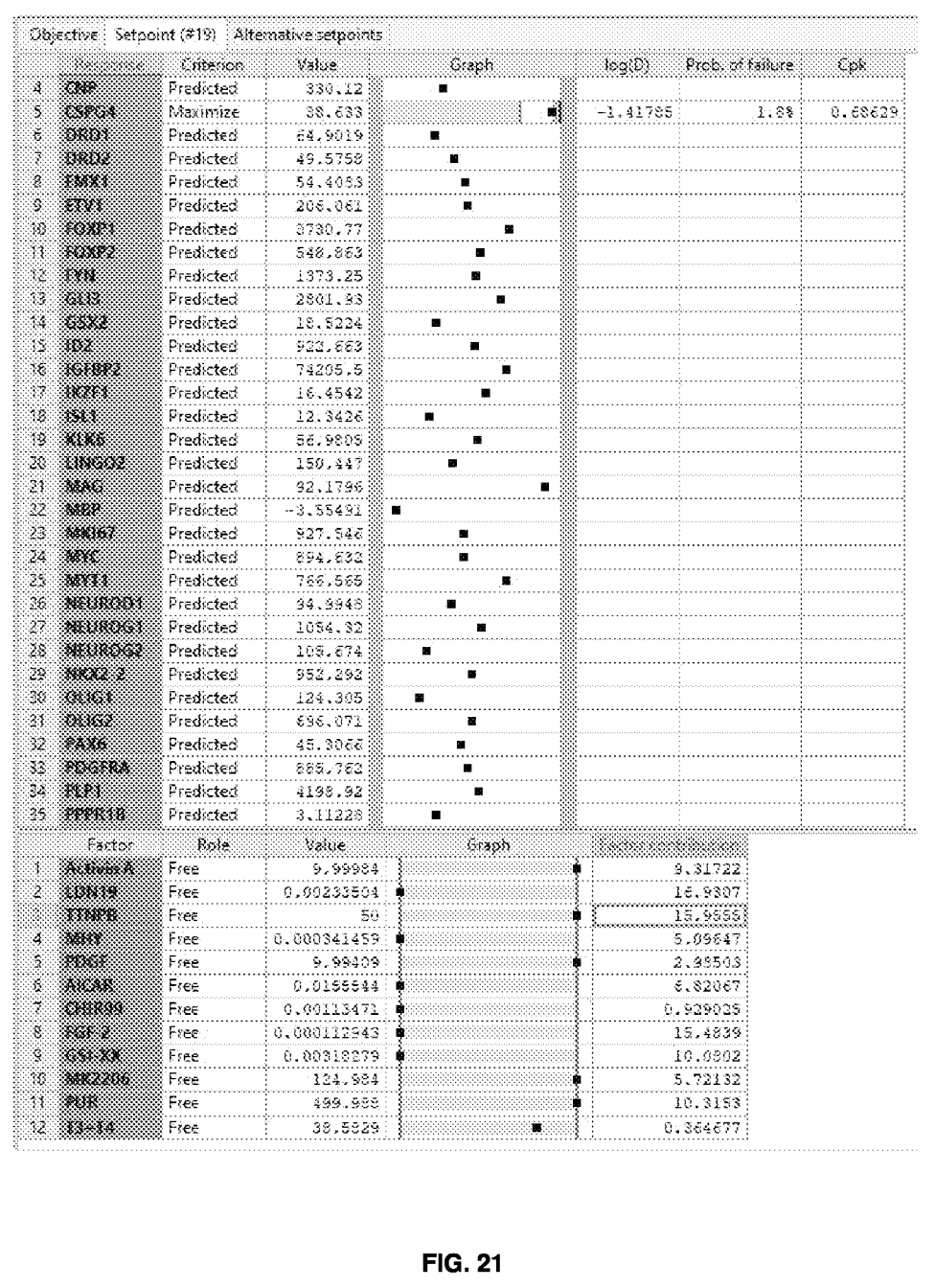

Objective | Setpoint (#19) | Alternative setpoints

| | Response | Criterion | Value | Graph | log(D) | Prob. of failure | Cpk |
|---|---|---|---|---|---|---|---|
| 4 | CNP | Predicted | 330.12 | | | | |
| 5 | CSPG4 | Maximize | 38.633 | | -1.41785 | 1.8% | 0.68629 |
| 6 | DRD1 | Predicted | 64.9019 | | | | |
| 7 | DRD2 | Predicted | 49.5758 | | | | |
| 8 | EMX1 | Predicted | 54.4053 | | | | |
| 9 | ETV1 | Predicted | 206.061 | | | | |
| 10 | FOXP1 | Predicted | 3730.77 | | | | |
| 11 | FOXP2 | Predicted | 548.863 | | | | |
| 12 | FYN | Predicted | 1373.25 | | | | |
| 13 | GLI3 | Predicted | 2801.83 | | | | |
| 14 | GSX2 | Predicted | 18.5224 | | | | |
| 15 | ID2 | Predicted | 922.663 | | | | |
| 16 | IGFBP2 | Predicted | 74205.5 | | | | |
| 17 | IKZF1 | Predicted | 16.4542 | | | | |
| 18 | ISL1 | Predicted | 12.3426 | | | | |
| 19 | KLK6 | Predicted | 56.9805 | | | | |
| 20 | LINGO2 | Predicted | 150.447 | | | | |
| 21 | MAG | Predicted | 92.1796 | | | | |
| 22 | MBP | Predicted | -3.55491 | | | | |
| 23 | MKI67 | Predicted | 927.546 | | | | |
| 24 | MYC | Predicted | 894.632 | | | | |
| 25 | MYT1 | Predicted | 766.565 | | | | |
| 26 | NEUROD1 | Predicted | 94.9948 | | | | |
| 27 | NEUROG1 | Predicted | 1054.32 | | | | |
| 28 | NEUROG2 | Predicted | 105.674 | | | | |
| 29 | NKX2-2 | Predicted | 952.292 | | | | |
| 30 | OLIG1 | Predicted | 124.305 | | | | |
| 31 | OLIG2 | Predicted | 696.071 | | | | |
| 32 | PAX6 | Predicted | 45.3066 | | | | |
| 33 | PDGFRA | Predicted | 885.762 | | | | |
| 34 | PLP1 | Predicted | 4198.92 | | | | |
| 35 | PPPR1B | Predicted | 3.11228 | | | | |

| | Factor | Role | Value | Graph | [illegible] |
|---|---|---|---|---|---|
| 1 | Activin A | Free | 9.99984 | | 9.31722 |
| 2 | LDN19 | Free | 0.00233504 | | 16.9307 |
| | TTNPB | Free | 50 | | 15.9555 |
| 4 | MHY | Free | 0.000341459 | | 5.09647 |
| 5 | PDGF | Free | 9.99409 | | 2.98503 |
| 6 | AICAR | Free | 0.0155544 | | 6.82067 |
| 7 | CHIR99 | Free | 0.00113471 | | 0.929025 |
| 8 | FGF-2 | Free | 0.000112943 | | 15.4839 |
| 9 | GSI-XX | Free | 0.00318279 | | 10.0802 |
| 10 | MK2206 | Free | 124.984 | | 5.72132 |
| 11 | PUR | Free | 499.999 | | 10.3153 |
| 12 | T3+T4 | Free | 38.5829 | | 0.364677 |

FIG. 21

Stage 2

Stage 3

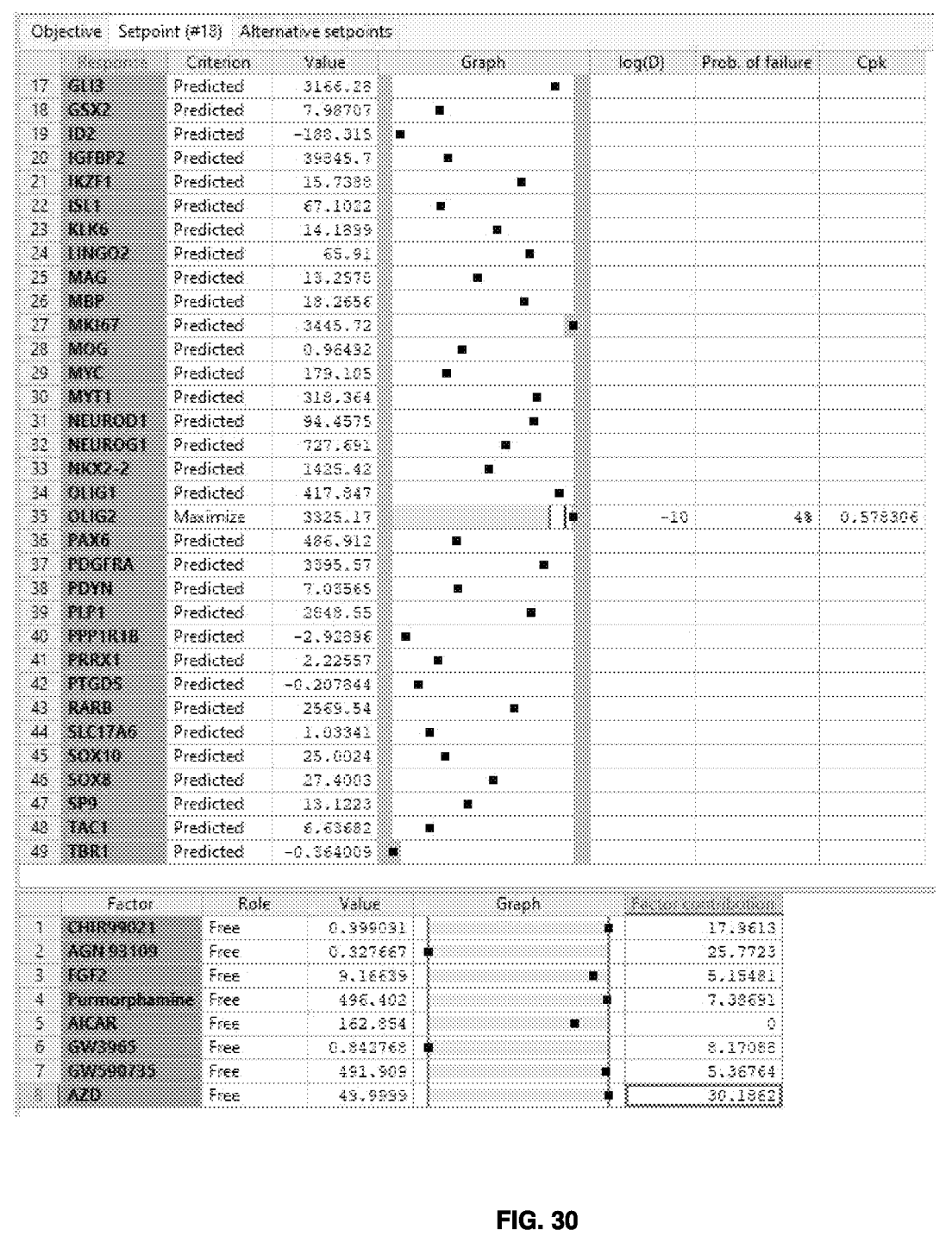

Objective | Setpoint (#18) | Alternative setpoints

| | [illegible] | Criterion | Value | Graph | log(D) | Prob. of failure | Cpk |
|---|---|---|---|---|---|---|---|
| 17 | GLI3 | Predicted | 3166.28 | | | | |
| 18 | GSX2 | Predicted | 7.98707 | | | | |
| 19 | ID2 | Predicted | -188.315 | | | | |
| 20 | IGFBP2 | Predicted | 39845.7 | | | | |
| 21 | IKZF1 | Predicted | 15.7388 | | | | |
| 22 | ISL1 | Predicted | 67.1022 | | | | |
| 23 | KLK6 | Predicted | 14.1839 | | | | |
| 24 | LINGO2 | Predicted | 65.91 | | | | |
| 25 | MAG | Predicted | 13.2575 | | | | |
| 26 | MBP | Predicted | 18.2656 | | | | |
| 27 | MKI67 | Predicted | 3445.72 | | | | |
| 28 | MOG | Predicted | 0.96432 | | | | |
| 29 | MYC | Predicted | 179.105 | | | | |
| 30 | MYT1 | Predicted | 318.364 | | | | |
| 31 | NEUROD1 | Predicted | 94.4575 | | | | |
| 32 | NEUROG1 | Predicted | 727.691 | | | | |
| 33 | NKX2-2 | Predicted | 1425.42 | | | | |
| 34 | OLIG1 | Predicted | 417.847 | | | | |
| 35 | OLIG2 | Maximize | 3325.17 | | -10 | 4% | 0.578306 |
| 36 | PAX6 | Predicted | 486.912 | | | | |
| 37 | PDGFRA | Predicted | 3395.57 | | | | |
| 38 | PDYN | Predicted | 7.03565 | | | | |
| 39 | PLP1 | Predicted | 2848.55 | | | | |
| 40 | PPP1R1B | Predicted | -2.92898 | | | | |
| 41 | PRRX1 | Predicted | 2.22557 | | | | |
| 42 | PTGDS | Predicted | -0.207844 | | | | |
| 43 | RARB | Predicted | 2569.54 | | | | |
| 44 | SLC17A6 | Predicted | 1.03341 | | | | |
| 45 | SOX10 | Predicted | 25.0024 | | | | |
| 46 | SOX8 | Predicted | 27.4003 | | | | |
| 47 | SP9 | Predicted | 13.1223 | | | | |
| 48 | TAC1 | Predicted | 6.63682 | | | | |
| 49 | TBR1 | Predicted | -0.364009 | | | | |

| | Factor | Role | Value | Graph | [illegible] |
|---|---|---|---|---|---|
| 1 | CHIR99021 | Free | 0.999031 | | 17.3613 |
| 2 | AGN 93109 | Free | 0.327667 | | 25.7723 |
| 3 | FGF2 | Free | 9.16639 | | 5.15481 |
| 4 | Purmorphamine | Free | 496.402 | | 7.38691 |
| 5 | AICAR | Free | 162.854 | | 0 |
| 6 | GW3965 | Free | 0.842768 | | 8.17086 |
| 7 | GW590735 | Free | 491.909 | | 5.36764 |
| 8 | AZD | Free | 49.9999 | | 30.1862 |

FIG. 30

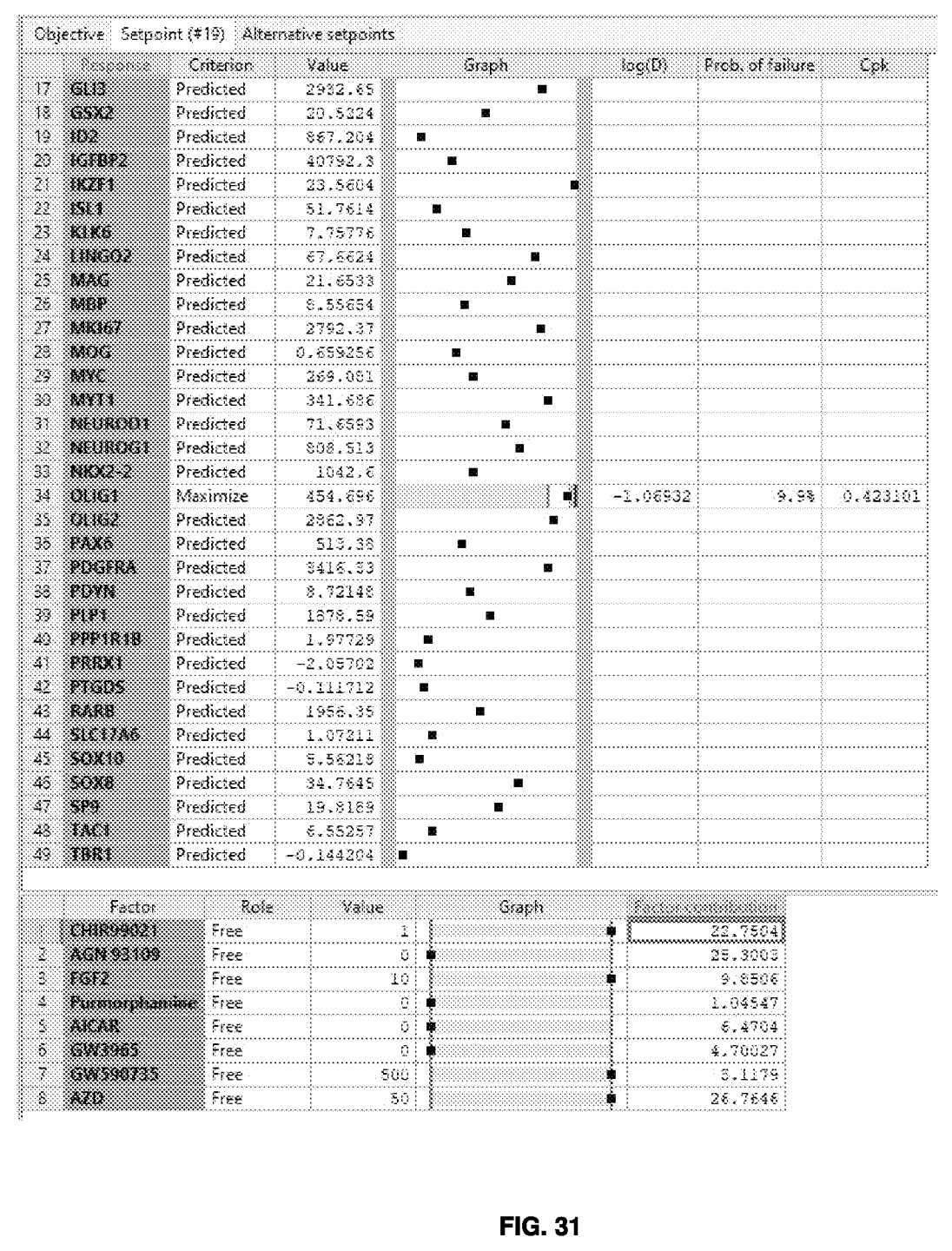

Objective | Setpoint (#19) | Alternative setpoints

| | Response | Criterion | Value | Graph | log(D) | Prob. of failure | Cpk |
|---|---|---|---|---|---|---|---|
| 17 | GLI3 | Predicted | 2932.65 | | | | |
| 18 | GSX2 | Predicted | 20.5324 | | | | |
| 19 | ID2 | Predicted | 867.204 | | | | |
| 20 | IGFBP2 | Predicted | 40792.3 | | | | |
| 21 | IKZF1 | Predicted | 23.5604 | | | | |
| 22 | ISL1 | Predicted | 51.7614 | | | | |
| 23 | KLK6 | Predicted | 7.75776 | | | | |
| 24 | LINGO2 | Predicted | 67.6624 | | | | |
| 25 | MAG | Predicted | 21.6533 | | | | |
| 26 | MBP | Predicted | 8.55654 | | | | |
| 27 | MKI67 | Predicted | 2792.37 | | | | |
| 28 | MOG | Predicted | 0.659256 | | | | |
| 29 | MYC | Predicted | 269.081 | | | | |
| 30 | MYT1 | Predicted | 341.686 | | | | |
| 31 | NEUROD1 | Predicted | 71.6593 | | | | |
| 32 | NEUROG1 | Predicted | 808.513 | | | | |
| 33 | NKX2-2 | Predicted | 1042.6 | | | | |
| 34 | OLIG1 | Maximize | 454.696 | | -1.06932 | 9.9% | 0.423101 |
| 35 | OLIG2 | Predicted | 2862.97 | | | | |
| 36 | PAX6 | Predicted | 513.38 | | | | |
| 37 | PDGFRA | Predicted | 3416.33 | | | | |
| 38 | PDYN | Predicted | 8.72148 | | | | |
| 39 | PLP1 | Predicted | 1878.59 | | | | |
| 40 | PPP1R1B | Predicted | 1.97729 | | | | |
| 41 | PRRX1 | Predicted | -2.05702 | | | | |
| 42 | PTGDS | Predicted | -0.111712 | | | | |
| 43 | RARB | Predicted | 1956.35 | | | | |
| 44 | SLC17A6 | Predicted | 1.07211 | | | | |
| 45 | SOX10 | Predicted | 5.56218 | | | | |
| 46 | SOX8 | Predicted | 34.7645 | | | | |
| 47 | SP9 | Predicted | 19.8169 | | | | |
| 48 | TAC1 | Predicted | 6.55257 | | | | |
| 49 | TBR1 | Predicted | -0.144204 | | | | |

| | Factor | Role | Value | Graph | |
|---|---|---|---|---|---|
| | CHIR99021 | Free | 1 | | 22.7504 |
| 2 | AGN 93109 | Free | 0 | | 25.3009 |
| 3 | FGF2 | Free | 10 | | 9.8506 |
| 4 | Purmorphamine | Free | 0 | | 1.04547 |
| 5 | AICAR | Free | 0 | | 6.4704 |
| 6 | GW3965 | Free | 0 | | 4.70027 |
| 7 | GW590735 | Free | 500 | | 3.1179 |
| 8 | AZD | Free | 50 | | 26.7646 |

FIG. 31

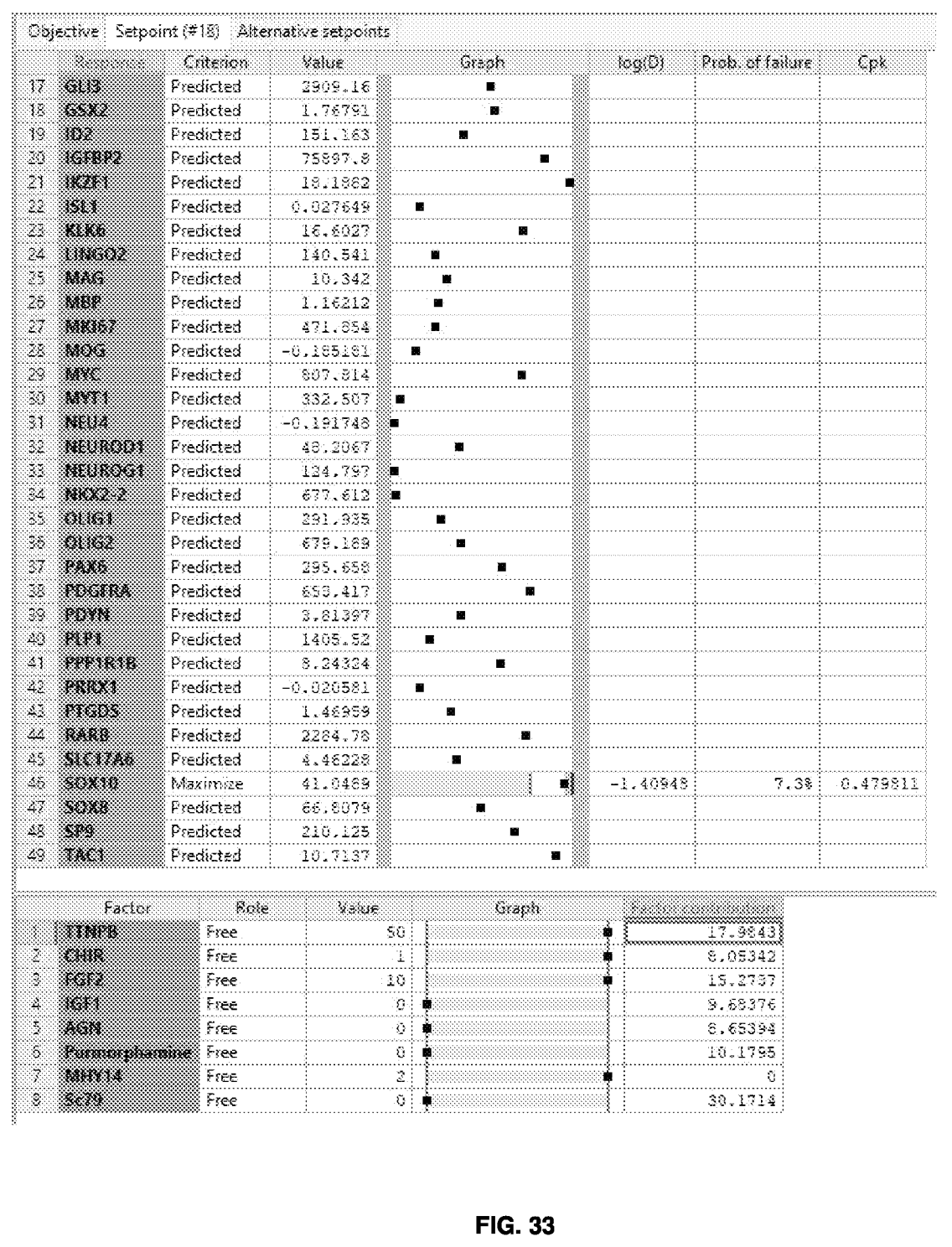

Objective | Setpoint (#18) | Alternative setpoints

| | Response | Criterion | Value | Graph | log(D) | Prob. of failure | Cpk |
|---|---|---|---|---|---|---|---|
| 17 | GLI3 | Predicted | 2909.16 | | | | |
| 18 | GSX2 | Predicted | 1.76791 | | | | |
| 19 | ID2 | Predicted | 151.163 | | | | |
| 20 | IGFBP2 | Predicted | 75897.8 | | | | |
| 21 | IKZF1 | Predicted | 18.1862 | | | | |
| 22 | ISL1 | Predicted | 0.027649 | | | | |
| 23 | KLK6 | Predicted | 16.6027 | | | | |
| 24 | LINGO2 | Predicted | 140.541 | | | | |
| 25 | MAG | Predicted | 10.342 | | | | |
| 26 | MBP | Predicted | 1.16212 | | | | |
| 27 | MKI67 | Predicted | 471.854 | | | | |
| 28 | MOG | Predicted | -0.185181 | | | | |
| 29 | MYC | Predicted | 807.814 | | | | |
| 30 | MYT1 | Predicted | 332.507 | | | | |
| 31 | NEU4 | Predicted | -0.191748 | | | | |
| 32 | NEUROD1 | Predicted | 48.2067 | | | | |
| 33 | NEUROG1 | Predicted | 124.797 | | | | |
| 34 | NKX2-2 | Predicted | 677.612 | | | | |
| 35 | OLIG1 | Predicted | 291.935 | | | | |
| 36 | OLIG2 | Predicted | 679.189 | | | | |
| 37 | PAX6 | Predicted | 295.658 | | | | |
| 38 | PDGFRA | Predicted | 653.417 | | | | |
| 39 | PDYN | Predicted | 3.81397 | | | | |
| 40 | PLP1 | Predicted | 1405.52 | | | | |
| 41 | PPP1R1B | Predicted | 8.24324 | | | | |
| 42 | PRRX1 | Predicted | -0.020581 | | | | |
| 43 | PTGDS | Predicted | 1.46959 | | | | |
| 44 | RARB | Predicted | 2284.78 | | | | |
| 45 | SLC17A6 | Predicted | 4.46228 | | | | |
| 46 | SOX10 | Maximize | 41.0469 | | -1.40948 | 7.3% | 0.479811 |
| 47 | SOX8 | Predicted | 66.8079 | | | | |
| 48 | SP9 | Predicted | 210.125 | | | | |
| 49 | TAC1 | Predicted | 10.7137 | | | | |

| | Factor | Role | Value | Graph | |
|---|---|---|---|---|---|
| 1 | TTNPB | Free | 50 | | 17.9843 |
| 2 | CHIR | Free | 1 | | 8.05342 |
| 3 | FGF2 | Free | 10 | | 15.2737 |
| 4 | IGF1 | Free | 0 | | 9.68376 |
| 5 | AGN | Free | 0 | | 6.65394 |
| 6 | Purmorphamine | Free | 0 | | 10.1795 |
| 7 | MHY14 | Free | 2 | | 0 |
| 8 | Sc79 | Free | 0 | | 30.1714 |

FIG. 33

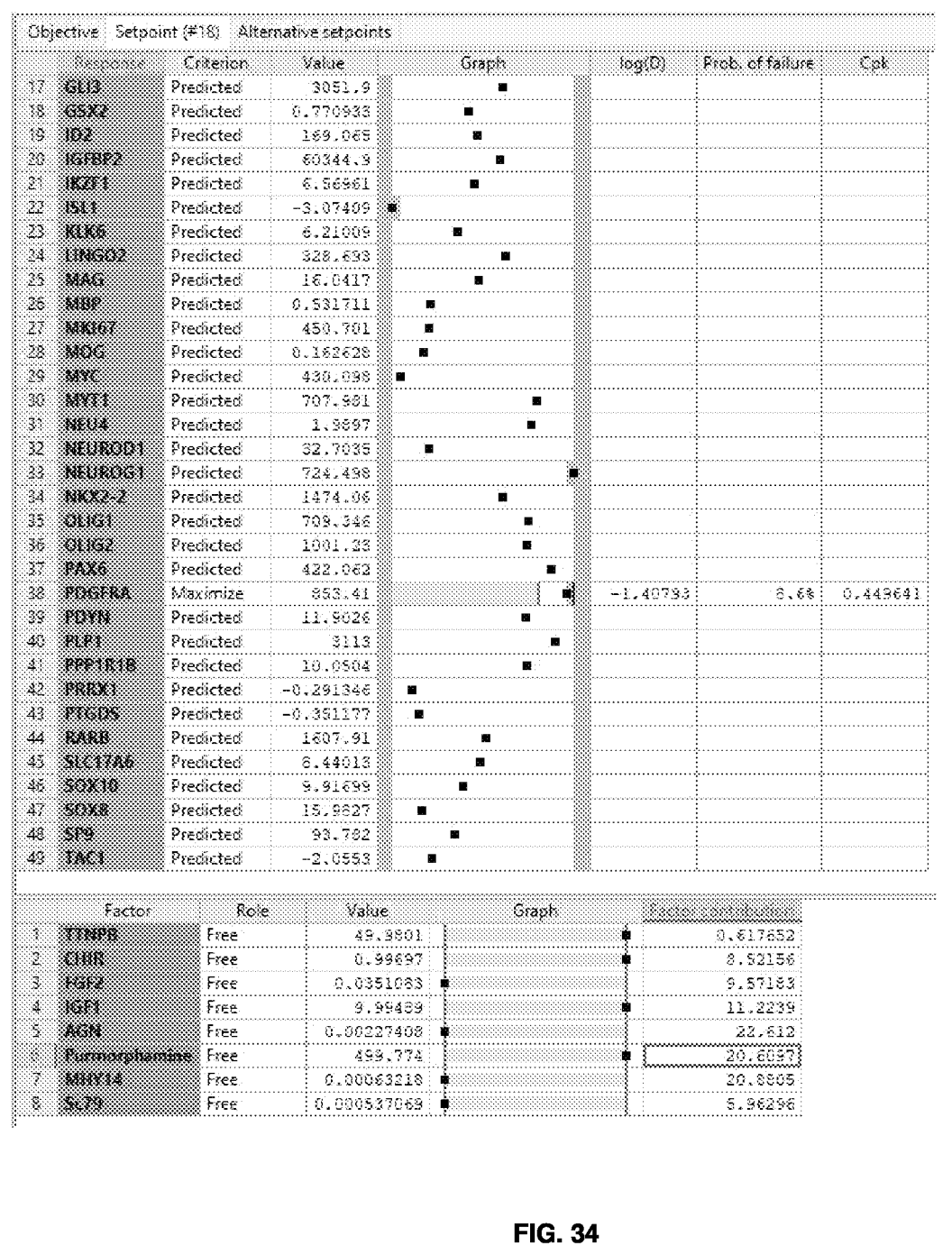

Objective | Setpoint (#18) | Alternative setpoints

| | Response | Criterion | Value | Graph | log(D) | Prob. of failure | Cpk |
|---|---|---|---|---|---|---|---|
| 17 | GLI3 | Predicted | 3051.9 | | | | |
| 18 | GSX2 | Predicted | 0.770933 | | | | |
| 19 | ID2 | Predicted | 169.065 | | | | |
| 20 | IGFBP2 | Predicted | 60344.9 | | | | |
| 21 | IKZF1 | Predicted | 6.56961 | | | | |
| 22 | ISL1 | Predicted | -3.07409 | | | | |
| 23 | KLK6 | Predicted | 6.21009 | | | | |
| 24 | LINGO2 | Predicted | 328.693 | | | | |
| 25 | MAG | Predicted | 16.0417 | | | | |
| 26 | MBP | Predicted | 0.531711 | | | | |
| 27 | MKI67 | Predicted | 450.701 | | | | |
| 28 | MOG | Predicted | 0.162628 | | | | |
| 29 | MYC | Predicted | 430.098 | | | | |
| 30 | MYT1 | Predicted | 707.981 | | | | |
| 31 | NEU4 | Predicted | 1.9897 | | | | |
| 32 | NEUROD1 | Predicted | 32.7035 | | | | |
| 33 | NEUROG1 | Predicted | 724.498 | | | | |
| 34 | NKX2-2 | Predicted | 1474.06 | | | | |
| 35 | OLIG1 | Predicted | 709.346 | | | | |
| 36 | OLIG2 | Predicted | 1001.33 | | | | |
| 37 | PAX6 | Predicted | 422.062 | | | | |
| 38 | PDGFRA | Maximize | 853.41 | | -1.40733 | 8.6% | 0.443641 |
| 39 | PDYN | Predicted | 11.9026 | | | | |
| 40 | PLP1 | Predicted | 3113 | | | | |
| 41 | PPP1R1B | Predicted | 10.0504 | | | | |
| 42 | PRRX1 | Predicted | -0.291346 | | | | |
| 43 | PTGDS | Predicted | -0.351177 | | | | |
| 44 | RARB | Predicted | 1607.91 | | | | |
| 45 | SLC17A6 | Predicted | 6.44013 | | | | |
| 46 | SOX10 | Predicted | 9.91699 | | | | |
| 47 | SOX8 | Predicted | 15.9827 | | | | |
| 48 | SP9 | Predicted | 93.782 | | | | |
| 49 | TAC1 | Predicted | -2.0553 | | | | |

| | Factor | Role | Value | Graph | Factor contribution |
|---|---|---|---|---|---|
| 1 | TTNPB | Free | 49.9801 | | 0.617652 |
| 2 | CHIR | Free | 0.99697 | | 8.52156 |
| 3 | FGF2 | Free | 0.0351063 | | 9.57183 |
| 4 | IGF1 | Free | 9.99489 | | 11.2239 |
| 5 | AGN | Free | 0.00227408 | | 22.612 |
| 6 | Purmorphamine | Free | 499.774 | | 20.6097 |
| 7 | MHY14 | Free | 0.00063218 | | 20.8805 |
| 8 | Sc79 | Free | 0.000537069 | | 5.96296 |

FIG. 34

| hiPSC | Pre-OPC | | OPC |
|---|---|---|---|
| Day 0 | Day 3 | Day 6 | Day 12 |
| CDM2 | CDM2 + Albumax II | | |
| LDN193189 | FGF-2 | | |
| XAV939 | AZD 3147 | Activin A | |
| Purmorphamine | | PDGF-AA | |
| GO6983 | MK2206 | | |
| TTNPB | | TTNPB | |
| Sc79 | | AICAR | |
| MHY1485 | | MHY1485 | |

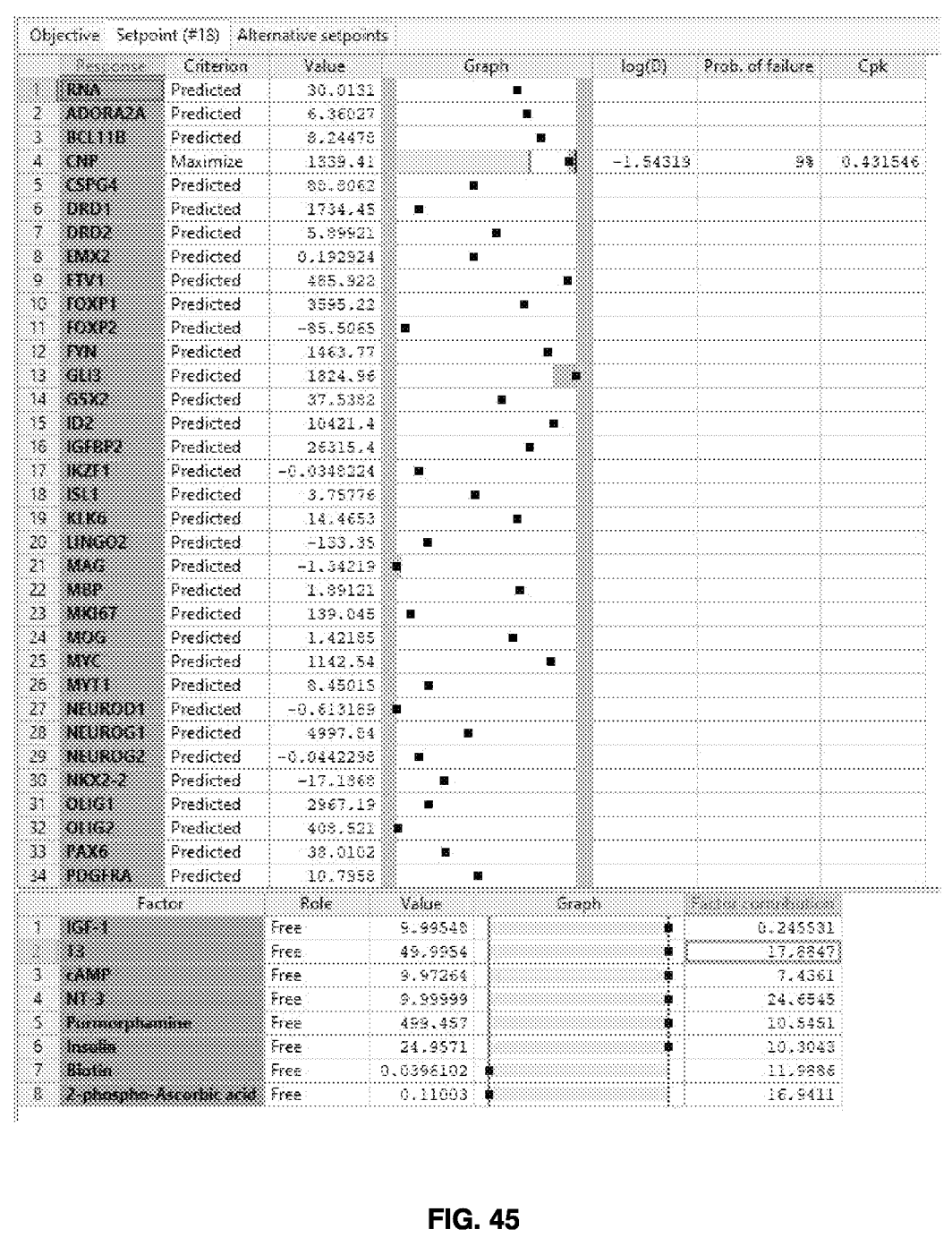

Objective | Setpoint (#18) | Alternative setpoints

| | Response | Criterion | Value | Graph | log(D) | Prob. of failure | Cpk |
|---|---|---|---|---|---|---|---|
| 1 | RNA | Predicted | 30.0131 | | | | |
| 2 | ADORA2A | Predicted | 6.36027 | | | | |
| 3 | BCL11B | Predicted | 8.24478 | | | | |
| 4 | CNP | Maximize | 1339.41 | | -1.54319 | 9% | 0.431546 |
| 5 | CSPG4 | Predicted | 88.8062 | | | | |
| 6 | DRD1 | Predicted | 1734.45 | | | | |
| 7 | DRD2 | Predicted | 5.89921 | | | | |
| 8 | EMX2 | Predicted | 0.192924 | | | | |
| 9 | ETV1 | Predicted | 485.922 | | | | |
| 10 | FOXP1 | Predicted | 3595.22 | | | | |
| 11 | FOXP2 | Predicted | -85.5065 | | | | |
| 12 | FYN | Predicted | 1463.77 | | | | |
| 13 | GLI3 | Predicted | 1824.96 | | | | |
| 14 | GSX2 | Predicted | 37.5382 | | | | |
| 15 | ID2 | Predicted | 10421.4 | | | | |
| 16 | IGFBP2 | Predicted | 26315.4 | | | | |
| 17 | IKZF1 | Predicted | -0.0348224 | | | | |
| 18 | ISL1 | Predicted | 3.75776 | | | | |
| 19 | KLK6 | Predicted | 14.4653 | | | | |
| 20 | LINGO2 | Predicted | -133.35 | | | | |
| 21 | MAG | Predicted | -1.34219 | | | | |
| 22 | MBP | Predicted | 1.89121 | | | | |
| 23 | MKI67 | Predicted | 139.045 | | | | |
| 24 | MOG | Predicted | 1.42185 | | | | |
| 25 | MYC | Predicted | 1142.54 | | | | |
| 26 | MYT1 | Predicted | 8.45015 | | | | |
| 27 | NEUROD1 | Predicted | -0.613189 | | | | |
| 28 | NEUROG1 | Predicted | 4997.84 | | | | |
| 29 | NEUROG2 | Predicted | -0.0442298 | | | | |
| 30 | NKX2-2 | Predicted | -17.1868 | | | | |
| 31 | OLIG1 | Predicted | 2967.19 | | | | |
| 32 | OLIG2 | Predicted | 408.521 | | | | |
| 33 | PAX6 | Predicted | 38.0102 | | | | |
| 34 | PDGFRA | Predicted | 10.7958 | | | | |

| | Factor | Role | Value | Graph | [illegible] |
|---|---|---|---|---|---|
| 1 | IGF-1 | Free | 9.99548 | | 0.245531 |
| | T3 | Free | 49.9954 | | 17.6847 |
| 3 | cAMP | Free | 9.97264 | | 7.4361 |
| 4 | NT-3 | Free | 9.99999 | | 24.6545 |
| 5 | Purmorphamine | Free | 499.457 | | 10.5451 |
| 6 | Insulin | Free | 24.9571 | | 10.3043 |
| 7 | Biotin | Free | 0.0396102 | | 11.9886 |
| 8 | 2-phospho-Ascorbic acid | Free | 0.11003 | | 16.9411 |

FIG. 45

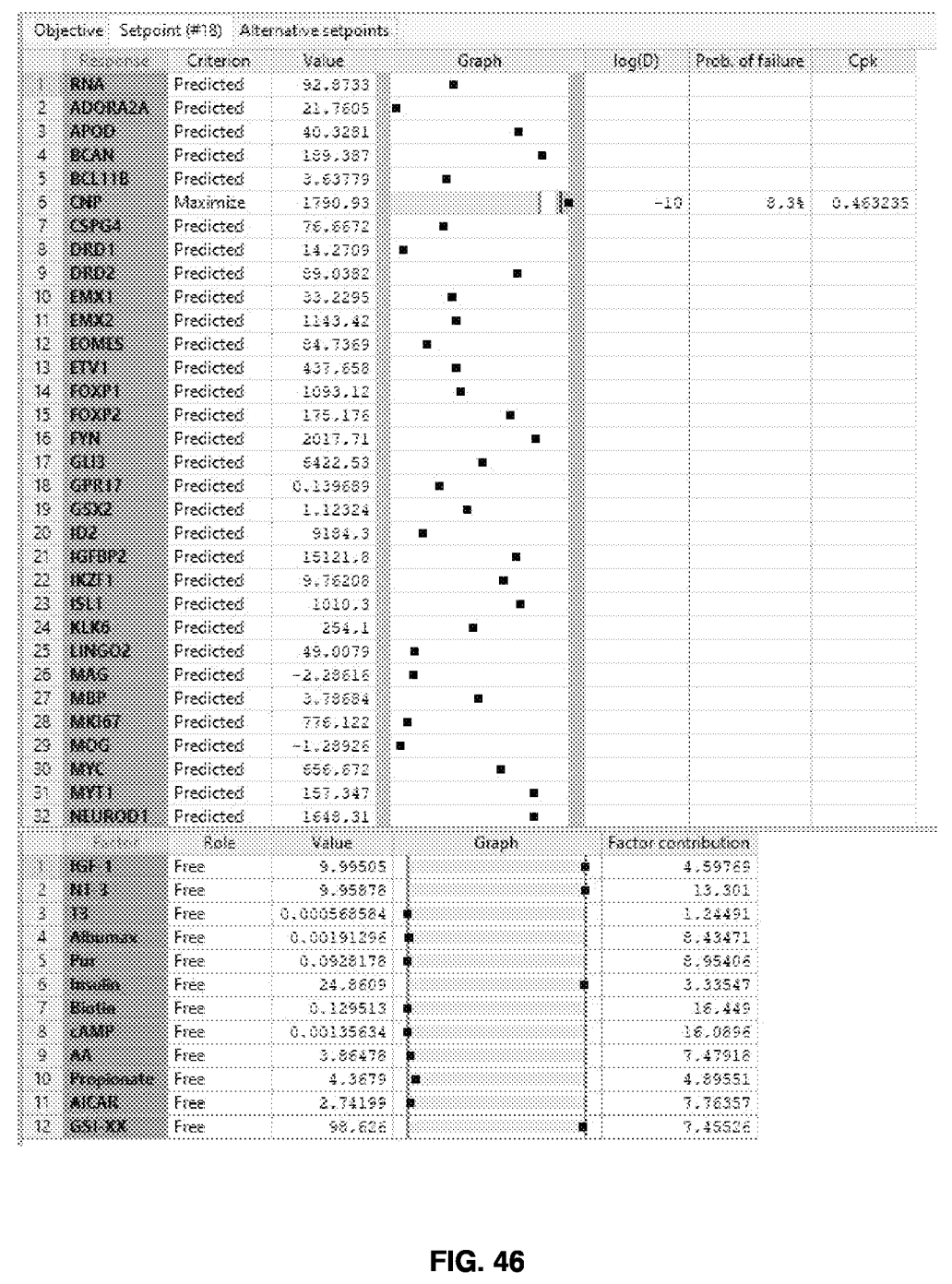

Objective | Setpoint (#18) | Alternative setpoints

| | Response | Criterion | Value | Graph | log(D) | Prob. of failure | Cpk |
|---|---|---|---|---|---|---|---|
| 1 | RNA | Predicted | 92.8733 | | | | |
| 2 | ADORA2A | Predicted | 21.7605 | | | | |
| 3 | APOD | Predicted | 40.3281 | | | | |
| 4 | BCAN | Predicted | 189.387 | | | | |
| 5 | BCL11B | Predicted | 3.63779 | | | | |
| 6 | CNP | Maximize | 1790.93 | | -10 | 8.3% | 0.463235 |
| 7 | CSPG4 | Predicted | 76.6672 | | | | |
| 8 | DRD1 | Predicted | 14.2709 | | | | |
| 9 | DRD2 | Predicted | 89.0382 | | | | |
| 10 | EMX1 | Predicted | 33.2295 | | | | |
| 11 | EMX2 | Predicted | 1143.42 | | | | |
| 12 | EOMES | Predicted | 84.7369 | | | | |
| 13 | ETV1 | Predicted | 437.658 | | | | |
| 14 | FOXP1 | Predicted | 1093.12 | | | | |
| 15 | FOXP2 | Predicted | 175.176 | | | | |
| 16 | FYN | Predicted | 2017.71 | | | | |
| 17 | GLI3 | Predicted | 6422.53 | | | | |
| 18 | GPR17 | Predicted | 0.139689 | | | | |
| 19 | GSX2 | Predicted | 1.12324 | | | | |
| 20 | ID2 | Predicted | 9184.3 | | | | |
| 21 | IGFBP2 | Predicted | 15121.8 | | | | |
| 22 | IKZF1 | Predicted | 9.76208 | | | | |
| 23 | ISL1 | Predicted | 1010.3 | | | | |
| 24 | KLK6 | Predicted | 254.1 | | | | |
| 25 | LINGO2 | Predicted | 49.0079 | | | | |
| 26 | MAG | Predicted | -2.28616 | | | | |
| 27 | MBP | Predicted | 3.78684 | | | | |
| 28 | MKI67 | Predicted | 776.122 | | | | |
| 29 | MOG | Predicted | -1.28926 | | | | |
| 30 | MYC | Predicted | 656.672 | | | | |
| 31 | MYT1 | Predicted | 157.347 | | | | |
| 32 | NEUROD1 | Predicted | 1648.31 | | | | |

| | Factor | Role | Value | Graph | Factor contribution |
|---|---|---|---|---|---|
| 1 | IGF-1 | Free | 9.99505 | | 4.59769 |
| 2 | NT-3 | Free | 9.95878 | | 13.301 |
| 3 | T3 | Free | 0.000568584 | | 1.24491 |
| 4 | Albumax | Free | 0.00191296 | | 8.43471 |
| 5 | Pur | Free | 0.0928178 | | 8.95406 |
| 6 | Insulin | Free | 24.8609 | | 3.33547 |
| 7 | Biotin | Free | 0.129513 | | 16.449 |
| 8 | cAMP | Free | 0.00135634 | | 16.0896 |
| 9 | AA | Free | 3.86478 | | 7.47918 |
| 10 | Propionate | Free | 4.3679 | | 4.89551 |
| 11 | AICAR | Free | 2.74199 | | 7.76357 |
| 12 | GSI-XX | Free | 98.626 | | 7.45526 |

FIG. 46

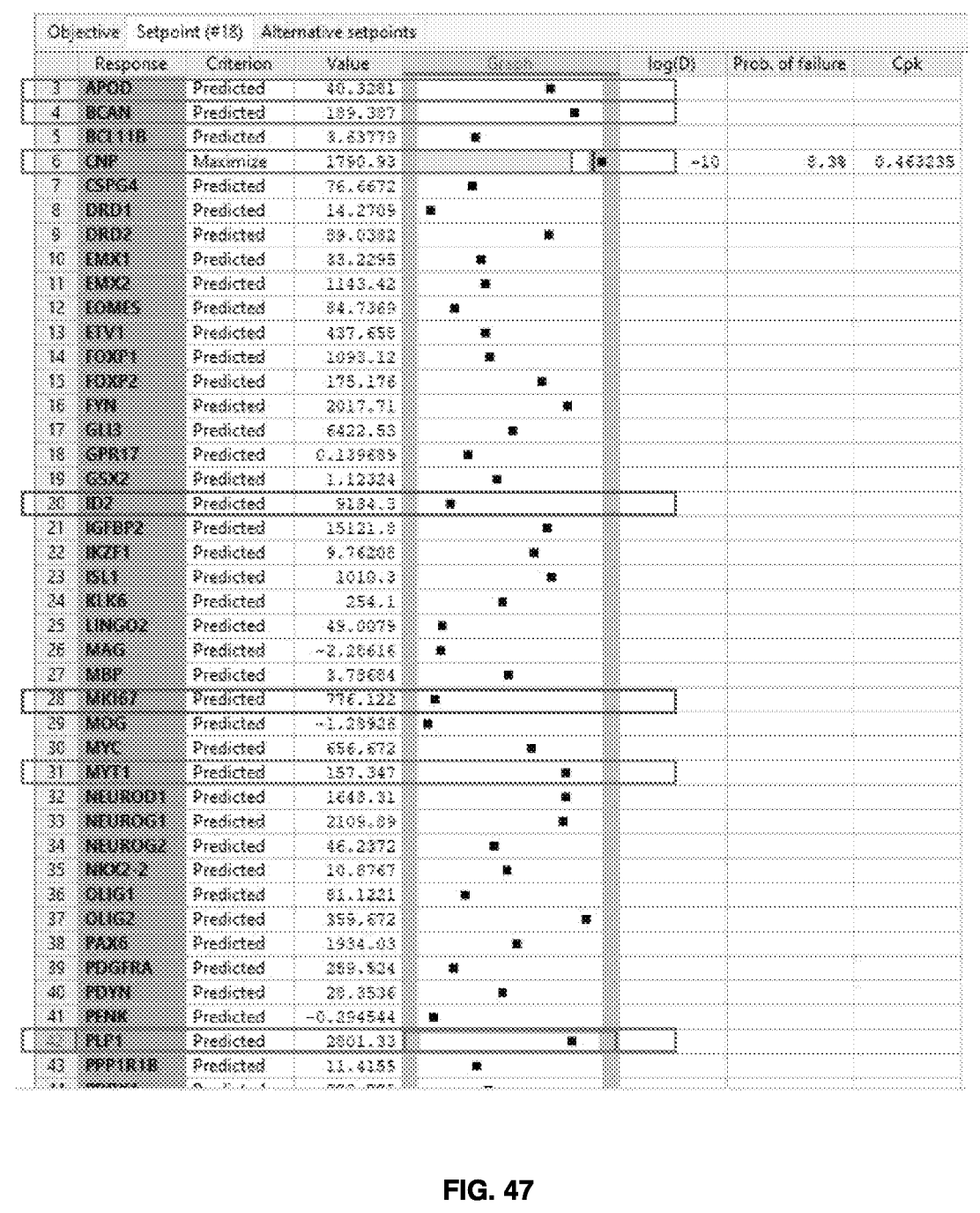

Objective | Setpoint (#18) | Alternative setpoints

| | Response | Criterion | Value | | log(D) | Prob. of failure | Cpk |
|---|---|---|---|---|---|---|---|
| 3 | APOD | Predicted | 40.3281 | | | | |
| 4 | BCAN | Predicted | 189.387 | | | | |
| 5 | BCL11B | Predicted | 3.63779 | | | | |
| 6 | CNP | Maximize | 1790.93 | | -10 | 9.3% | 0.463235 |
| 7 | CSPG4 | Predicted | 76.6672 | | | | |
| 8 | DRD1 | Predicted | 14.2709 | | | | |
| 9 | DRD2 | Predicted | 89.0382 | | | | |
| 10 | EMX1 | Predicted | 33.2295 | | | | |
| 11 | EMX2 | Predicted | 1143.42 | | | | |
| 12 | EOMES | Predicted | 84.7369 | | | | |
| 13 | ETV1 | Predicted | 437.659 | | | | |
| 14 | FOXP1 | Predicted | 1093.12 | | | | |
| 15 | FOXP2 | Predicted | 175.176 | | | | |
| 16 | FYN | Predicted | 2017.71 | | | | |
| 17 | GLI3 | Predicted | 6422.53 | | | | |
| 18 | GPR17 | Predicted | 0.139889 | | | | |
| 19 | GSX2 | Predicted | 1.12324 | | | | |
| 20 | ID2 | Predicted | 9184.3 | | | | |
| 21 | IGFBP2 | Predicted | 15121.8 | | | | |
| 22 | IKZF1 | Predicted | 9.76208 | | | | |
| 23 | ISL1 | Predicted | 1010.3 | | | | |
| 24 | KLK6 | Predicted | 254.1 | | | | |
| 25 | LINGO2 | Predicted | 49.0079 | | | | |
| 26 | MAG | Predicted | -2.28616 | | | | |
| 27 | MBP | Predicted | 3.78684 | | | | |
| 28 | MKI67 | Predicted | 776.122 | | | | |
| 29 | MOG | Predicted | -1.29928 | | | | |
| 30 | MYC | Predicted | 656.672 | | | | |
| 31 | MYT1 | Predicted | 157.347 | | | | |
| 32 | NEUROD1 | Predicted | 1648.31 | | | | |
| 33 | NEUROG1 | Predicted | 2109.89 | | | | |
| 34 | NEUROG2 | Predicted | 46.2372 | | | | |
| 35 | NKX2-2 | Predicted | 10.8767 | | | | |
| 36 | OLIG1 | Predicted | 81.1221 | | | | |
| 37 | OLIG2 | Predicted | 359.672 | | | | |
| 38 | PAX6 | Predicted | 1934.03 | | | | |
| 39 | PDGFRA | Predicted | 289.934 | | | | |
| 40 | PDYN | Predicted | 28.3536 | | | | |
| 41 | PENK | Predicted | -0.394544 | | | | |
| 42 | PLP1 | Predicted | 2801.33 | | | | |
| 43 | PPP1R1B | Predicted | 11.4155 | | | | |

FIG. 47

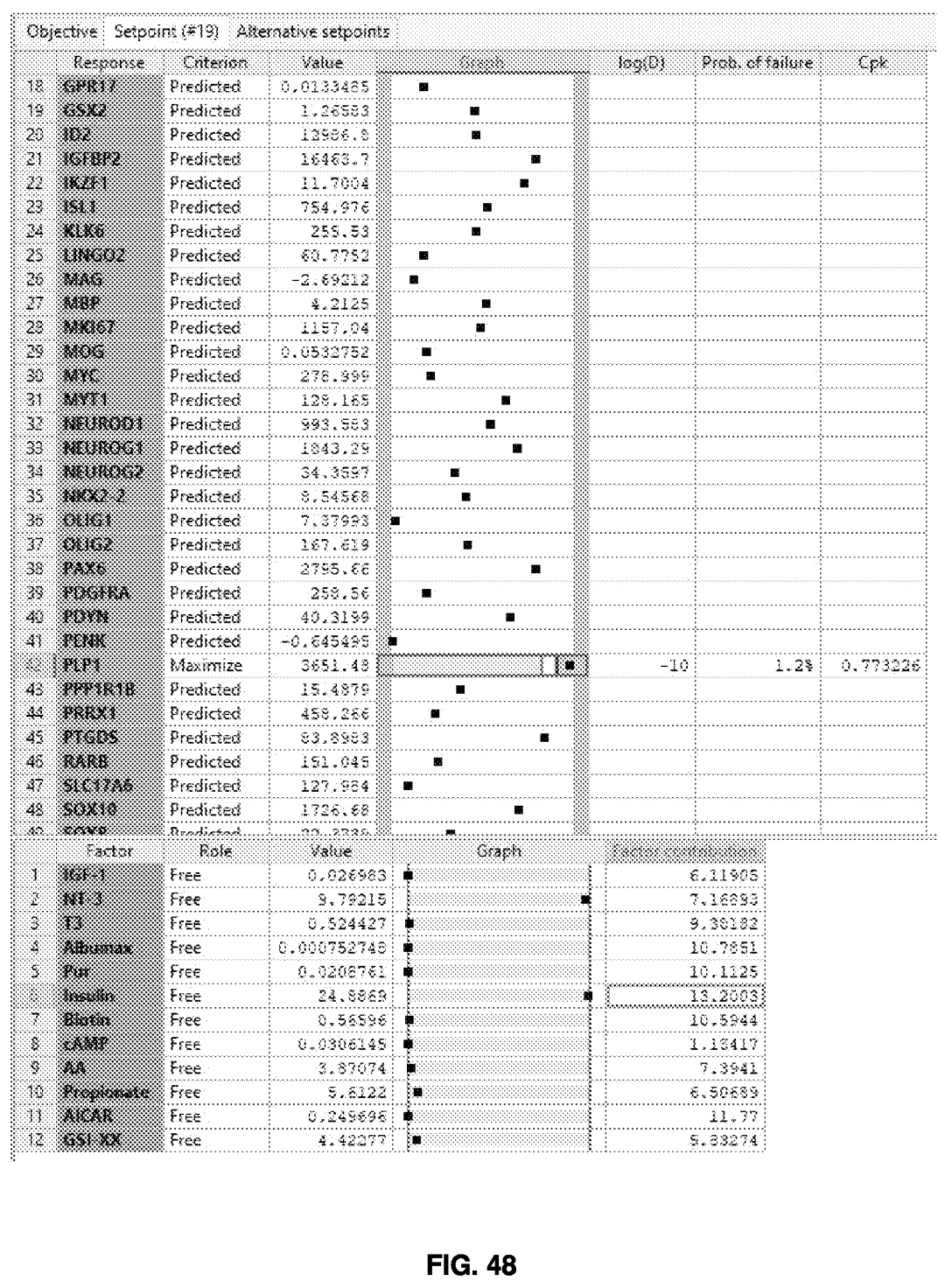

Objective | Setpoint (#19) | Alternative setpoints

| | Response | Criterion | Value | Graph | log(D) | Prob. of failure | Cpk |
|---|---|---|---|---|---|---|---|
| 18 | GPR17 | Predicted | 0.0133485 | | | | |
| 19 | GSX2 | Predicted | 1.26583 | | | | |
| 20 | ID2 | Predicted | 12986.8 | | | | |
| 21 | IGFBP2 | Predicted | 16463.7 | | | | |
| 22 | IKZF1 | Predicted | 11.7004 | | | | |
| 23 | ISL1 | Predicted | 754.976 | | | | |
| 24 | KLK6 | Predicted | 255.53 | | | | |
| 25 | LINGO2 | Predicted | 60.7752 | | | | |
| 26 | MAG | Predicted | -2.69212 | | | | |
| 27 | MBP | Predicted | 4.2125 | | | | |
| 28 | MKI67 | Predicted | 1157.04 | | | | |
| 29 | MOG | Predicted | 0.0532752 | | | | |
| 30 | MYC | Predicted | 278.999 | | | | |
| 31 | MYT1 | Predicted | 128.165 | | | | |
| 32 | NEUROD1 | Predicted | 993.583 | | | | |
| 33 | NEUROG1 | Predicted | 1843.29 | | | | |
| 34 | NEUROG2 | Predicted | 34.3597 | | | | |
| 35 | NKX2-2 | Predicted | 8.54568 | | | | |
| 36 | OLIG1 | Predicted | 7.37993 | | | | |
| 37 | OLIG2 | Predicted | 167.619 | | | | |
| 38 | PAX6 | Predicted | 2795.66 | | | | |
| 39 | PDGFRA | Predicted | 258.56 | | | | |
| 40 | PDYN | Predicted | 40.3199 | | | | |
| 41 | PENK | Predicted | -0.645495 | | | | |
| | PLP1 | Maximize | 3651.48 | | -10 | 1.2% | 0.773226 |
| 43 | PPP1R18 | Predicted | 15.4879 | | | | |
| 44 | PRRX1 | Predicted | 458.266 | | | | |
| 45 | PTGDS | Predicted | 83.8983 | | | | |
| 46 | RARB | Predicted | 151.045 | | | | |
| 47 | SLC17A6 | Predicted | 127.984 | | | | |
| 48 | SOX10 | Predicted | 1726.68 | | | | |
| 49 | [illegible] | Predicted | [illegible] | | | | |

| | Factor | Role | Value | Graph | [illegible] |
|---|---|---|---|---|---|
| 1 | IGF-1 | Free | 0.026983 | | 6.11905 |
| 2 | NT-3 | Free | 9.79215 | | 7.16893 |
| 3 | T3 | Free | 0.524427 | | 9.30182 |
| 4 | Albumax | Free | 0.000752748 | | 10.7851 |
| 5 | Pur | Free | 0.0208761 | | 10.1125 |
| | Insulin | Free | 24.8869 | | 13.2003 |
| 7 | Biotin | Free | 0.56596 | | 10.5944 |
| 8 | cAMP | Free | 0.0306145 | | 1.13417 |
| 9 | AA | Free | 3.87074 | | 7.3941 |
| 10 | Propionate | Free | 5.6122 | | 6.50689 |
| 11 | AICAR | Free | 0.249696 | | 11.77 |
| 12 | GSI-XX | Free | 4.42277 | | 5.83274 |

FIG. 48

METHODS AND COMPOSITIONS FOR GENERATING OLIGODENDROCYTE PROGENITOR CELLS

RELATED APPLICATION

This application claims priority to U.S. Provisional Application No. 63/396,073, filed Aug. 8, 2022, and U.S. Provisional Application No. 63/400,222, filed Aug. 23, 2022, the entire contents of the prior applications are hereby incorporated by reference in their entirety.

GOVERNMENT LICENSED RIGHTS

This invention was made with government support under Grant Number: W911NF-17-3-0003 awarded by the U.S. ARMY ACC-AGP-RTP. The government has certain rights in the invention.

BACKGROUND OF THE INVENTION

Oligodendrocytes (OLs) are a type of glial cells that synthesize the myelin sheath around axons. Thus, they are critical for nerve conduction in the central nervous system (CNS). A greater understanding of oligodendrocyte biology is likely to be very important in the development of therapies for the treatment of neurodegenerative disorders, including demyelinating diseases, such as multiple sclerosis and leukodystrophies, as well as amyotrophic lateral sclerosis (ALS), which can involve demyelination later in the course of the disease. Additionally, radiation therapy to the brain can be associated with the side-effect of oligodendrocyte depletion, leading to cognitive decline and/or impairment of motor coordination.

Since mature human oligodendrocytes are not readily isolatable from human subjects, human oligodendrocyte cell lines have been developed to allow study of the cells. However, immortalized cell lines may not mimic the full biology of the native cells and are not suitable for therapeutic uses. Thus, the ability to generate human oligodendrocytes in vitro, such as from stem cells, is highly desirable. Various protocols have been reported for differentiation of oligodendrocytes from human pluripotent stem cells. However, these protocols remain inefficient and variable in terms of oligodendrocyte yield and require very long differentiation times to generate myelin basic protein (MBP)-positive oligodendrocytes.

An early protocol used a four-step process (Hu et al. (2009) *Nature Protocols* 4:1614-1622; see also Wang et al. (2013) *Cell Stem Cell* 12:252-264). The protocol first involved induction of human embryonic stem cells (hESCs) to differentiate into neuroepithelial cells for two weeks, forming neural-tube like rosettes, followed by a 10 day treatment with retinoic acid (RA) and sonic hedgehog (SHH), leading to OLIG2-expressing progenitors. Treatment with fibroblast growth factor (FGF2) for another 10 days led to conversion to OLIG2 and NKX2.2-expressing pre-OPCs. Finally, the pre-OPCs were cultured for an additional 8-9 weeks in the absence of FGF2 to differentiate into OPCs, expressing markers such as platelet-derived growth factor receptor alpha (PDGFRα), SOX10 and NG2. Thus, using this protocol, it required approximately 24 days to generate OLIG2-expressing progenitors and approximately 34 days to generate OLIG2 and NKX2.2-expressing pre-OPCs, with about 100 days needed to obtain mature Ols. A variant of this protocol was reported by Douvaras et al. (*Stem Cell Reports* (2014) 3:250-259), but still required about 20 days to obtain pre-OPCs and about 50 days to obtain OPCs, including culture with exogenously-added growth factors PDGF, IGF-1 and HGF.

Subsequently, alternative protocols have been reported, yet these protocols still utilized an approximately week-long neural induction and patterning phase (also referred to as neuralization), followed by induction of cells expressing pre-OPC and OPC markers using media that included exogenously-added growth factors, such as FGF2, PDGF, IGF-1 and/or HGF depending on the protocol (see e.g., Piao et al. (2015) *Cell Stem Cell* 16:198-210; Douvaras & Fossati (2015) *Nature Protocols* 10:1143-1154; Livesey et al. (2016) *Stem Cells* 34:1040-1053; and Yamashita et al. (2017) *PLOS One* 12: e0171947).

More recently, a protocol has been reported in which hESCs were first neurally induced to generate neural progenitor cells (NPCs), followed by overexpression of the SOX10 transcription factor in the NPCs (via viral transduction) and expansion in the presence of bFGF, leading to generation of MBP-positive oligodendrocytes in only about 20 days (Garcia-Leon et al. (2018) *Stem Cell Reports* 10:655-672). Furthermore, transient and partial inhibition of the SHH pathway transcription factor GLI1 in neural stem cells (generated by neuralization) by a small molecule inhibitor GANT61 was found to generate OPCs that were more migratory and could differentiate earlier toward myelin-producing oligodendrocytes (Namchaiw et al. (2019) *Stem Cell Res & Therapy* 10:272).

Accordingly, while some progress has been, there remains a need for efficient and robust methods and compositions for generating oligodendrocyte progenitor cells from human pluripotent stem cells.

SUMMARY OF THE INVENTION

This disclosure provides methods of generating human oligodendrocyte progenitor cells (OPCs) from pre-OPCs using chemically-defined culture media that allows for generation of SOX10+ OLIG2+ NKX2.2+ OPCs in as little as nine days of culture starting from pre-OPCs. The pre-OPCs can be obtained from culture of pluripotent stem cells in a chemically-defined culture media for three days, thereby providing an overall twelve day protocol for generating OPCs from pluripotent stem cells. The disclosure also provides methods of generating CD9+A2B5+O4+CNPase+ pre-myelinating oligodendrocytes from the OPCs by further differentiation of the OPCs for six days in another chemically-defined culture media of the disclosure.

The disclosure provides two alternate culture protocols for generating OPCs from pre-OPCs, referred to herein as version 1 and version 2. Each of these protocols comprises two stages (stages 2 and 3) whereas the starting protocol for generating pre-OPCs from pluripotent stem cell comprises a single stage (stage 1), for an overall three stage protocol to generate OPCs. Non-limiting representative protocols for generating OPCs are illustrated schematically in FIG. 42 and FIG. 43. The disclosure further provides culture protocols for generating pre-myelinating oligodendrocytes (preOLs) from OPCs using a stage 4 culture medium. A representative stage 4 protocol for generating preOLs is illustrated schematically in FIG. 44.

Each culture media for the different stages comprises small molecule agents that either agonize or antagonize particular signaling pathway activity in the pluripotent stem cells such that differentiation along the OPC lineage is promoted, leading to cellular maturation and expression of OPC-associated biomarkers. The methods of the disclosure have the advantage that they bypass the neural induction step of prior art protocols and allow for direct differentiation of pluripotent stem cells to pre-OPCs and OPCs, thereby significantly shortening the time needed to generate pre-OPCs and OPCs. Moreover, the use of small molecule agents in the culture media allows for precise control of the culture components.

Accordingly, in one aspect, the disclosure pertains to a method of generating human SOX10+ OLIG2+ NKX2-2+ oligodendrocyte progenitor cells (OPCs) comprising:

(a) culturing human OLIG2+ pre-oligodendrocyte progenitor cells (pre-OPCs) in a culture media comprising an FGFR pathway agonist, an mTOR pathway antagonist, an SHH pathway agonist, an AKT pathway antagonist and an AKT pathway agonist on day 0-3 to obtain a population of cells; and (b) culturing the population of cells from step (a) in a culture media comprising an FGFR pathway agonist, an activin receptor (AR) pathway agonist, a PDGFR pathway agonist, an AKT pathway antagonist, a retinoic acid (RA) pathway agonist, an AMPK pathway agonist and an mTOR pathway agonist on day 3-9, such that SOX10+ OLIG2+ NKX2-2+ OPCs are generated.

The above method corresponds to the stage 2 and stage 3 culture media of the version 1 protocol. In another embodiment, the method further comprises the obtaining the human OLIG2+ pre-OPCs by culturing human pluripotent stem cells in a culture media comprising a retinoic acid (RA) pathway agonist, an Akt pathway agonist, an mTOR pathway agonist, a WNT pathway antagonist, an SHH pathway agonist, a BMP pathway antagonist and a PKC pathway antagonist on day −3-0 (i.e., three days of culture to obtain pre-OPCs from pluripotent stem cells, prior to differentiating the pre-OPCs to OPCs). This corresponds to the stage 1 culture media for obtaining pre-OPCs.

In an embodiment, the FGFR pathway agonist is FGF2. In an embodiment, the FGFR pathway agonist is FGF2, which is present in the culture media in step (a) and step (b) at a concentration of 10 ng/ml. Other suitable FGFR pathway agonists and concentration ranges are disclosed herein.

In an embodiment, the mTOR pathway antagonist is AZD 3147. In an embodiment, the mTOR pathway antagonist is AZD 3147, which is present in the culture media at a concentration of 15 nM. Other suitable mTOR pathway antagonists and concentration ranges are disclosed herein.

In an embodiment, the SHH pathway agonist is Purmorphamine. In an embodiment, the SHH pathway agonist is Purmorphamine, which is present in the culture media at a concentration of 500 nM. Other suitable SHH pathway agonists and concentration ranges are disclosed herein.

In an embodiment, the Akt pathway antagonist is MK2206. In an embodiment, the Akt pathway antagonist is selected from the group consisting of MK2206, which is present in the culture media in step (a) and in step (b) at a concentration of 125 nM. Other suitable Akt pathway antagonists and concentration ranges are disclosed herein.

In an embodiment, the Akt pathway agonist is Sc79. In an embodiment, the Akt pathway agonist is Sc79, which is present in the culture media at a concentration of 2 μM. Other suitable Akt pathway agonists and concentration ranges are disclosed herein.

In an embodiment, the AR pathway agonist is Activin A. In an embodiment, the AR pathway agonist is Activin A, which is present in the culture media at a concentration of 10 ng/ml. Other suitable AR pathway agonists and concentration ranges are disclosed herein.

In an embodiment, the PDGFR pathway agonist is PDGF-AA. In an embodiment, the PDGFR pathway agonist is PDGF-AA, which is present in the culture media at a concentration of 10 ng/ml.

In an embodiment, the RA pathway agonist is TTNPB. In an embodiment, the RA pathway agonist is TTNPB, which is present in the culture media at a concentration of 50 nM. Other suitable RA pathway agonists and concentration ranges are disclosed herein.

In an embodiment, the AMPK pathway agonist is AICAR. In an embodiment, the AMPK pathway agonist is AICAR, which is present in the culture media at a concentration of 200 μM. Other suitable AMPK pathway agonists and concentration ranges are disclosed herein.

In an embodiment, the mTOR pathway agonist is MHY1485. In an embodiment, the mTOR pathway agonist is MHY1485, which is present in the culture media at a concentration of 2 μM. Other suitable mTOR pathway agonists and concentration ranges are disclosed herein.

In another aspect, the disclosure provides to a culture media for obtaining oligodendrocyte progenitor cells (OPCs) comprising an FGFR pathway agonist, an mTOR pathway antagonist, an SHH pathway agonist, an AKT pathway antagonist and an AKT pathway agonist (corresponding to the version 1 stage 2 media). In another aspect, the disclosure provides a culture media for obtaining oligodendrocyte progenitor cells (OPCs) comprising an FGFR pathway agonist, an activin receptor (AR) pathway agonist, a PDGFR pathway agonist, an AKT pathway antagonist, a retinoic acid (RA) pathway agonist, an AMPK pathway agonist and an mTOR pathway agonist (corresponding to the version 1 stage 3 media). Isolated cell cultures, comprising OLIG2+ OPCs cultured in one of the aforementioned culture media, are also provided.

In yet another aspect, the disclosure pertains to a method of generating human SOX10+ OLIG2+ NKX2-2+ oligodendrocyte progenitor cells (OPCs) comprising:

(a) culturing human OLIG2+ pre-oligodendrocyte progenitor cells (pre-OPCs) in a culture media comprising an FGFR pathway agonist, an mTOR pathway antagonist, an SHH pathway agonist and a WNT pathway agonist on day 0-6 to obtain a population of cells; and (b) culturing the population of cells from step (a) in a culture media comprising an FGFR pathway agonist, an IGF-1 pathway agonist and a retinoic acid (RA) pathway agonist on day 6-9, such that SOX10+ OLIG2+ NKX2-2+ OPCs are generated.

The above method corresponds to the stage 2 and stage 3 culture media of the version 2 protocol. In another embodiment, the method further comprises obtaining the human OLIG2+ pre-OPCs by culturing human pluripotent stem cells in a culture media comprising a retinoic acid (RA) pathway agonist, an Akt pathway agonist, an mTOR pathway agonist, a WNT pathway antagonist, an SHH pathway agonist, a BMP pathway antagonist and a PKC pathway antagonist on day −3-0 (i.e., three days of culture to obtain pre-OPCs from pluripotent stem cells, prior to differentiating the pre-OPCs to OPCs). This corresponds to the stage 1 culture media for obtaining pre-OPCs.

In an embodiment, the FGFR pathway agonist is FGF2. In an embodiment, the FGFR pathway agonist is FGF2, which is present in the culture media in step (a) and step (b) at a concentration of 10 ng/ml. Other suitable FGFR pathway agonists and concentration ranges are disclosed herein.

In an embodiment, the mTOR pathway antagonist is AZD 3147. In an embodiment, the mTOR pathway antagonist is AZD 3147, which is present in the culture media at a concentration of 100 nM. Other suitable mTOR pathway antagonists and concentration ranges are disclosed herein.

In an embodiment, the SHH pathway agonist is Purmorphamine. In an embodiment, the SHH pathway agonist is Purmorphamine, which is present in the culture media at a concentration of 500 nM. Other suitable SHH pathway agonists and concentration ranges are disclosed herein.

In an embodiment, the WNT pathway agonist is CHIR99021. In an embodiment, the WNT pathway agonist is CHIR99021, which is present in the culture media at a concentration of 1 μM. Other suitable WNT pathway agonists and concentration ranges are disclosed herein.

In an embodiment, the IGF-1 pathway agonist is IGF-1. In an embodiment, the IGF-1 pathway agonist is IGF-1, which is present in the culture media at a concentration of 10 ng/ml. Other suitable IGF-1 pathway agonists and concentration ranges are disclosed herein.

In an embodiment, the RA pathway antagonist is AGN193109. In an embodiment, the RA pathway antagonist is AGN193109, which is present in the culture media at a concentration of 100 nM. Other suitable RA pathway antagonists and concentration ranges are disclosed herein.

In another aspect, the disclosure provides to a culture media for obtaining oligodendrocyte progenitor cells (OPCs) comprising an FGFR pathway agonist, an mTOR pathway antagonist, an SHH pathway agonist and a WNT pathway agonist (corresponding to the version 2 stage 2 media). In another aspect, the disclosure provides a culture media for obtaining oligodendrocyte progenitor cells (OPCs) comprising an FGFR pathway agonist, an IGF-1 pathway agonist and a retinoic acid (RA) pathway agonist (corresponding to the version 2 stage 3 media). Isolated cell cultures, comprising OLIG2+ OPCs cultured in one of the aforementioned culture media, are also provided.

In another aspect, the disclosure pertains to compositions and methods of the stage 4 protocol for generating pre-myelinating oligodendrocytes (preOLs) from OPCs. In on embodiment, the disclosure pertains to a method of generating CD9+A2B5+O4+CNPase+ pre-myelinating oligodendrocytes (preOLs) comprising culturing SOX10+ OLIG2+ NKX2-2+ OPCs in a culture media comprising an IGF1R pathway agonist, a TrkC pathway agonist, a PDGFR pathway agonist, a thyroid hormone receptor agonist and an insulin receptor agonist such that CD9+A2B5+O4+CNPase+ preOLs are generated. In an embodiment, the OPCs are cultured in the culture media for six days to generate the preOLs.

In one embodiment, the IGF1R pathway agonist is selected from the group consisting of IGF-1, IGF-2, insulin, Rg5, IGF-1 30-41, Demethylasterriquinone B1, IGF1-Ado, X10, mecasermin, and combinations thereof. In one embodiment, the IGF1R pathway agonist is IGF-1. In one embodiment, IGF-1 is present in the culture media at a concentration of 10 ng/ml.

In one embodiment, the TrkC pathway agonist is selected from the group consisting of neurotrophin-3 (NT-3), peptidomimetics based on β-turns of NT-3, LM22B 10, GNF 5837, and combinations thereof. In one embodiment, the TrkC pathway agonist is NT-3. In one embodiment, NT-3 is present in the culture media at a concentration of 10 ng/ml.

In one embodiment, the PDGFR pathway agonist is PDGF-AA. In one embodiment, PDGF-AA is present in the culture media at a concentration of 10 ng/ml.

In one embodiment, the thyroid hormone receptor agonist is selected from the group consisting of T3, T4, Resmetirom, TRb agonist 3 (Compound 3), Sobetirome, Tiratricol, and combinations thereof. In one embodiment, the thyroid hormone receptor agonist is T3. In one embodiment, T3 is present in the culture media at a concentration of 50 nM.

In one embodiment, the insulin receptor agonist is selected from the group consisting of insulin, IGF-1, IGF-2, Demethylasterriquinone B1, MK-5160, MK-1092, and combinations thereof. In one embodiment, the insulin receptor agonist is insulin. In one embodiment, insulin is present in the culture media at a concentration of 20 μg/ml.

In another aspect, the disclosure pertains to a stage 4 media for generating preOLs. In an embodiment, the stage 4 culture media comprises an IGF1R pathway agonist, a TrkC pathway agonist, a PDGFR pathway agonist, a thyroid hormone receptor agonist and an insulin receptor agonist. In embodiments, the IGF1R pathway agonist is IGF-1, the TrkC pathway agonist is NT-3, the PDGFR pathway agonist is PDGF-AA, the thyroid hormone receptor agonist is T3 and the insulin receptor agonist is insulin. In an embodiment, the media comprises IGF-1 at 10 ng/ml, NT-3 at 10 ng/ml, PDGF-AA at 10 ng/ml, T3 at 50 nM and insulin at 20 μg/ml.

The stage 4 media can be combined with the stage 2/stage 3 media (version 1 or version 2) to generate preOLs from preOPCs. Accordingly, in one embodiment for the version 1 protocol, the disclosure pertains to a method of generating human CD9+A2B5+O4+CNPase+ pre-myelinating oligodendrocytes (preOLs) comprising:

(a) culturing human OLIG2+ pre-oligodendrocyte progenitor cells (pre-OPCs) in a culture media comprising an FGFR pathway agonist, an mTOR pathway antagonist, an SHH pathway agonist, an AKT pathway antagonist and an AKT pathway agonist on day 0-3 to obtain a population of cells;
(b) culturing the population of cells from step (a) in a culture media comprising an FGFR pathway agonist, an activin receptor (AR) pathway agonist, a PDGFR pathway agonist, an AKT pathway antagonist, a retinoic acid (RA) pathway agonist, an AMPK pathway agonist and an mTOR pathway agonist on day 3-9, such that SOX10+ OLIG2+ NKX2-2+ OPCs are generated; and
(c) culturing the population of cells from step (b) in a culture media comprising an IGF1R pathway agonist, a TrkC pathway agonist, a PDGFR pathway agonist, a thyroid hormone receptor agonist and an insulin receptor agonist on days 9-15 such that CD9+A2B5+O4+CNPase+ preOLs are generated.

In one embodiment for the version 2 protocol, the disclosure pertains to a method of generating human CD9+A2B5+O4+CNPase+ pre-myelinating oligodendrocytes (preOLs) comprising:

(a) culturing human OLIG2+ pre-oligodendrocyte progenitor cells (pre-OPCs) in a culture media comprising an FGFR pathway agonist, an mTOR pathway antagonist, an SHH pathway agonist and a WNT pathway agonist on day 0-6 to obtain a population of cells;
(b) culturing the population of cells from step (a) in a culture media comprising an FGFR pathway agonist, an IGF-1 pathway agonist and a retinoic acid (RA) pathway agonist on day 6-9, such that SOX10+ OLIG2+ NKX2-2+ OPCs are generated; and
(c) culturing the population of cells from step (b) in a culture media comprising an IGF1R pathway agonist, a TrkC pathway agonist, a PDGFR pathway agonist, a thyroid hormone receptor agonist and an insulin receptor agonist on days 9-15 such that CD9+A2B5+O4+CNPase+ preOLs are generated.

In yet another embodiment, the above methods that combine stages 2, 3 and 4, further comprise obtaining the human OLIG2+ pre-OPCs by culturing human pluripotent stem cells in a culture media comprising a retinoic acid (RA) pathway agonist, an Akt pathway agonist, an mTOR pathway agonist, a WNT pathway antagonist, an SHH pathway agonist, a BMP pathway antagonist and a PKC pathway antagonist on day −3-0 (i.e., three days of culture to obtain pre-OPCs from pluripotent stem cells, prior to differentiating the pre-OPCs to OPCs). This corresponds to the stage 1 culture media for obtaining pre-OPCs, to thereby provide methods combining the stage 1, 2, 3 and 4 protocols for generating preOLs.

In one embodiment, the human pluripotent stem cells are induced pluripotent stem cells (iPSCs). In another embodiment, the human pluripotent stem cells are embryonic stem cells.

In one embodiment, the human pluripotent stem cells are attached to vitronectin-coated plates during culturing.

Other features and advantages of the invention will be apparent from the following detailed description and claims.

BRIEF DESCRIPTION OF THE DRAWINGS

FIG. 1 shows results from an HD-DoE model of an 8-factor experiment optimized for maximum expression of NKX2-2. The upper section of the model shows the prediction of expression level of pre-selected 53 genes when optimized for NKX2-2. The lower section of the model shows the effectors that were tested in this model and their contribution to maximum expression of NKX2-2. The value column refers to required concentration of each effector to mimic the model.

FIG. 2 shows the results from an HD-DoE model of an 8-factor experiment optimized for maximum expression of PDGFRA. Upper and lower sections are as described for FIG. 1. This condition highlights the effector PD0325901 with factor contribution of 30.05 as an important input for high expression of PDGFRA.

FIG. 4 shows the results from an HD-DoE model of a 13-factor experiment optimized for maximum expression of OTX2. This model introduced MK2206, PD0325901, CHIR99021, LDN193189, Go6983 and PD173074 as positive effectors on expression of OTX2.

FIG. 5 shows the results from an HD-DoE model of a 13-factor experiment optimized for maximum expression of FEZF2. This model confirmed the positive effect of LDN193189, MK2206 and PD0325901 on patterning the cells and introduced three other factors including SC79, XAV939 and Purmorphamine-500 nM.

FIG. 11 shows the results from an HD-DoE model of a 12-factor experiment optimized for maximum expression of OLIG2. The upper section of the model shows the prediction of expression levels of pre-selected 53 genes when optimized for OLIG2. The lower section of the model shows the effectors that were tested in this model and their contribution to maximum expression of OLIG2. The value column refers to required concentration of each effector to mimic the model.

FIG. 13 shows the results from an HD-DoE model of a 12-factor experiment optimized for maximum expression of OLIG2. Upper and lower sections, and value column, are as in FIG. 11. This model highlights the effector Purmorphamine, with factor contribution of 13.03, and AGN193109, with factor contribution of 18.3, as two important inputs for maximal and minimal expression of OLIG2, respectively.

FIG. 14 shows the results from an HD-DoE model of a 12-factor experiment applied on stage 1 pre-OPCs to generate a recipe for stage 2 of differentiation. Upper and lower sections, and value column, are as in FIG. 11. This model is optimized for maximum expression of OLIG2. This model highlights the role of Purmorphamine in expression of OLIG2 with a factor contribution of 16.9.

FIG. 16 shows the results of an HD-DoE model of an 8-factor experiment applied on stage 2 early oligodendrocyte progenitors to generate a recipe for stage 3 of differentiation. Upper and lower sections, and value column, are as in FIG. 11. This model highlights the positive role of Activin A and TTNPB on expression of OLIG1, with factor contributions of 50.2 and 19.1 respectively.

FIG. 17 shows the results of an HD-DoE model of an 8-factor experiment applied on stage 2 early-OPCS. Upper and lower sections, and value column, are as in FIG. 11. This model is optimized for maximum expression of PDGFRa. This model highlights the effector TTNPB, with a factor contribution of 71.6, and Linoleic acid, with a factor contribution of 22.1, as two important inputs for maximum expression of PDGFRa.

FIG. 18 shows the results from an HD-DoE model of an 8-factor experiment applied on stage 2 early-OPCs. Upper and lower sections, and value column, are as in FIG. 11. This model highlights the positive role TTNPB on expression of SOX10, with a factor contribution of 8, while all the other factors have a negative regulatory impact.

FIG. 20 shows the results from an HD-DoE model of a 12-factor experiment applied on stage 2 early-OPCs to generate a recipe for stage 3 of differentiation. Upper and lower sections, and value column, are as in FIG. 11. This model is optimized for maximum expression of SOX10. This model highlights the role of MK2206 and MHY1485 in expression of SOX10, with factor contributions of 16.2 and 11.5, respectively.

FIG. 21 shows the results from an HD-DoE model of a 12-factor experiment applied on stage 2 early-OPCs to generate a recipe for stage 3 of differentiation. Upper and lower sections, and value column, are as in FIG. 11. This model is optimized for maximum expression of CSPG4. This model highlights the role of TTNPB and Activin A in expression of CSPG4, with factor contributions of 15.9 and 9.3, respectively.

FIG. 25A shows expression levels of genes of interest in the presence of all finalized effectors. FIG. 25B shows expression levels of genes of interest in the absence of one finalized effector at a time while the others are present. FIG. 25C shows expression levels of genes of interest in the presence and absence of the remaining finalized factor, Purmorphamine.

FIG. 26A shows expression levels of genes of interest in the presence of both effectors. FIG. 26B shows expression levels of genes of interest in the absence of one finalized effector at a time while the other is present.

FIG. 27A shows expression levels of genes of interest in the presence of the four finalized effectors. FIG. 27B shows expression levels of genes of interest in the absence of one finalized effector at a time while the others are present.

FIG. 30 shows the results from an HD-DoE model of an 8-factor experiment optimized for maximum expression of OLIG2. The upper section of the model shows the prediction of expression levels of pre-selected 53 genes when optimized for OLIG2. The lower section of the model shows the effectors that were tested in this model and their contribution to maximum expression of OLIG2. The value column refers to the required concentration of each effector to mimic the model.

FIG. 31 shows the results from an HD-DoE model of an 8-factor experiment optimized for maximum expression of OLIG1. This model highlights the effector AZD3147, with a factor contribution of 26.76, and Purmorphamine, with a factor contribution of 22.75, as two important inputs for maximal expression of OLIG1.

FIG. 33 shows the results from an HD-DoE model of an 8-factor experiment optimized for maximum expression of SOX10. This model highlights the effector TTNPB, with a factor contribution of 17.98, and FGF-2, with factor contribution of 15.3, as two important inputs for maximal expression of SOX10.

FIG. 34 shows the results from an HD-DoE model of an 8-factor experiment optimized for maximum expression of PDGFRa. This model highlights the effector Purmorphamine, with a factor contribution of 20.61, and IGF-1, with a factor contribution of 11.2, as two important inputs for maximal expression of SOX10.

FIG. 45 shows the results from an HD-DoE model of an 8-factor experiment optimized for maximum expression of CNP. Upper section of the model shows the prediction of expression level of pre-selected 53 genes when optimized for CNP. Lower section of the model shows the effectors that were tested in this model and their contribution to maximum expression of CNP. The value column refers to required concentration of each effector to mimic the model.

FIG. 46 shows the results from an HD-DoE model of a 12-factor experiment optimized for maximum expression of CNP. This condition highlights the effector NT-3, with a factor contribution of 13.3, and Biotin, with a factor contribution of 16.5, as two important inputs for maximal and minimal expression of CNP, respectively.

FIG. 47 shows the results from an HD-DoE model of a 12-factor experiment optimized for maximum expression of CNP. When CNP is maximally expressed, multiple other oligodendrocyte genes including APOD, BCAN, MYT1 and PLP1 are also upregulated, as shown by the red frames. Concurrently, ID2 and MKI67 that are expressed in oligodendrocyte progenitor stage are downregulated, shown by blue frame.

FIG. 48 shows the results from an HD-DoE model of a 12-factor experiment optimized for maximum expression of PLP1. This condition highlights the effector Insulin, with a factor contribution of 13.2, and AICAR, with a factor contribution of 11.8, as two important inputs for maximal and minimal expression of PLP1, respectively.

DETAILED DESCRIPTION OF THE INVENTION

Figure 3:
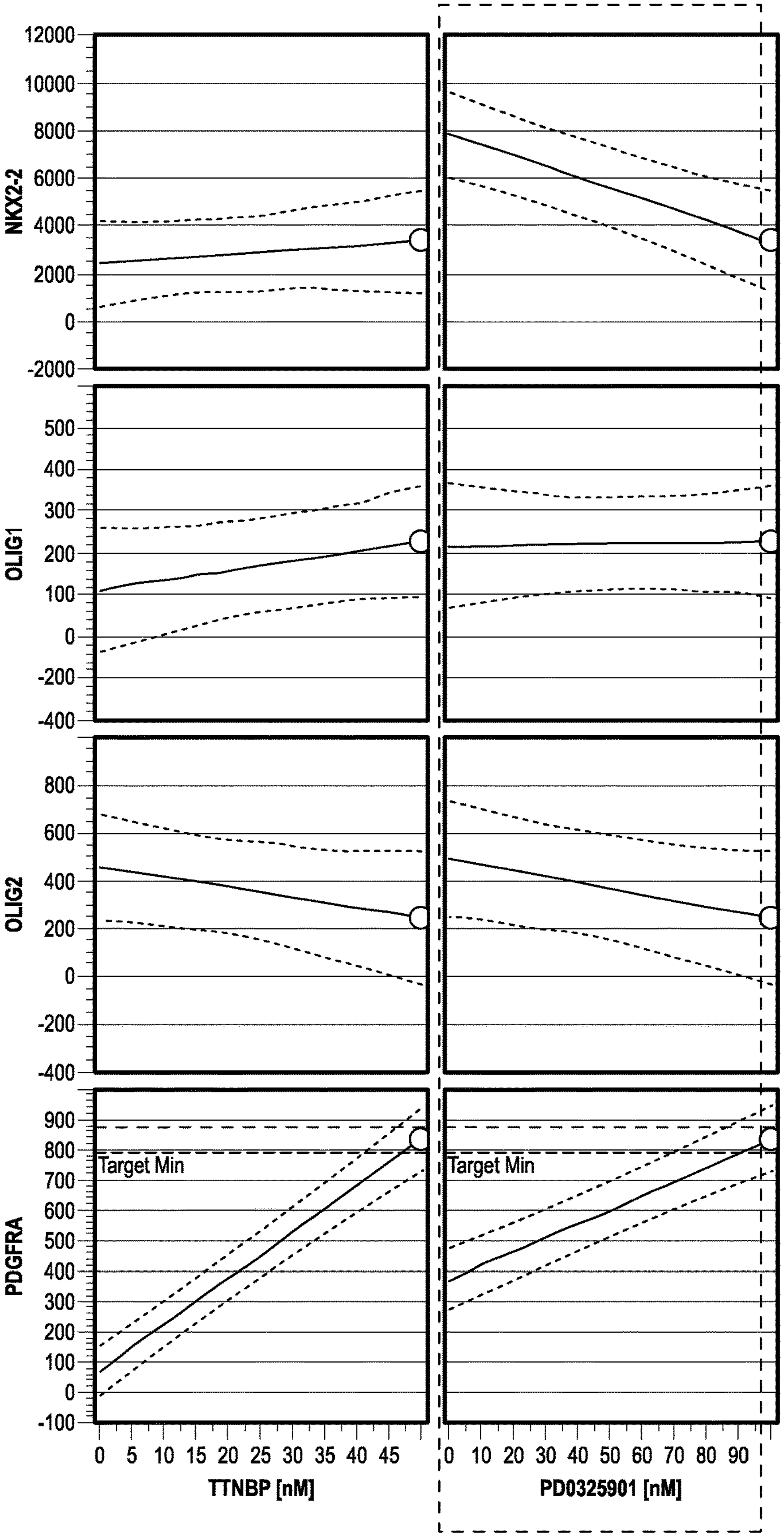
FIG. 3 shows the dynamic profile of expression levels of NKX2-2, OLIG1, OLIG2 and PDGFRA genes relative to the concentration of 8 effectors tested. The positive impact of TTNPB, MHY1485 and PD0325901 on expression of PDGFRA and their factor contribution is shown by the slope of the plots for each effector. The dotted box highlights the opposite impact of PD0325901 on NKX2-2 and OLIG2 compared to PDGFRA.
Figure 3:
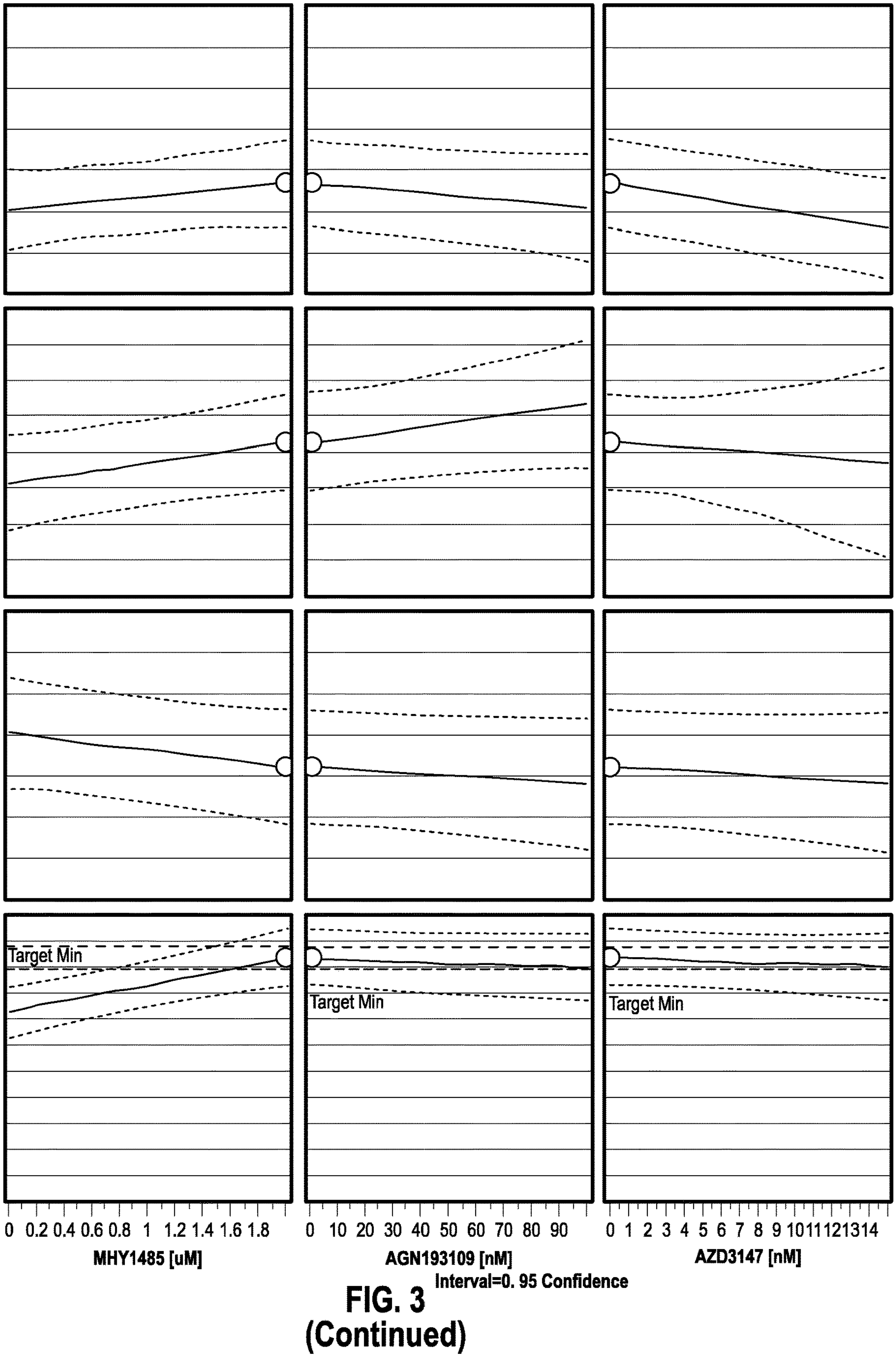
Figure 3:
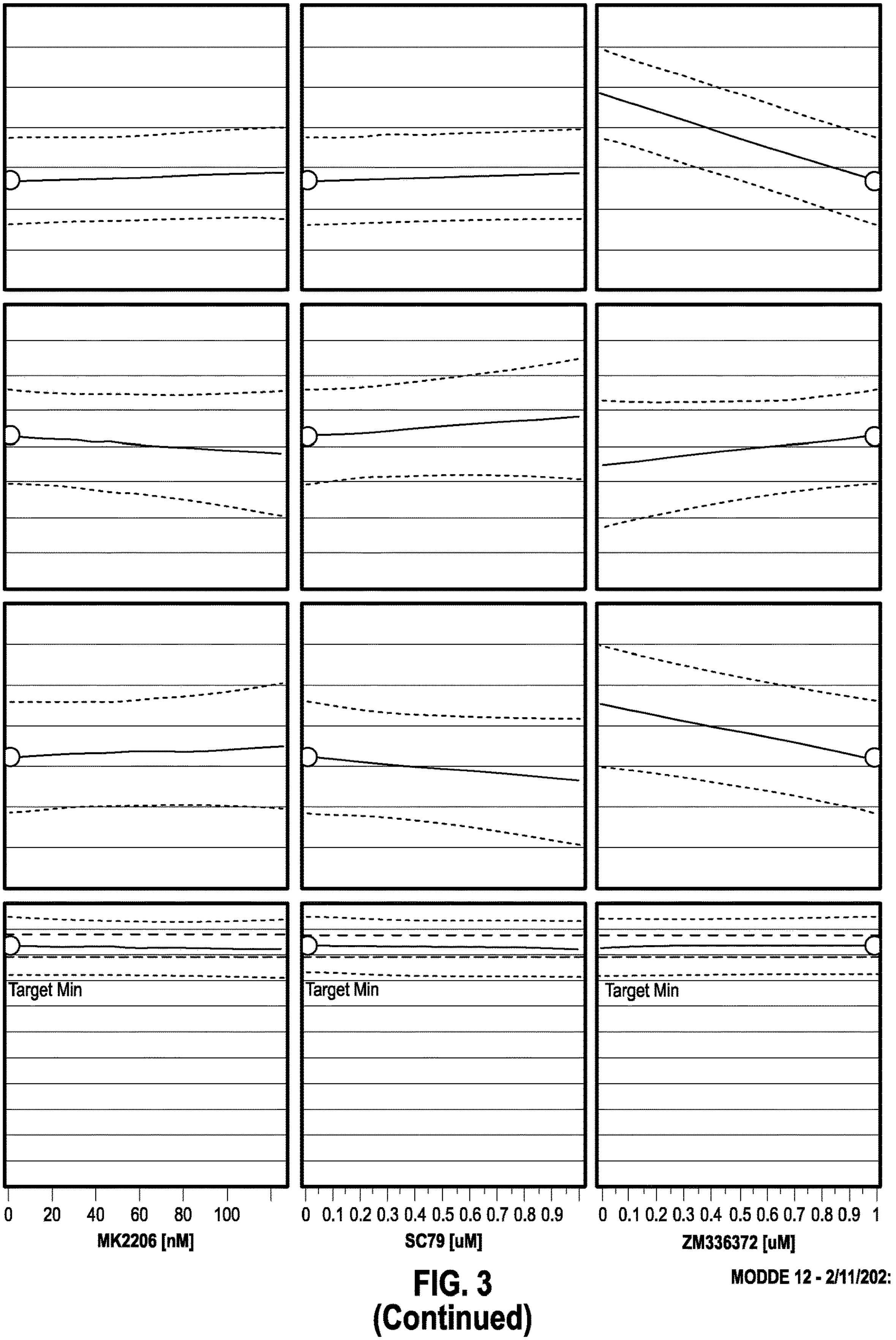

Described herein are methodologies and compositions that allow for the generation of SOX10+ OLIG2+ NKX2-2+ OPCs from human pre-OPCs, which themselves can be generated from human pluripotent stem cells, under chemically-defined culture conditions using a small molecule based approach. The OPCs can be further differentiated using the methodologies and compositions described herein to generate CD9+A2B5+O4+CNPase+ preOLs under chemically-defined culture conditions. The methods of the disclosure have the advantage that the starting pluripotent stem cells do not go through neural induction, which many prior art protocols use. This allows for generation of OLIG2+ pre-OPCs in as little as three days, which is significantly shorter than current protocols, which average 10 days to generate pre-OPCs. The pre-OPCs can be further differentiated to SOX10+ OLIG2+ NKX2-2+ OPCs in as little as more nine days, leading to a total of 12 days to generate OPCs from pluripotent stem cells. PreOLs can be obtained from the OPCs within six more days of culture in the appropriate media, allowing for obtention of preOLs from pluripotent stem cells in as little as 18 days, whereas other approaches take significantly longer (e.g., 50-70 days).

As described in Examples 1, 5, 8 and 10, a High-Dimensional Design of Experiments (HD-DoE) approach was used to simultaneously test multiple process inputs (e.g., small molecule agonists or antagonists) on output responses, such as gene expression. These experiments allowed for the identification of chemically-defined culture media, comprising agonists and/or antagonists of particular signaling pathways, that is sufficient to generate pre-OPCs, OPCs or preOLs in a very short amount of time. The optimized culture media was further validated by a factor criticality analysis, which examined the effects of eliminating individual agonist or antagonist agents, as described in Examples 2, 6 and 10. Immunohistochemistry further confirmed the phenotype of the cells generated by the differentiation protocol, as described in Examples 3, 7, 9 and 11.

Pre-OPCs can be differentiated into OPCs using one of two alternative protocols described herein. These alternative protocols are referred to herein as version 1 (described further in Example 5) and version 2 (described further in Example 8), with each protocol comprising two stages. As used herein, the first culture media that generates pre-OPCs from pluripotent stem cells in three days is referred to as the stage 1 media and the second and third culture media that generate OPCs from pre-OPCs in an additional nine days are referred to as the stage 2 media and the stage 3 media.

Figure 42:
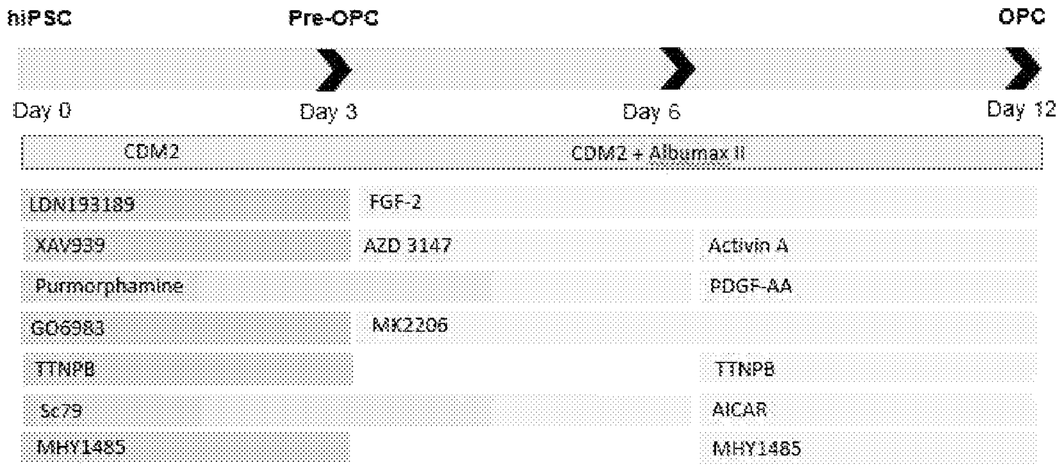
FIG. 42 is a schematic diagram of a representative example of the three stage protocol for obtaining oligodendrocyte progenitors from pluripotent stem cells described herein, wherein the version 1 protocol is used for stages 2 and 3.

An exemplary 3-stage culture protocol for generating OPCs from pluripotent stem cells using the version 1 protocol for stages 2 and 3 is illustrated schematically in FIG. 42. As shown, the stage 1 media is used for three days (days 0-3), the stage 2 media is used for three days (days 3-6), and the stage 3 media is used for six days (days 6-12).

Figure 43:
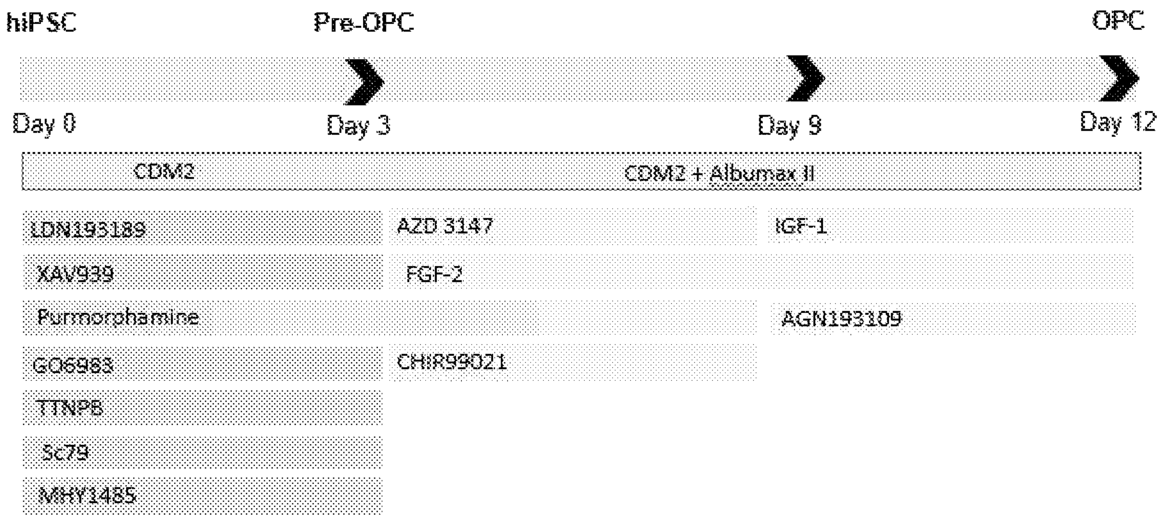
FIG. 43 is a schematic diagram of a representative example of the three stage protocol for obtaining oligodendrocyte progenitors from pluripotent stem cells described herein, wherein the version 2 protocol is used for stages 2 and 3.

An exemplary 3-stage culture protocol for generating OPCs from pluripotent stem cells using the version 2 protocol for stages 2 and 3 is illustrated schematically in FIG. 43. As shown, the stage 1 media is used for three days (days 0-3), the stage 2 media is used for six days (days 3-9), and the stage 3 media is used for three days (days 9-12).

The OPCs generated by either the version 1 protocol or the version 2 protocol for stages 2 and 3 can be further differentiated to preOLs in a stage 4 protocol. An exemplary stage 4 culture protocol for generating preOLs from OPCs is illustrated schematically in FIG. 44. As shown, the stage 1 media is used for three days (days 0-3), the stage 2 & 3 media are used for nine days (days 3-12), and the stage 4 media is used for six days (days 12-18).

Various aspects of the invention are described in further detail in the following subsections.

I. Cells

The starting cells used in the cultures of the disclosure for generating pre-OPCs are human pluripotent stem cells. As used herein, the term "human pluripotent stem cell" (abbreviated as hPSC) refers to a human stem cell that has the capacity to differentiate into a variety of different cell types. The term "pluripotent" as used herein refers to a cell with the capacity, under different conditions, to differentiate to cell types characteristic of all three germ cell layers (endoderm, mesoderm and ectoderm). Pluripotent cells are characterized primarily by their ability to differentiate to all three germ layers, for example, using a nude mouse and teratomas formation assay. Pluripotency can also be evidenced by the expression of embryonic stem (ES) cell markers, although the preferred test for pluripotency is the demonstration of the capacity to differentiate into cells of each of the three germ layers.

Human pluripotent stem cells include, for example, induced pluripotent stem cells (iPSC) and human embryonic stem cells, such as ES cell lines. Non-limiting examples of induced pluripotent stem cells (iPSC) include 19-11-1, 19-9-7 or 6-9-9 cells (e.g, as described in Yu, J. et al. (2009) *Science* 324:797-801). Non-limiting examples of human embryonic stem cell lines include ES03 cells (WiCell Research Institute) and H9 cells (Thomson, J. A. et al. (1998) *Science* 282:1145-1147). Human pluripotent stem cells (PSCs) express cellular markers that can be used to identify cells as being PSCs. Non-limiting examples of pluripotent stem cell markers include TRA-1-60, TRA-1-81, TRA-2-54, SSEA1, SSEA3, SSEA4, CD9, CD24, OCT3, OCT4, NANOG and/or SOX2. Since the methods of generating pre-OPCs and/or OPCs of the disclosure are used to differentiate (maturate) the starting pluripotent stem cell population, in various embodiments the pre-OPC and/or OPC cell populations generated by the methods of the disclosure lack expression of one or more stem cell markers selected from the group consisting of TRA-1-60, TRA-1-81, TRA-2-54, SSEA1, SSEA3, SSEA4, CD9, CD24, OCT3, OCT4, NANOG and/or SOX2.

The starting cells used in the cultures of the disclosure for generating OPCs are human pre-OPCs, such as the pre-OPCs generated from pluripotent stem cells as described herein.

The pluripotent stem cells and pre-OPCs are subjected to culture conditions, as described herein, that induce cellular differentiation. As used herein, the term "differentiation" refers to the development of a cell from a more primitive stage towards a more mature (i.e., less primitive) cell, typically exhibiting phenotypic features of commitment to a particular cellular lineage. An early progenitor cell that can be derived from human PSCs by neural induction (neuralization) is a neural precursor cell (NPC). As used herein, a "neural precursor cell" or "NPC" refers to a stem cell-derived progenitor cell that expresses the type VI intermediate filament protein Nestin. Since the methods of generating pre-OPCs and/or OPCs of the disclosure avoid the use of neural induction, and thus do not generate NPCs, in various embodiments the cell populations generated by the methods of the disclosure lack Nestin-positive cells.

In one embodiment, the cells generated by the methods of the disclosure are pre-oligodendrocyte progenitor cells (pre-OPCs). As used herein, a "pre-oligodendrocyte progenitor cells" or "pre-OPC" refers to a stem cell-derived progenitor cell that expresses the cellular markers OLIG2 and NKX2.2. A pre-OPC may express additional markers, including but not limited to: OTX2 (anterior neuroectoderm biomarker), FEZF2 (anterior ectoderm biomarker), and/or OLIG1.

In one embodiment, the cells generated by the methods of the disclosure are oligodendrocyte progenitor cells (OPCs), which are more differentiated (more mature) cells than pre-OPCs. As used herein, an "oligodendrocyte progenitor cells" or "OPC" refers to a stem cell-derived progenitor cell that expresses the cellular markers SOX10, OLIG2 and NKX2.2, as well as PDGFRa. An OPC may express additional markers, non-limiting example of which include OTX2 (anterior neuroectoderm biomarker), FEZF2 (anterior ectoderm biomarker), and/or OLIG1.

In one embodiment, the cells generated by the methods of the disclosure are pre-myelinating oligodendrocytes (pre-OLs), which are more differentiated (more mature) cells than OPCs. As used herein, a "pre-myelinating oligodendrocyte" or "preOL" refers to an oligodendrocyte lineage cell that expresses the cellular markers CD9, A2B5, O4 and CNPase.

The pre-OLs generated by the methods of the disclosure can be further cultured in vitro to generate mature oligodendrocytes (OL). Markers of mature OLs include but are not limited to myelin basic protein (MBP) and O4.

II. Culture Media Components

The method of the disclosure for generating pre-OPCs, OPCs or preOLs comprise culturing human pluripotent stem cells in a culture media comprising specific agonist and/or antagonists of cellular signaling pathways.

As described in Example 1 (stage 1 protocol), a culture media comprising a retinoic acid (RA) pathway agonist, an Akt pathway agonist and an mTOR pathway agonist was sufficient to generate OLIG2 and NKX2.2-expressing pre-OPCs in as little as three days. Inclusion of additional agents optimized for expression of other markers, including PDGFRa as a marker of OPC differentiation. In other embodiments, the culture media further comprises at least one additional agent selected from the group consisting of WNT pathway antagonists, SHH pathway agonists, BMP pathway antagonists and PKC pathway antagonists. In one embodiment, the culture media further comprises a WNT pathway antagonist. In one embodiment, the culture media further comprises an SHH pathway agonist. In one embodiment, the culture media further comprises a BMP pathway antagonist. In one embodiment, the culture media further comprises a PKC pathway antagonist. In one embodiment, the culture media further comprises a WNT pathway antagonist and an SHH pathway agonist, wherein the differentiated cells express OTX2 and FEZF2, in addition to OLIG2 and NKX2.2.

In one embodiment, the culture media of stage 1 to generate pre-OPCs comprises a retinoic acid (RA) pathway agonist, an Akt pathway agonist, an mTOR pathway agonist, a WNT pathway antagonist, an SHH pathway agonist, a BMP pathway antagonist and a PKC pathway antagonist. In one embodiment, the differentiated cells are OPCs expressing at least OLIG2, NKX2.2 and PDGFRa (and may express additional markers, such as OTX2, FEZF2 and/or OLIG1).

Pre-OPCs can be further differentiated to SOX10+ OLIG2+ NKX2-2+ OPCs by further culture in the stage 2 and stage 3 media according to either the version 1 or version 2 protocol (as illustrated schematically in FIG. 42 and FIG. 43).

As described in Examples 5 and 8, two alternative culture protocols have been developed for generating human OPCs from pre-OPCs, referred to as version 1 and version 2, with each version comprised of two stages, referred to as stage 2 and stage 3. The stage 2 and stage 3 protocols can be combined with the stage 1 protocol described herein for generating pre-OPCs from pluripotent stem cells to thereby allow for generating human OPCs from pluripotent stem cells in as little as twelve days.

As described in Example 5 (the version 1 protocol for stages 2 and 3), culture of pre-OPCs in (i) a culture media comprising an FGFR pathway agonist, an mTOR pathway antagonist, an SHH pathway agonist, an AKT pathway antagonist and an AKT pathway agonist for three days (e.g., day 0-3 of culture), followed by culture of the resultant cells in (ii) a culture media comprising an FGFR pathway agonist, an activin receptor (AR) pathway agonist, a PDGFR pathway agonist, an AKT pathway antagonist, a retinoic acid (RA) pathway agonist, an AMPK pathway agonist and an mTOR pathway agonist for six days (e.g., days 3-9 of culture) was sufficient to generate SOX10+ OLIG2+ NKX2-2+ OPCs.

As described in Example 8 (the version 2 protocol for stages 2 and 3), culture of pre-OPCs in (i) a culture media comprising an FGFR pathway agonist, an mTOR pathway antagonist, an SHH pathway agonist and a WNT pathway agonist for six days (e.g., day 0-6 of culture), followed by culture of the resultant cells in (ii) a culture media comprising an FGFR pathway agonist, an IGF-1 pathway agonist and a retinoic acid (RA) pathway antagonist, for three days (e.g., days 6-9 of culture) was sufficient to generate SOX10+ OLIG2+ NKX2-2+ OPCs.

Figure 44:
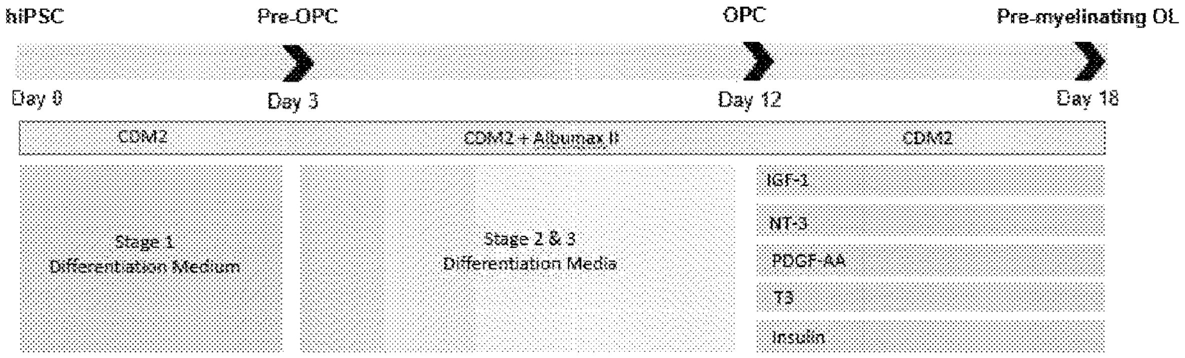
FIG. 44 is a schematic diagram of a representative example of the stage 4 protocol for generating pre-myelinating OLs from OPCs.

OPCs can be further differentiated to CD9+A2B5+O4+ CNPase preOLs by further culture in stage 4 media (as illustrated schematically in FIG. 44).

As described in Example 10 and 11, culture of SOX10+ OLIG2+ NKX2-2+ OPCs in a culture media comprising an IGF1R agonist, a TrkC agonist, a PDGFR agonist, a thyroid hormone receptor agonist and an insulin receptor agonist was sufficient to generate CD9+ A2B5+ CNPase+ O4+ pre-OLs.

As used herein, an "agonist" of a cellular signaling pathway is intended to refer to an agent that stimulates (upregulates) the cellular signaling pathway. Stimulation of the cellular signaling pathway can be initiated extracellularly, for example by use of an agonist that activates a cell surface receptor involved in the signaling pathway (e.g., the agonist can be a receptor ligand). Additionally or alternatively, stimulation of cellular signaling can be initiated intracellularly, for example by use of a small molecule agonist that interacts intracellularly with a component(s) of the signaling pathway.

As used herein, an "antagonist" of a cellular signaling pathway is intended to refer to an agent that inhibits (downregulates) the cellular signaling pathway. Inhibition of the cellular signaling pathway can be initiated extracellularly, for example by use of an antagonist that blocks a cell surface receptor involved in the signaling pathway. Additionally or alternatively, inhibition of cellular signaling can be initiated intracellularly, for example by use of a small molecule antagonist that interacts intracellularly with a component(s) of the signaling pathway.

Retinoic acid (RA) pathway agonists, Akt pathway agonists, mTOR pathway agonists, WNT pathway antagonists, SHH pathway agonists, BMP pathway antagonists, PKC pathway antagonists FGFR pathway agonists, WNT pathway agonists, IGF-1 pathway agonists, mTOR pathway antagonists, RA pathway antagonists, Akt pathway antagonists, activin receptor (AR) pathway agonists, PDGFR pathway agonists and AMPK pathway agonists are known in the art and commercially available. They are used in the culture media at a concentration effective to achieve the desired outcome, e.g., generation of pre-OPCs and/or OPCs expressing markers of interest. Non-limiting examples of suitable agonist and antagonists agents, and effective concentration ranges, are described further below.

Agonists of the RA pathway are used in the stage 1 media and in the version 1 stage 3 media and include agents, molecules, compounds, or substances capable of stimulation of a retinoic acid receptor (RAR) that is activated by both all-trans retinoic acid and 9-cis retinoic acid. There are three RARs: RAR-alpha, RAR-beta and RAR-gamma, which are encoded by the RARA, RARB, RARG genes, respectively. Different retinoic acid analogs have been synthesized that can activate the retinoic acid pathway. Non-limiting examples of such compounds include TTNPB (agonist of RAR-alpha, beta and gamma), AM 580 (RARalpha agonist), CD 1530 (potent and selective RARgamma agonist), CD 2314 (selective RARbeta agonist), Ch 55 (potent RAR agonist), BMS 753 (RARalpha-selective agonist), Tazarotene (receptor-selective retinoid; binds RAR-beta and -gamma), Isotretinoin (endogenous agonist for retinoic acid receptors; inducer of neuronal differentiation), and AC 261066 (RARβ2 agonist). In some embodiments, the RA signaling pathway agonist is selected from the group consisting of: i) a retinoid compound, ii) a retinoid X receptor (RXR) agonist, and iii) a 25 retinoic acid receptor (RARs) agonist. In particular embodiments, the RA pathway agonist is selected from the group consisting of: retinoic acid, Sr11237, adapalene, EC23, 9-cis retinoic acid, 13-cis retinoic acid, 4-oxo retinoic acid, and All-trans Retinoic Acid (ATRA).

Accordingly, in one embodiment, the RA pathway agonist is selected from the group consisting of TTNPB, AM 580, CD 1530, CD 2314, CD 437, Ch 55, BMS 753, BMS 961, Tazarotene, Isotretinoin, Tretinoin, Tamibarotene, ATRA, AC 261066, AC 55649, retinoic acid (RA), Sr11237, adapalene, EC23, 9-cis retinoic acid, 13-cis retinoic acid, 4-oxo retinoic acid, and All-trans Retinoic Acid (ATRA), and combinations thereof. In one embodiment, the RA pathway agonist is present in the culture media at a concentration within a range of 5-500 mM, or 10-100 nM or 25-75 nM. In one embodiment, the RA pathway agonist is TTNPB. In one embodiment, the RA pathway agonist is TTNPB, which is present in the culture media at a concentration within a range of 5-500 nM, or 10-100 nM or 25-75 nM. In one embodiment, the RA pathway agonist is TTNPB, which is present in the culture media at a concentration of 50 nM in the stage 1 media, the stage 3 media (version 1) or both.

Agonists of the Akt pathway include agents, molecules, compounds, or substances capable of stimulating (activating) the signaling pathway of one or more of the serine/threonine kinase Akt family members, which include Akt1 (also designated PKB or RacPK), Akt2 (also designated PKBβ or RaePK-β) and Akt 3 (also designated PKBγ or thyoma viral proto-oncogene 3). In one embodiment, the Akt pathway agonist is a pan-Akt activator. In one embodiment, the Akt pathway agonist is selected from the group consisting of Sc79, Demethyl-Coclaurine, LM22B-10, YS-49, YS-49 monohydrate, Demethylasterriquinone B1, Recilisib, N-Oleyol glycine, NSC45586 sodium, Periplocin, CHPG sodium salt, Bilobalide, 6-hydorxyflavone, Musk ketone, SEW2871, 8-Prenylnaringenin, Razuprotafib, and combinations thereof. In one embodiment, the Akt pathway agonist is SC79. In one embodiment, the Akt pathway agonist is present in the culture media at a concentration within a range of 0.1-10 μM. In one embodiment, the Akt pathway agonist is SC79. In one embodiment, the Akt pathway agonist is SC79, which is present in the culture media at a concentration of 0.1-10 μM, or 0.5-5 μM, or 0.5-3.0 μM or 0.5-2.5 μM. In one embodiment, the Akt pathway agonist is SC79, which is present in the culture media of stage 1 at a concentration of 1 μM. In one embodiment, the Akt pathway agonist is SC79, which is present in the culture media of stage 2 (version 1) at a concentration of 2 μM.

Agonists of the mTOR (mammalian target of rapamycin) pathway include agents, molecules, compounds, or substances capable of stimulating (activating) signaling through mTOR, a PI3K-related kinase family member which is a core component of the mTORC1 and mTORC2 complexes. In one embodiment, the mTOR pathway agonist is selected from the group consisting of MHY1485, 3BDO, Salidroside, L-Leucine, NV-5138, Testosterone; 3-benzyl-5-((2-nitrophenoxy)methyl)-dihydrofuran-2(3H)-one (3BDO); NV-5138 hydrochloride, NV-5138, L-leucine-d1, L-leucine-2-13C,15N, Leucine-13C6, L-leucine-d7, L-leucine-d10, L-leucin-d2, l-leucine-d3, L-leucine-1802, L-leucine-13C, L-leucine-2-13C, L-leucine-13C6-15N, L-leucine-15N, L-leucine-1-13C,15N, and combinations thereof. In one embodiment, the mTOR pathway agonist is present in the culture media at a concentration within a range of 0.1-10 μM, or 0.5-5 μM, or 0.5-3.0 μM or 0.5-2.5 μM. In one embodiment, the mTOR pathway agonist is MHY1485. In one embodiment, the mTOR pathway agonist is MHY1485, which is present in the culture media at a concentration of 0.1-10 μM, or 0.5-5 μM, or 0.5-3.0 μM or 0.5-2.5 μM. In one embodiment, the mTOR pathway agonist is MHY1485, which is present in the culture media of stage 1 at a concentration of 1 μM. In one embodiment, the mTOR pathway agonist is MHY1485, which is present in the culture media of stage 3 (version 1) at a concentration of 2 μM.

Antagonists of the WNT pathway include agents, molecules, compounds, or substances capable of inhibiting (downregulating) the canonical Wnt/β-catenin signaling pathway, which biologically is activated by binding of a Wnt-protein ligand to a Frizzled family receptor. In one embodiment, the WNT pathway antagonist is selected from the group consisting of XAV939, ICG001, Capmatinib, endo-IWR-1, IWP-2, IWP-4, MSAB, CCT251545, KY02111, NCB-0846, FH535, LF3, WIKI4, Triptonide, KYA1797K, JW55, JW 67, JW74, Cardionogen 1, NLS-StAx-h, TAK715, PNU 74654, iCRT3, WIF-1, DKK1, and combinations thereof. In one embodiment, the WNT pathway antagonist is present in the culture media at a concentration within a range of 10-500 nM, 50-250 nM or 50-150 nM. In one embodiment, the WNT pathway antagonist is XAV939. In one embodiment, the WNT pathway antagonist is XAV939, which is present in the culture media at a concentration of 10-500 nM, 50-250 nM or 50-150 nM. In one embodiment, the WNT pathway antagonist is XAV939, which is present in the culture media of stage 1 at a concentration of 100 nM.

Agonists of the SHH (sonic hedgehog) pathway include agents, molecules, compounds, or substances capable of stimulating (activating) signaling through the SHH pathway, which biologically involves binding of SHH to the Patched-1 (PTCH1) receptor and transduction through the Smoothened (SMO) transmembrane protein. In one embodiment, the SHH pathway agonist is selected from the group consisting of Purmorphamine, GSA 10, SHH, SAG, and combinations thereof. In one embodiment, the SHH pathway agonist is present in the culture media at a concentration within a range of 100-1000 nM, or 250-750 nM or 400-600 nM. In one embodiment, the SHH pathway antagonist is Purmorphamine. In one embodiment, the SHH pathway antagonist is Purmorphamine, which is present in the culture media at a concentration of 100-1000 nM, or 250-750 nM or 400-600 nM. In one embodiment, the SHH pathway antagonist is Purmorphamine, which is present in the culture media of stage 1, stage 2 (version 1) and/or stage 2 (version 2) at a concentration of 500 nM.

Antagonists of the BMP (bone morphogenetic protein) pathway include agents, molecules, compounds, or substances capable of inhibiting (downregulating) the BMP signaling pathway, which biologically is activated by binding of BMP to a BMP receptor, which are activin receptor-like kinases (ALK) (e.g., type I BMP receptor, including but not limited to ALK2 and ALK3). In one embodiment, the BMP pathway antagonist is selected from the group consisting of LDN193189, DMH1, DMH2, Dorsopmorphin, K02288, LDN214117, LDN212854, folistatin, ML347, Noggin and combinations thereof. In one embodiment, the BMP pathway antagonist is present in the culture media at a concentration within a range of 100-1000 nM, 150-750 nM, 100-500 nM, or 150-350 nM. In one embodiment, the BMP pathway antagonist is LDN193189. In one embodiment, the BMP pathway antagonist is LDN193189, which is present in the culture media at a concentration of 100-1000 nM, 150-750 nM, 100-500 nM, or 150-350 nM. In one embodiment, the BMP pathway antagonist is LDN193189, which is present in the culture media of stage 1 at a concentration of 250 nM.

Antagonists of the PKC (protein kinase C) pathway include agents, molecules, compounds, or substances capable of inhibiting (downregulating) a PKC signaling pathway, which biologically is mediated by a PKC family member. The PKC family of serine/threonine kinases comprises fifteen isozymes, including the "classical" PKC subcategory, which contain the isoforms α, β1, β2 and γ. In one embodiment, the PKC pathway antagonist inhibits the activity of at least one (and in other embodiments, at least two or three) PKC enzyme selected from PKCα, PKCβ1, PKCβ2 and PKCγ. In one embodiment, the PKC pathway antagonist is selected from the group consisting of Go 6983, Sotrastaurin, Enzastaurin, Staurosporine, LY31615, Go 6976, GF 109203X, Ro 31-8220 Mesylate, and combinations thereof. In one embodiment, the PKC pathway antagonist is present in the culture media at a concentration within a range of 10-500 nM, 50-300 nM, 50-150 nM or 75-150 nM. In one embodiment, the PKC pathway antagonist is Go 6983. In one embodiment, the PKC pathway antagonist is Go 6983, which is present in the culture media at a concentration of 10-500 nM, 50-300 nM, 50-150 nM or 75-150 nM. In one embodiment, the PKC pathway antagonist is Go 6983, which is present in the culture media of stage 1 at a concentration of 110 nM.

Agonists of the FGFR pathway include agents, molecules, compounds, or substances capable of stimulating (upregulating) a fibroblast growth factor receptor signaling pathway, which biologically is activated by binding of an FGF to an FGFR. In an embodiment, the FGFR agonist is FGF2, SUN11602, or combinations thereof. In an embodiment, the FGFR pathway agonist is present in the culture media at a concentration within a range of 1-20 ng/ml, 5-15 ng/ml, 7.5-12.5 ng/ml, 9-11 ng/ml or at a concentration of 10 ng/ml. In an embodiment, the FGFR agonist is FGF2 (e.g., recombinant human FGF2). In an embodiment, the FGFR agonist is FGF2 which is present in the culture media of stage 1 and/or stage 2 (versions 1 and 2) and/or stage 3 (versions 1 and 2) at a concentration within a range of 1-20 ng/ml, 5-15 ng/ml, 7.5-12.5 ng/ml, 9-11 ng/ml or at a concentration of 10 ng/ml.

Agonists of the WNT pathway include agents, molecules, compounds, or substances capable of stimulating (upregulating) the canonical Wnt/β-catenin signaling pathway, which biologically is activated by binding of a Wnt-protein ligand to a Frizzled family receptor. In one embodiment, a WNT pathway agonist is a glycogen synthase kinase 3 (Gsk3) inhibitor. In one embodiment, the WNT pathway agonist is selected from the group consisting of CHIR99021, CHIR98014, SB 216763, SB 415286, LY2090314, 3F8, A 1070722, AR-A 014418, BIO, BIO-acetoxime, AZD1080, WNT3A, alsterpaullone, indirubin-3-oxime, 1-azakenpaullone, kenpaullone, TC-G 24, TDZD 8, TWS 119, NP 031112, AT 7519, KY 19382, AZD2858, and combinations thereof. In one embodiment, the WNT pathway agonist is present in the culture media at a concentration within a range of 0.3-3.0 μM, 0.5-2.0 μM, 0.75-1.5 μM or 0.9-1.1 μM. In one embodiment, the WNT pathway agonist is CHIR99021. In one embodiment, the WNT pathway agonist is CHIR99021, which is present in the culture media at a concentration within a range of 0.3-3.0 μM, 0.5-2.0 μM, 0.75-1.5 μM or 0.9-1.1 μM. In one embodiment, the WNT pathway agonist is CHIR99021, which is present in the culture media of stage 2 (version 2) at a concentration of 1.0 μM.

Agonists of the IGF-1 (insulin-like growth factor 1) pathway include agents, molecules, compounds, or substances capable of stimulating (activating) signaling through the IGF-1 pathway. In one embodiment, the IGF-1 pathway agonist is selected from the group consisting of IGF-1, IGF-2, insulin, Rg5, IGF-1 30-41, Demethylasterriquinone B1, IGF1-Ado, X10, mecasermin, and combinations thereof. In one embodiment, the IGF-1 pathway agonist is present in the culture media at a concentration within a range of 2-20 ng/ml, 5-15 ng/ml or 7.5-12.5 ng/ml. In one embodiment, the IGF-1 pathway agonist is IGF-1. In one embodiment, the IGF-1 pathway agonist is IGF-1, which is present in the culture media at a concentration of 2-20 ng/ml, 5-15 ng/ml or 7.5-12.5 ng/ml. In one embodiment, the IGF-1 pathway agonist is IGF-1, which is present in the culture media of stage 3 (version 2) at a concentration of 10 ng/ml. In one embodiment, the IGF-1 pathway agonist is IGF-1, which is present in the culture media of stage 4 at a concentration of 10 ng/ml.

Antagonists of the mTOR (mammalian target of rapamycin) pathway include agents, molecules, compounds, or substances capable of inhibiting (downregulating) an mTOR signaling pathway, wherein mTOR is a PI3K-related kinase family member which is a core component of the mTORC1 and mTORC2 complexes. In one embodiment, the mTOR pathway antagonist is selected from the group consisting of AZD 3147, Dactolisib, Rapamycin, Everolimus, AZD 8055, Temsirolimus, PI-103, NU7441, BC-LI-0186, eCF 309, ETP 45658, Niclosamide, Omipalisib, PF 04691502, PF 05212384, Torin1, Torin 2, WYE 687, XL 388, STK16-IN-1, PP 242, Torkinib, Ridaforolimus, Sapanisertib, Voxtalisib, and combinations thereof. In one embodiment, the mTOR pathway antagonist is present in the culture media at a concentration within a range of 5-200 nM, 10-150 nM or 15-100 nM. In one embodiment, the mTOR pathway antagonist is AZD 3147. In one embodiment, the mTOR pathway antagonist is AZD 3147, which is present in the culture media at a concentration within a range of 5-200 nM, 10-150 nM or 15-100 nM. In one embodiment, the mTOR pathway antagonist is AZD 3147, which is present in the culture media of stage 2 (version 1) at a concentration of 15 nM. In one embodiment, the mTOR pathway antagonist is AZD 3147, which is present in the culture media of stage 2 (version 2) at a concentration of 100 nM.

Antagonists of the retinoic acid (RA) pathway include agents, molecules, compounds, or substances capable of inhibiting (downregulating) an RA signaling pathway. In one embodiment, the RA pathway antagonist is selected from the group consisting of AGN193109, BMS 195614, CD 2665, ER 50891, LE 135, LY 2955303, MM11253, and combinations thereof. In one embodiment, the RA pathway antagonist is present in the culture media at a concentration within a range of 50-300 nM, 75-250 nM, 100-200 nM or 90-110 nM. In one embodiment, the RA pathway antagonist is AGN193109. In one embodiment, the RA pathway antagonist is AGN193109, which is present in the culture media at a concentration within a range of 50-300 nM, 75-250 nM, 100-200 nM or 90-110 nM. In one embodiment, the RA pathway antagonist is AGN193109, which is present in the culture media of stage 3 (version 2) at a concentration of 100 nM.

Antagonists of the AKT pathway include agents, molecules, compounds, or substances capable of inhibiting (downregulating) the signaling pathway of one or more of the serine/threonine kinase AKT family members, which include AKT1 (also designated PKB or RacPK), AKT2 (also designated PKBβ or RacPK-β) and AKT 3 (also designated PKBγ or thyoma viral proto-oncogene 3). In one embodiment, the AKT pathway antagonist is selected from the group consisting of MK2206, GSK690693, Perifosine (KRX-0401), Ipatasertib (GDC-0068), Capivasertib (AZD5363), PF-04691502, AT 7867, Triciribine (NSC154020), ARQ751, Miransertib (ab235550), Borussertib, Cerisertib, Akti1/2, CCT128930, A 674563, PHT 427, Miltefosine, AT 13148, ML 9, BAY 1125976, Oridonin, TIC10, Pectolinarin, Akti IV, 10-DEBC, API-1, SC 66, FPA 124, API-2, Urolithin A, and combinations thereof. In one embodiment, the AKT pathway antagonist is present in the culture media at a concentration within a range of 25-300 nM, 50-250 nM, 75-200 nM or 100-150 nM. In one embodiment, the AKT pathway antagonist is MK2206. In one embodiment, the AKT pathway antagonist is MK2206, which is present in the culture media at a concentration within a range of 25-300 nM, 50-250 nM, 75-200 nM or 100-150 nM. In one embodiment, the AKT pathway antagonist is MK2206, which is present in the culture media of stage 2 (version 1) and/or stage 3 (version 1) at a concentration of 125 nM.

Agonists of the activin receptor (AR) pathway include agents, molecules, compounds, or substances capable of stimulating (activating) signaling through the AR pathway. In one embodiment, the AR pathway agonist is selected from the group consisting of Activin A, Alantolactone, and combinations thereof. In one embodiment, the AR pathway agonist is present in the culture media at a concentration within a range of 2-20 ng/ml, 5-15 ng/ml or 7.5-12.5 ng/ml. In one embodiment, the AR pathway agonist is Activin A. In one embodiment, the AR pathway agonist is Activin A, which is present in the culture media at a concentration of 2-20 ng/ml, 5-15 ng/ml or 7.5-12.5 ng/ml. In one embodiment, the AR pathway agonist is Activin A, which is present in the culture media of stage 3 (version 1) at a concentration of 10 ng/ml.

Agonists of the PDGFR (platelet-derived growth factor receptor) pathway include agents, molecules, compounds, or substances capable of stimulating (activating) signaling through the PDGFR pathway. In one embodiment, the PDGFR pathway agonist is PDGF-AA. In one embodiment, the PDGFR pathway agonist is present in the culture media at a concentration within a range of 2-20 ng/ml, 5-15 ng/ml or 7.5-12.5 ng/ml. In one embodiment, the PDGFR pathway agonist is PDGF-AA, which is present in the culture media at a concentration of 2-20 ng/ml, 5-15 ng/ml or 7.5-12.5 ng/ml. In one embodiment, the PDGFR pathway agonist is PDGF-AA, which is present in the culture media of stage 3 (version 1) at a concentration of 10 ng/ml. In one embodiment, the PDGFR pathway agonist is PDGF-AA, which is present in the culture media of stage 4 at a concentration of 10 ng/ml.

Agonists of the AMPK (5' AMP-activated protein kinase) pathway include agents, molecules, compounds, or substances capable of stimulating (activating) signaling through the AMPK pathway. In one embodiment, the AMPK pathway agonist is selected from the group consisting of AICAR, metformin, Kazinol B, Marein, Amarogentin, A 769662, PF 06409577, metformin hydrochloride, ZLN 024, ZLN 024 hydrochloride, Nilotinib, Phenformin, Nilotinib hydrochloride monohydrate, Adenosine 5'-monophosphate monohydrate, Hispidulin, MK 8722, Euphorbiasteroid, ASP4132, GSK621, EX229 (compound 991), Trans-feluric acid, O-304, MK 3903, BAM 15, ligustroflavone, ETC-1002, BC1618, IMM-H007, IM156, Chikusetsusaponin IVa, Poricoic acid A, 7-Methoxyisoflavone, Urolithin B, Danthron, Demethyleneberberine, AMPK activator 1, AMPK activator 2, AMPK activator 4, Malvidin-3-O-arabinoside chloride, RSVA 405, Etilefrin, COH-SR4, Buformin, Buformin hydrochloride, PT1, Bempedoic acid, 3a-Hydrocymogrol, Ampkinone, and combinations thereof. In one embodiment, the AMPK pathway agonist is present in the culture media at a concentration within a range of 50-500 μM, 100-300 μM, 150-250 μM or 175-225 μM. In one embodiment, the AMPK pathway agonist is AICAR, which is present in the culture media at a concentration of 50-500 μM, 100-300 μM, 150-250 μM or 175-225 μM. In one embodiment, the AMPK pathway agonist is AICAR, which is present in the culture media of stage 3 (version 1) at a concentration of 200 μM.

Agonists of the TrkC (tropomyosin-related kinase receptor C) pathway include agents, molecules, compounds, or substances capable of stimulating (activating) signaling through the TrkC pathway. In one embodiment, the TrkC pathway agonist is selected from the group consisting of neurotrophin-3 (NT-3), peptidomimetics based on β-turns of NT-3, LM22B 10, GNF 5837, and combinations thereof. In one embodiment, the TrkC pathway agonist is NT-3. In one embodiment, the TrkC pathway agonist is present in the culture media at a concentration within a range of 2-20 ng/ml, 5-15 ng/ml or 7.5-12.5 ng/ml. In one embodiment, the TrkC pathway agonist is NT-3, which is present in the culture media at a concentration of 2-20 ng/ml, 5-15 ng/ml or 7.5-12.5 ng/ml. In one embodiment, the TrkC pathway agonist is NT-3, which is present in the culture media of stage 4 at a concentration of 10 ng/ml.

Agonists of thyroid hormone receptor (THR) include agents, molecules, compounds, or substances capable of stimulating (activating) signaling through the thyroid hormone receptor pathway. In one embodiment, the thyroid hormone receptor agonist is selected from the group consisting of T3, T4, Resmetirom, TRb agonist 3 (Compound 3), Sobetirome, Tiratricol, and combinations thereof. In one embodiment, the THR agonist is present in the culture media at a concentration within a range of 10-100 nM, or 25-75 nM or 40-60 nM or at 50 nM. In one embodiment, the THR agonist is T3. In one embodiment, the THR agonist is T3, which is present in the culture media at a concentration of 10-100 nM, or 25-75 nM or 40-60 nM or at 50 nM. In one embodiment, the THR agonist is T3, which is present in the culture media of stage 4 at a concentration of 50 nM.

Agonists of insulin receptor (IR) include agents, molecules, compounds, or substances capable of stimulating (activating) signaling through the insulin receptor pathway. In one embodiment, the insulin receptor agonist is selected from the group consisting of insulin, IGF-1, IGF-2, Demethylasterriquinone B1, MK-5160, MK-1092, and combinations thereof. In one embodiment, the insulin receptor agonist is present in the culture media at a concentration within a range of 4-40 μg/ml, 10-30 μg/ml or 15-25 μg/ml or at 20 μg/ml. In one embodiment, the insulin receptor agonist is insulin, which is present in the culture media at a concentration of 4-40 μg/ml, 10-30 μg/ml or 15-25 μg/ml. In one embodiment, the insulin receptor agonist is insulin, which is present in the culture media of stage 4 at a concentration of 20 μg/ml.

When an agonist or antagonist is used in more than one step of the method, in one embodiment it is the same particular agonist or antagonist that is used for each step in which the agent is present in the culture media. In another embodiment, different agonists or antagonists that affect the same signaling pathway are used in different steps of the method.

When an agonist or antagonist is used in more than one step of the method, in one embodiment it is the same concentration of the same agonist or antagonist that is used for each step in which the agent is present in the culture media. In another embodiment, different concentrations of the same agonist or antagonist are used in different steps of the method.

III. Culture Conditions

In combination with the chemically-defined and optimized culture media described in subsection II above, the methods of generating pre-OPCs, OPCs and preOLs of the disclosure utilize standard culture conditions established in the art for cell culture. For example, cells can be cultured at 37° C. and 5% $CO_2$ conditions. Cells can be cultured in standard culture vessels or plates, such as 96-well plates. In certain embodiments, the starting pluripotent stem cells are adhered to plates, preferably coated with an extracellular matrix material such as vitronectin. In one embodiment, the stem cells are cultured on a vitronectin coated culture surface (e.g., vitronectin coated 96-well plates).

Pluripotent stem cells can be cultured in commercially-available media prior to differentiation. For example, stem cells can be cultured for at least one day in Essential 8 Flex media (Thermo Fisher #A2858501) prior to the start of the differentiation protocol. In a non-limiting exemplary embodiment, stem cells are passaged onto vitronectin (Thermo Fisher #A14700) coated 96-well plates at 150,000 cells/$cm^2$ density and cultured for one day in Essential 8 Flex media prior to differentiation.

To begin the differentiation protocol, the media the stem cells are being cultured in is changed to a basal differentiation media that has been supplemented with signaling pathway agonists and/or antagonists as described above in subsection II. A basal differentiation media can include, for example, a commercially-available base supplemented with additional standard culture media components needed to maintain cell viability and growth, but lacking serum (the basal differentiation media is a serum-free media) or any other exogenously-added growth factors, such as FGF2, PDGF, IGF or HGF. In a non-limiting exemplary embodiment, a basal differentiation media contains 1×IMDM (Thermo Fisher #12440046), 1× F12 (Thermo Fisher #11765047), poly(vinyl alcohol) (Sigma #p8136) at 1 mg/ml, chemically defined lipid concentrate (Thermo Fisher #11905031) at 1%, 1-thioglycerol (Sigma #M6145) at 450 uM, Insulin (Sigma #11376497001) at 0.7 ug/ml and transferrin (Sigma #10652202001) at 15 ug/ml. In one embodiment, this basal media is supplemented with Albumax II.

The culture media typically is changed regularly to fresh media. For example, in one embodiment, media is changed every 24 hours.

To generate pre-OPCs, OPCs, and/or preOLs, the stem cells are cultured in the optimized culture media for sufficient time for cellular differentiation and expression of pre-OPC-, OPC- or preOL-associated markers. As described in Example 1, it has been discovered that culture of stem cells in the optimized stage 1 culture media for as little as 72 hours (3 days) was sufficient for pre-OPC differentiation. Accordingly, in one embodiment, stem cells are cultured for at least 72 hours. In other embodiments, stem cells are cultured for at least 60, 64, 68, 72, 76, 80, 84, 88, 92 or 96 hours.

As described in Example 5, it has been discovered that culture of pre-OPCs in the optimized stage 2 culture media for as little as 72 hours (3 days) was sufficient for pre-OPC differentiation. Accordingly, in one embodiment, pre-OPCs are cultured for at least 72 hours in stage 2 (version 1) culture media. In other embodiments, pre-OPCs are cultured for at least 60, 64, 68, 72, 76, 80, 84, 88, 92 or 96 hours in stage 2 (version 1) culture media. It further has been discovered that further culture of the cells in the optimized stage 3 media for as little as 6 days (144 hours) was sufficient for OPC differentiation. Accordingly, in one embodiment, cells are cultured for at least 144 hours in stage 3 (version 1) culture media. In other embodiments, the cells are cultured for at least 132, 136, 140, 144, 150, 154 or 158 hours in stage 3 (version 1) culture media.

As described in Example 8, it has been discovered that culture of pre-OPCs in the optimized stage 2 culture media for as little as 6 days (144 hours) was sufficient for cell differentiation. Accordingly, in one embodiment, pre-OPCs are cultured for at least 144 hours in stage 2 (version 2) culture media. In other embodiments, pre-OPCs are cultured for at least 132, 136, 140, 144, 150, 154 or 158 hours in stage 2 (version 2) culture media. It further has been discovered that further culture of the cells in the optimized stage 3 media for as little 72 hours (3 days) was sufficient for OPC differentiation. Accordingly, in one embodiment, cells are cultured for at least 72 hours in stage 3 (version 2) culture media. In other embodiments, the cells are cultured for at least 60, 64, 68, 72, 76, 80, 84, 88, 92 or 96 hours in stage 3 (version 2) culture media.

As described in Example 10, it has been discovered that culture of OPCs in the optimized stage 4 culture media for as little as 6 days (144 hours) was sufficient for cell differentiation to preOLs. Accordingly, in one embodiment, OPCs are cultured for at least 144 hours in stage 4 culture media. In other embodiments, OPCs are cultured for at least 132, 136, 140, 144, 150, 154 or 158 hours in stage 4 culture media.

IV. Uses

The methods and compositions of the disclosure for generating pre-OPCs, OPCs and preOLs allow for efficient and robust availability of these cell populations for a variety of uses. For example, the methods and compositions can be used in the study of oligodendrocyte development and biology to assist in the understanding of oligodendrocyte-related diseases and disorders. For example, the pre-OPCs, OPCs and/or preOLs generated using the methods of the disclosure can be further purified according to methods established in the art using agents that bind to surface markers expressed on the cells. Accordingly, in one embodiment, the disclosure provides a method of isolating pre-oligodendrocyte progenitor cells (pre-OPCs), oligodendrocyte progenitor cells (OPCs) or pre-myelinating oligodendrocytes (preOLs), the method comprising: contacting OLIG2-expressing pre-OPCs or OPCs, or CD9+ preOLs, generated by a method of the disclosure with at least one binding agent that binds to a cell surface marker expressed by the pre-OPCs, OPCs or preOLs; and isolating cells that bind to the binding agent to thereby isolate the pre-OPCs, OPCs or preOLs.

In one embodiment, the binding agent is an antibody, e.g., a monoclonal antibody (mAb) that binds to the cell surface marker. Non-limiting examples of suitable OPC cell surface markers include PDGFRa, O4 and A2B5. Cells that bind the antibody can be isolated by methods known in the art, including but not limited to fluorescent activated cell-sorting (FACS) and magnetic activated cell sorting (MACS).

Progenitors of the oligodendrocyte lineage also are contemplated for use in the treatment of various oligodendrocyte-related diseases and disorders, through delivery of the cells to a subject having the disease or disorder. Examples of oligodendrocyte-related diseases and disorders include, but are not limited to, multiple sclerosis (MS), progressive multifocal leukoencephalopathy, periventricular leukomalacia, certain leukodystrophies and amyotrophic lateral sclerosis (ALS).

V. Compositions

In other aspects, the disclosure provides compositions related to the methods of generating pre-OPCs and OPCs, including culture media and cell cultures, as well as isolated progenitor cells and cell populations.

In one aspect, the disclosure provides a culture media for obtaining oligodendrocyte progenitor cells (OPCs) comprising an FGFR pathway agonist, an mTOR pathway antagonist, an SHH pathway agonist, an AKT pathway antagonist and an AKT pathway agonist (corresponding to the version 1 stage 2 media). In another aspect, the disclosure provides a culture media for obtaining oligodendrocyte progenitor cells (OPCs) comprising an FGFR pathway agonist, an activin receptor (AR) pathway agonist, a PDGFR pathway agonist, an AKT pathway antagonist, a retinoic acid (RA) pathway agonist, an AMPK pathway agonist and an mTOR pathway agonist (corresponding to the version 1 stage 3 media).

In another aspect, the disclosure provides a culture media for obtaining oligodendrocyte progenitor cells (OPCs) comprising an FGFR pathway agonist, an mTOR pathway antagonist, an SHH pathway agonist and a WNT pathway agonist (corresponding to the version 2 stage 2 media). In another aspect, the disclosure provides a culture media for obtaining oligodendrocyte progenitor cells (OPCs) comprising an FGFR pathway agonist, an IGF-1 pathway agonist and a retinoic acid (RA) pathway agonist (corresponding to the version 2 stage 3 media).

In another aspect, the disclosure provides a culture media for obtaining pre-myelinating oligodendrocytes (preOLs) comprising an IGF1R pathway agonist, a TrkC pathway agonist, a PDGFR pathway agonist, a thyroid hormone receptor agonist and an insulin receptor agonist.

In one aspect, the disclosure provides isolated cell cultures comprising OPCs cultured in one of the culture media disclosed herein. In one embodiment, the disclosure provides an isolated cell culture comprising OLIG2+ OPCs cultured in a culture media comprising an FGFR pathway agonist, an mTOR pathway antagonist, an SHH pathway agonist, an AKT pathway antagonist and an AKT pathway agonist (corresponding to the version 1 stage 2 media). In another embodiment, the disclosure provides an isolated cell culture comprising OLIG2+ OPCs cultured in a culture media comprising an FGFR pathway agonist, an activin receptor (AR) pathway agonist, a PDGFR pathway agonist, an AKT pathway antagonist, a retinoic acid (RA) pathway agonist, an AMPK pathway agonist and an mTOR pathway agonist (corresponding to the version 1 stage 3 media).

In another embodiment, the disclosure provides an isolated cell culture comprising OLIG2+ OPCs cultured in a culture media comprising an FGFR pathway agonist, an mTOR pathway antagonist, an SHH pathway agonist and a WNT pathway agonist (corresponding to the version 2 stage 2 media). In another embodiment, the disclosure provides an isolated cell culture comprising OLIG2+ OPCs cultured in a culture media comprising an FGFR pathway agonist, an IGF-1 pathway agonist and a retinoic acid (RA) pathway agonist (corresponding to the version 2 stage 3 media).

In another embodiment, the disclosure provides an isolated cell culture comprising CD9+ preOLs cultured in a culture media comprising an IGF1R pathway agonist, a TrkC pathway agonist, a PDGFR pathway agonist, a thyroid hormone receptor agonist and an insulin receptor agonist.

The present invention is further illustrated by the following examples, which should not be construed as further limiting. The contents of figures and all references, patents and published patent applications cited throughout this application are expressly incorporated herein by reference.

EXAMPLES

Example 1: Culture Protocol Development for Generation of Stem Cell-Derived Oligodendrocyte Progenitors In this example, a culture media recipe for generation of oligodendrocyte progenitors was developed that can guide human pluripotent stem cells to differentiate to oligodendrocyte progenitors expressing NKX2-2 and OLIG2 after 3 days in culture. These cells can be further differentiated to mature oligodendrocytes.

This example utilizes a method of High-Dimensional Design of Experiments (HD-DoE), as previously described in Bukys et al. (2020) *Iscience* 23:101346. The method employs computerized design geometries to simultaneously test multiple process inputs and offers mathematical modeling of a deep effector/response space. The method allows for finding combinatorial signaling inputs that control a complex process, such as during cell differentiation. It allows testing of multiple plausible critical process parameters, as such parameters impact output responses, such as gene expression. Because gene expression provides hallmark features of the phenotype of, for example, a human cell, the method can be applied to identify, and understand, which signaling pathways control cell fate. In the current example, the HD-DOE method was applied with the intent to find conditions for induction of oligodendrocyte progenitor-expressed genes, directly from the pluripotent stem cell state.

Specifically, to develop a novel method to generate oligodendrocytes, the impact of agonists and antagonists of multiple signaling pathways (herein called effectors) were tested on expression of two sets of 53 pre-selected genes after a 3-day treatment. These effectors are small molecules that are commonly used during stepwise differentiation of stem cells to specific fates. Choice of the effectors were based on current literature on neural induction in anterior ectoderm and differentiation of stem cells to oligodendrocytes.

HD-DoE #1

To test the effectors, experiments with at least 8 factors were designed that can assess the response of cells to 48 or more different combinations of effectors in a range of concentrations. To analyze the models, we focused on expression of genes expressed during early development of anterior neuroectoderm and oligodendrocytes including NKX2-2, OLIG2, OLIG1, and PDGFRA. The impact of each effector on gene expression level is defined by a parameter called factor contribution that is calculated for each effector during the modeling.

As shown in the results summarized in FIG. 1, one model specifically showed promising results on upregulation of NKX2-2 and OLIG2 genes when optimized for maximum expression of NKX2-2 at 12480.6. This model tested 8 factors: PD0325901, MK2206, TTNPB, SC79, MHY1485, ZM336372, AGN193109 and AZD3147.

Out of the eight factors tested, three of them, namely TTNPB (agonist of retinoic acid pathway), SC79 (agonist of Akt signaling pathway) and MHY1485 (agonist of mTOR signaling pathway), had significant positive effect on expression of targeted genes, with TTNPB having the most impact with factor contribution of 31.3 and MHY1485 with factor contribution of 13.8 and SC79 at 1.47. These factors could bring up expression of NKX2-2 and OLIG2 significantly. OLIG1 and PDGFRA had average expression levels (129.9 and 346.45 respectively) which is compatible with the pattern of gene expression during oligodendrocyte differentiation.

As shown in the results summarized in FIG. 2, normalized expression of PDGFRA in this model could reach up to 832.9 which was the highest expression level out of all models and therefore, the model was also optimized for maximum expression of PDGFRA. This setting showed that TTNPB (agonist of retinoic acid pathway) and MHY1485 (agonist of mTOR signaling pathway) also have a positive effect on upregulation of PGFRA with factor contribution of 49.01 and 13.4, respectively. It was also observed that PD0325901 can have a significant positive effect on this gene with factor contribution of 30.6. Because of low factor contribution of ZM336372 (<1), this factor was not included in the recipe. In this condition, OLIG1 had average expression level at 228.36 similar to conditions of optimization of NKX2-2. One difference in this condition was downregulation of OLIG2 gene from 1049.4 at previous condition to 241.9.

As shown in the results summarized in FIG. 3, out of effectors with positive contribution to expression levels of NKX2-2, OLIG2 or PDGFRA, two factors were negatively impacting NKX2-2 and OLIG2 expression levels. Thus, these two factors, PD0325901 and ZM336372, were eliminated from list of candidates for the recipe of oligodendrocyte differentiation.

Thus, this first HD-DoE screening identified a culture media lacking exogenously-added growth factors and comprising an agonist of retinoic acid pathway, an agonist of Akt signaling pathway and an agonist of mTOR signaling pathway as sufficient to lead to the generation of OLIG2-expressing OPCs from pluripotent stem cells after 3 days (72 hours) of culture.

HD-DoE #2

To further enhance the conditions for oligodendrocyte differentiation from pluripotency, we performed an additional HD-DoE experiment. We obtained additional gene regulatory models that were used for preparation of a differentiation protocol. The basis of this was a 13-factor HD-DoE experiment with focus on initiation of differentiation of cells toward anterior neuroectoderm. In this model, we focused on expression of FEZF2 and OTX2.

As shown in the results summarized in FIG. 4, the model was optimized for highest expression of OTX2 at 12755.9. According to the model of high expression of OTX2, seven effectors had positive contribution including MK2206, PD0325901, CHIR99021, LDN193189, Go6983, PD173074 and BLU9931 with highest factor contribution of 22.2 for MK2206 and lowest factor contribution of 1.7 for PD173074 and BLU9931.

As shown in the results summarized in FIG. 5, the model was optimized for highest expression of FEZF2 at 4466. When the model was optimized for maximum expression level of FEZF2, three effectors including LDN193189 with factor contribution of 19.5, PD0325901 with factor contribution of 14.6 and MK2206 with factor contribution of 12.3 were common with previous condition and three new effectors including purmorphamine-500 nM, XAV939 and SC79 were introduced.

Figure 6:
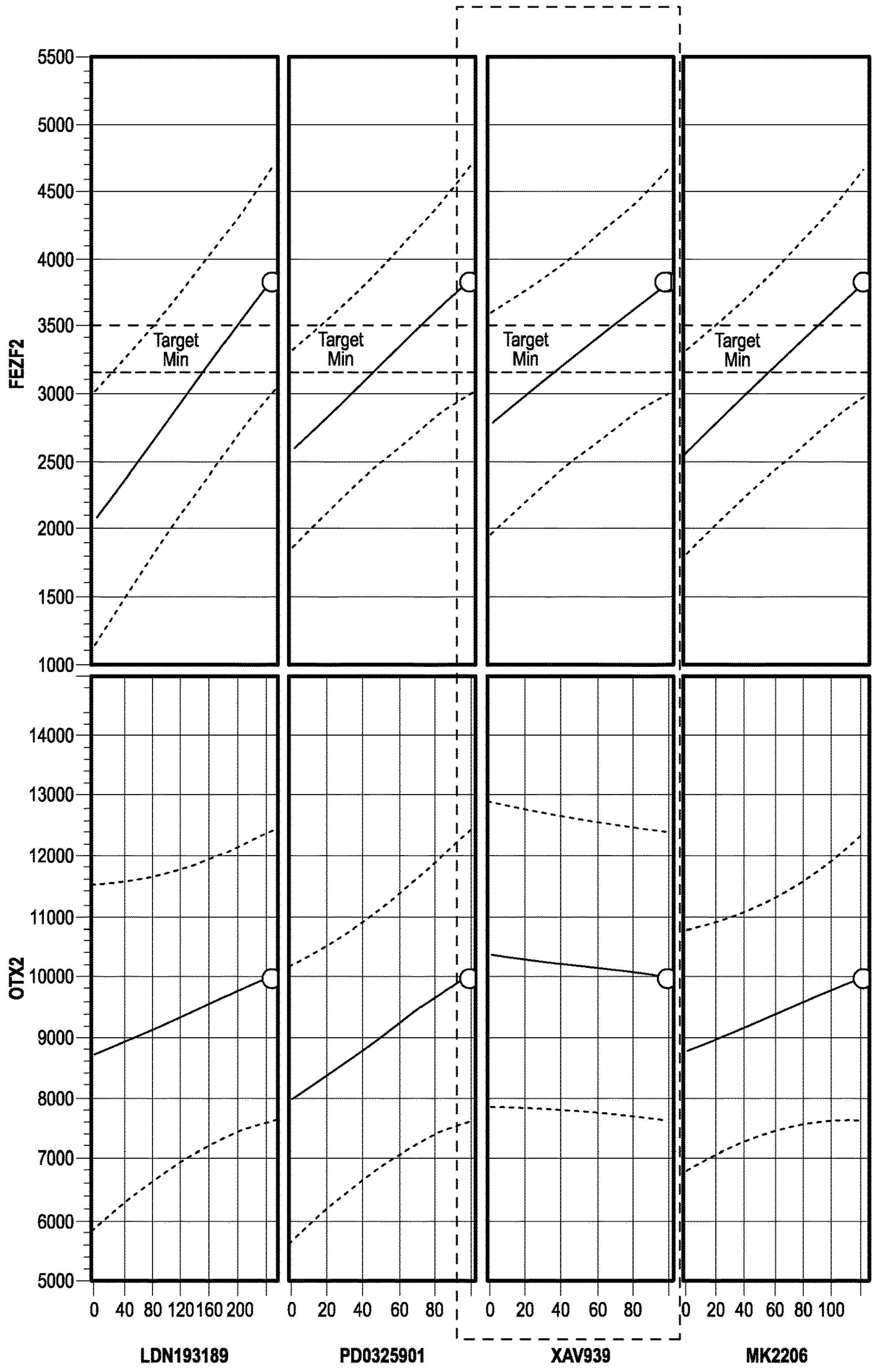
FIG. 6 shows the dynamic profile of expression level of OTX2 and FEZF2 relative to the concentration of 13 factors tested in this model. XAV939 and Purmorphamine-500 nM have a significant positive impact on the expression of FEZF2 and no significant negative impact on the expression of OTX2.
Figure 6:
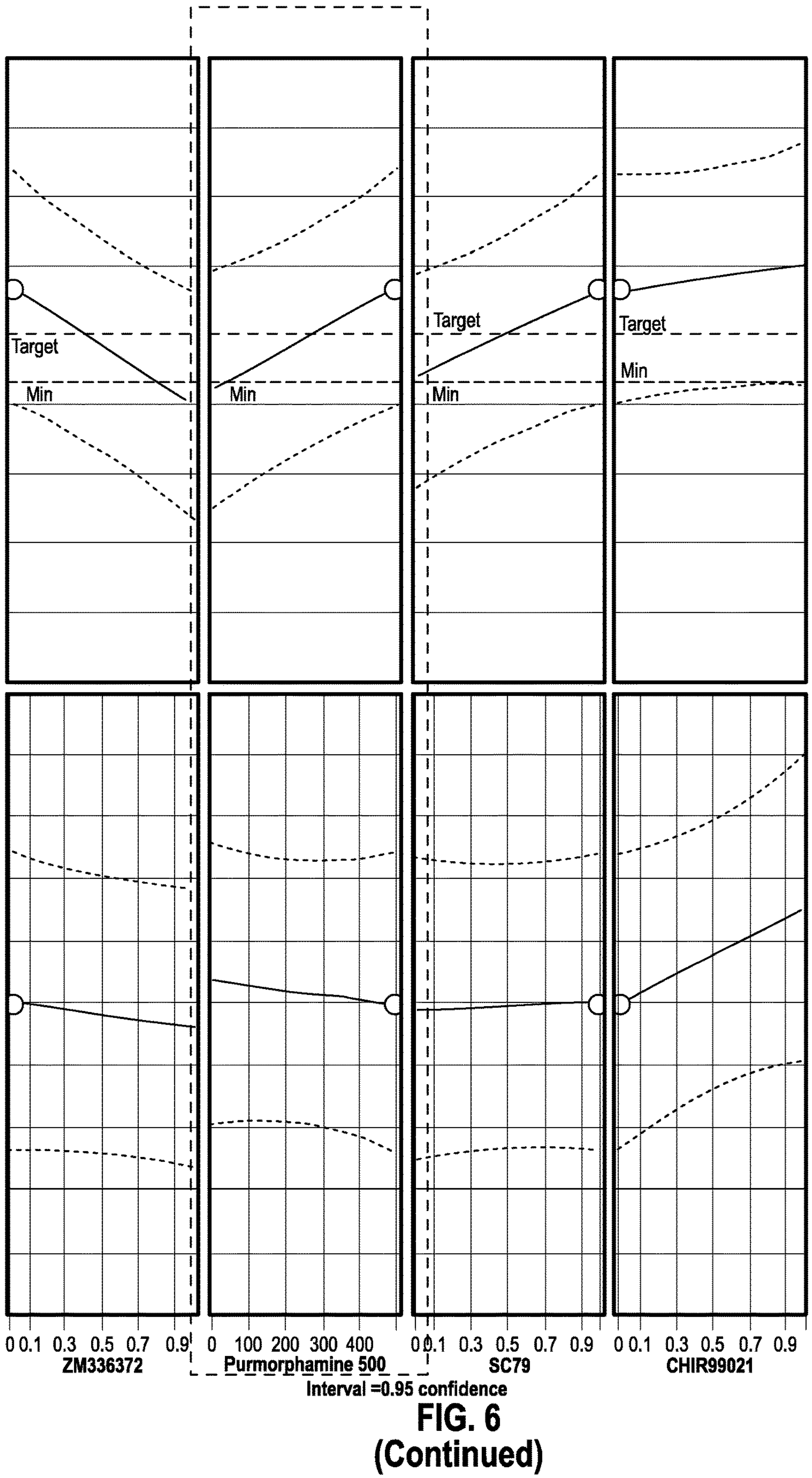
Figure 6:
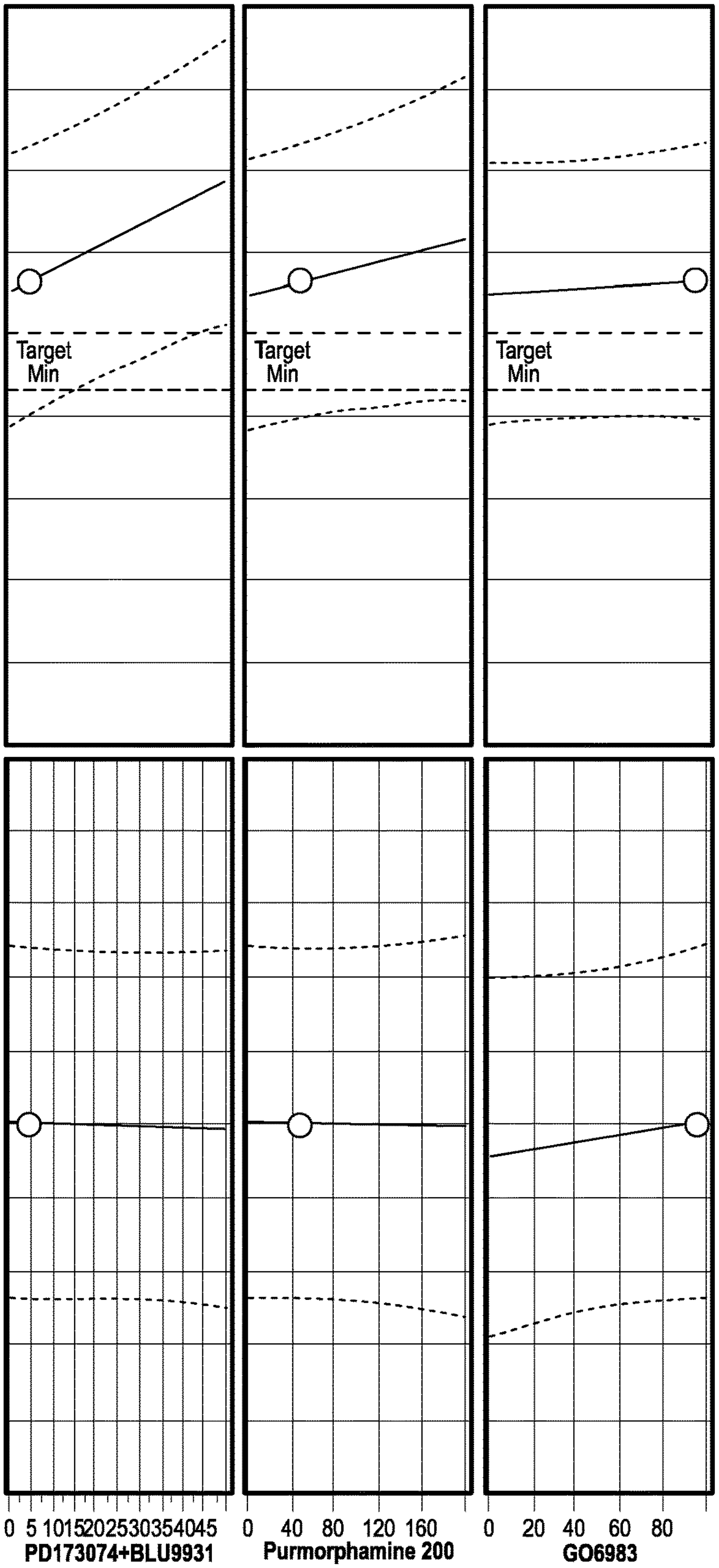
Figure 6:
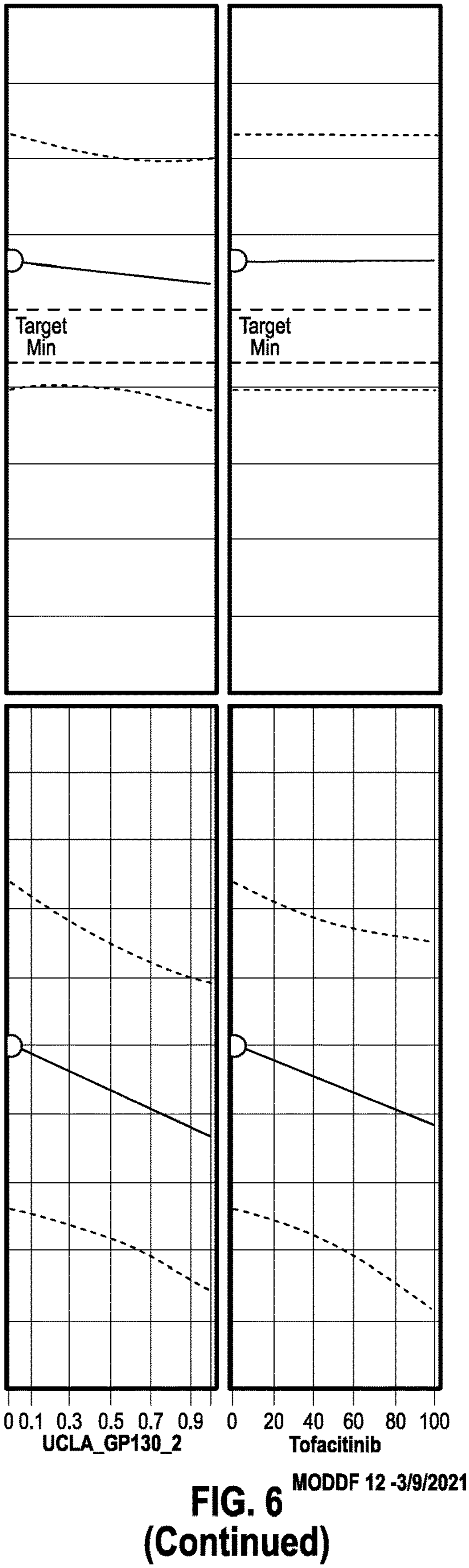

As shown in the results summarized in FIG. 6, to fine-tune the recipe and find the optimum combination of factors for high expression of both OTX2 and FEZF2, dynamic profiling analysis was done. According to this analysis, XAV939 (inhibitor of WNT signaling pathway) and Purmorphamine (agonist of SHH signaling pathway and known for ventralizing the cells during development of regions of the brain) had significant positive effects on expression of FEZF2 and no negative impact on expression level of OTX2. Therefore, these two factors were added to the optimized culture recipe.

In addition to inclusion of factors that promoted expression of OPC-associated surface markers, certain factors that inhibited expression of such markers were eliminated from the optimized culture recipe. CHIR99021, which is the agonist of WNT signaling pathway, was eliminated. MK2206 and PD0325901 were also eliminated, since according to the 8-factor model, they had negative effect on expression of oligodendrocyte genes. PD173074 and BLU9931 were also eliminated because of low factor contribution of 1.7.

Summary

Considering both models, culture conditions that maximized differentiation of human induced pluripotent stem cells to cells having oligodendrocyte progenitor cell (OPC) identity, leading to elevated expression of OTX2, FEZF2, NKX2-2 and OLIG2, included the following effector inputs: TTNPB (RA pathway agonist), SC79 (Akt pathway agonist), MHY1485 (mTOR pathway agonist), Purmorphamine (SHH pathway agonist), XAV939 (WNT pathway antagonist), LDN193189 (BMP pathway antagonist) and Go6983 (PKC pathway antagonist).

Example 2: Factor Criticality Analysis of OPC-Inducing Culture Conditions

To assess the factor criticality of each component in the optimized culture media described in Example 1, we performed in-silico prediction analysis of the outcome under conditions in which individual effectors was eliminated, while keeping others present. To do this, we used dynamic profile analysis at setpoint, while comparing the expression level of genes of interest in absence of each factor. Since expression of genes of interest reveal whether the desired outcome is reachable, this factor criticality analysis revealed the extent of importance of each input effector.

Figure 7A:
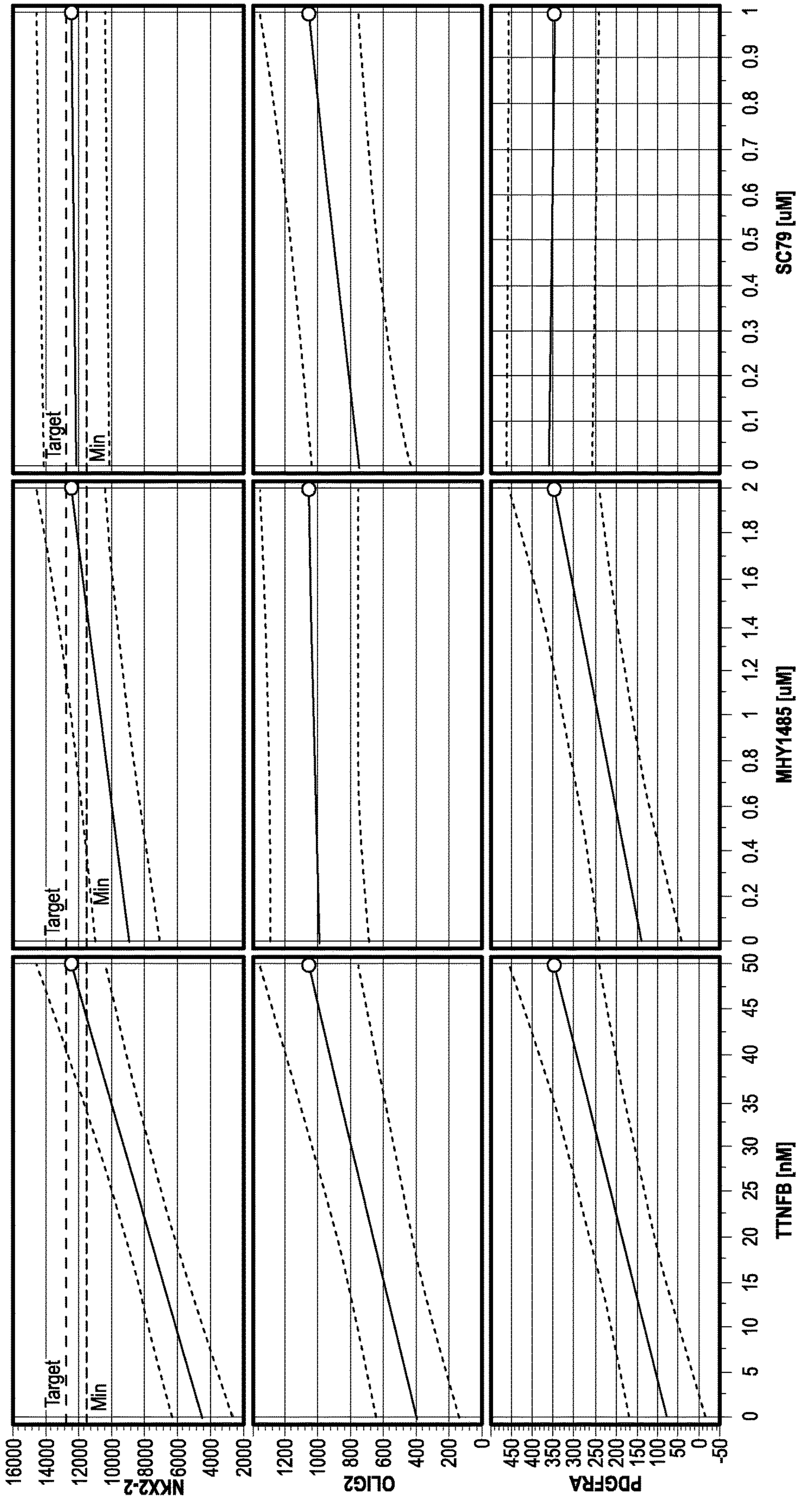
FIG. 7A-7D shows the dynamic profile analysis of the elimination process in an 8-factor modeling experiment and its effect on expression of NKX2-2, OLIG2 and PDGFRA.
Figure 7B:
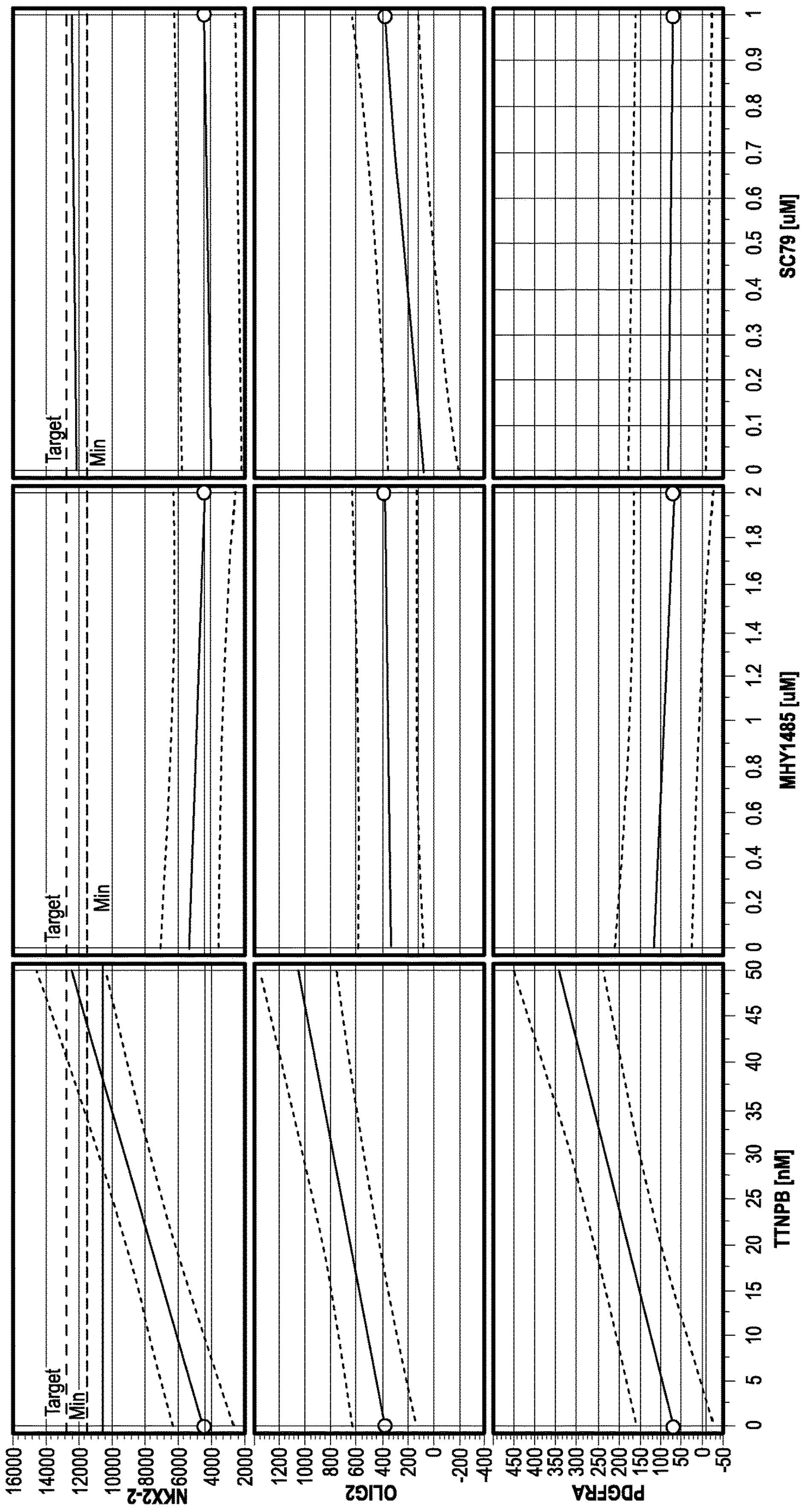
Figure 7C:
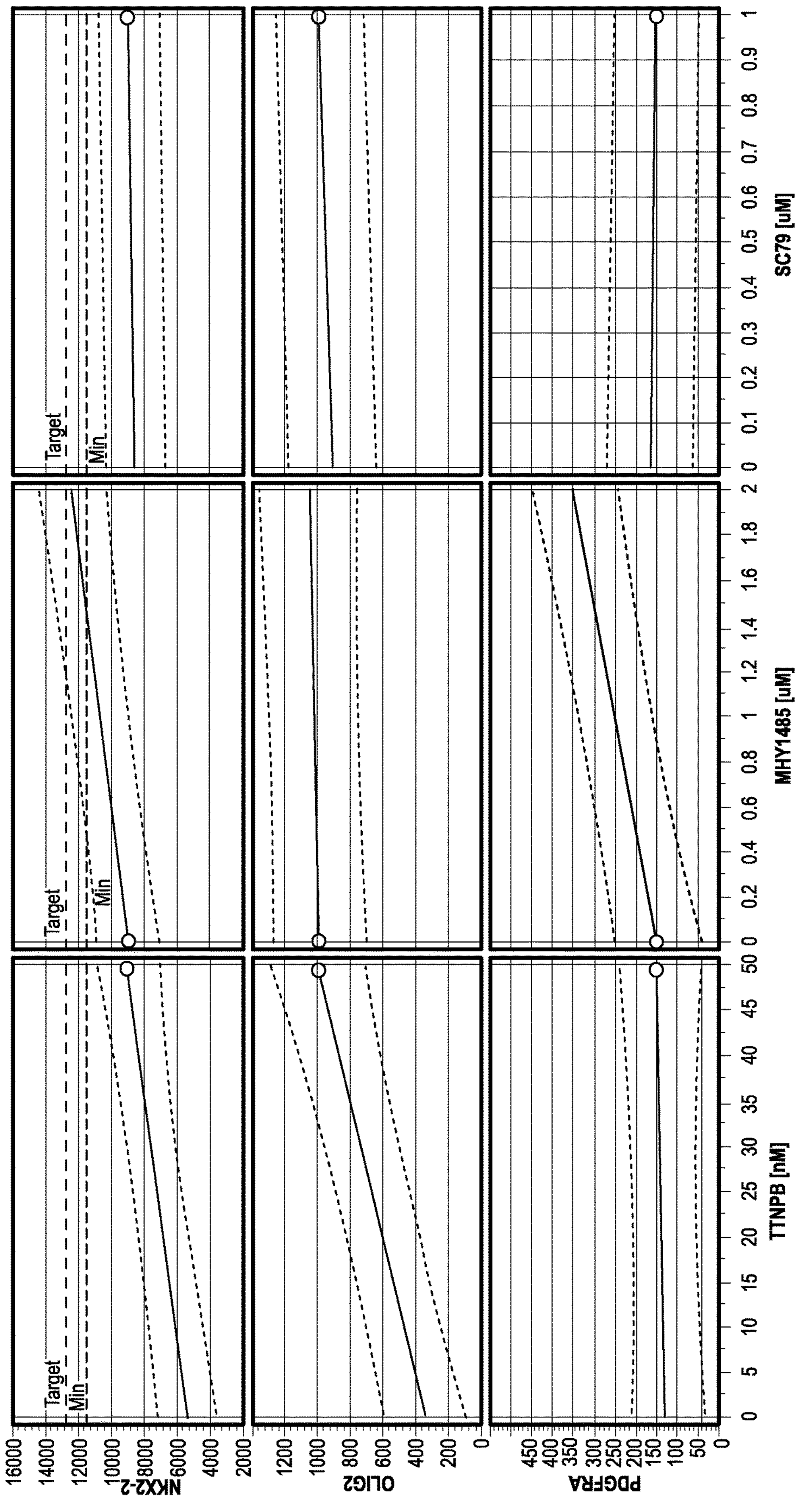
Figure 7D:
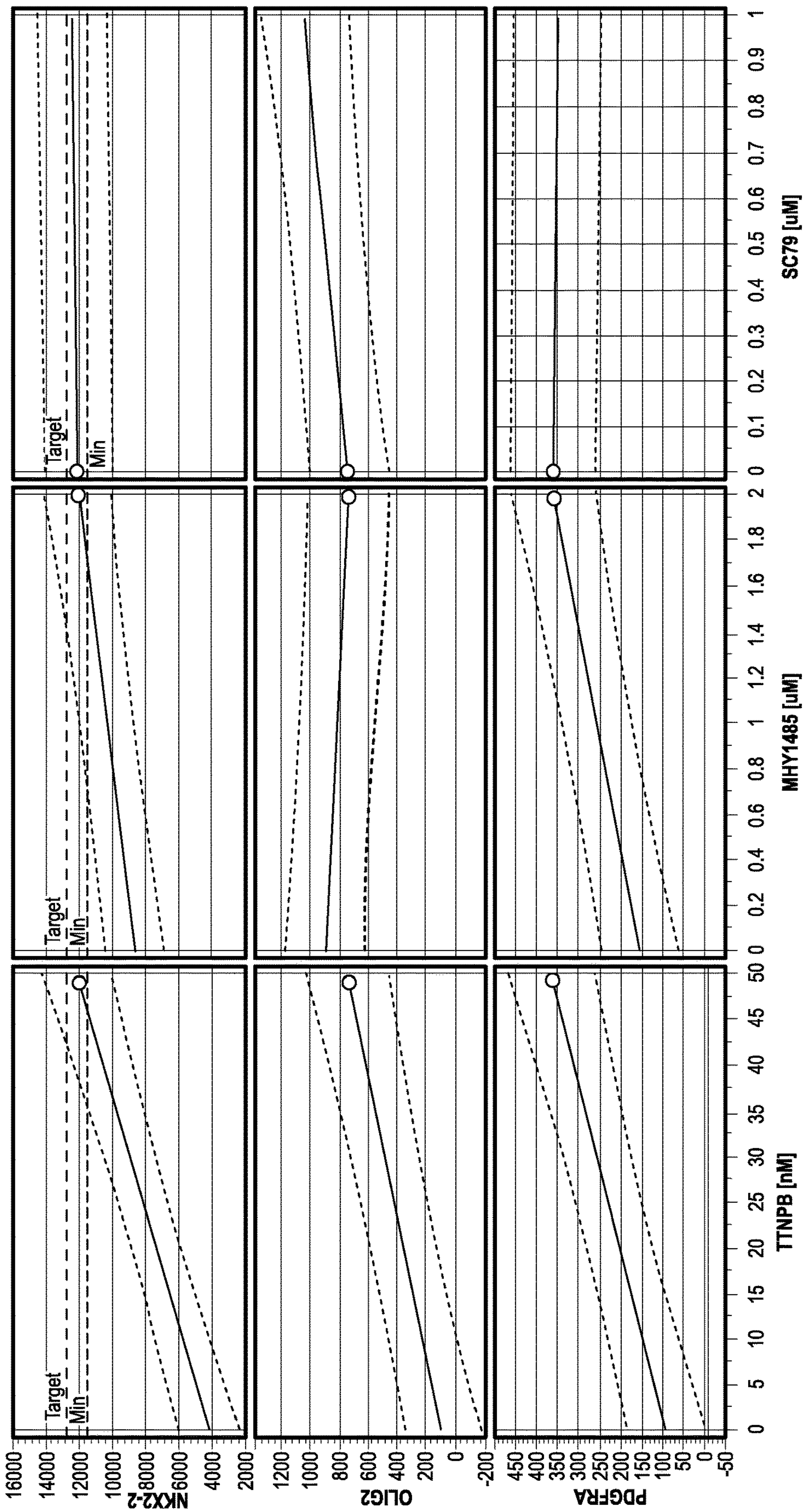
Figure 8A:
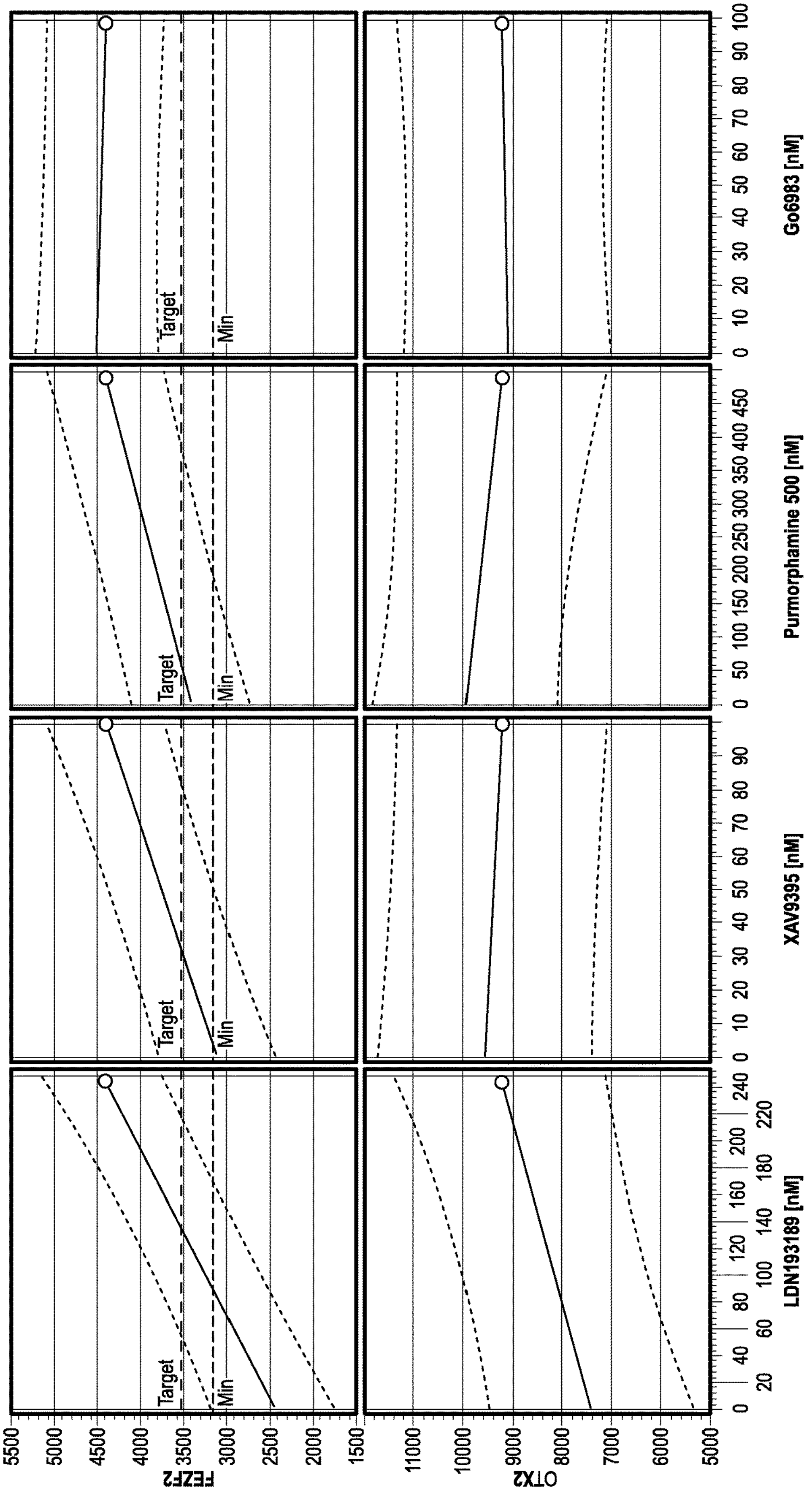
FIG. 8A-8D shows the dynamic profile analysis of the elimination process in a 13-factor modeling experiment and its effect on expression of FEZF2 and OTX2.
Figure 8B:
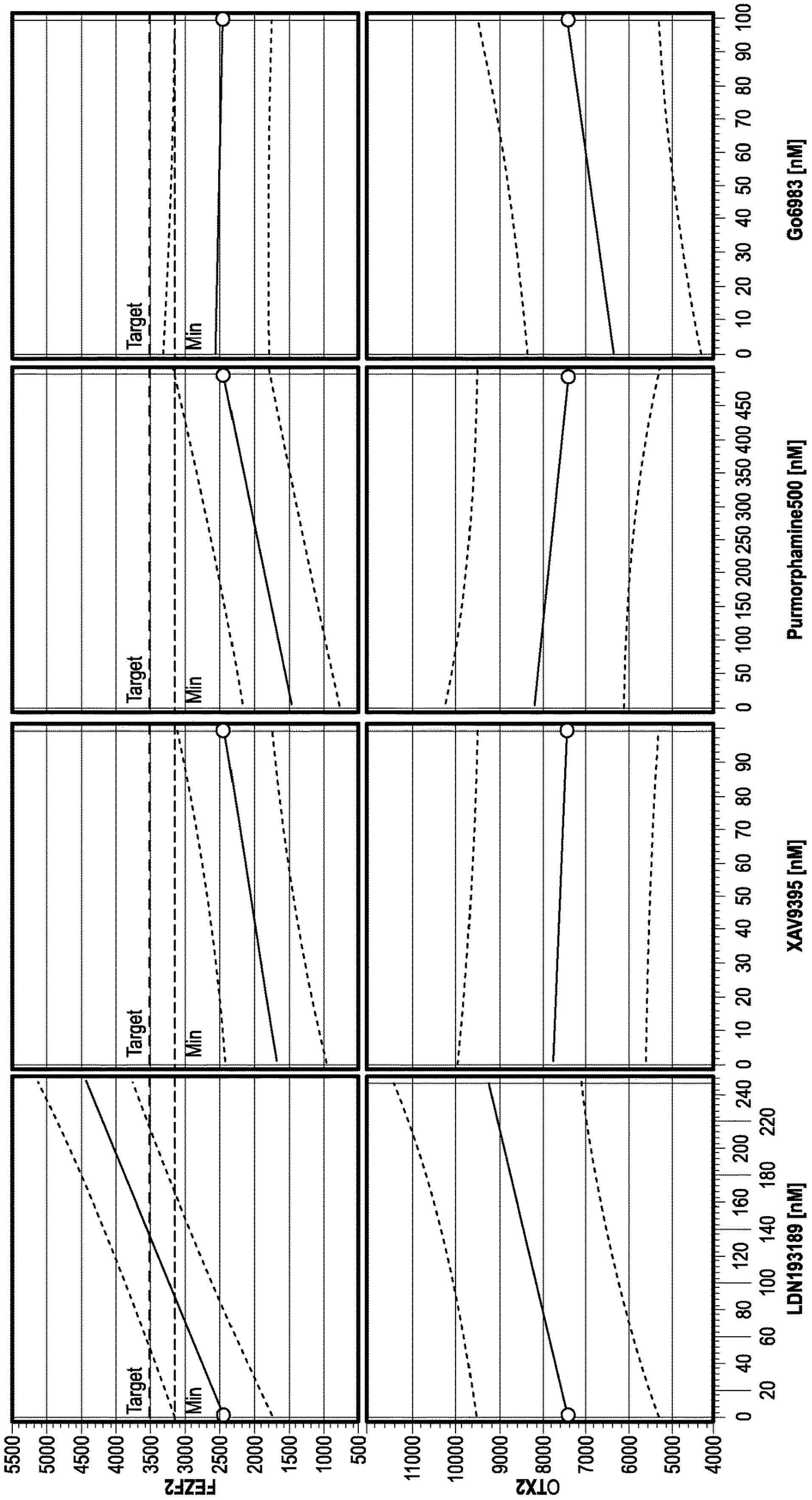
Figure 8C:
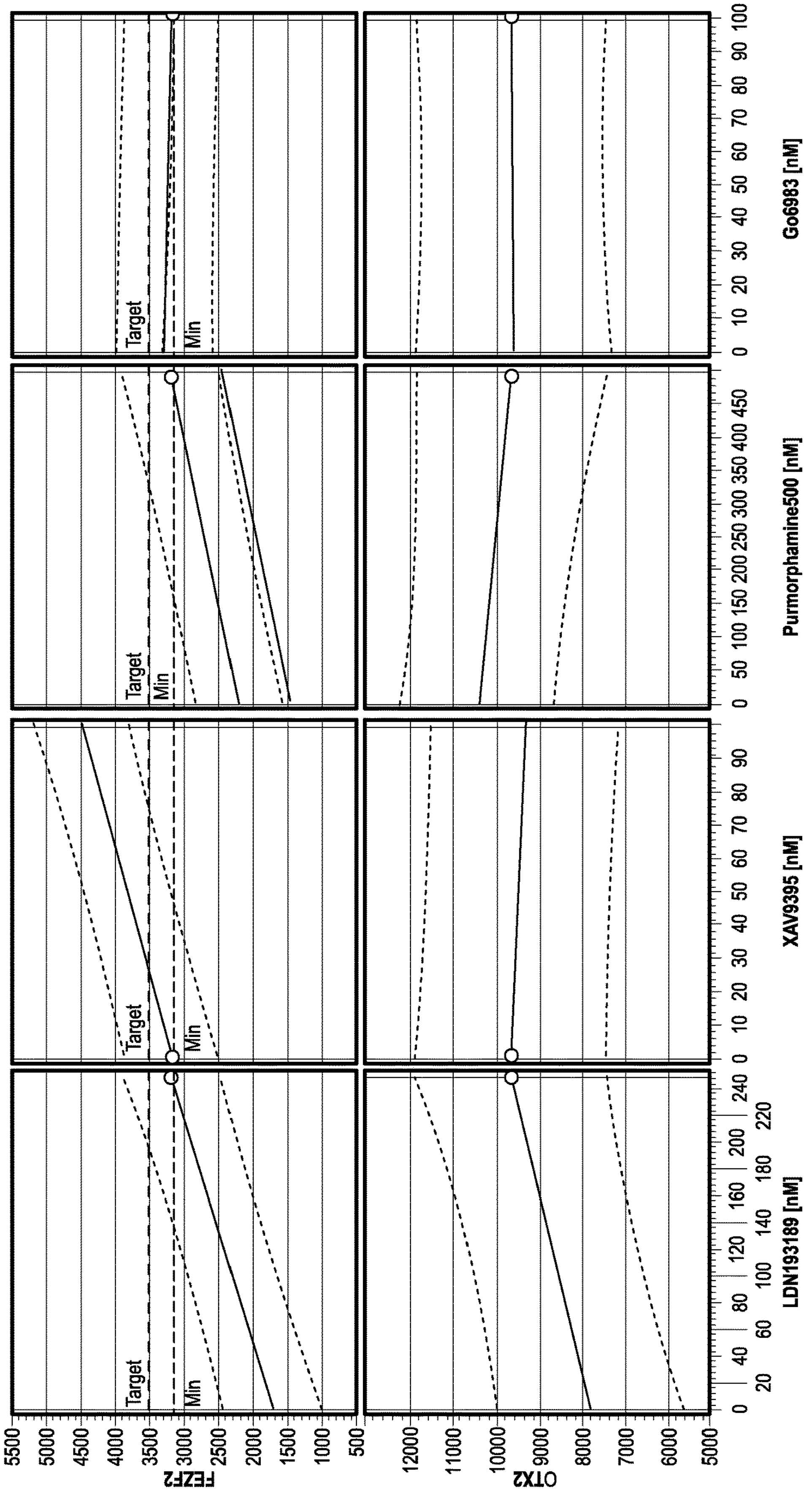
Figure 8D:
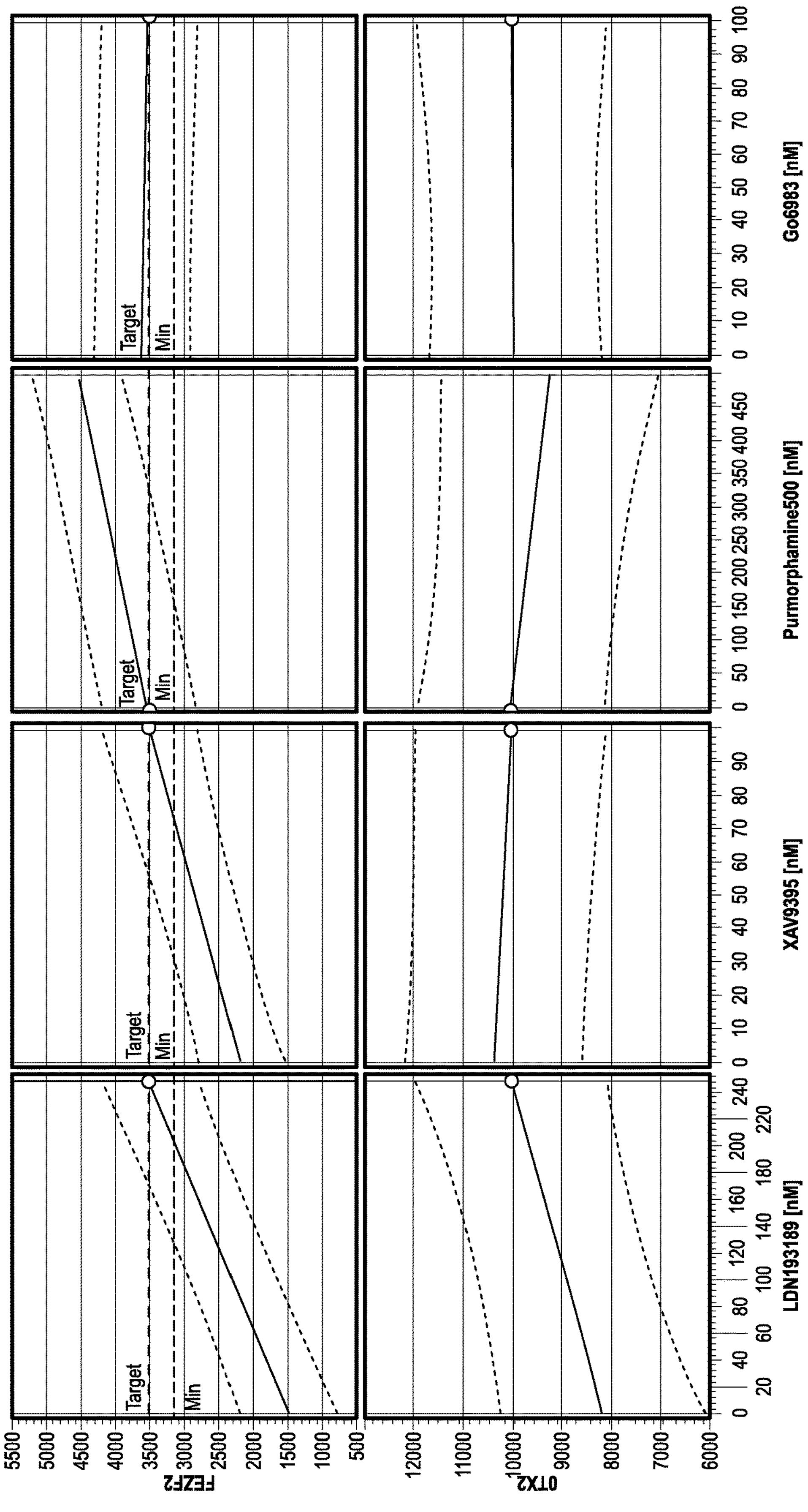

FIG. 7A-7D summarize the results for the factor criticality analysis of the effectors TTNPB (RA pathway agonist), SC79 (Akt pathway agonist) and MHY1485 (mTOR pathway agonist). FIG. 7A shows the expression level of the OPC genes of interest in presence of TTNPB, MHY1485 and SC79 when the model is otherwise optimized for maximum expression of NKX2-2. As shown in FIG. 7B, upon removal of TTNPB, the predicted expression levels of NKX2-2, OLIG2 and PDGFRA dropped significantly from more than 12000 to 4500 for NKX2-2, 1000 to 400 for OLIG2 and 350 to less than 100 for PDGFRA. This outcome signifies a significant deleterious effect on expression of all the desired markers when the RA pathway agonist is removed. As shown in FIG. 7C, when MHY1485 was removed, again expression levels decreased, however, not as drastically as previous condition. As shown in FIG. 7D, when SC79 was removed, only a small shift in the plots was observed, which suggests this factor is less critical than TTNPB and MHY1485 for attaining maximal OPC marker induction.

FIG. 8A-8D summarize the results for the factor criticality analysis of the effectors Purmorphamine (SHH pathway agonist), XAV939 (WNT pathway antagonist), LDN193189 (BMP pathway antagonist) and Go6983 (PKC pathway antagonist). To attain the desired patterning of the oligodendrocyte population to anterior region of the brain, these additional factor inputs were queried, such as FEZF2 and OTX2. Expression levels of FEZF2 and OTX2 were examined in absence of either LDN193189, XAV, Purmorphamine or Go6983, when the model was optimized for maximum expression of FEZF2. The most significant change was observed in absence of LDN193189 which led to almost 50% reduction in expression of FEZF2 (from 4500 to 2500). Expression of OTX2 was also reduced from 9000 to 7000, which was the lowest in all four elimination processes. When XAV939 and Purmorphamine were removed, expression level of FEZF2 decreased to 3000 and 3500 respectively, while expression of OTX2 was only slightly higher in both cases. When Go6983 was removed, we did not observe any significant changes in the expression level of genes of interest, therefore suggesting G06983 being optional related to control of FEZF2 and OTX2.

Example 3: Immunocytochemistry Validation of Stem Cell-Derived OPCs

Figure 9:
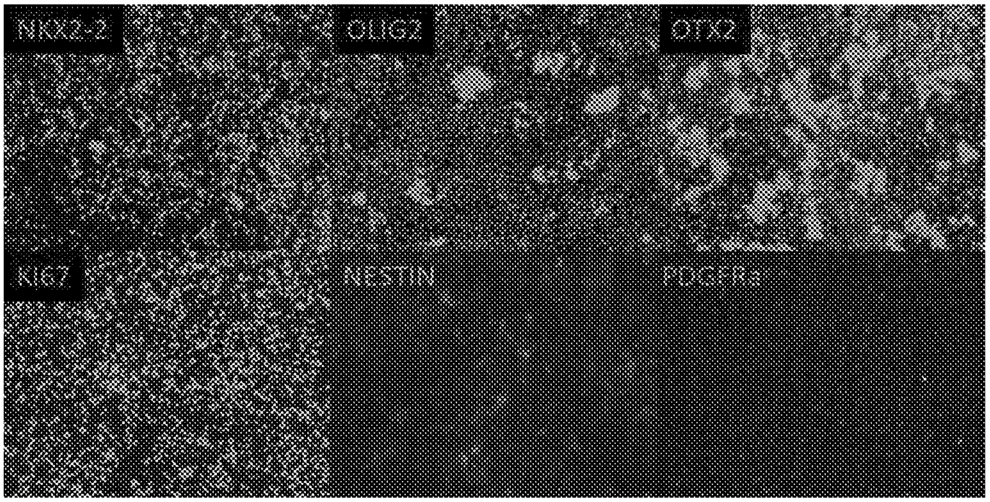
FIG. 9 shows photographs of images of cells cultured in the optimized OPC differentiation media after three days. Cells were stained with oligodendrocyte and neural biomarkers. Cells express anterior neuroectoderm biomarkers including OTX2 and NKX2-2 along with OPC specific biomarker OLIG2. NESTIN and PDGFRa, which are neuronal and late OPC biomarkers respectively, are not present. Expression of KI67 shows the proliferative state of precursor cells.

To further validate the optimized culture media described in Example 1, cells were cultured in the optimized media for 3 days and immunocytochemistry was used to assess expression of biomarkers of anterior neuroectoderm and oligodendrocyte progenitors. Biomarkers included OTX2 and oligodendrocyte precursor biomarkers including NKX2-2, OLIG2 and PDGF. Nestin, an early neuronal marker was used to distinguish between neural stem cells and oligodendrocyte progenitors. Ki67 was also used to confirm the proliferation of cells after induction. Representative immunohistochemistry results are shown in FIG. 9. These immunocytochemistry images confirmed that most of the cells expressed OTX2. However, there was no trace of the neuronal biomarker Nestin detected, confirming that the differentiated OPC population lacks neural stem cells. Expression of OLIG2 and NKX2-2 was also observed in more than 90% of the cells, thereby confirming the oligodendrocyte lineage of the cells. None of the cells expressed PDGFR which was expected since this gene is expressed at later stages of differentiation of oligodendrocytes.

Example 4: RNA-sea Validation of Stem Cell-Derived Pre-OPC

Figure 10A:
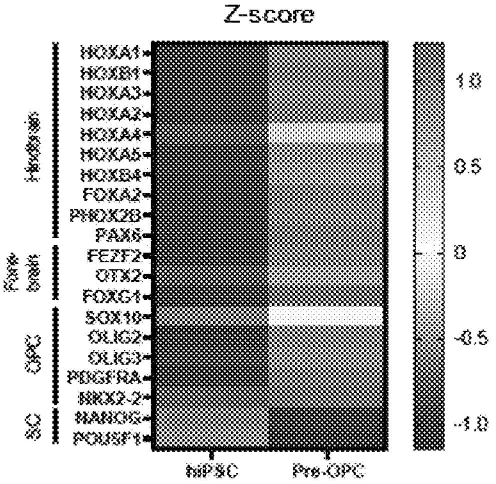
FIG. 10A-10B shows RNA-seq data of cells cultured in optimized OPC differentiation media after three days. Expression level of stem cell genes NANOG and POU5F1 were decreased while genes involved in early development of brain regions and oligodendrocyte lineage were elevated.
Figure 10B:
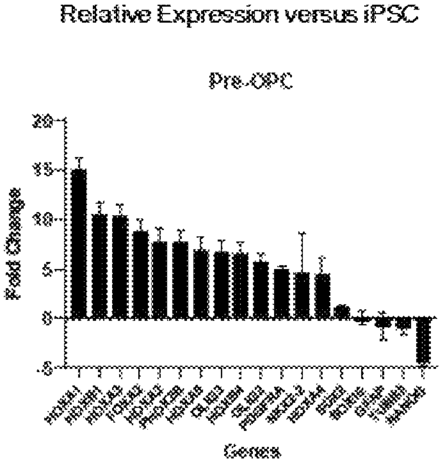

RNA sequencing was used to obtain a gene profile of cells cultured in the differentiation media detailed in Examples 1 and 2. hiPSCs were cultured for 3 days in the media and RNA from the generated cells was sequenced by standard RNA-seq analysis. The results in FIG. 10A show normalized expression levels of selected genes representative of various regions of the brain, early oligodendrocyte identity (NKX2-2, OLIG2, PDGFRa) and stem cell state (NANOG, POU5F1) in three replicates at day 0 and day 3. The results demonstrated that the level of stem cell genes decreased in pre-OPC cells while the level of oligodendrocyte genes increased, which validated the differentiation of hiPSCs to oligodendrocyte lineage using the differentiation media. The results of FIG. 10B show differential expression and fold change of the selected genes, with HOXA1 at highest level (15) and OLIG2, NKX2-2 and PDGFRa at 5. This data demonstrates the ability of developed recipe as a stage 1 media in directing the cells toward oligodendrocyte identity.

Example 5: Culture Protocol Development for Generation of Stem Cell-Derived Oligodendrocyte Progenitors Expressing SOX10, OLIG2 and NKX2-2

In the example, a stepwise differentiation protocol for the generation of oligodendrocyte progenitors was developed that can guide human pluripotent stem cells to progenitors expressing SOX10, NKX2-2 and OLIG2 after 12 days in culture. Differentiated cells also express other oligodendrocyte progenitor markers, including PDGFRa and NG2. After treating the cells with stage 1 pre-OPC media for 3 days as described in Example 1, cells are cultured for three days in stage 2 media, followed by six days in stage 3 media. These cells can be further differentiated to mature oligodendrocytes. The full three stage protocol is illustrated schematically in FIG. 42.

To develop the oligodendrocyte differentiation recipes, the impact of various agonist and antagonists (effectors) on differentiation of pre-OPCs was investigated using an HD-DoE method. These effectors were chosen based on available literature on developmental biology and differentiation of stem cells, as well as mouse and human single cell RNA-seq data from oligodendrocytes at the time.

These experiments led to generation of the stage 2 recipe, shown below in Table 1, and the stage 3 recipe, shown below in Table 2.

TABLE 1

Validated factors in stage 2 recipe

| Effectors | Role | concentration |
|---|---|---|
| FGF2 | FGF pathway activator | 10 ng/ml |
| Purmorphamine | SHH agonist | 500 nM |
| MK2206 | AKT antagonist | 125 nM |
| SC79 | AKT agonist | 2 uM |
| AZD3147 | mTOR antagonist | 15 nM |

TABLE 2

Validated factors in stage 3 recipe

| Effectors | Role | concentration |
|---|---|---|
| FGF2 | FGF pathway activator | 10 ng/ml |
| Activin A | TGF-b superfamily activator | 10 ng/ml |
| PDGF-AA | PDGFR pathway | 10 ng/ml |
| MK2206 | AKT inhibitor | 125 nM |
| TTNPB | RA agonist | 50 nM |
| AICAR | AMPK agonist | 200 uM |
| MHY1485 | mTOR agonist | 2 uM |

To engineer the recipe of stage 2 of differentiation, cells were first cultured in the stage 1 media described in Example 1 and then treated with combinations of 8 or 12 factors for 3 days and the gene expression of cells in each condition was modeled. At this point, due to short duration of culture (only six days in vitro), we decided to focus on maximal expression of OLIG2 and maintenance of high expression of NKX2-2, while initiating expression of SOX10, OLIG1 and PDGFRa, to guide the cells towards oligodendrocyte fate (Emery and Lu (2015). *Cold Spring Harb Perspect Biol.* 7:a020461; Perlman et al. (2020). *Glia* 68:1291-1303; Goldman and. Kuypers (2015) *Development* 142:3983-95).

In one 12-factor model, the individual and combinatorial impact of SUN 11602 an agonist for FGF signaling pathway, FGF2, Activin A an activator of one of the receptors of TGF-b superfamily, A 8301, an inhibitor of TGF-b pathway, CHIR99021 a WNT activator, AGN193109 a RA antagonist, MK2206 an AKT inhibitor, Purmorphamine an agonist of SHH signaling pathway, AZD3147 an antagonist of mTOR pathway, MHY1485 an agonist of mTOR pathway, SC79 an agonist of AKT pathway and G06983 an inhibitor of PKC pathway, were tested. This model demonstrated the potential to regulate pre-OPCs to highly express OLIG2, NKX2-2 and PDGFRa. When optimized for maximum expression of OLIG2 at 1841.6, multiple factors showed positive regulatory effect including FGF-2, with highest the factor contribution of 12.9, MK2206 and AZD3147, with factor contributions of 5.3 and 5.2, respectively, SC79, with a factor contribution of 3.6, and SUN 11602 and Activin A, both with factor contributions smaller than 3 (FIG. 11). AGN193109, MHY1485 and GO6983 had the highest negative impact on expression of OLIG2, with factor contributions of 23.2, 22.5 and 10.2, respectively. Within the specifications of attaining 80% maximal expression of OLIG2, this complex media composition had a Cpk value (process capability index) of 0.43, with a corresponding to a 9.6% risk of failure.

Figure 12:
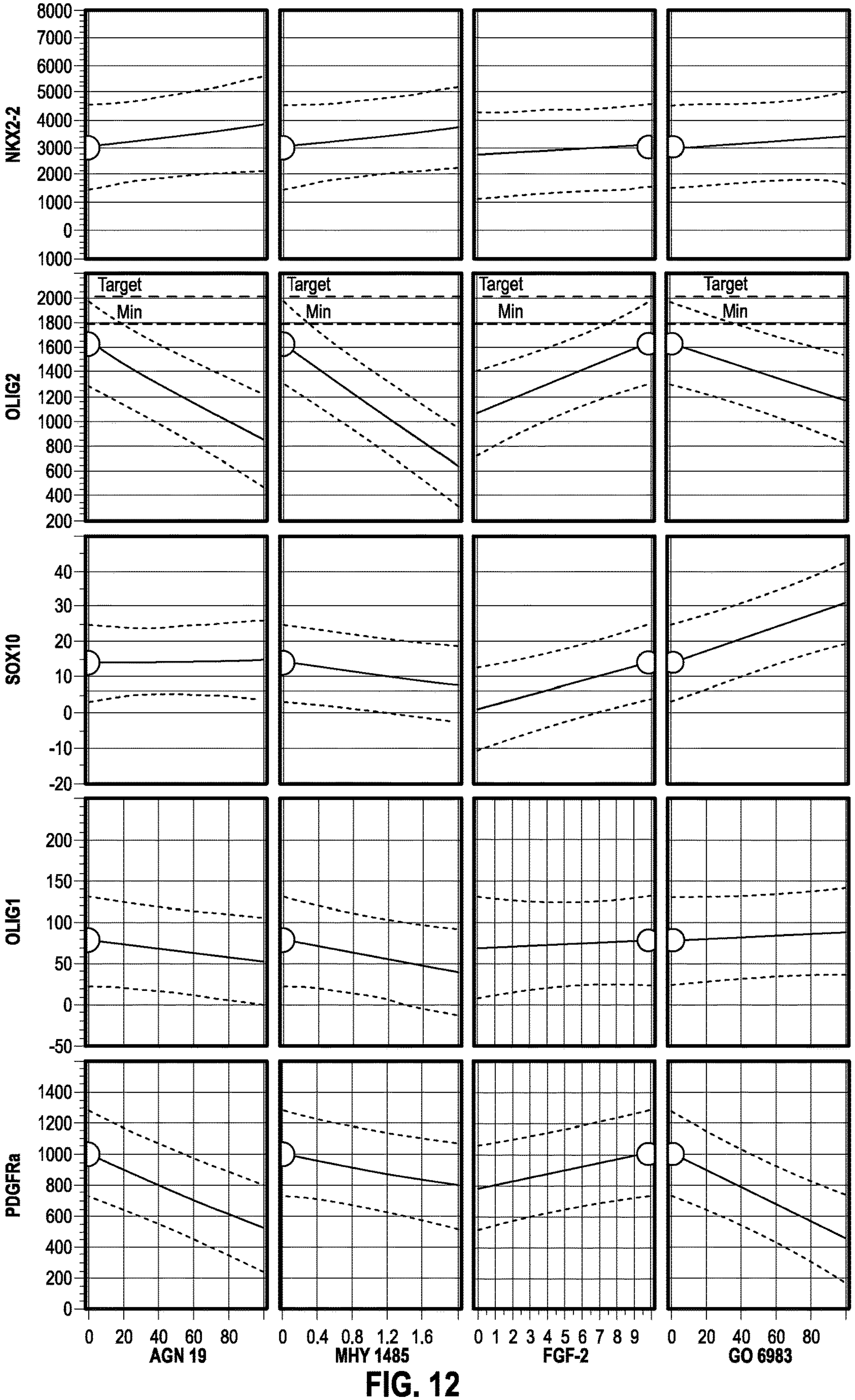
FIG. 12 shows the dynamic profile analysis of expression levels of NKX2-2, OLIG2, SOX10, OLIG1 and PDGFRa relative to concentration of 12 effectors. The positive impact of FGF-2 and MK2206 on expression of OLIG2 and their factor contributions are shown by the slope of the plots for each effector.
Figure 12:
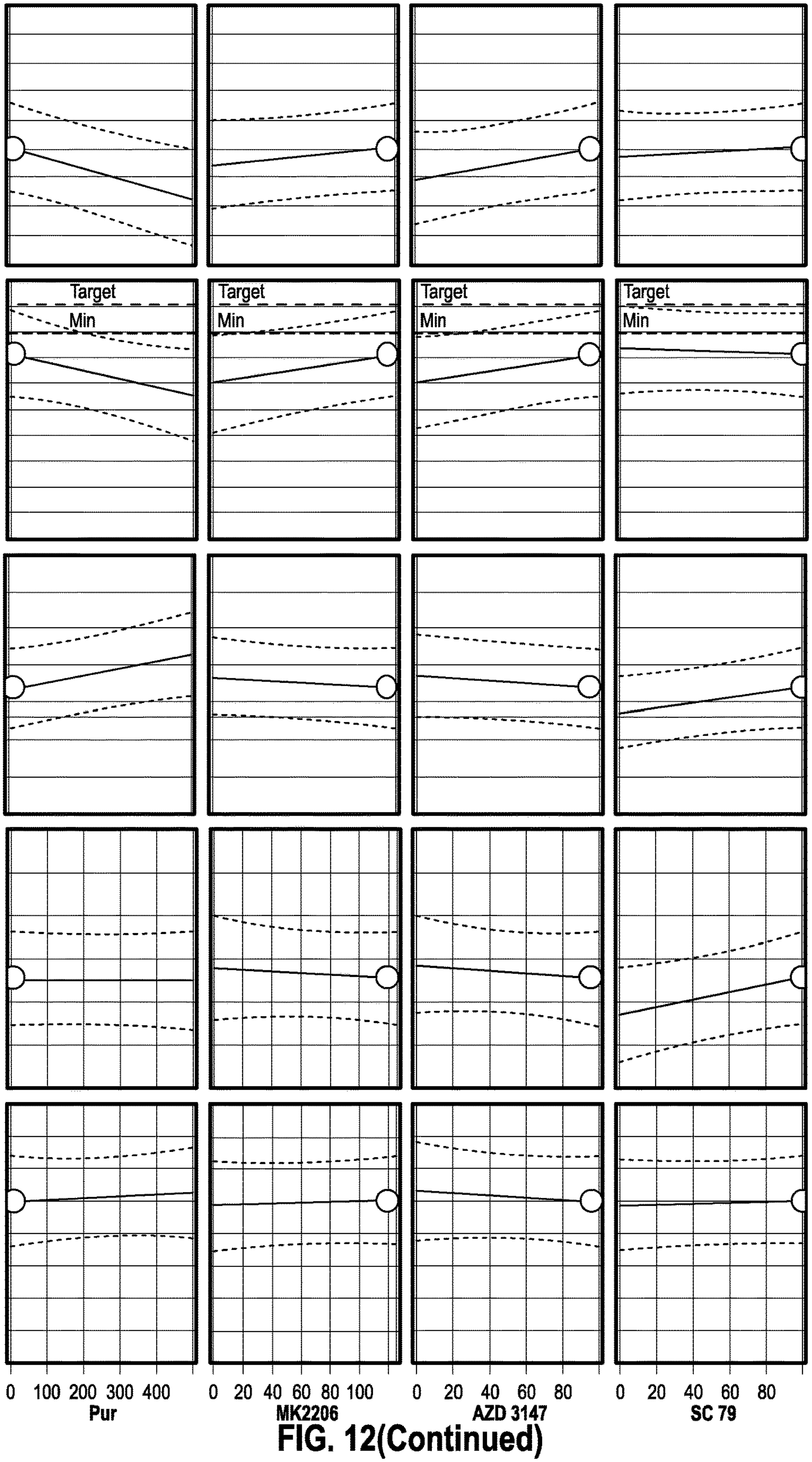
Figure 12:
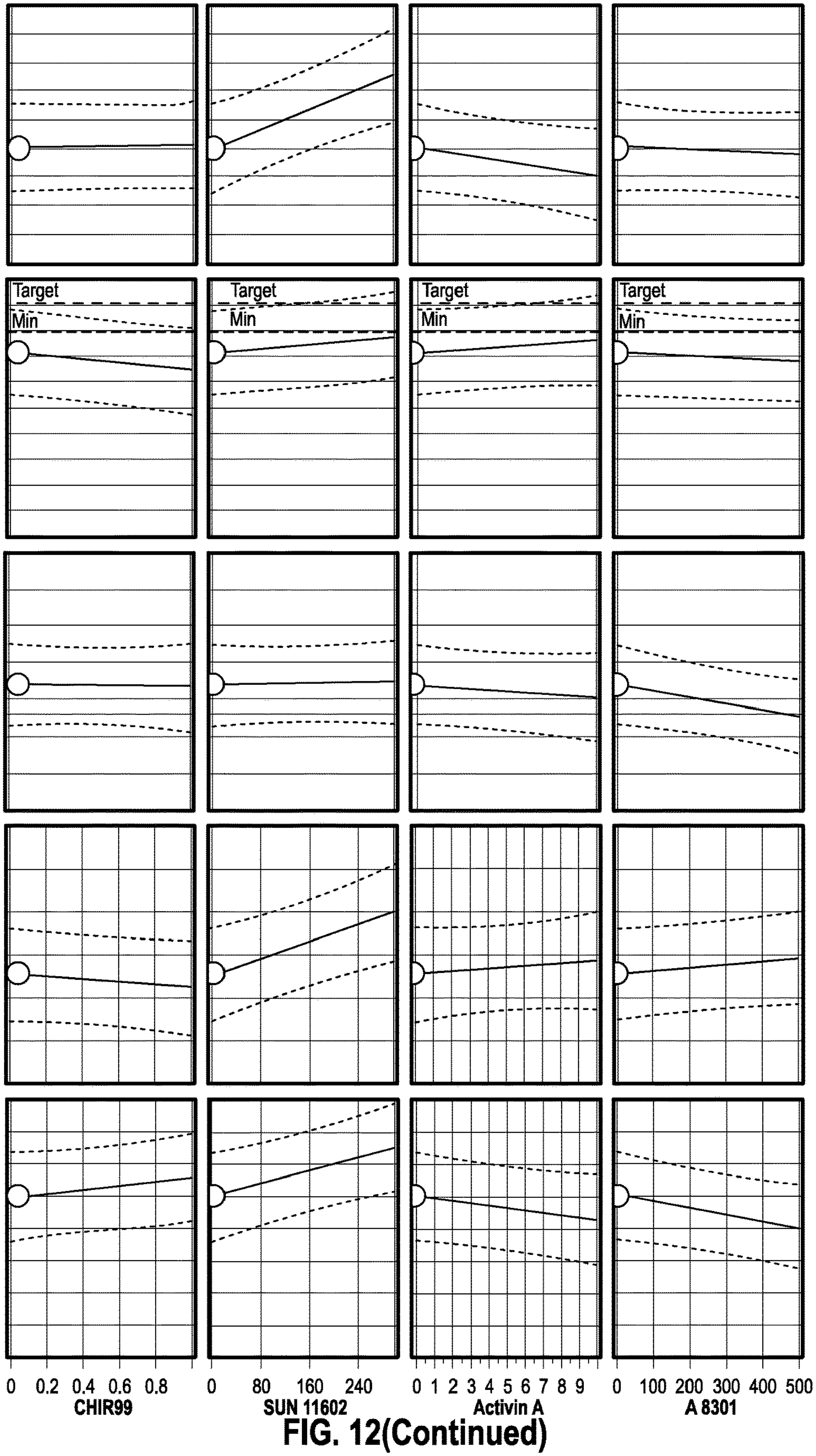

Dynamic profile analysis was used to assess the expression levels of other genes of interests, such as NKX2-2, OLIG1 and SOX10, while the model is maximized for OLIG2. Activin A and SUN 11602 were brought down to zero due to their very low factor contribution. We observed when the model is optimized, the expression level of NKX2-2 is at 3000, PDGFRa at 1000, OLIG1 at 80 and SOX10 at 15 (FIG. 12). According to the analysis, the four compounds showing positive impact on OLIG2 with factor contribution larger than 3, including FGF2, MK2206, SC79, AZD3147, are either positive for the other genes or don't have any significant effect on their expression level. Therefore, we did not exclude any of these four factors from the candidate recipe. We also observed that even though Purmorphamine and GO6983 have a negative effect on OLIG2 (factor contribution of 7.2 and 10.22), they positively regulate the expression of SOX10. Therefore, the impact of these two compounds was investigated on the other selected genes, and it was concluded that because GO6983 has a significant negative impact on PDGFRA, it should not be included in the recipe.

To gain more information about the effect of Purmorphamine on differentiation of pre-OPCs to a more committed cell population, we tested this factor in two other models. In a 12-factor model, we included Purmorphamine, FGF2, AGN193109 and CHIR99021 along with 8 new inputs including TTNPB, Biotin, Insulin, propionate, DBZ, Yhhu3792, LDN193189 and Y-27632. When optimized for OLIG2 at 3299.4, Purmorphamine showed a strong positive impact with factor contribution of 13 (FIG. 13). Within the specifications of attaining 80% maximal expression of OLIG2, this complex media composition had a Cpk value (process capability index) of 0.68, with a corresponding to a 0.1% risk of failure. In another 12-factor model, Purmorphamine was tested along with A 8301, CHIR99021, Dexamethasone, T3+T4, PD0325901, ZM336372, DBZ, BMP7, PD173074, SANT-1 and PDGF-AA. When optimized for OLIG2 at 644.6, Purmorphamine had the highest positive impact on its expression, with a factor contribution of 16.9 (FIG. 14). Within the specifications of attaining 80% maximal expression of OLIG2, this complex media composition had a Cpk value (process capability index) of 0.95, with a corresponding to a 0.22% risk of failure.

Figure 15:
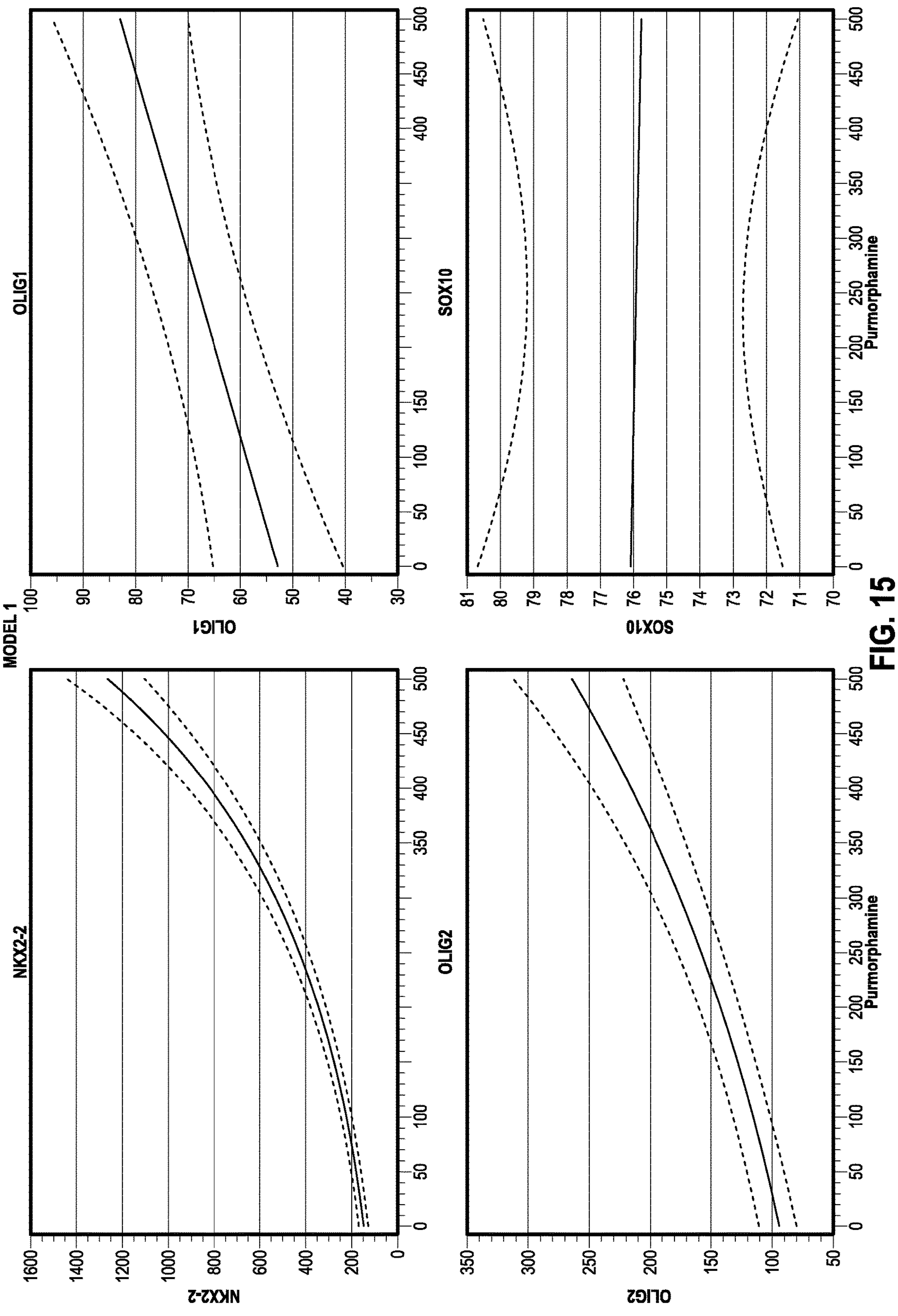
FIG. 15 are factor effect plots showing expression level of NKX2-2, OLIG2, OLIG1 and SOX10 relative to concentration of Purmorphamine in two separate 12-factor models.
Figure 15:
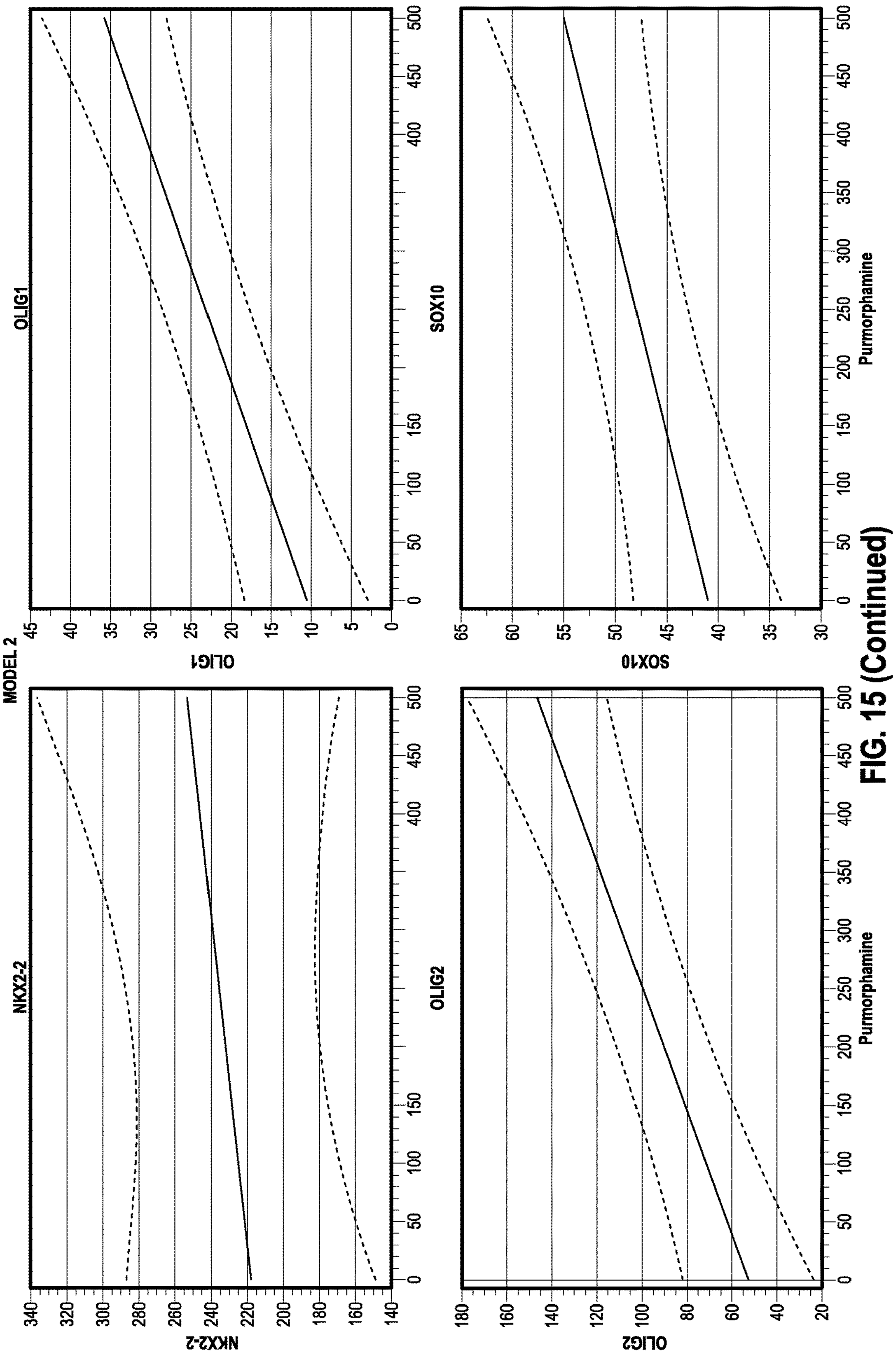

We also investigated the individual effect of the factor on the rest of the selected genes in both models and observed a positive trend for SOX10, OLIG1 and NKX2-2 (FIG. 15).

Therefore, considering these models, a candidate recipe for stage 2 consisting of FGF2, Purmorphamine, MK2206, SC79 and AZD3147 was made. This recipe is able to maximize differentiation of cells to robust and elevated expression of OLIG2, NKX2-2 and initial expression of SOX10 and PDGFRa. This recipe was further validated by immunocytochemistry assay (see Example 7).

To further differentiate the cells to an oligodendrocyte progenitor identity, additional HD-DoE experiments were performed on the cells that were cultured in stage 1 and stage 2 differentiation media. After 3 days, gene expression of cells in different combinatorial conditions were investigated. At this time, we focused on maximal expression of signature oligodendrocyte progenitor genes such as SOX10, OLIG1 and PDGFRa (Goldman and Kuypers (2015) *Development* 142:3983-95; Marques et al. (2016) *Science* 352:1326-1329). In one 8-factor model, individual and combinatorial effects of LDN193189, SUN 11602, Activin A, Biotin, TTNPB, Isoproterenol, linoleic acid and T3+T4 were tested. When the model was optimized for maximum expression of OLIG1 at 256, Activin A and TTNPB had the highest positive impact, with factor contributions of 50.2 and 19.11, respectively (FIG. 16). LDN193189 and SUN 11602, also positively regulated its expression with factor contribution of 10.8 and 3.7. Within the specifications of attaining 80% maximal expression of OLIG1, this complex media composition had a Cpk value (process capability index) of 0.46, with a corresponding to a 8.1% risk of failure.

The same model was also optimized for maximum expression of PDGFRa at 3510.9. Two factor specifically, TTNPB and Linoleic acid determined the expression level of PDGFRa with factor contribution of 71.6 and 22.1, respectively (FIG. 17). Within the specifications of attaining 80% maximal expression of PDGFRa, this complex media composition had a Cpk value (process capability index) of 0.54, with a corresponding to a 5.2% risk of failure. The model was also optimized for highest expression of SOX10 at 18.8. In this optimization, TTNPB was the only input that could elevate the expression level of the selected gene (FIG. 18).

Figure 19:
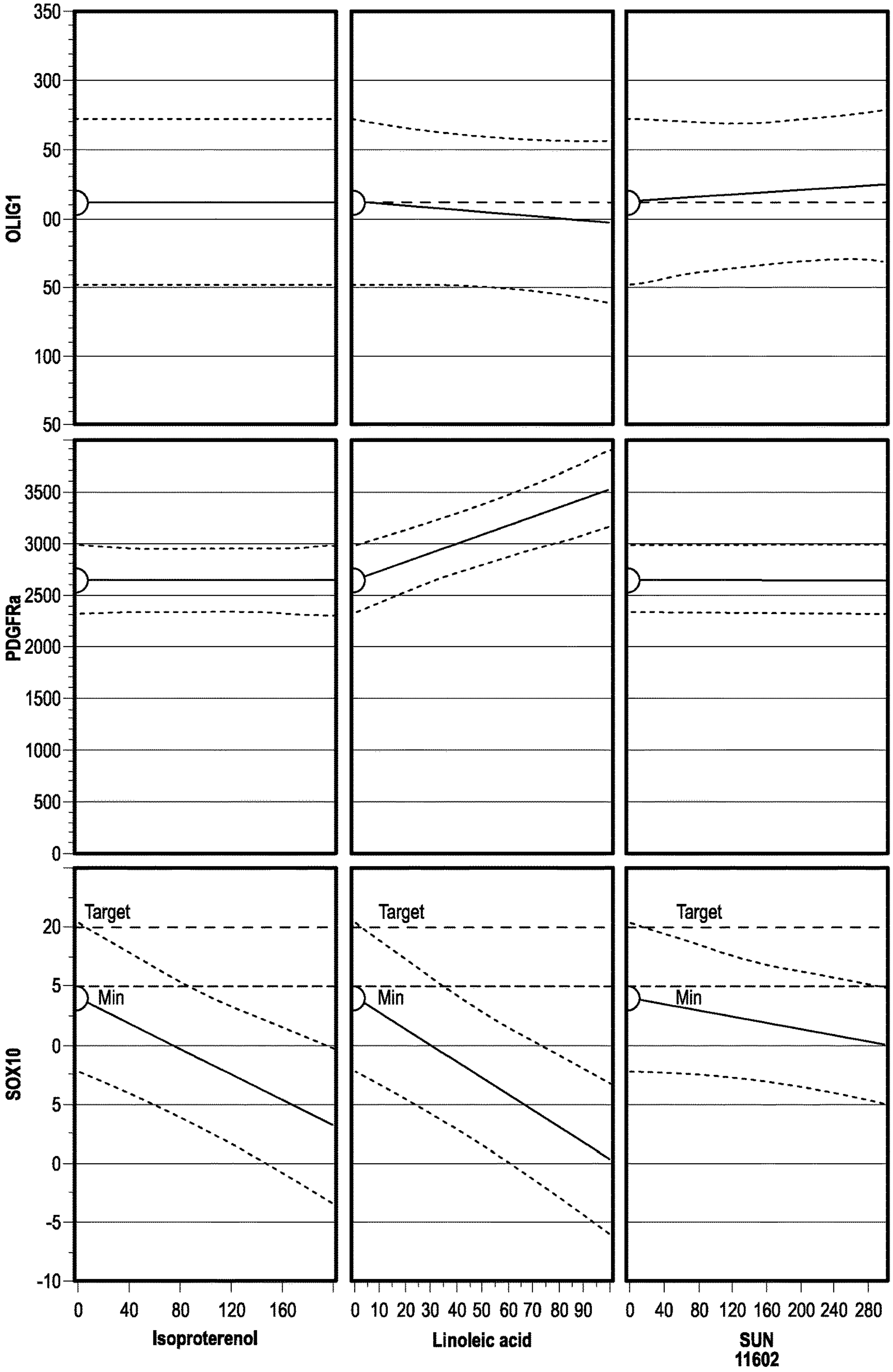
FIG. 19 shows the dynamic profile analysis of expression levels of OLIG1, PDGFRa and SOX10 relative to the concentration of 8 factors. The positive impact of TTNPB on expression of PDGFRa and OLIG1 and their factor contributions are shown by slope of the plots for each effector.
Figure 19:
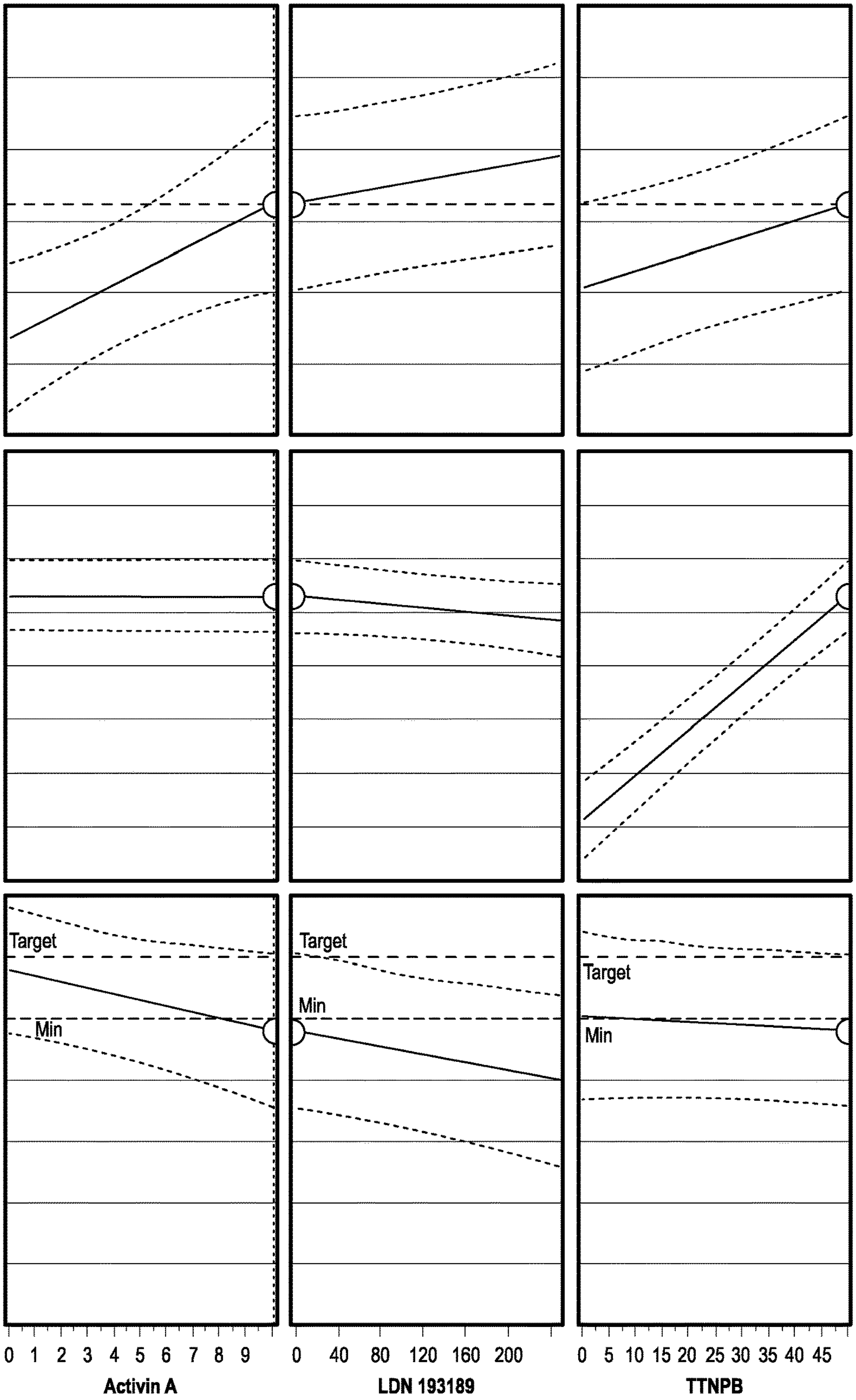
Figure 19:
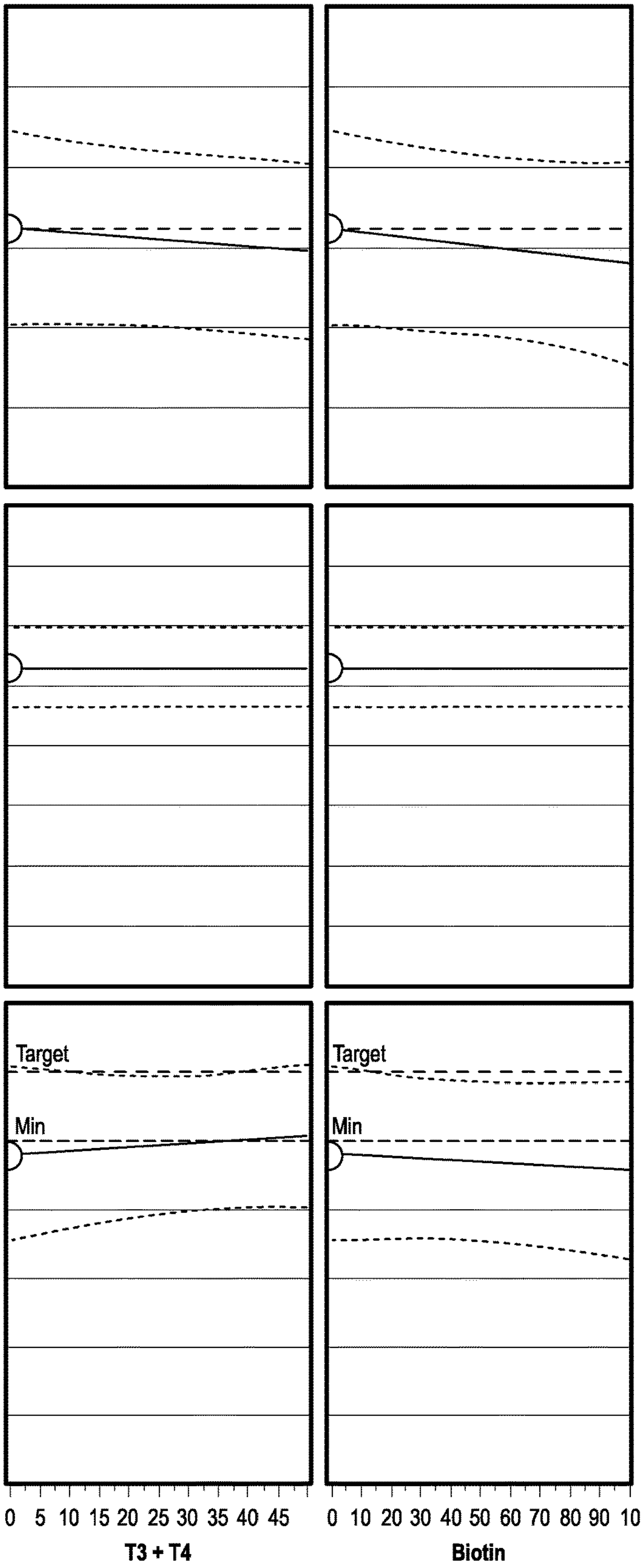

Dynamic profile analysis was utilized to explore combination sets that can optimize expression of all three selected genes. Out of all effectors, TTNPB was the only factor with positive impact on all three genes (FIG. 19). Since Activin A is the main compound regulating expression level of OLIG1, we investigated the changes in the plots after addition of Activin A and observed that expression level of SOX10 is still in the target range and PDGFRa is expressed at a high level too (2520). Addition of the other compounds resulted in lower expression levels of two out of three genes and therefore, only Activin A and TTNPB were added to the candidate recipe for stage 3.

In another model, the effects of Activin A and TTNPB along with LDN193189, MHY1485, PDGF-AA, AICAR, FGF2, CHIR99021, DBZ, MK2206, Purmorphamine and T3+T4 were tested on gene profile of differentiating cells. When this model was optimized for maximum expression of SOX10 at 54.7, we observed Activin A again had positive regulatory impact on its expression, with factor contribution of 4.7. Other positive factors included MK2206, with the highest factor contribution at 16.2, MHY1485 at 11.49, CHIR99021 at 9.6, DBZ at 9.3, FGF2 at 3.6 and PDGF-AA, with factor contribution less than 3 (FIG. 20). Within the specifications of attaining 80% maximal expression of SOX10, this complex media composition had a Cpk value (process capability index) of 0.47, with a corresponding to a 7.7% risk of failure.

In this model, we also investigated the conditions of expression of another important OPC gene, CSPG4 (Goldman and Kuypers (2015) *Development* 142:3983-95: van Tilborg et al. (2018) *Glia* 66:221-238). When the model was optimized for maximum expression of CSPG4 at 38.6, five factors demonstrated positive regulatory behavior, including TTNPB, with the highest factor contribution at 15.96, and Purmorphamine, Activin A, MK2206 and PDGF-AA, with factor contributions of 10.3, 9.3, 5.2, and 2.9, respectively. In this model, LDN193189 had the most negative impact with factor contribution of 16.9 (FIG. 21). Within the specifications of attaining 80% maximal expression of CSPG4, this complex media composition had a Cpk value (process capability index) of 0.69, with a corresponding to a 1.8% risk of failure.

Figure 22:
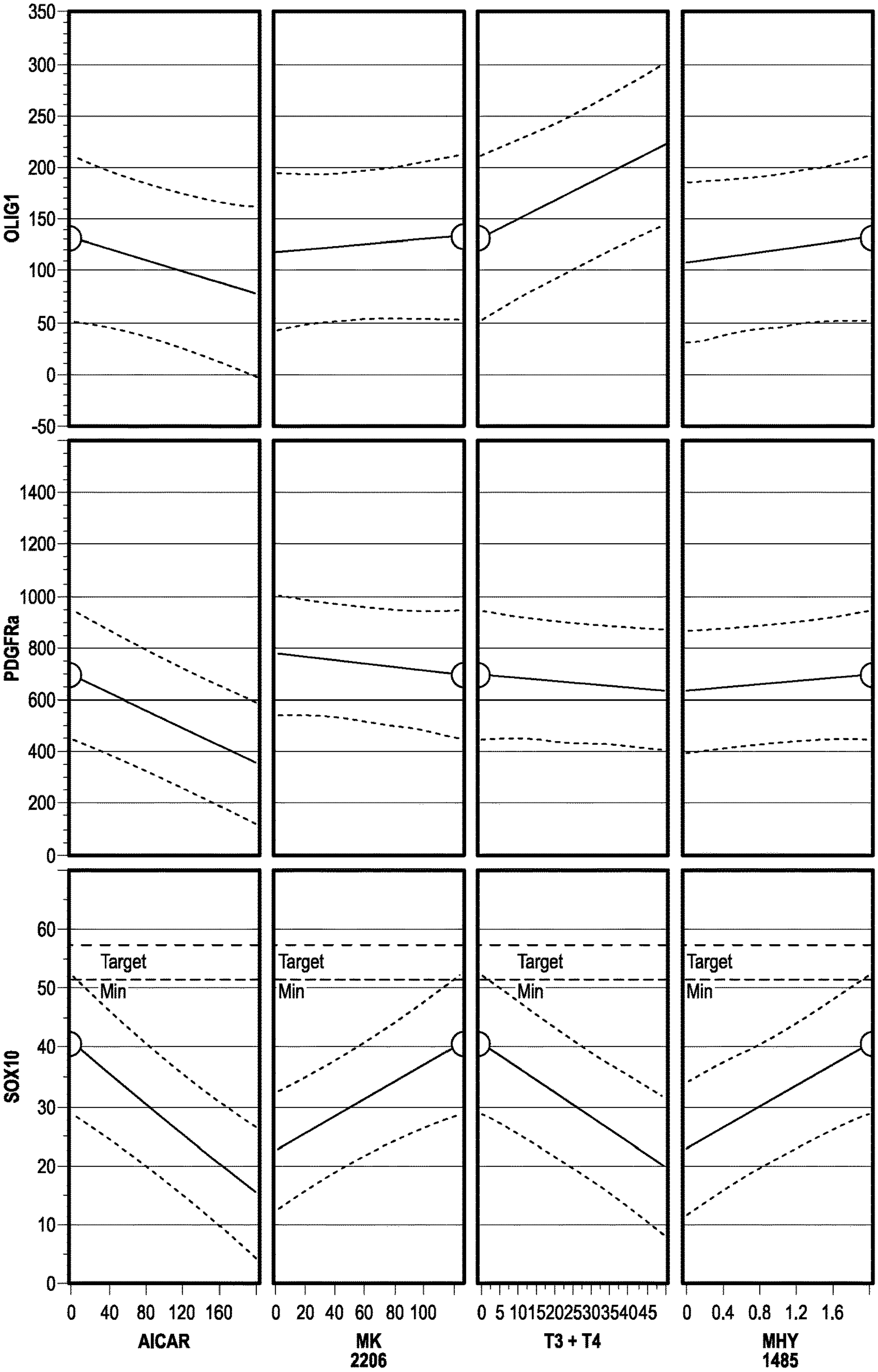
FIG. 22 shows the dynamic profile analysis of expression levels of OLIG1, PDGFRa and SOX10 relative to the concentration of four of 12 factors. The positive impact of MK2206 and DBZ on levels of expression of SOX10 and their factor contributions are shown by slope of the plots for each effector.
Figure 22:
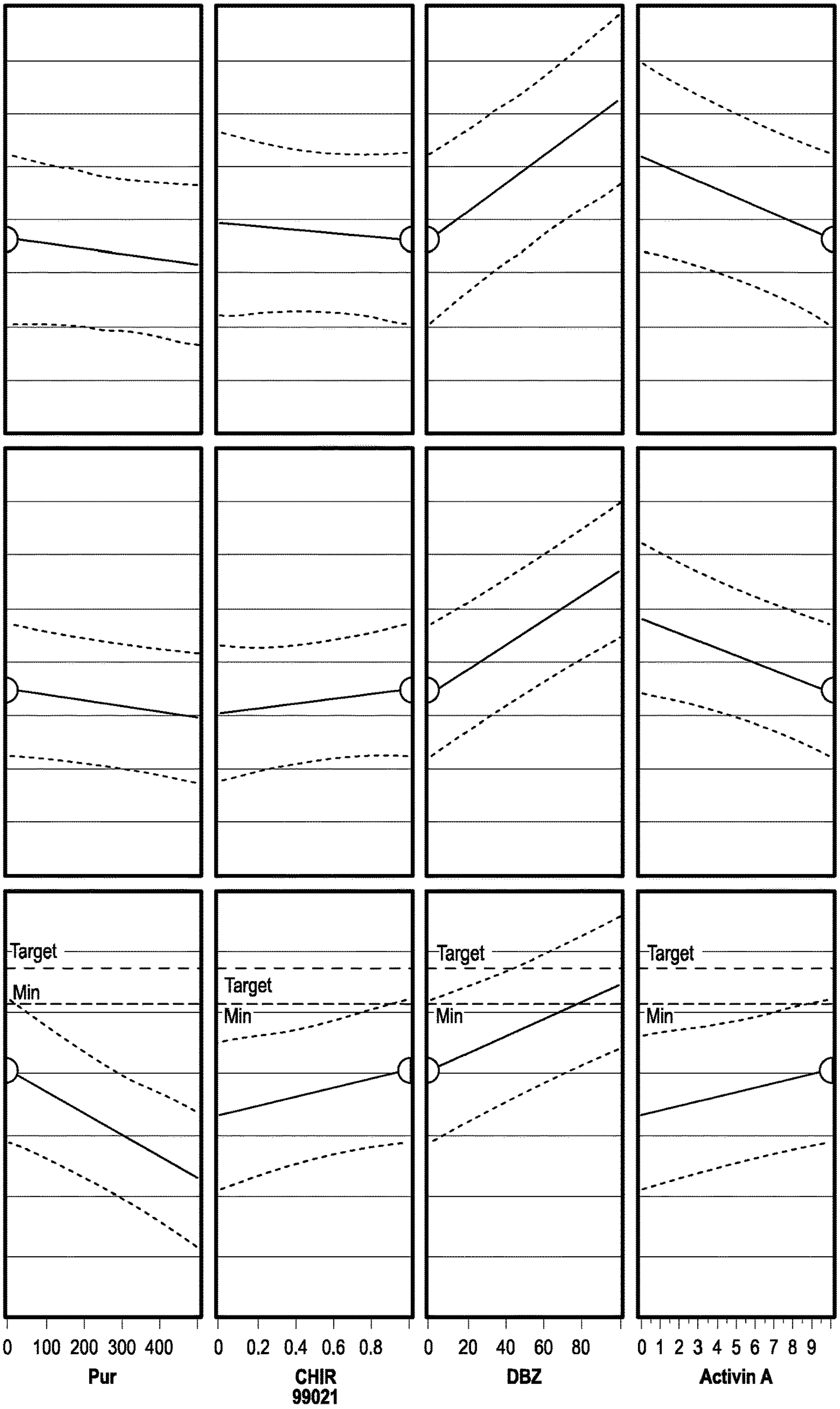
Figure 22:
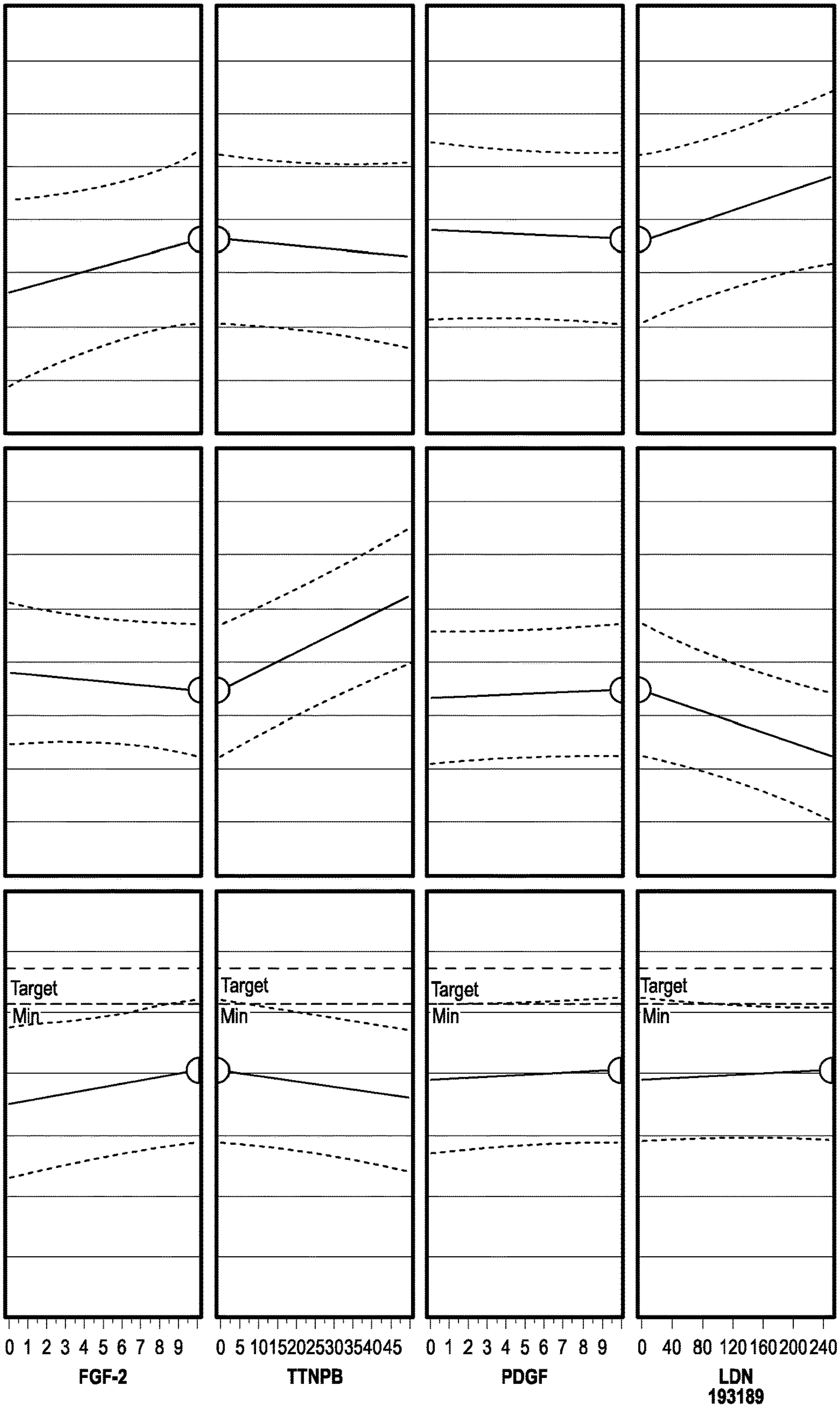
Figure 23:
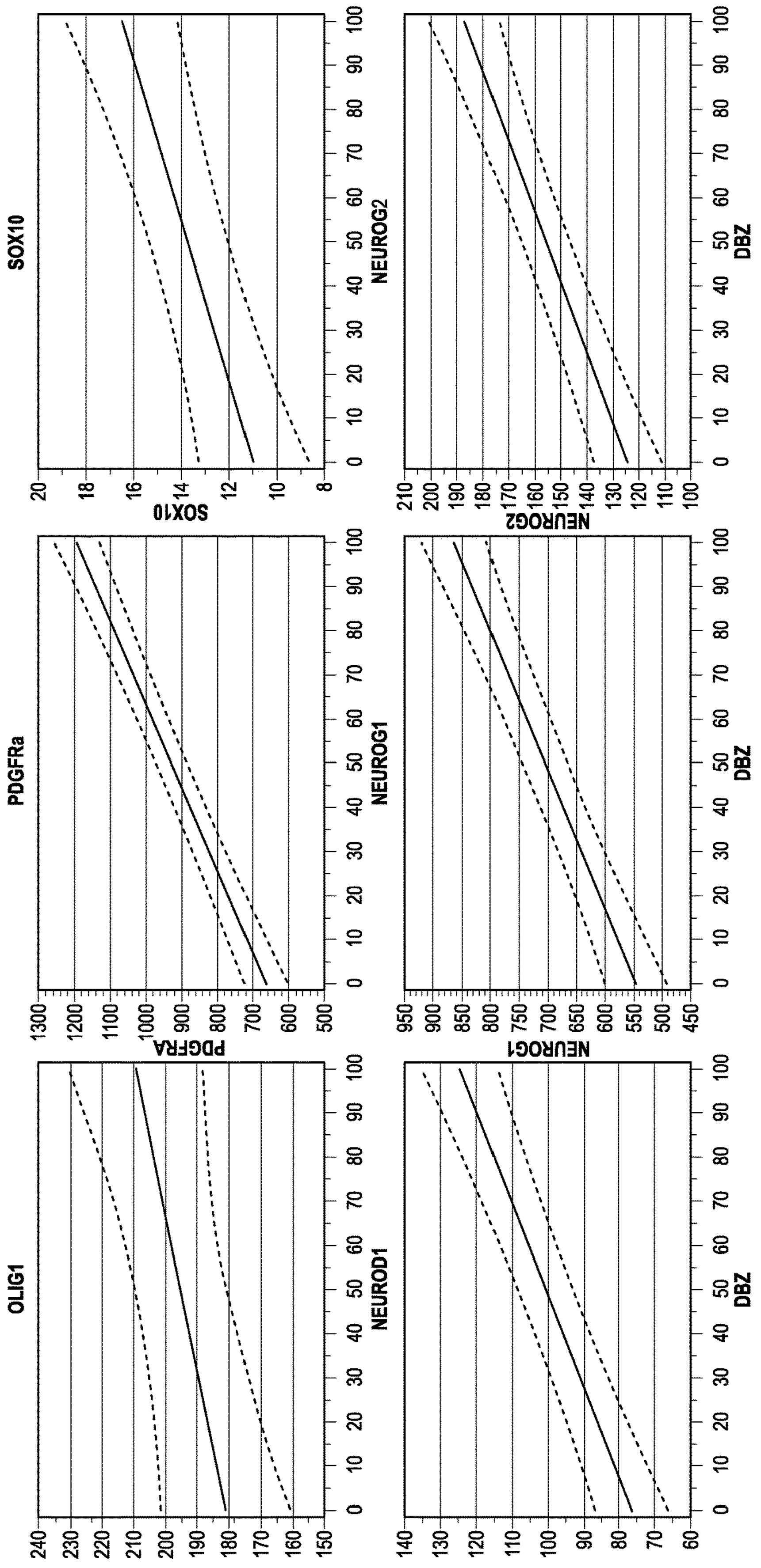
FIG. 23 shows factor effect plots demonstrating expression levels of OPC genes, including OLIG1, PDGFRa, SOX10, and neuronal genes, including NEUROD1, NEUROG1 and NEUROG2, relative to the concentration of DBZ. As the concentrations of DBZ increases, the expression of genes of both groups increases too.

Dynamic profile analysis was used to better assess the impact of the factors on our selected genes and find the combination set that can optimize their expression (FIG. 22). According to this analysis, even though Activin A has a positive effect on SOX10, it decreases level of PDGFRa and OLIG1. However, previous model showed that depending on other factors present in the recipe, Activin A can be positive for OLIG1 as well. Moreover, SOX10 is one of the main transcription factors of oligodendrocytes, along with OLIG2 and NKX2-2, that has shown the potential to commit the stem cells to oligodendrocytes in reprogramming efforts (Wang et al. (2014) *Proc Natl Acad Sci USA* 111:E2885-94; Garciá-León et al. (2018) *Stem Cell Reports* 10:655-672). DBZ demonstrated a positive effect on all three genes, however it also increases neuronal genes (FIG. 23). One of the main challenges of differentiating cells to oligodendrocyte fate is controlling the mixed population and increasing the purity of the culture by committing more cells to oligodendrocyte over neuronal identity. Therefore, DBZ was excluded from the final recipe. MK2206, MHY1485, FGF2 and PDGF-AA, which are positive regulators of SOX10, either positively increased the expression level of PDGFRa and OLIG1 or did not have a significant negative impact on their expression and therefore they were included in the final recipe.

Figure 24:
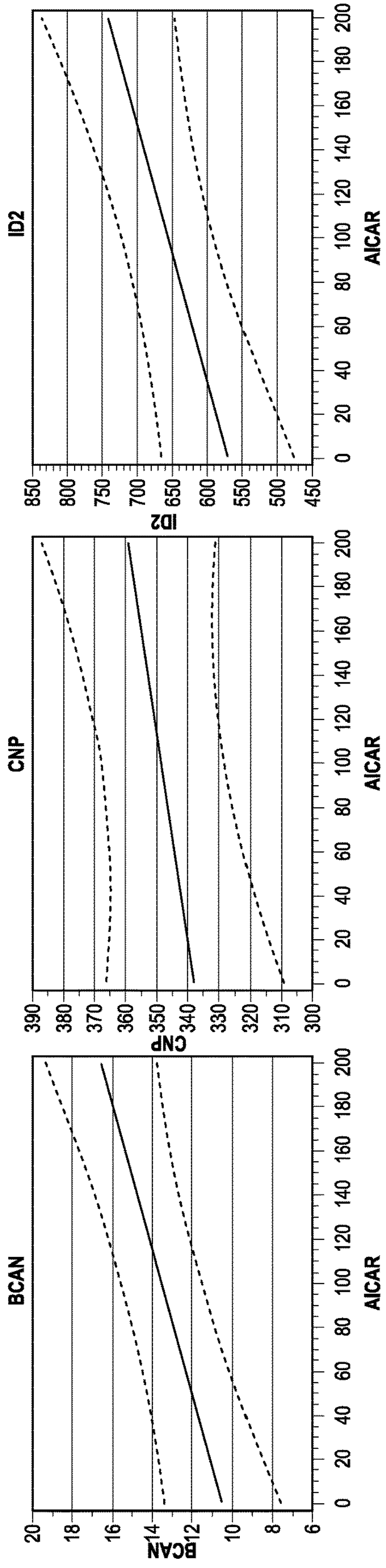
FIG. 24 shows factor effect plots demonstrating expression levels of late OPC genes, including BCAN, CNP and ID2, relative to the concentration of AICAR. As the concentration of AICAR increases, the expression of genes of both groups increases too.

At this point, we investigated the expression profile of a larger group of genes defining oligodendrocyte progenitor population at a later stage, including ID2, CNP and BCAN (Perlman et al. (2020). *Glia* 68:1291-1303; Goldman and Kuypers (2015) *Development* 142:3983-95). In this model, these genes were expressed at 1900, 660 and 44, respectively. AICAR was identified as the factor that positively regulates this group of genes (FIG. 24).

Therefore, considering the models, a candidate recipe for stage 3 consisting of Activin A, TTNPB, FGF2, PDGF-AA, MK2206, MHY1485 and AICAR was made. This recipe should be able to maximize differentiation of cells as such relate to robust and elevated expression of SOX10, PDGFRa and OLIG1. This recipe was further validated by immunocytochemistry assay (see Example 7).

Example 6: Factor Criticality Analysis of Stem Cell Derived Oligodendrocyte Progenitor-Inducing Culture Conditions To assess the impact of the elimination of each validated factor, we again used dynamic profile analysis and compared the expression levels of genes of interest in the absence of each finalized factor while others were kept present. Since expression levels of genes of interest reveal whether the desired outcome is reachable, this factor criticality analysis revealed the extent of importance of each input effector.

Figure 25A:
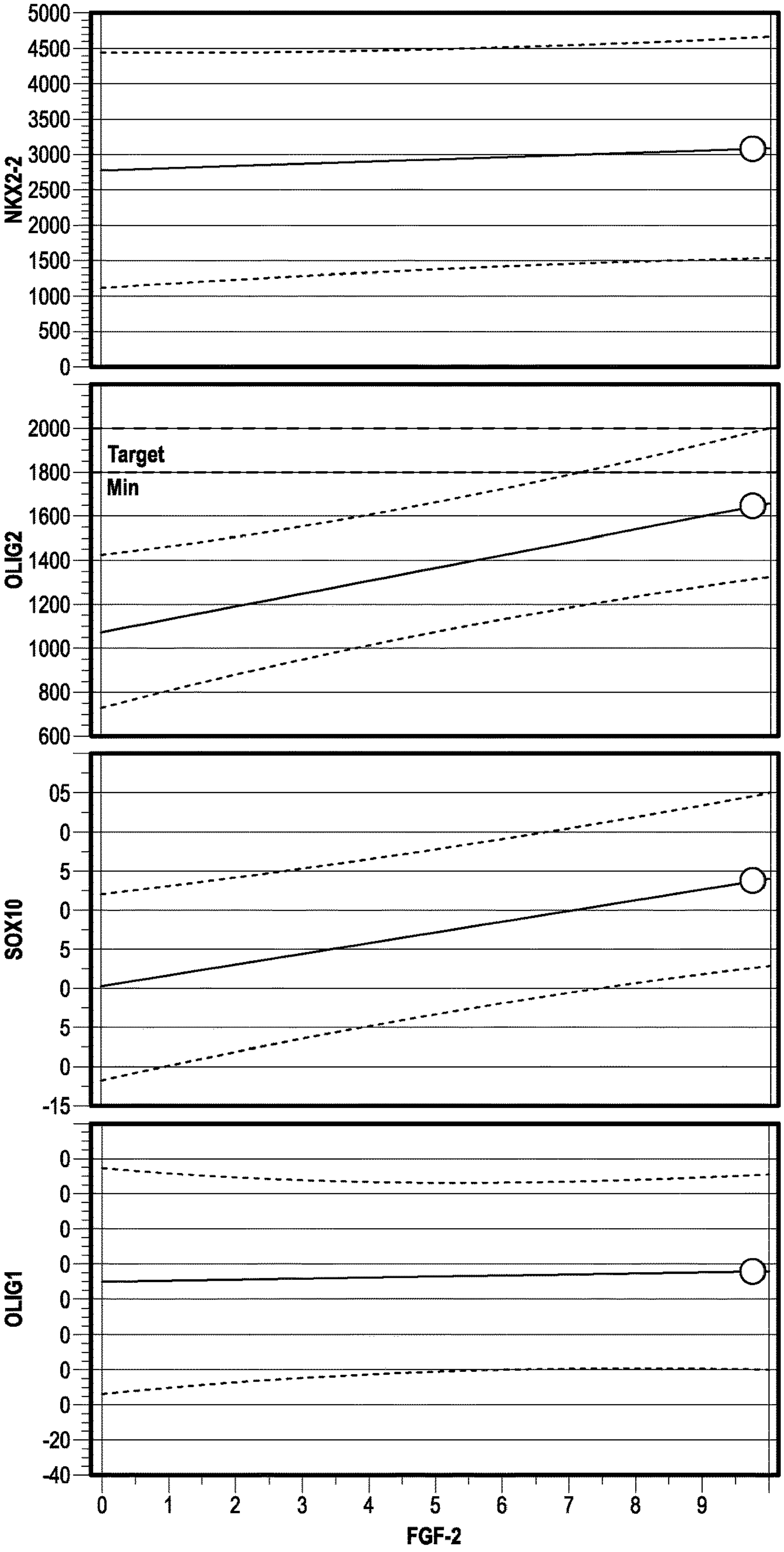
FIG. 25A-25C show the dynamic profile of expression levels of NKX2-2. OLIG2, SOX10 and OLIG1 relative to the concentration of four of the finalized effectors in the recipe of stage 2 differentiation media.
Figure 25A:
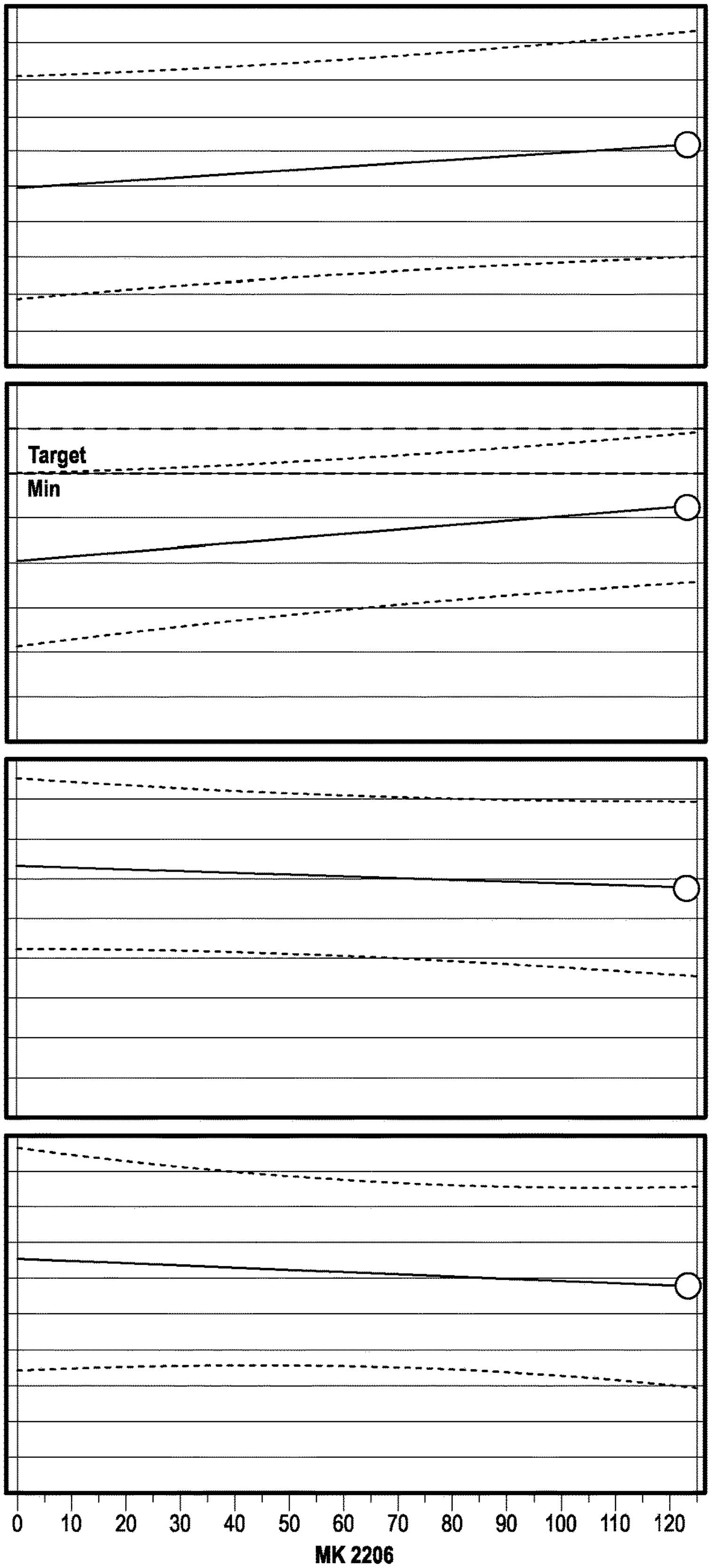
Figure 25A:
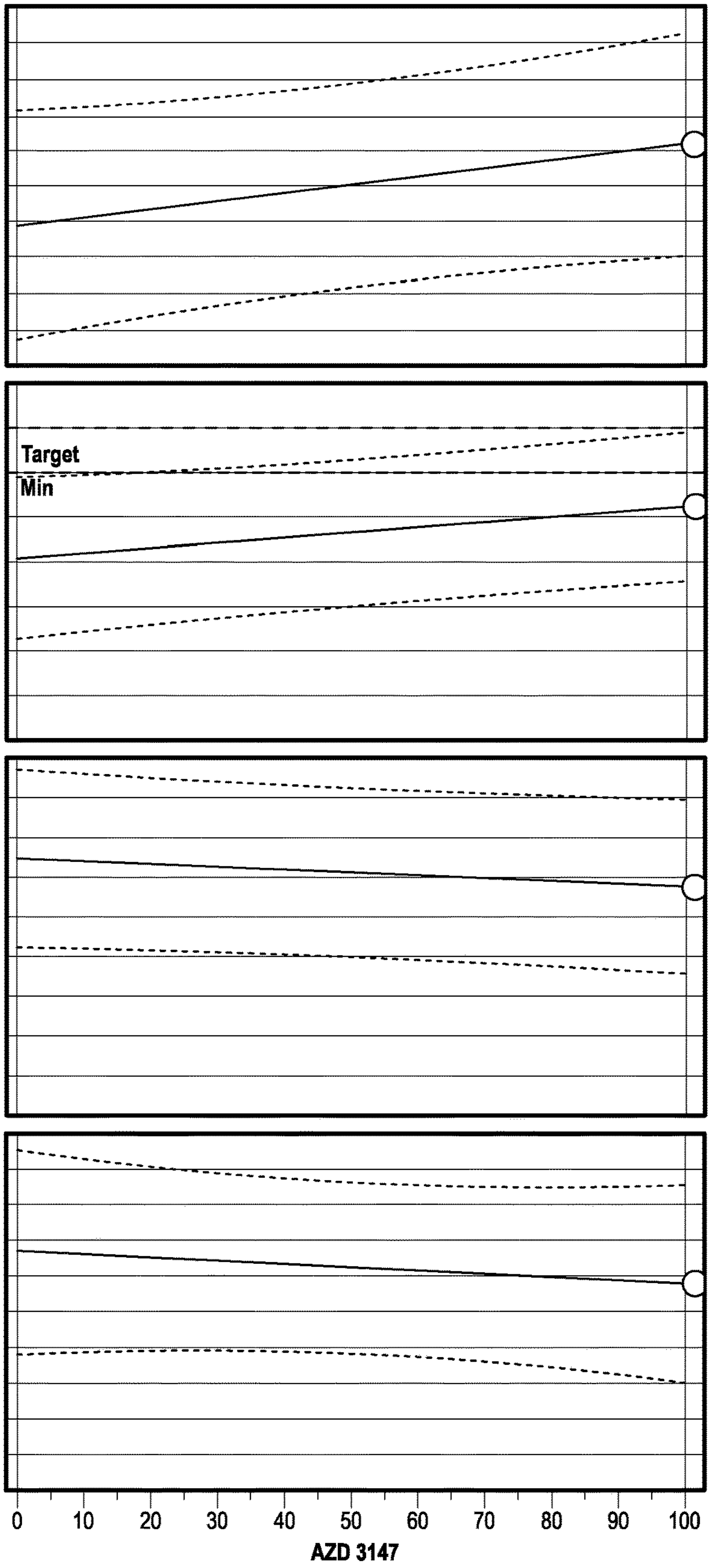
Figure 25A:
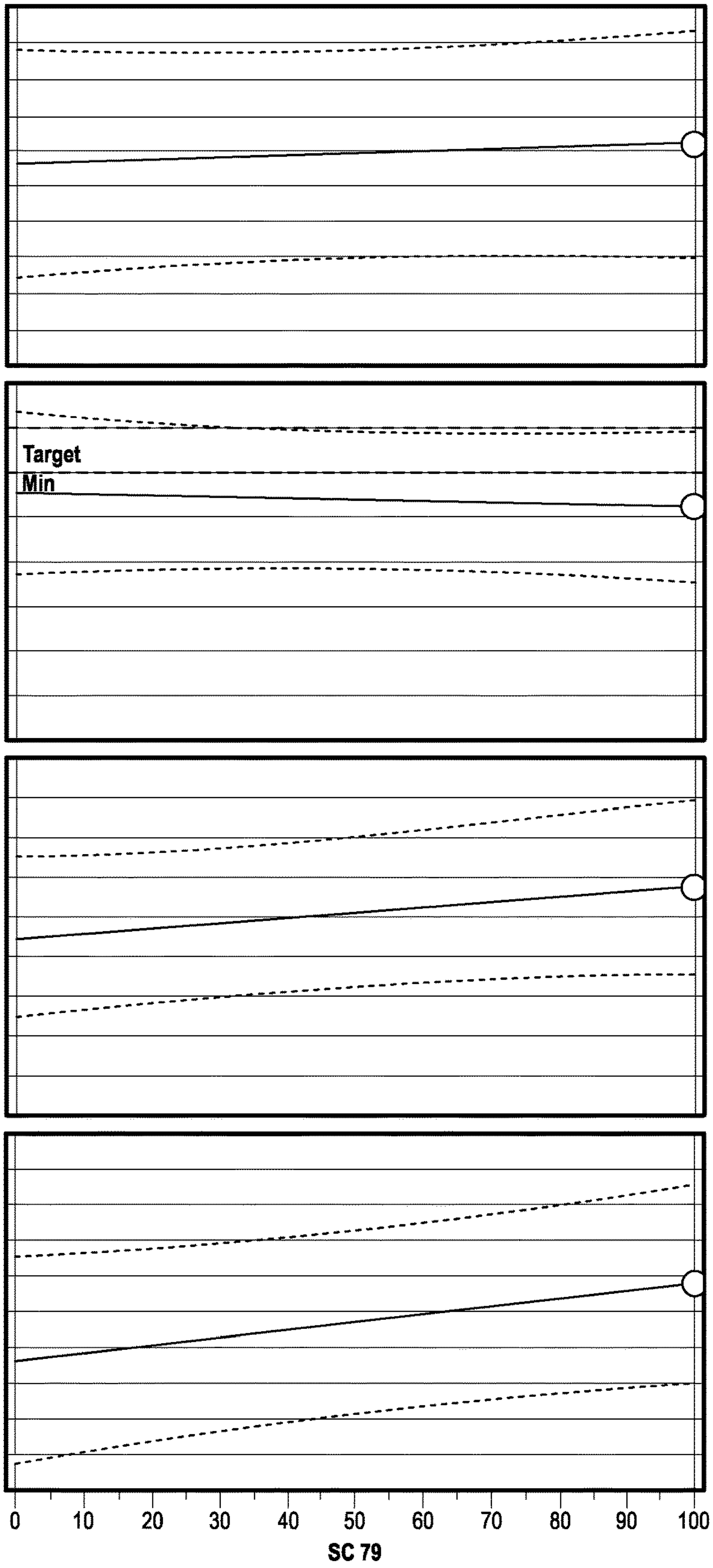
Figure 25B:
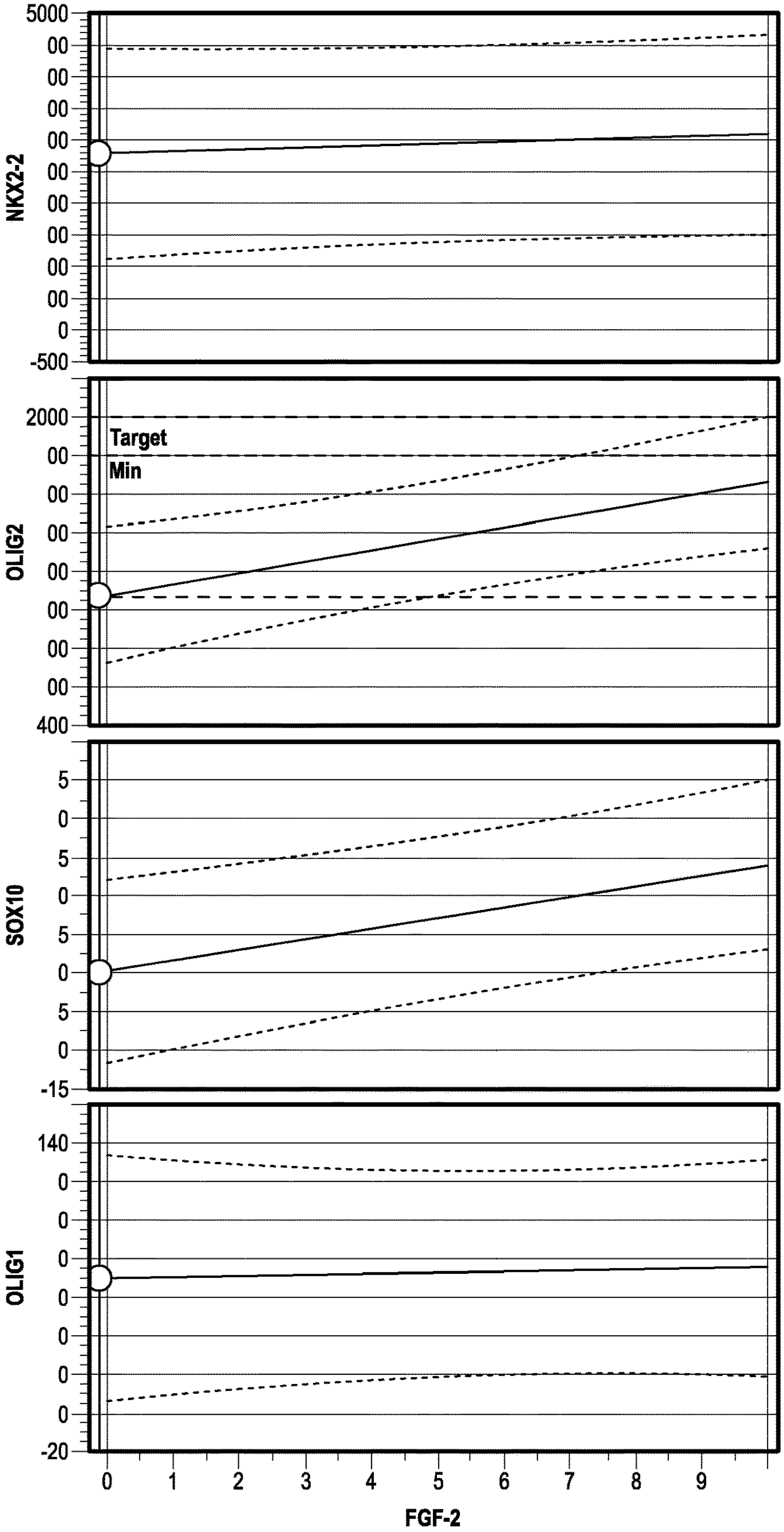
Figure 25B:
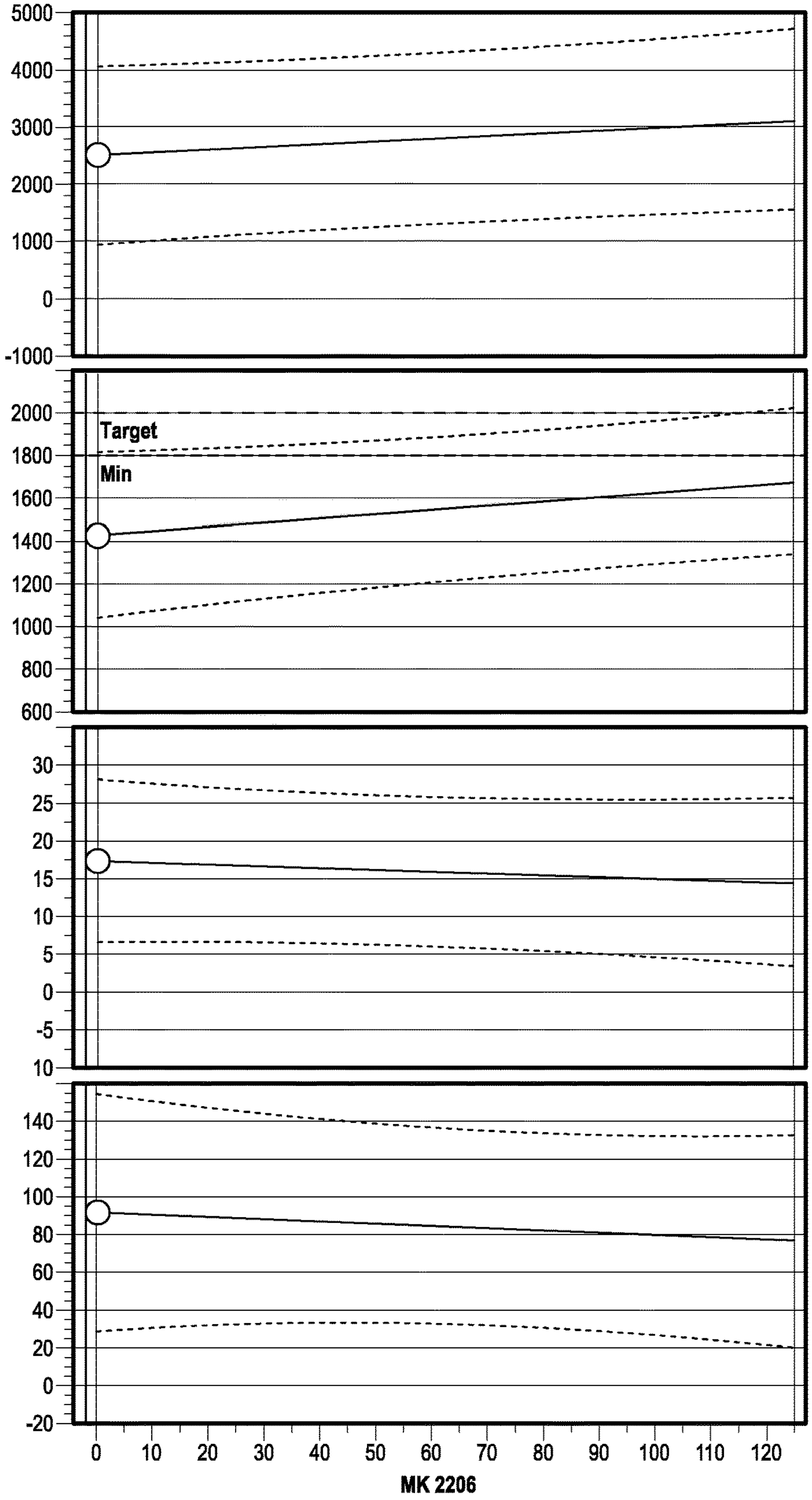
Figure 25B:
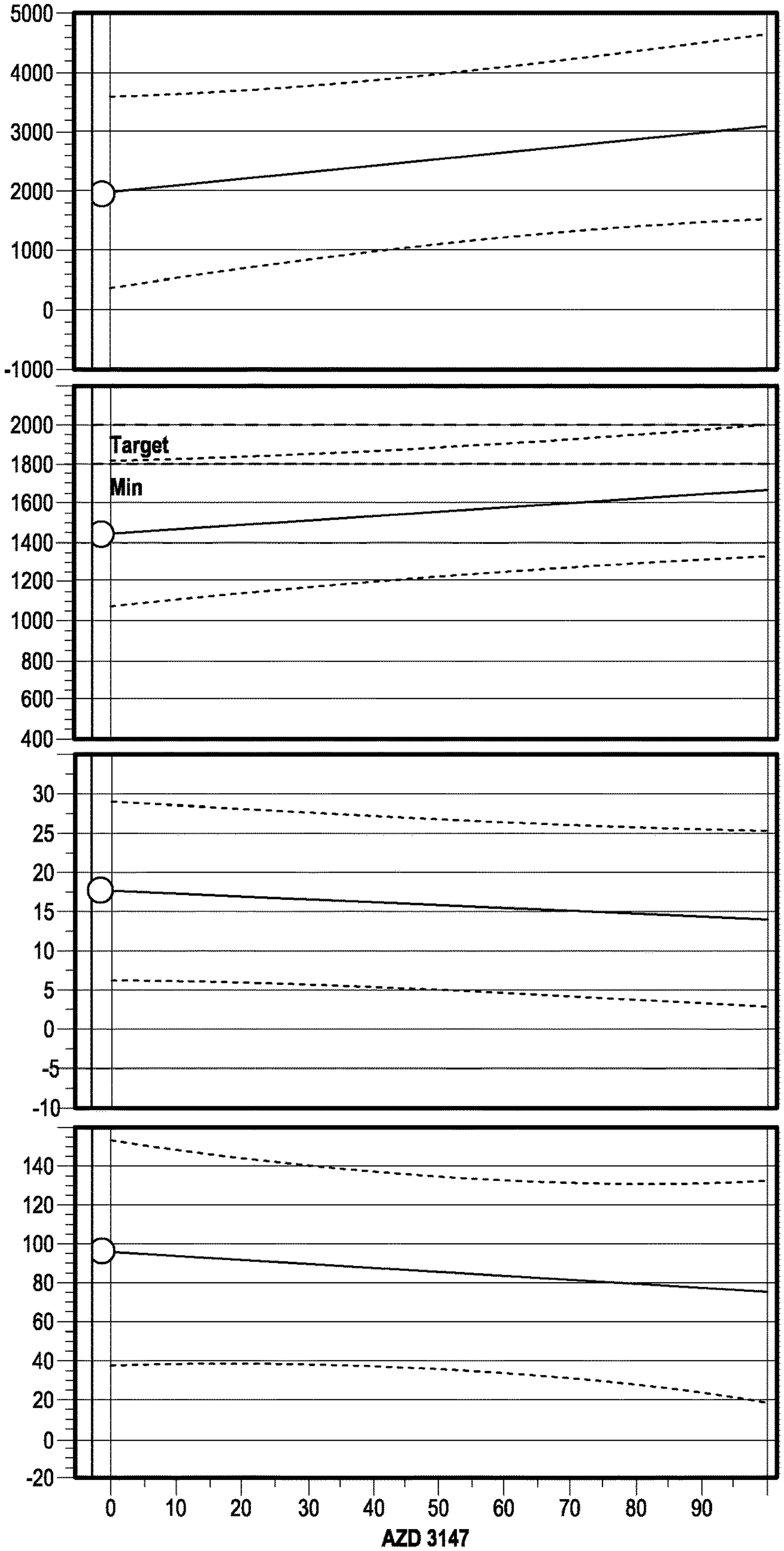
Figure 25B:
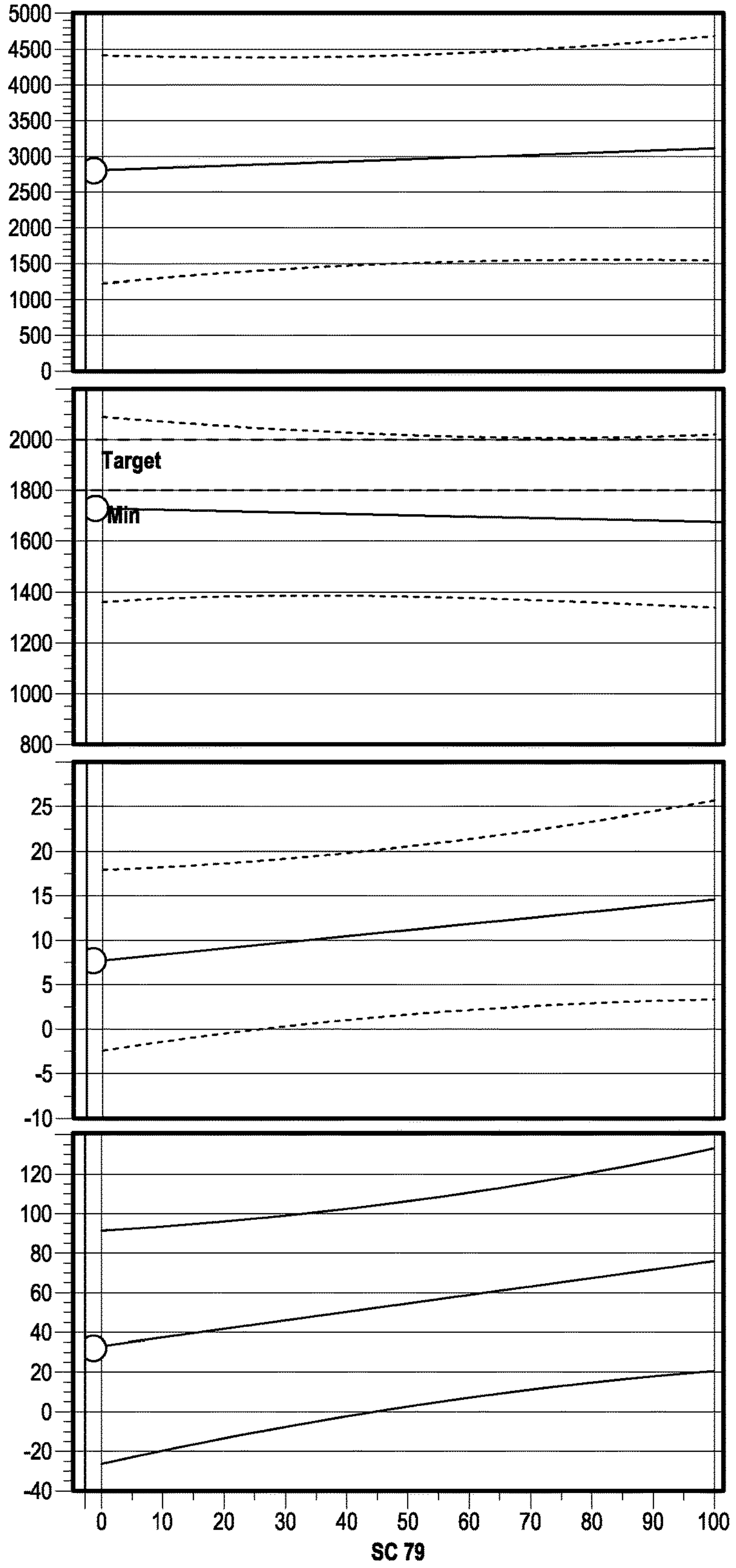

In the stage 2 recipe of Example 5, each of the finalized factors were removed in their respective models while other factors were present and the expression levels of genes of interest were assessed compared to the presence of all factors. The results are shown in FIG. 25A-25B. When FGF-2 was excluded from the recipe, the expression levels of OLIG2 and SOX10 decreased from 1600 to 1000 and from 15 to 0, respectively. The levels of NKX2-2 and OLIG1 also decreased from 3100 to 2800 and from 75 to 65, respectively. When MK2206 was removed, the expression level of OLIG2 decreased from 1600 to 1400 and the level of NKX2-2 significantly decreased from 3100 to 2400. OLIG1 and SOX10 had a slight increase in their expression from 75 to 90 and 15 to 17. When AZD3147 was removed, we observed a similar trend showing a decrease in the levels of OLIG2 and NKX2-2 to 1400 and 1800 respectively, while the level of SOX10 and OLIG1 slightly increased to 17 and 100, respectively. When SC79 was excluded from the recipe, the levels of NKX2-2, SOX10 and OLIG1 dropped to 2800, 7 and 25, respectively. We noticed an increase in the level of OLIG2 from 1600 to 1700.

Figure 25C:
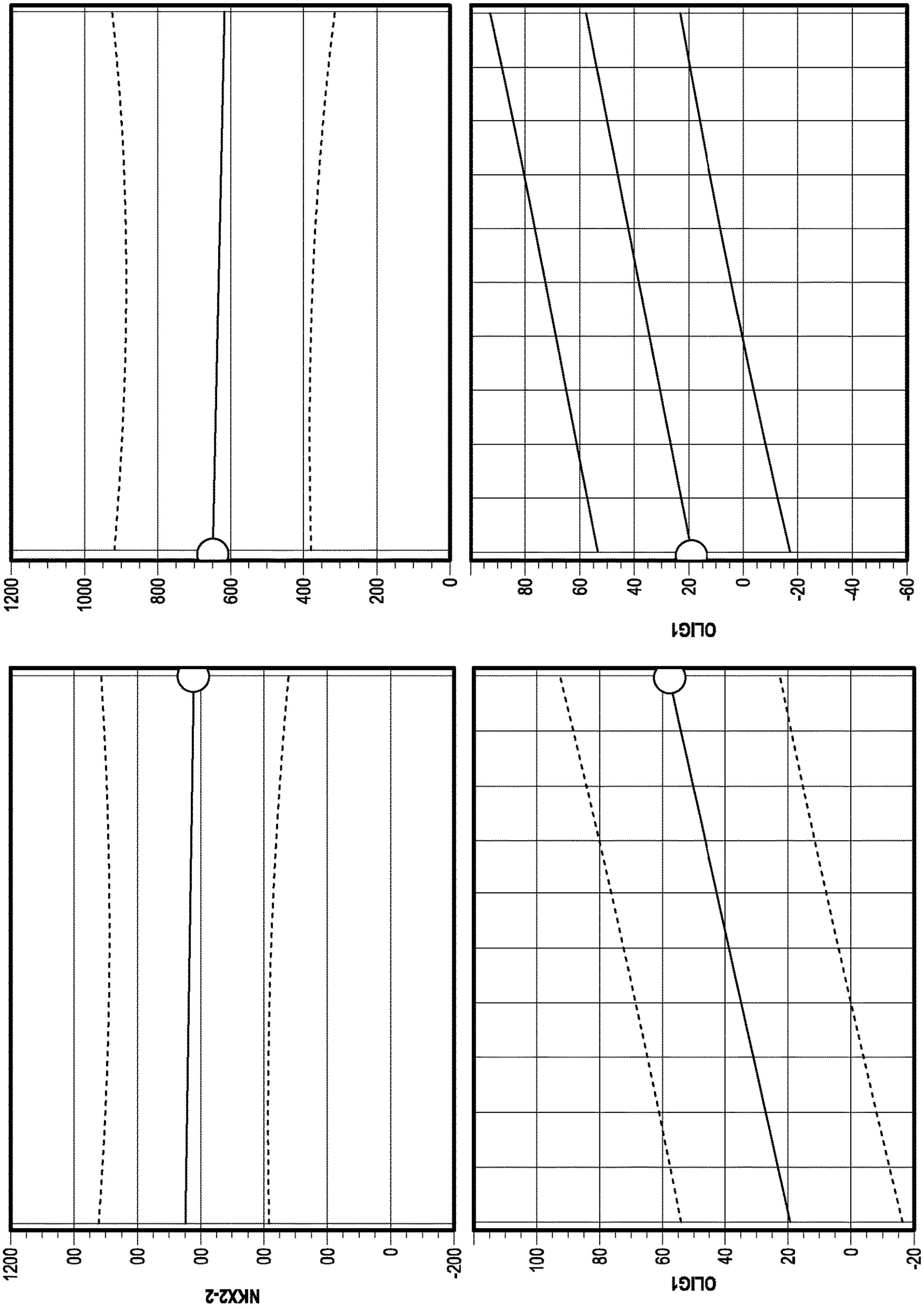
Figure 25C:
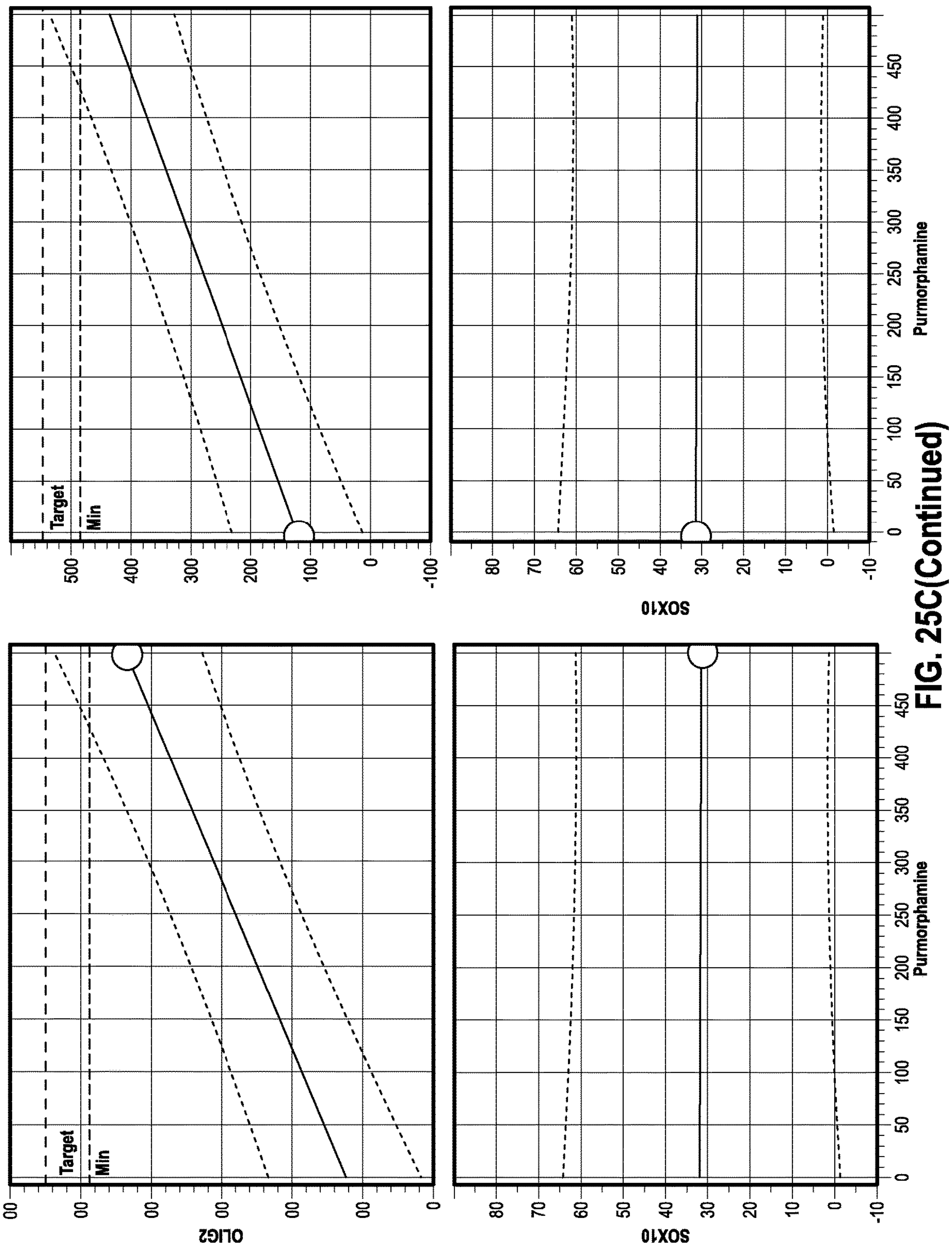

In another model, the criticality of including Purmorphamine in the recipe was determined by tracking the expression levels of genes of interest in the presence and absence of this compound. When Purmorphamine was removed, the levels of OLIG1 and OLIG2 decreased from 60 to 20 and 430 to 105, respectively (FIG. 25C).

Figure 26A:
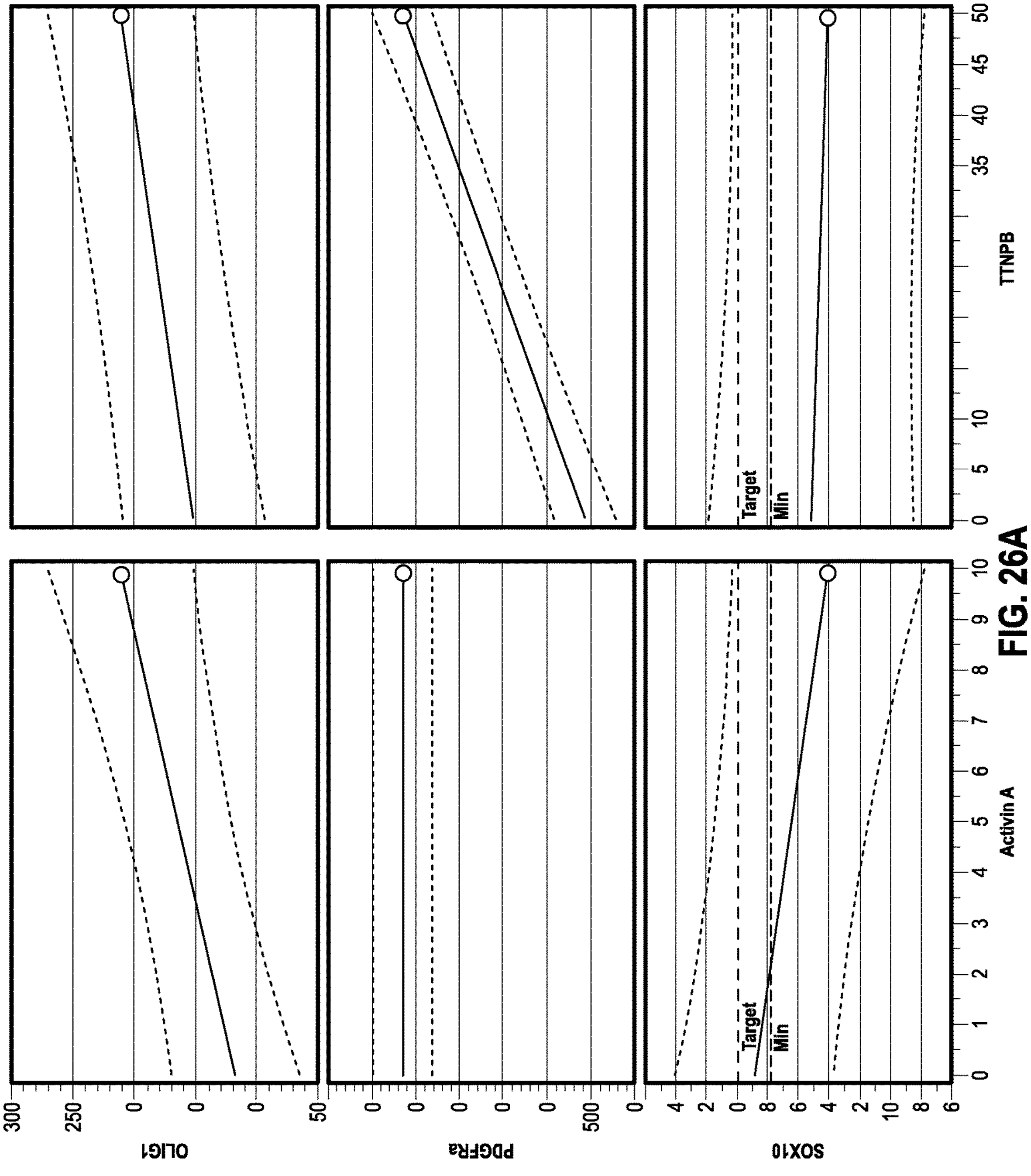
FIG. 26A-26B shows the dynamic profile of expression levels of OLIG1, PDGFRa and SOX10 relative to the concentration of two of the finalized effectors in recipe of stage 3 differentiation media.
Figure 26B:
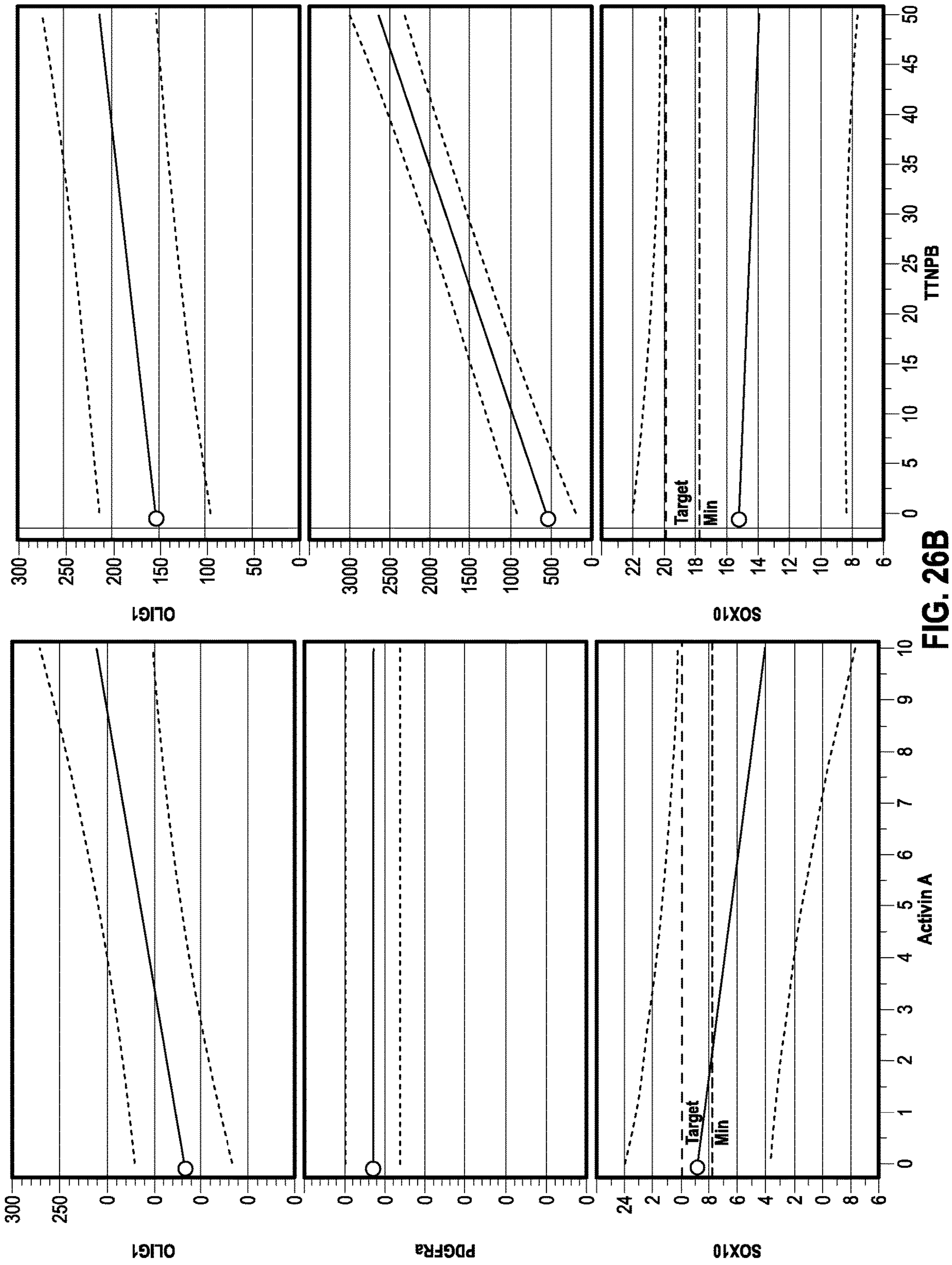

In the stage 3 recipe, each of the finalized factors were excluded while other factors were kept present and the expression levels of SOX10, PDGFRa and OLIG1 were assessed compared to the presence of all factors. In one model, in the absence of TTNPB, the level of PDGFRa and OLIG1 drastically dropped from 2600 to 400 and from 210 to 150. When Activin A was excluded from the recipe, the level of OLIG1 decreased to 120 while the level of PDGFRa did not change. In the absence of Activin A, the expression level of SOX10 increased from 14 to 19 and when TTNPB was removed we observed a slight change in its expression from 14 to 15 (FIG. 26A-26B).

Figure 27A:
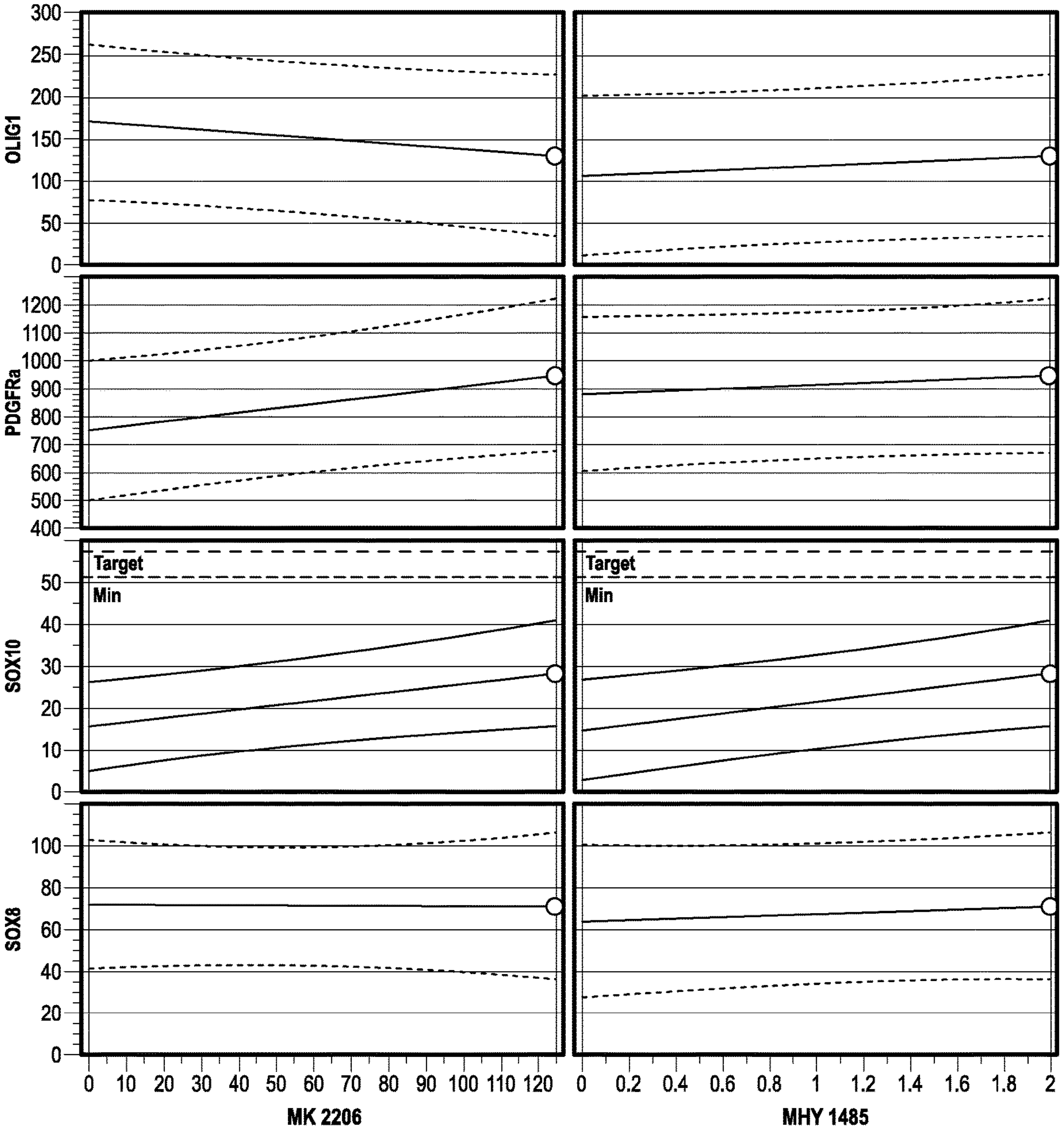
FIG. 27A-27B shows the dynamic profile of expression levels of OLIG1, PDGFRa, SOX10 and SOX8 relative to the concentration of four of the finalized effectors in the recipe of stage 3 differentiation media.
Figure 27A:
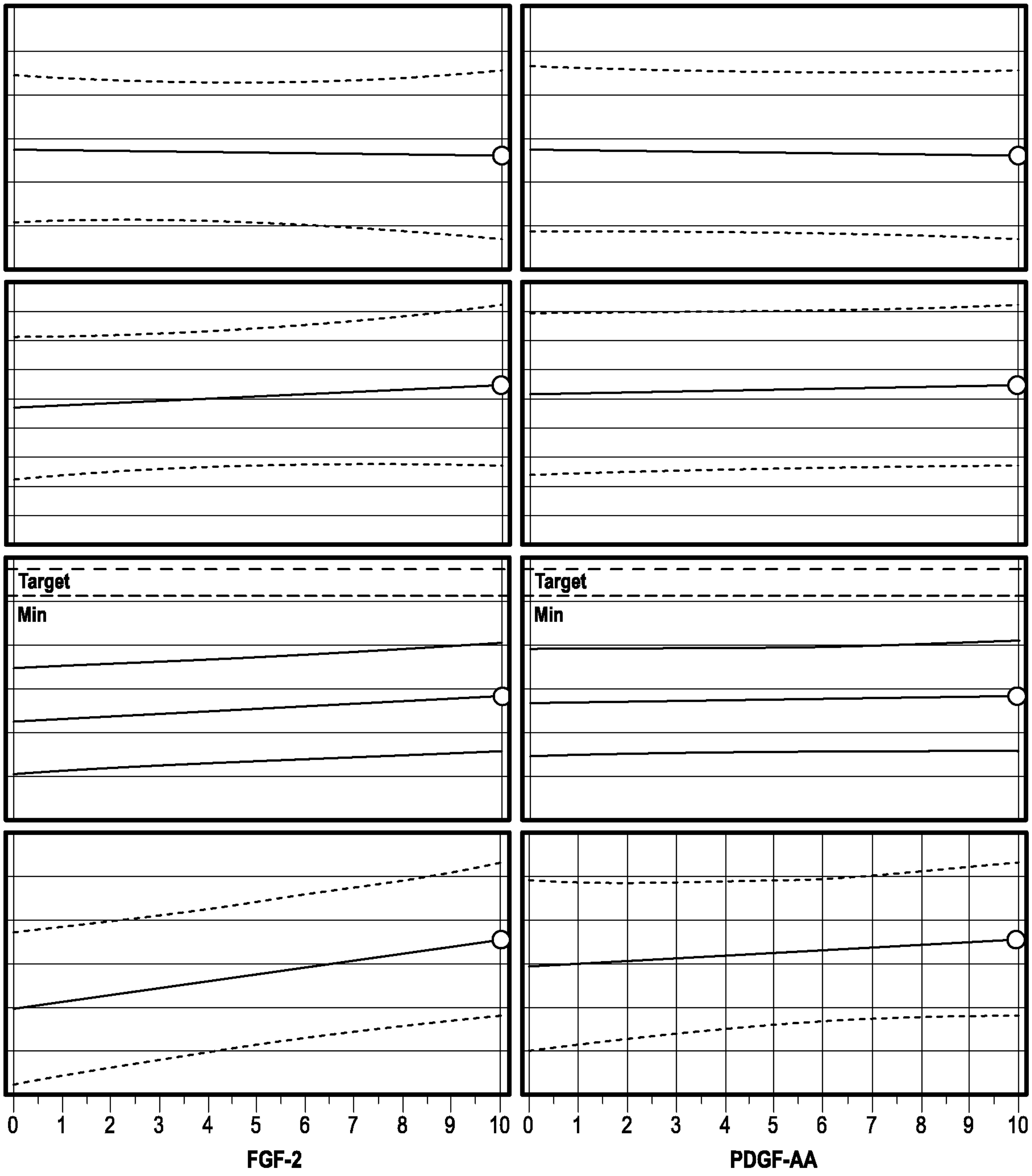
Figure 27B:
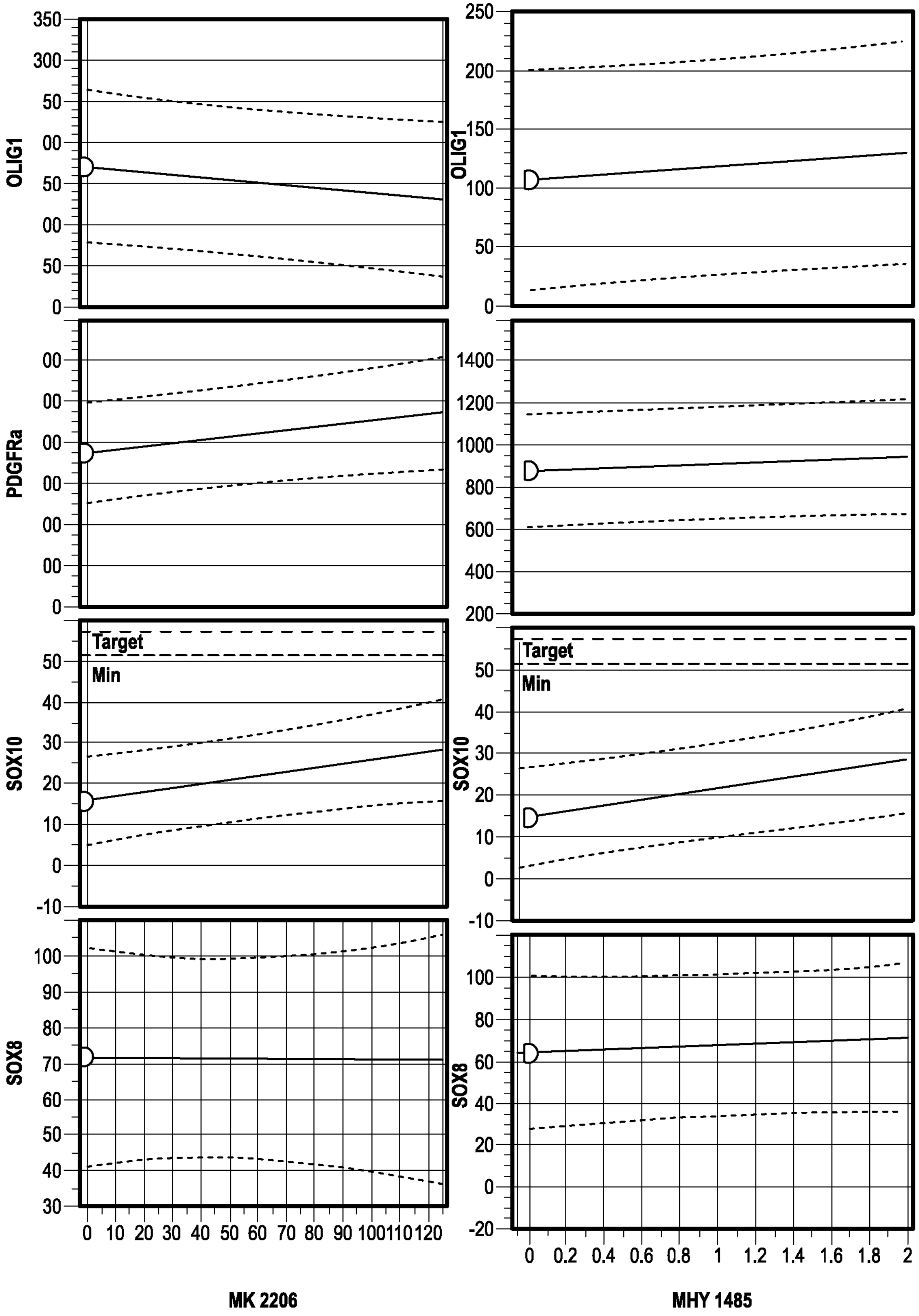
Figure 27B:
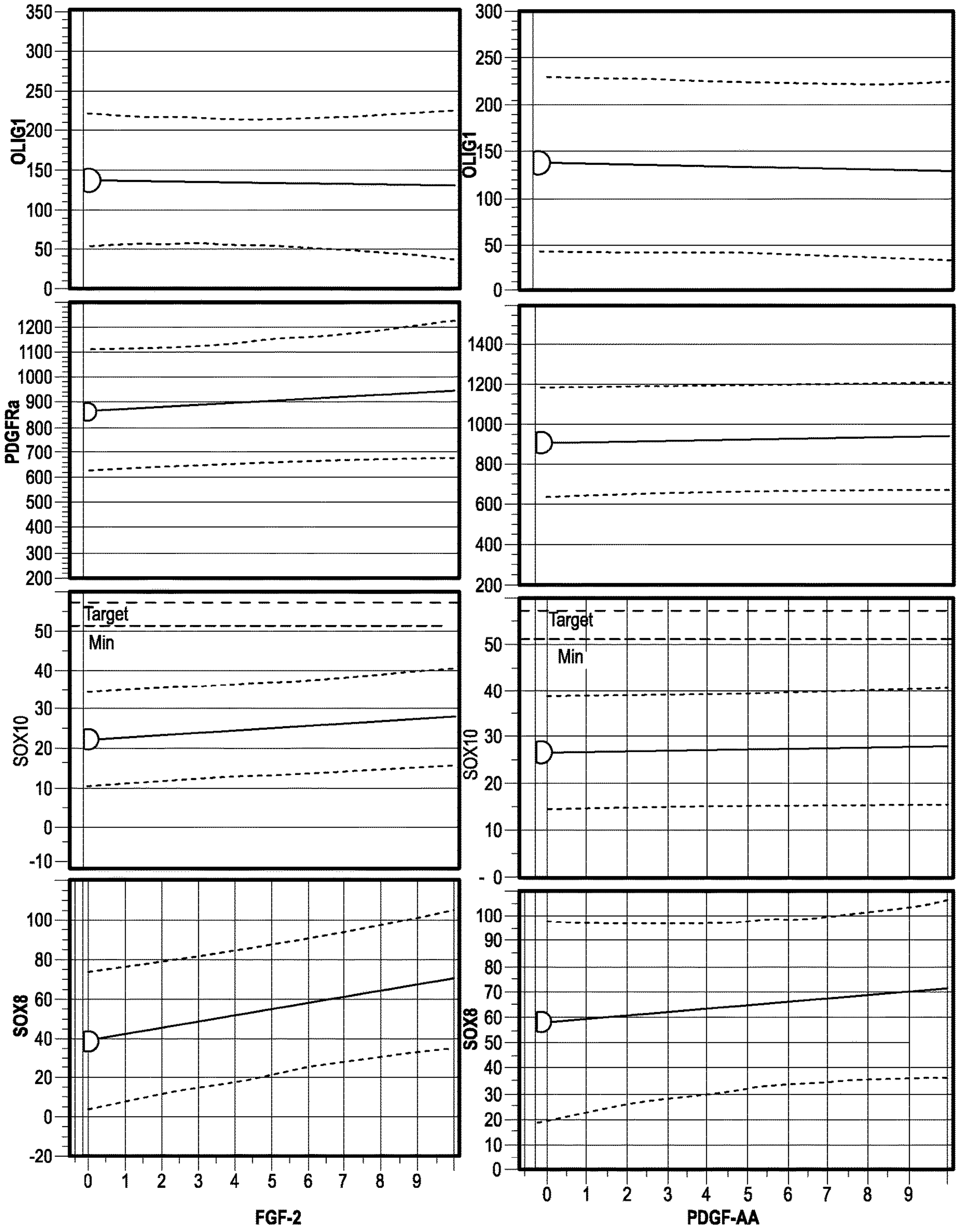

In another model, to determine the combinatorial effect of MK2206, MHY1485, FGF-2 and PDGF-AA on gene profile of cells in the presence of other factors in final recipe, the expression levels of OLIG1, PDGFRa, SOX8 and SOX10 were compared in the absence of each factor (FIG. 27A-27B). When FGF-2 was removed, the level of PDGFRa, SOX8 and SOX10 was decreased from 920 to 860, 70 to 40 and 30 to 20, respectively. The level of OLIG1 did not change. Removing MK2206 resulted in an increase in the level of OLIG1 from 130 to 170 while the expression levels of SOX10 and PDGFRa decreased to 15 and 750, respectively. The level of SOX8 did not change. When MHY1485 was removed, the expression levels of SOX8, SOX10, PDGFRa and OLIG1 dropped to 60, 15, 850 and 110, respectively. When PDGF-AA was excluded from the recipe, the level of SOX8 decreased to 60 while the other three genes had slight changes.

In summary, factor criticality analysis demonstrated the importance of inclusion of each of the compounds in the recipes of the stage 2 and stage 3 differentiation media described in Example 5.

Example 7: Immunocytochemistry Validation of Stem Cell-Derived Oligodendrocyte Progenitors Expressing SOX10 and PDGFRa To further validate the optimized culture media described in Example 5, cells were treated with stage 1 differentiation media for 3 days, stage 2 differentiation media for 3 days and stage 3 differentiation media for 6 days, then standard immunocytochemistry assays were used to assess expression of biomarkers of early oligodendrocyte progenitors at the end of stage 2 and late oligodendrocyte progenitors at the end of stage 3. Biomarkers tested included OPC-specific markers, such as SOX10, OLIG2, NKX2-2, PDGFR, NG2 (CSPG4) and A2B5, along with the pan neuronal marker TUBB3 to determine the homogeneity of the culture.

Figure 28:
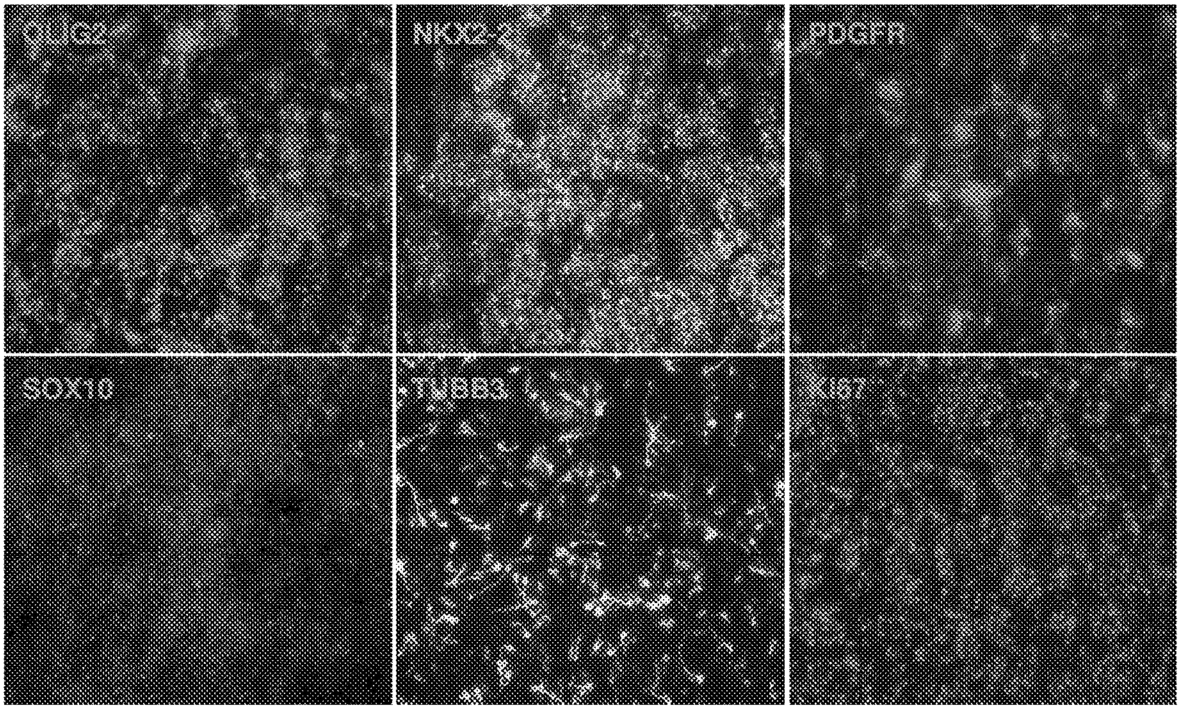
FIG. 28 show photographs of fluorescence images of hiPSC-derived early oligodendrocyte progenitors at the end of stage 2. Cells are stained with OPC biomarkers, including NKX2-2, OLIG2, SOX10 and PDGFRa, the pan neuronal biomarker TUBB3 and the proliferation marker KI67. At this stage, cells were positive for all the markers expected at the early progenitor state.

Immunocytochemistry images of cells at the end of stage 2 (Day 6 in culture) confirmed the expression of OLIG2 and NKX2-2 and the initial expression of SOX10 and PDGFRa in differentiated cells. Expression of KI67 in the cells showed that most of the cells were still proliferating, which was expected at the progenitor stage (FIG. 28). TUBB3 was also detected in less than 50% of the cells, which showed the culture was not 100% glial cell.

Figure 29:
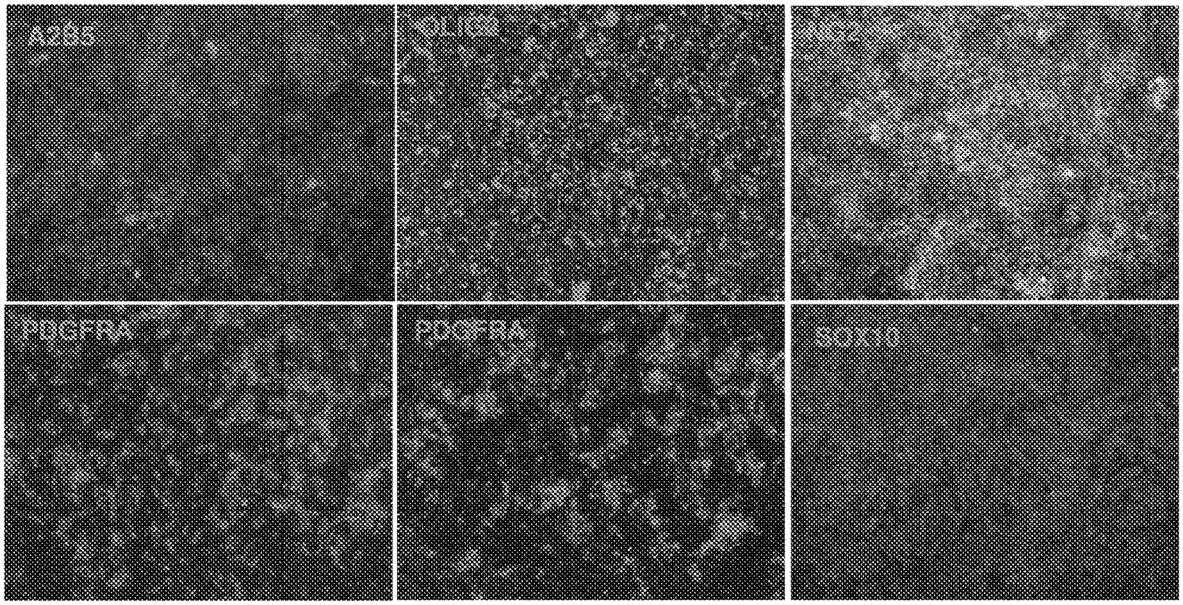
FIG. 29 shows photographs of fluorescence images of oligodendrocyte progenitors at the end of stage 3. Cells are stained with OPC markers, including OLIG2, PDGFRa, SOX10, NG2 and A2B5. At this stage, cells were positive for all expected biomarkers and their oligodendrocyte identity was confirmed.

The results of immunocytochemistry assays on hiPSC-derived cells at the end of stage 3 (day 12 in culture), confirmed the expression of SOX10 and PDGFRa in differentiated cells (FIG. 29). Cells were able to maintain the expression of OLIG2 and we also detected NG2 (CSPG4) and A2B5 in some of the cells.

Detection of SOX10 and PDGFRa in differentiated cells by the end of stage 3 of differentiation confirmed the robustness and high conversion potential of the stage-wise recipes described in Example 5 for differentiation of human induced pluripotent stem cells to oligodendrocyte progenitors after 12 days in vitro.

Example 8: Culture Protocol Development for Generation of Stem Cell-Derived Oligodendrocyte Progenitors Expressing SOX10, OLIG2 and NKX2-2

In the example, an alternative stepwise differentiation protocol for the generation of oligodendrocyte progenitors to that described in Example 5 was developed that can guide human pluripotent stem cells to progenitors expressing SOX10, NKX2-2 and OLIG2 after 12 days in culture. Differentiated cells also express other oligodendrocyte progenitor markers including PDGFRa and NG2. The two stage protocol described in this example is referred to as version 2, whereas the two stage protocol described in Example 5 is referred to as version 1.

For the protocol, after treating the cells with stage 1 pre-OPC media (as described in Example 1) for 3 days, cells are cultured for six days in stage 2 media, followed by three days in stage 3 media. These cells can be further differentiated to mature oligodendrocytes. The full three stage protocol is illustrated schematically in FIG. 43.

To develop the oligodendrocyte differentiation recipes, the impact of various agonist and antagonists (effectors) on differentiation of pre-OPCs using an HD-DoE method was investigated. These effectors were chosen based on the available literature on developmental biology and differentiation of stem cells, as well as mouse and human single cell RNA-seq data from oligodendrocytes at the time.

These experiments led to generation of the stage 2 recipe shown below in Table 3 and the stage 3 recipe shown below in Table 4.

TABLE 3

| Validated factors in stage 2 recipe | | |
|---|---|---|
| Effectors | Role | Concentration |
| FGF-2 | FGF pathway activator | 10 ng/ml |
| Purmorphamine | SHH agonist | 500 nM |
| CHIR99021 | WNT agonist | 1 uM |
| AZD3147 | mTOR antagonist | 100 nM |

TABLE 4

| Validated factors in stage 3 recipe | | |
|---|---|---|
| Effectors | Role | Concentration |
| FGF-2 | FGF pathway activator | 10 ng/ml |
| IGF-1 | IGFR activator | 10 ng/ml |
| AGN193109 | RA antagonist | 100 nM |

To engineer the recipe of stage 2 of differentiation, cells were first cultured in the stage 1 media described in Example 1, then, 48 or 96 different combinations of effectors generated using Design-of-Experiments compression through D-optimality were robotically prepared. The effector combinations were prepared in a basal media and were subsequently added to the cells, which were then allowed to differentiate. Three days later RNA extraction was performed, and gene expression was obtained using quantitative PCR analysis. The data was normalized and modeled using partial least squares regression analysis to the effector design, resulting in the generation of gene-specific models, which after model tuning for maximal predictive power, provided explanation of the effectors ability to control the expression of individual genes, combinatorically, and individually. Solutions within the tested space could then be explored to address desirability.

At this point, due to short duration of culture (only six days in vitro) we decided to focus on maximal expression of OLIG2 and maintenance of high expression of NKX2-2, while initiating expression of SOX10, OLIG1 and PDGFRa, to guide the cells towards oligodendrocyte fate (Emery and Lu (2015). *Cold Spring Harb Perspect Biol.* 7:a020461; Perlman et al. (2020). *Glia* 68:1291-1303; Goldman and Kuypers (2015) *Development* 142:3983-95). In one 8-factor model, the individual and combinatorial impact of CHIR99021 (a WNT pathway agonist), AGN193109 (an RA pathway antagonist), FGF-2 (an FGFR agonist), Purmorphamine (an SHH pathway agonist), AICAR (an AMPK agonist), GW3965 (an LXR pathway agonist), GW590735 (a PPAR-a agonist) and AZD3147 (a mTOR antagonist) on further differentiation of cells were tested. This model demonstrated the potential to regulate pre-OPCs to highly express OLIG2, OLIG1, NKX2-2 and PDGFRa. When the model was optimized for maximum expression of OLIG2 at 3325, multiple factors showed positive regulatory effect including AZD3147 with highest factor contribution at 30.2, CHIR99021, Purmorphamine, FGF-2 and GW590735 with factor contribution of 17.96, 7.39, 5.2 and 5.4, respectively (FIG. 30). AGN193109 had the highest negative impact on its expression, with a factor contribution of 25.8. Within the specifications of attaining 80% maximal expression of OLIG2, this complex media composition had a Cpk value (process capability index) of 0.58, with a corresponding to a 4% risk of failure.

This model was also optimized for maximum expression of OLIG1 at 454.7 and we observed, similar to optimization of OLIG2, AZD3147 had the highest positive impact on its regulation with a factor contribution of 26.7 and AGN193109 had the highest negative impact with a factor contribution of 25.3 (FIG. 31). Other factors with positive impact included CHIR99021, FGF-2 and GW590735, with factor contributions of 22.8, 9.9 and 3.1, respectively. Within the specifications of attaining 80% maximal expression of OLIG1, this complex media composition had a Cpk value (process capability index) of 0.42, with a corresponding to a 9.9% risk of failure.

Figure 32:
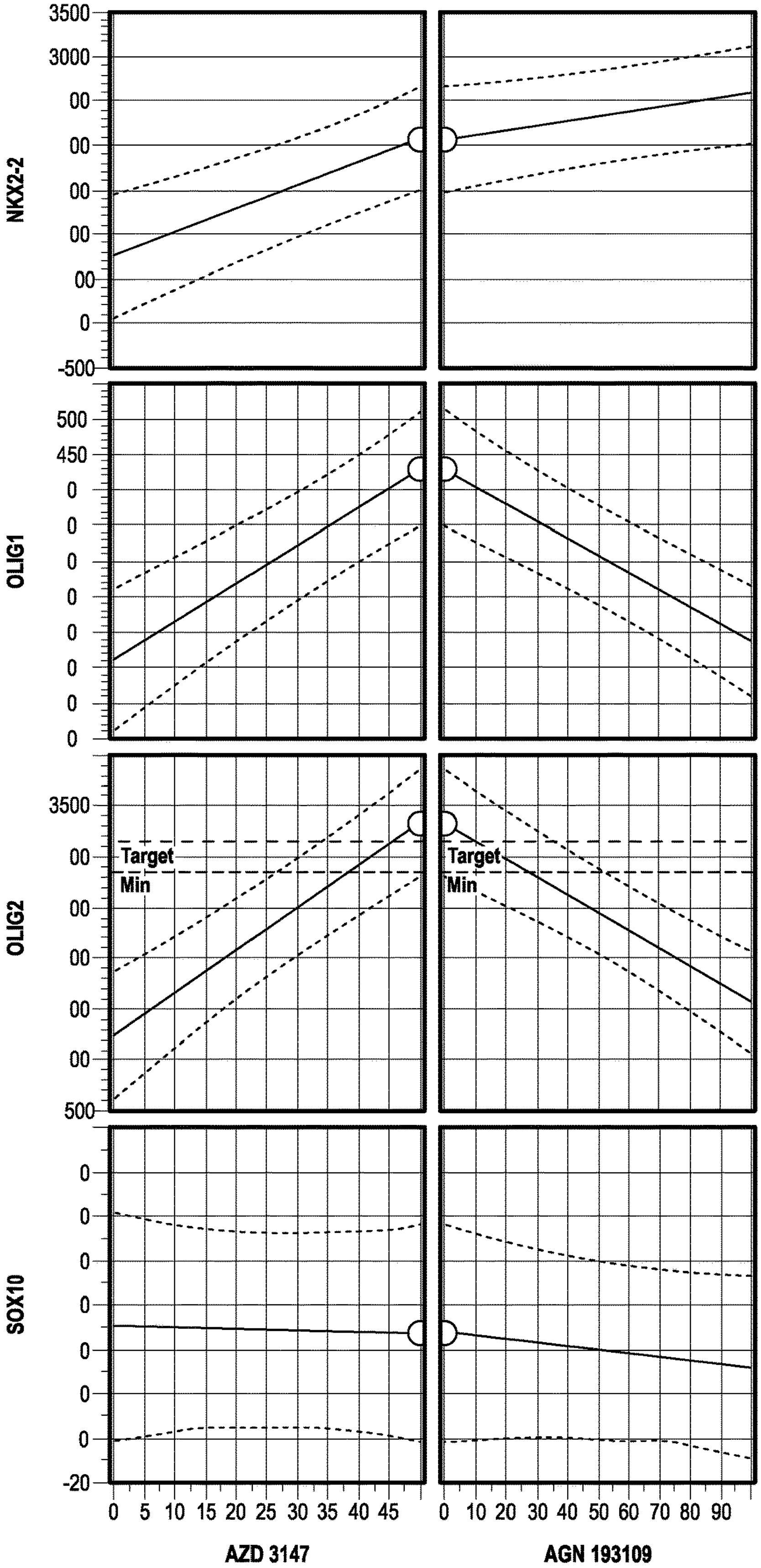
FIG. 32 shows the dynamic profile analysis of expression levels of NKX2-2, OLIG2, SOX10 and OLIG1 relative to the concentration of 8 effectors. The positive impact of AZD3147 and CHIR99021 on expression of OLIG2 and their factor contributions are shown by slope of the plots for each effector.
Figure 32:
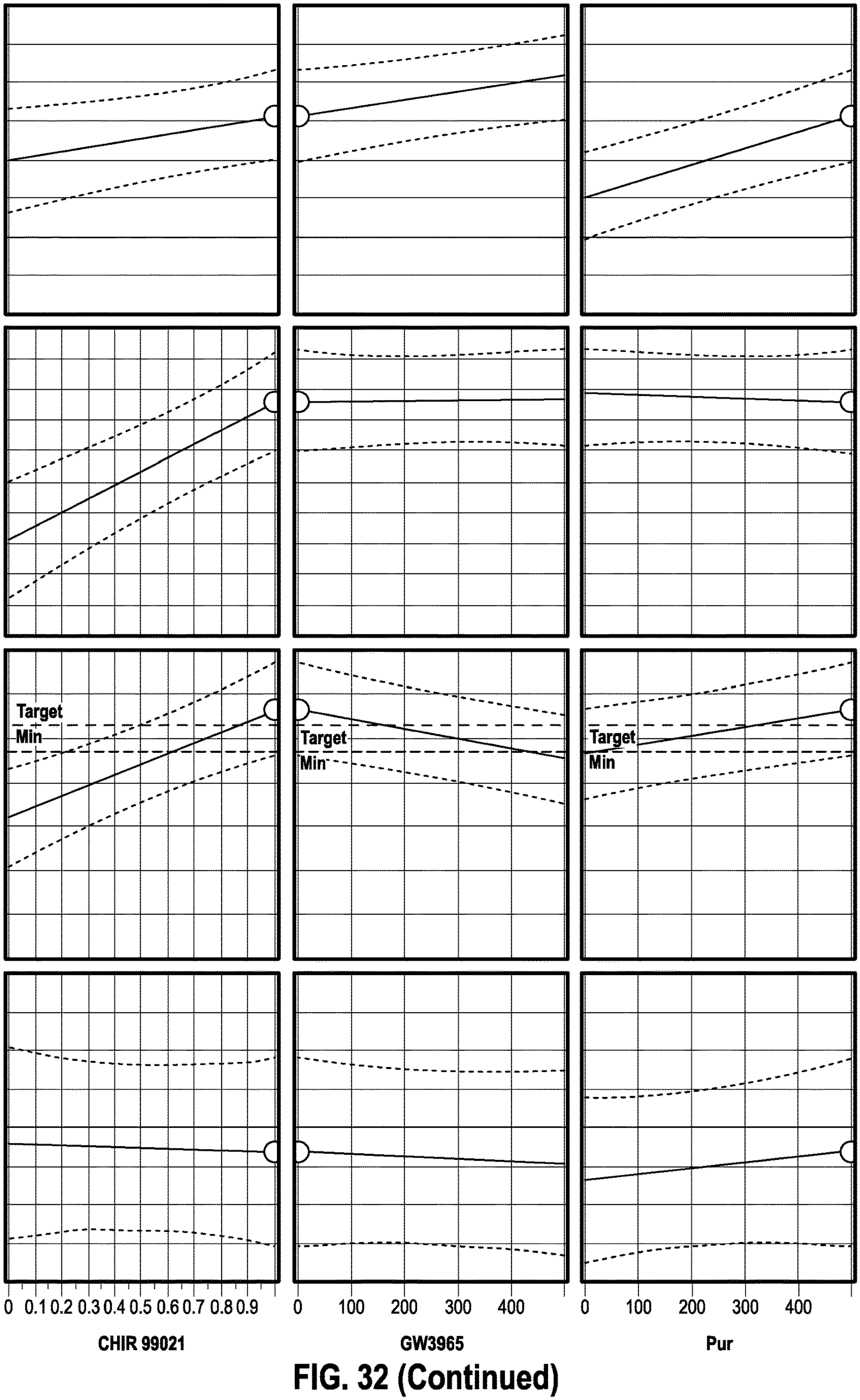
Figure 32:
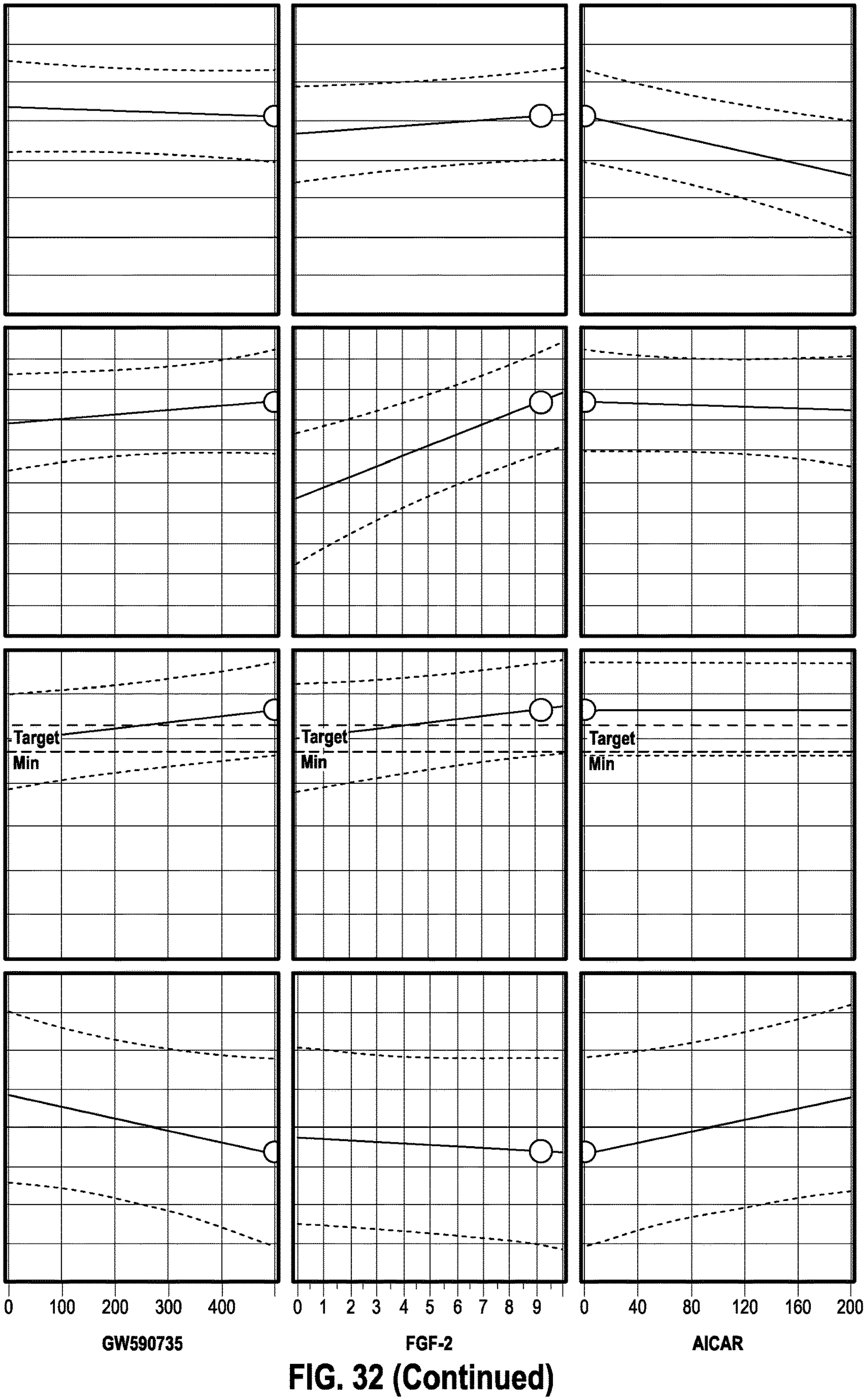

Dynamic profile analysis was used to assess the expression levels of other genes of interests, such as NKX2-2 and SOX10, while the model was maximized for OLIG2. When the model was optimized, the expression level of NKX2-2 was at 2000, OLIG1 at 440 and SOX10 at 15 (FIG. 32). According to the analysis, four of the five compounds showing a positive impact on OLIG2 expression, including FGF-2, Purmorphamine, CHIR99021 and AZD3147, also had a positive impact on NKX2-2 expression, while FGF-2, CHIR99021, AZD 3147 and GW590735 had a positive impact for OLIG1 expression. Even though Purmorphamine did not significantly improve expression of OLIG1, it was a significant positive regulator for both OLIG2 and NKX2-2, which are the target genes at stage 2 and therefore the positive common factors for these two genes were included in the candidate recipe of stage 2 differentiation media. The negative impact of GW590735 on SOX10 and NKX2-2 expression led us to exclude it from the final recipe.

Therefore, considering these models, a candidate recipe for stage 2 consisting of FGF2, Purmorphamine, CHIR99021 and AZD3147 was made. This recipe should be able to maximize differentiation of cells for robust and elevated expression of OLIG2, NKX2-2 and initial expression of SOX10. This recipe was further validated by immunocytochemistry assay (see Example 9).

To further differentiate the cells to an oligodendrocyte progenitor identity, additional HD-DoE experiments were performed on the cells that were cultured in stage 1 and stage 2 differentiation media. After 3 days, gene expression of cells in different combinatorial conditions were investigated. At this time, we focused on maximal expression of signature oligodendrocyte progenitor genes such as SOX10, OLIG1 and PDGFRa (Goldman and Kuypers (2015) *Development* 142:3983-95: Marques et al. (2016) *Science* 352:1326-1329). In one 8-factor model, individual and combinatorial effects of TTNPB (an RA agonist), CHIR99021, FGF-2, IGF-1, AGN193109, Purmorphamine, MHY1485 (a mTOR pathway agonist) and SC79 (an AKT pathway agonist) were tested to guide the cells toward a SOX10/PDGFRa positive population. When optimized for SOX10 at 41.04, TTNPB and FGF-2 showed the highest positive impact, with factor contributions of 17.98 and 15.3, respectively. CHIR99021 was also positive, with a factor contribution of 8.1 (FIG. 33). SC 79 had the highest negative impact, with a factor contribution of 30.2. Within the specifications of attaining 80% maximal expression of SOX10, this complex media composition had a Cpk value (process capability index) of 0.47, with a corresponding to a 7.3% risk of failure.

When this model was optimized for maximum expression of PDGFRa at 853.4, Purmorphamine had the highest positive impact, with a factor contribution of 20.6. Other positive factors were IGF-1, with a factor contribution of 11.2, CHIR99021, with a factor contribution of 8.5 and TTNPB, with a factor contribution below 1 (FIG. 34). Within the specifications of attaining 80% maximal expression of PDGFRa, this complex media composition had a Cpk value (process capability index) of 0.45, with a corresponding to a 8.6% risk of failure.

Figure 35:
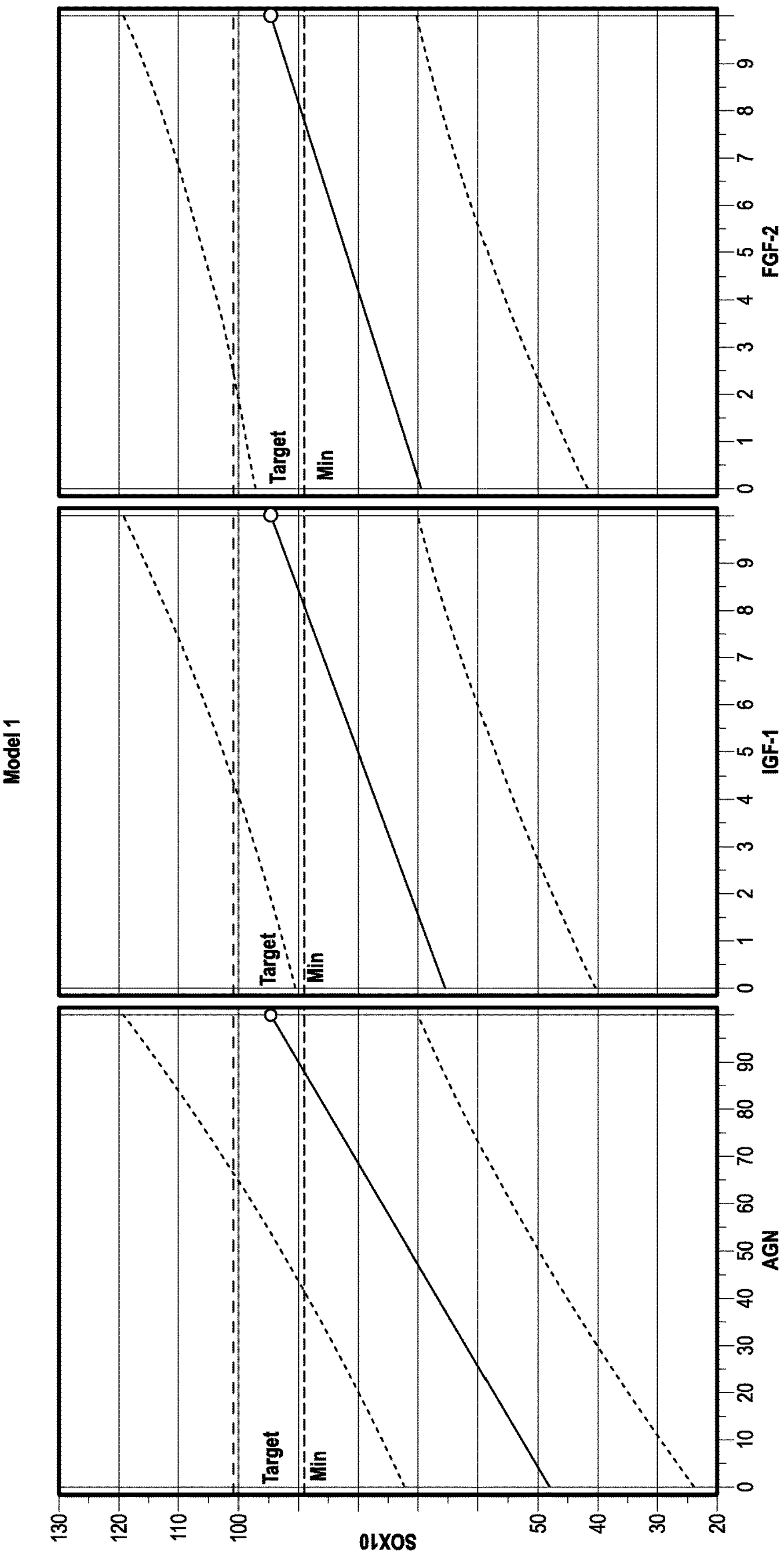
FIG. 35 shows factor effect plots showing expression level of SOX10 relative to the concentrations of IGF-1, FGF-2 and AGN193109 in a 12-factor model (model on the left) and IGF-1 and FGF-2 in an 8-factor model (model on the right).
Figure 35:
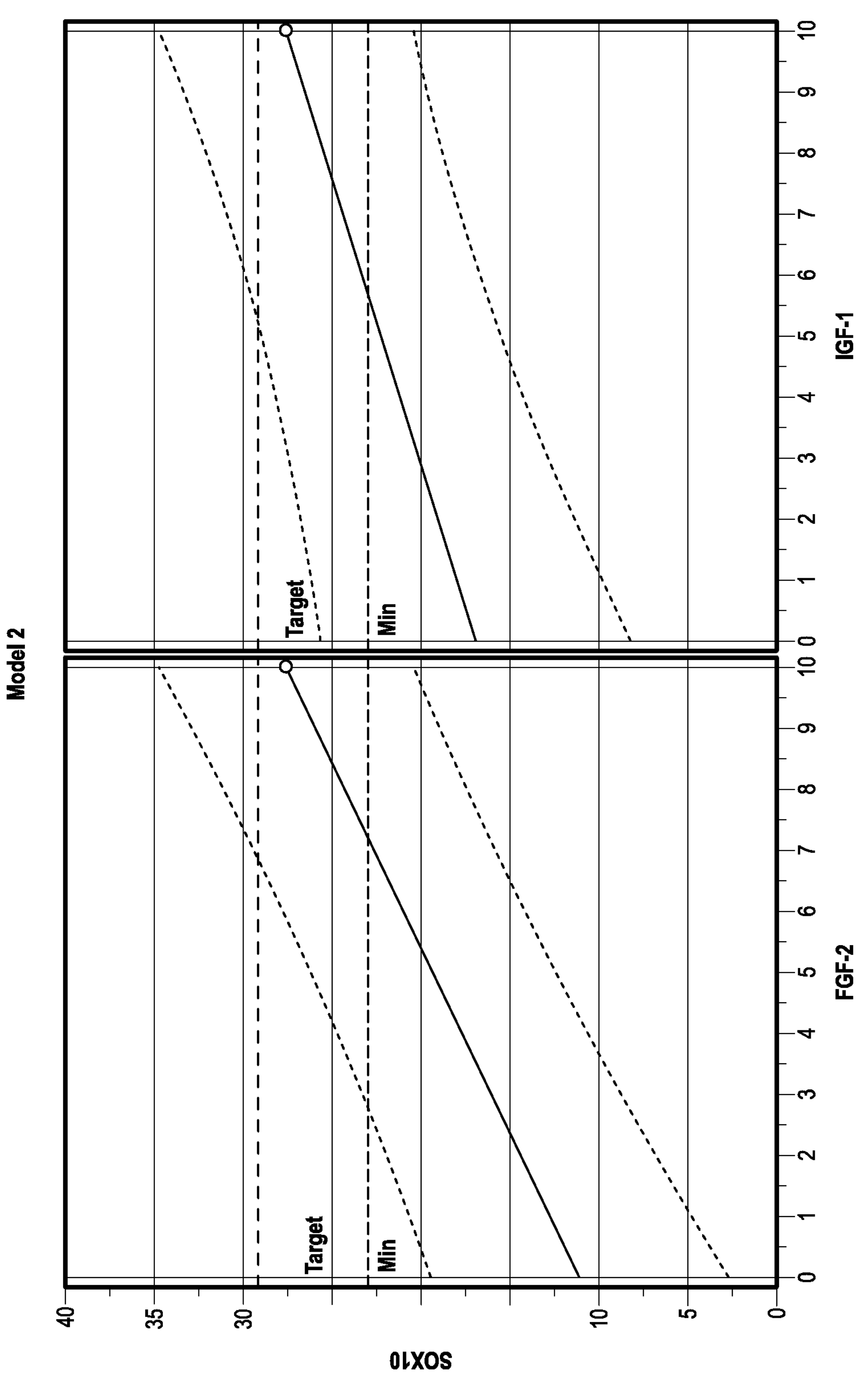

According to literature, proteins such as FGF-2, IGF-1, PDGF-AA and NT-3 play an important role in oligodendrocyte differentiation (Goldman and Kuypers (2015) *Development* 142:3983-95). In the first model, FGF-2 had positive regulatory impact only on the expression level of SOX10 and IGF-1 on PDGFRa. Therefore, to further understand the impact of IGF-1 and FGF-2 on differentiation of cells and confirm their positive role, we included these factors in two other models and optimized the models for maximum expression of SOX10. This gene is one of the main transcription factors of oligodendrocytes, along with OLIG2 and NKX2-2 that has shown the potential to commit the stem cells to oligodendrocytes in reprogramming efforts (Wang et al, (2014) *Proc Natl Arad Sri USA* 111:E2885-94; García-León et al. (2018) *Stem Cell Reports* 10:655-672). In both models, IGF-1 and FGF-2 had a positive impact on the expression level of SOX10, at expression level of 95 and 25 (FIG. 35). AGN193109 was also demonstrated to have a positive effect on increasing level of SOX10, with a factor contribution of 16.

Figure 36:
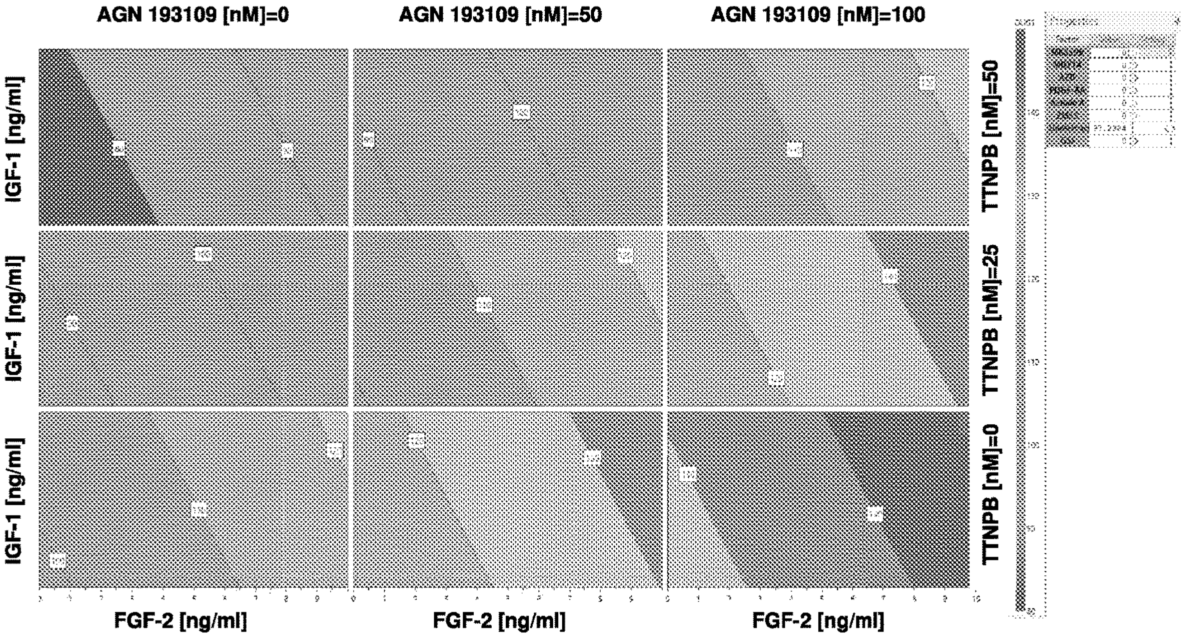
FIG. 36 shows contour plots modeling the expression level of OLIG1 relative to the concentration of IGF-1, FGF-2, TTNPB and AGN193109 in an 8-factor model while all the other factors are excluded. The concentration of AGN193109 is shown on top axis, TTNPB on the right axis, IGF-1 on the left axis and FGF-2 on the bottom axis. The expression level of OLIG1 is demonstrated in a spectrum going from red, the highest level to blue, the lowest level. The space at bottom right corner shows the highest expression level at presence of IGF-1, FGF-2 and AGN193109.

In previous model, it was observed that TTNPB positively regulated one of the OPC genes and since TTNPB and AGN193109 have opposing functions in RA signaling pathway, we decided to investigate expression level of another OPC gene, OLIG1, in the presence of AGN193109, TTNPB, FGF-2 and IGF-1 (FIG. 36). In this analysis, the highest and lowest expression levels are shown on a spectrum from red to blue and each of the four axes represent one compound. OLIG1 expression was maximized when TTNPB was at the lowest and AGN193109 and FGF-2 were at highest concentration, and even though IGF-1 demonstrated lower impact on expression of OLIG1, it still positively regulated its level.

Figure 37:
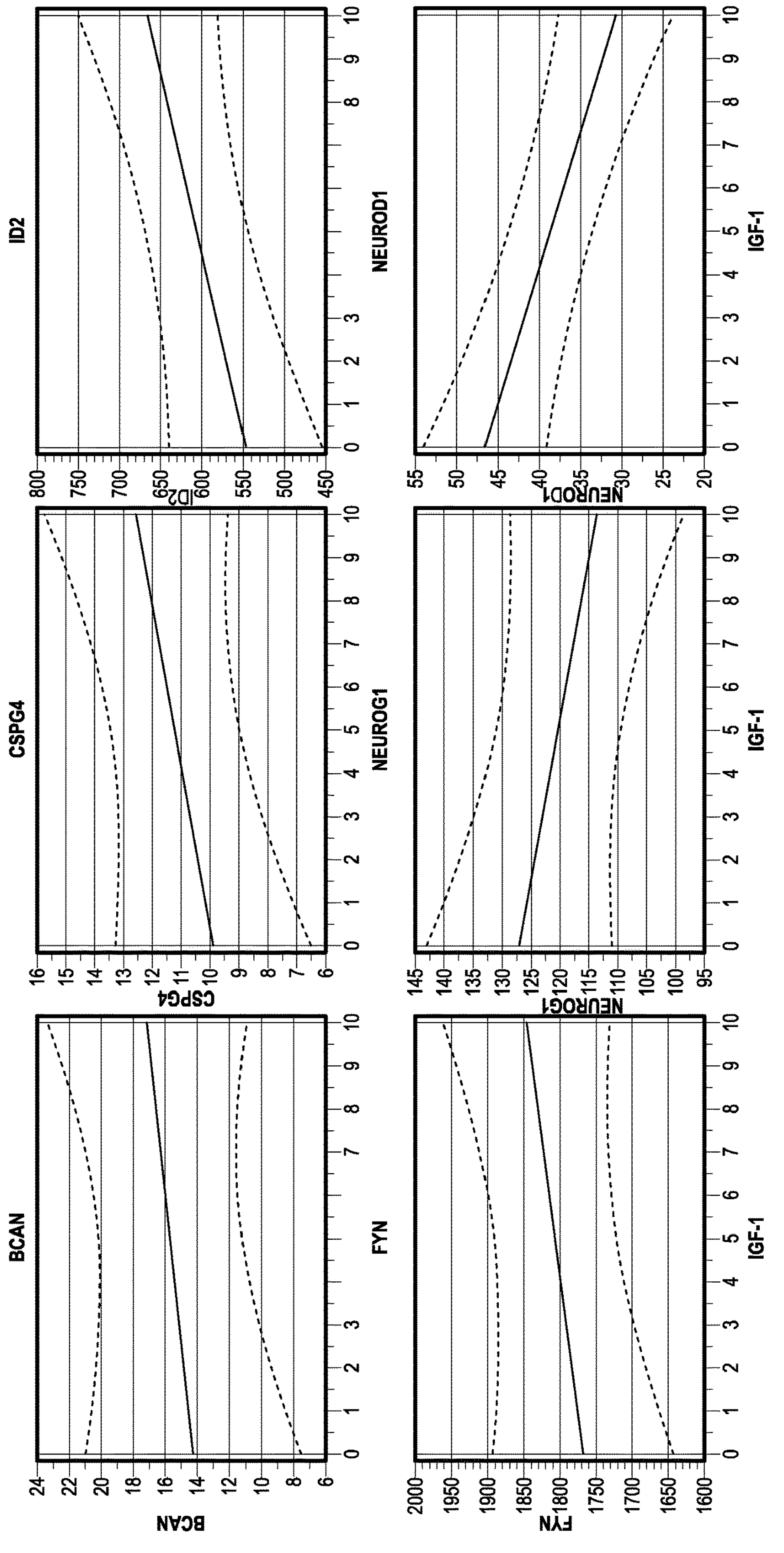
FIG. 37 shows factor effect plots demonstrating expression levels of late OPC genes, including BCAN, CSPG4, ID2 and FYN, and neuronal genes, including NEUROG1 and NEUROD1, relative to the concentration of IGF-1. As the concentration of IGF-1 increases, the expression levels of OPC genes of interest increase while the expression levels of neuronal genes drop.
Figure 38:
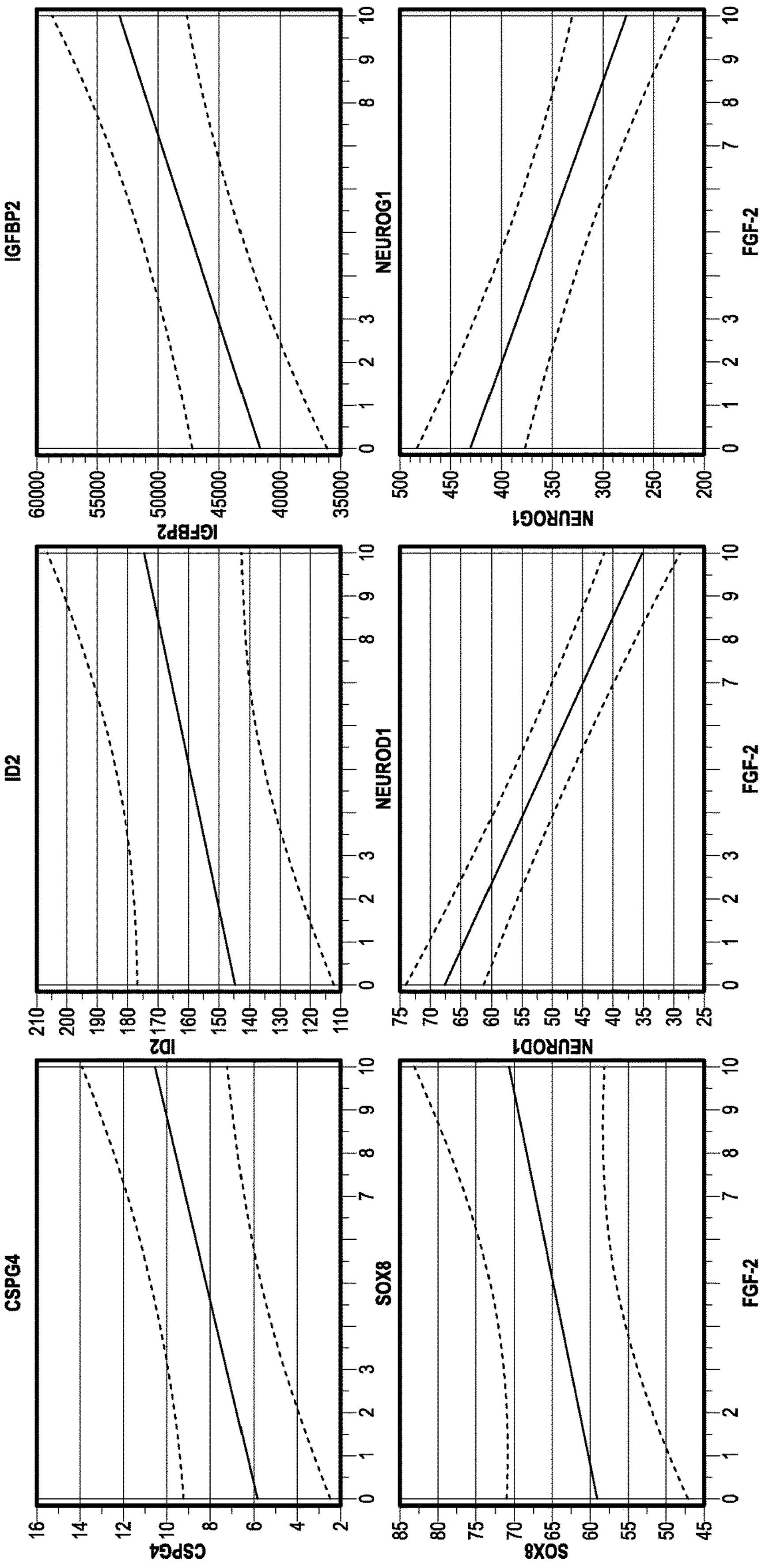
FIG. 38 shows factor effect plots demonstrating expression levels of late OPC genes, including CSPG4, ID2, IGFBP2 and SOX8, and neuronal genes, including NEUROG1 and NEUROD1, relative to the concentration of FGF-2. As the concentration of FGF-2 increases, the expression levels of OPC genes of interest increase while the expression levels of neuronal genes drop.
Figure 39:
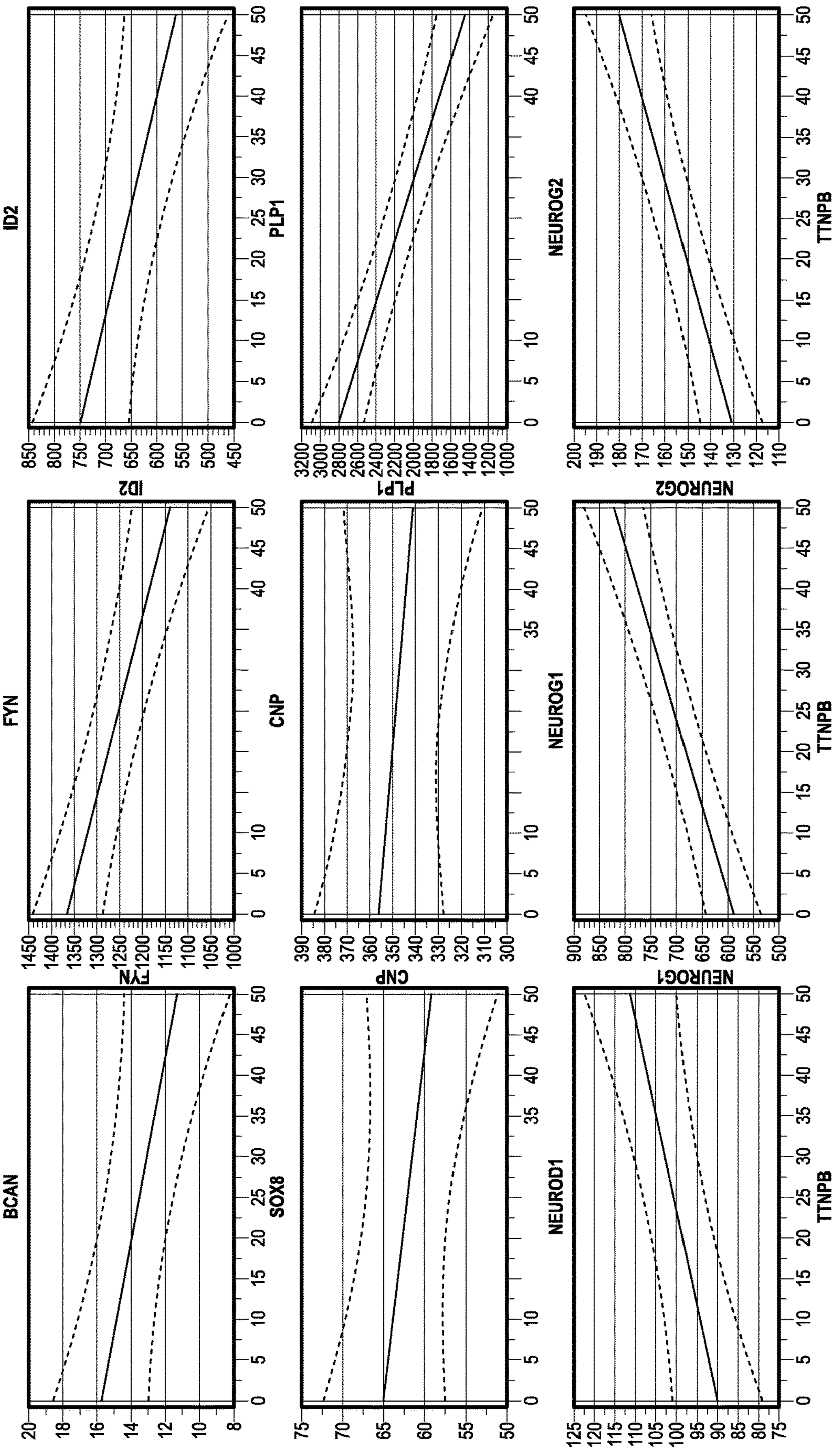
FIG. 39 shows factor effect plots demonstrating expression level of late OPC genes, including BCAN, ID2, FYN, CNP, PLP1 and SOX8, and neuronal genes, including NEUROG1, NEUROG2 and NEUROD1, relative to the concentration of TTNPB. As the concentration of TTNPB increases, the expression levels of OPC genes drop while the expression levels of neuronal genes increase.

To confirm the impact of TTNPB, FGF-2 and IGF-1 on a bigger scale, we investigated the expression profile of a larger group of genes defining late oligodendrocyte progenitor population, such as ID2, CSPG4, FYN, SOX8, PLP1 and BCAN (Perlman et al. (2020). *Glia* 68:1291-1303; Goldman and Kuypers (2015) *Development* 142:3983-95; van Tilborg et al. (2018) *Glia* 66:221-238) and neuronal genes such as NEUROD1, NEUROG1 and NEUROG2 in presence of IGF-1, FGF-2 or TTNPB. FIG. 37 shows factor plots of various genes in the presence of IGF-1 and the observed expression levels of OPC genes increased as the concentration of IGF-1 increased, while neuronal genes decreased. This confirms the positive impact of IGF-1 on commitment of cells to an oligodendrocyte fate over a neuronal fate. FIG. 38 shows the same analysis for FGF-2 and it was observed that the presence of FGF-2 increased the expression levels of OPC genes while decreasing the expression levels of neuronal genes. However, in the presence of TTNPB, the predicted behavior of genes changed, and an opposite trend was observed in the plots, demonstrating the negative effect of TTNPB on OPC genes and its positive effect on neuronal genes (FIG. 39).

Therefore, considering the models, a candidate recipe for stage 3 consisting of FGF-2, IGF-1 and AGN193109 was made. This recipe was able to maximize differentiation of cells to robust and elevated expression levels of SOX10, PDGFRa and OLIG1. This recipe was further validated by immunocytochemistry assay (see Example 9).

Example 9: Immunocytochemistry Validation of Stem Cell-Derived Oligodendrocyte Progenitors Expressing SOX10 and PDGFRa To further validate the optimized culture media described in Example 8, cells were treated with stage 1 differentiation media for 3 days, stage 2 differentiation media for 6 days and stage 3 differentiation media for 3 days, then standard immunocytochemistry assays were used to assess expression of biomarkers of early oligodendrocyte progenitors at the end of stage 2 and late oligodendrocyte progenitors at the end of stage 3. Biomarkers tested included OPC-specific markers, such as SOX10, OLIG2, NKX2-2, PDGFR and NG2 (CSPG4), along with the pan neuronal marker beta-III tubulin (TUBB3) to determine the homogeneity of the culture.

Figure 40:
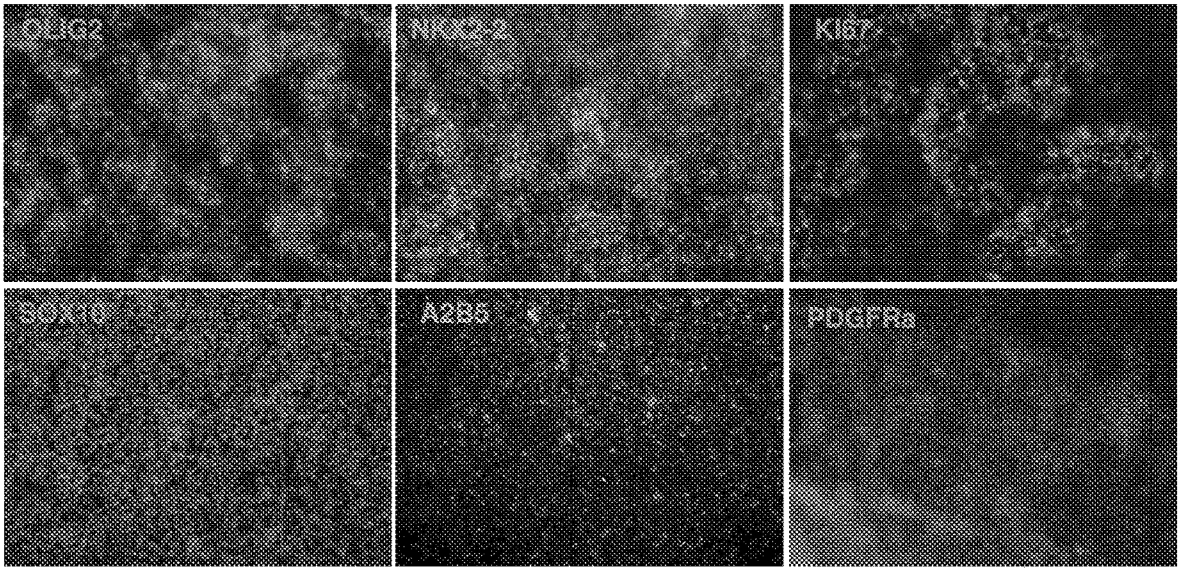
FIG. 40 shows photographs of fluorescence images of hiPSC-derived early oligodendrocyte progenitors at the end of stage 2. Cells are stained with OPC biomarkers, including NKX2-2, OLIG2, SOX10, A2B5 and PDGFRa, and the proliferation marker KI67. At this stage, cells were positive for all the markers expected at the early progenitor state.

Immunocytochemistry images of cells at the end of stage 2 (Day 9 in culture) confirmed the expression of OLIG2, NKX2-2 and SOX10 and initial expression of PDGFRa in differentiated cells (FIG. 40). Expression of KI67 in the cells showed that most of the cells were still proliferating, which was expected at progenitor stage.

Figure 41:
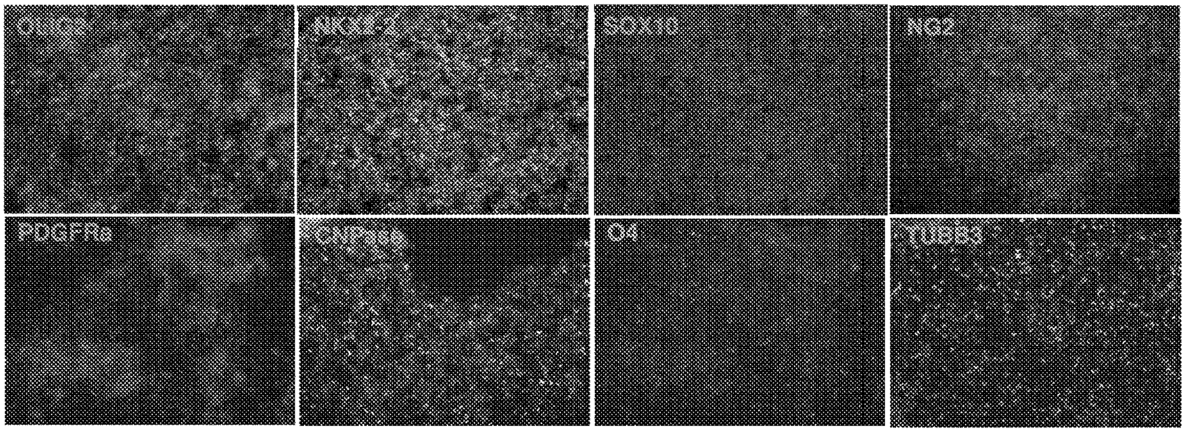
FIG. 41 shows photographs of fluorescence images of oligodendrocyte progenitors at the end of stage 3. Cells are stained with OPC markers, including OLIG2, NKX2-2, PDGFRa, SOX10, NG2, CNP and O4, and the pan neuronal marker TUBB3. At this stage, cells were positive for all expected biomarkers and their oligodendrocyte identity was confirmed.

Results of immunocytochemistry assay on hiPSC-derived cells at the end of stage 3 (day 12 in culture), confirmed the expression of SOX10, PDGFRa and NG2 (CSPG4) in differentiated cells. The cells were able to maintain expression of OLIG2. Additionally, the late OPC marker CNP was detected in more than half of the cells and initial expression of O4 in some of the cells in the culture was observed (FIG. 41). TUBB3 was also detected in less than half of the culture, which shows there is heterogeneity in the culture.

Detection of SOX10 and PDGFRa expression in differentiated cells by the end of stage 3 of differentiation confirmed the robustness and high conversion potential of the stage-wise recipe described in Example 8 for differentiation of human induced pluripotent stem cells to oligodendrocyte progenitors after 12 days in vitro.

Example 10: Culture Protocol Development for Generation of Stem Cell-Derived Pre-Myelinating Oligodendrocytes Expressing CNP, CD9 and O4

In this example, a culture protocol was developed for generating pre-myelinating oligodendrocytes from pre-OPC, referred to herein as the stage 4 protocol. As described in the earlier examples, a stepwise 3-stage differentiation protocol was developed that guides human pluripotent stem cells to progenitors expressing SOX10, NKX2-2 and OLIG2 after 12 days in culture. Differentiated cells also express other oligodendrocyte progenitor markers including PDGFRa and NG2. These cells can be further matured to pre-myelinating oligodendrocytes, that express CNP, CD9 and O4, after 6 days of culture in the stage 4 differentiation medium described herein. In a population of cell, initial expression of myelination marker MBP is also observed.

To develop the stage 4 oligodendrocyte differentiation recipes, the impact of various agonist and antagonists (effectors) on differentiation of pre-OPCs was investigated using the HD-DoE method described in earlier examples. These effectors were chosen based on available literature on developmental biology, differentiation of stem cells, as well as mouse and human single cell RNA-seq data from oligodendrocytes at the time.

These experiments led to generation of the stage 4 recipe, shown below in Table 5. A representative schematic diagram of the stage 4 culture protocol is shown in FIG. 44.

TABLE 5

Validated Factors in Stage 4 Recipe

| Effectors | Role | Concentration |
|---|---|---|
| IGF-1 | IGF-1 receptor activator | 10 ng/ml |
| PDGF-AA | PDGFR pathway | 10 ng/ml |
| NT-3 | TrkC agonist | 10 ng/ml |
| T3 | Thyroid hormone receptor agonist | 50 nM |
| Insulin | Inuslin receptor agonist | 20 ug/ml |

To engineer the recipe of stage 4 of differentiation, 48 or 96 different combinations of effectors generated using Design-of-Experiments compression through D-optimality were robotically prepared. The effector combinations were prepared in a basal media and were subsequently added to the cells, which were treated with the stage 1, stage 2 and stage 3 differentiation media as described in the earlier examples to generate OPCs. The resultant OPCs were then replated onto a 96-well plate. 3 to 7 days later RNA extraction was performed, and gene expression was obtained using quantitative PCR analysis. The data were normalized and modeled using partial least squares regression analysis to the effector design, resulting in the generation of gene-specific models, which after model tuning for maximal Q2 predictive power, provided explanation of the effectors ability to control the expression of individual genes, combinatorially, and individually. Solutions within the tested space could then be explored to address desirability.

To guide the differentiation of OPCs to oligodendrocytes, expression of post mitotic genes, such as CNP and PLP1 (Goldman and Kuypers (2015) *Development* 142:3983-95; Emery and Lu (2015) *Cold Spring Harb Perspect Biol.* 7:a020461; Tiane et al. (2019) *Cells* 8:1236) was focused on. In one model, the effect of NT-3, T3, Insulin, Biotin, IGF-1, Purmorphamine, cAMP and 2-phospho-ascorbic acid was tested on gene profile of differentiating cells. When optimized for maximal expression of CNP at 1339, multiple inputs showed positive regulatory impact on its expression (FIG. 45), including NT-3, with a factor contribution of 24, T3, with a factor contribution of 18, Purmorphamine, with a factor contribution of 10, Insulin, with a factor contribution of 10, and cAMP, with a factor contribution of 7. IGF-1 also had a positive regulatory effect, but the factor contribution was below 1. Biotin and ascorbic acid were the only factors with a negative impact with factor contributions of 12 and 17. Within the specifications of attaining 80% maximal expression of CNP, this complex media composition had a Cpk value (process capability index) of 0.43, corresponding to a 9% risk of failure.

Based on the initial results, the effect of the tested 8 factors in combination was investigated with an additional four factors that are expected to promote the differentiation of oligodendrocytes (Wang et al. (1998) *Neuron* 21:63-75; Weng et al. (2017) *Sci Rep.* 7:1705; Benarroch (2009) *Neurology* 72:1779-1785; Shi et al. (2019) *Exp Ther Med,* 18:1258-1266). In this HD-DoE model, the impact of IGF-1, NT-3, T3, Insulin, Purmorphamine, Biotin, Ascorbic acid, Albumax, cAMP, propionate, AICAR and gamma secretase inhibitor-XX (GSI-XX), a Notch pathway inhibitor, was tested on differentiation of OPCs after 6 days in culture. When optimized for CNP at 1790, NT-3, IGF-1, Insulin and GSI-XX had positive impact on maximizing its expression, with factor contribution of 13, 5, 3 and 7, respectively (FIG. 46). Biotin and cAMP, both with factors contribution of 16, had the highest negative impact on maximizing CNP. T3 also showed a negative effect; however, its factor contribution was relatively low at 1.2. Within the specifications of attaining 80% maximal expression of CNP, this complex media composition had a Cpk value (process capability index) of 0.46, corresponding to an 8.3% risk of failure.

When the model was optimized for expression of CNP, other oligodendrocyte genes, such as PLP1, MYT1, APOD and BCAN, were also upregulated, with expression levels of 2800, 157, 40, 189 and 72, respectively, while the proliferation marker MKI67 was minimized (FIG. 47). This gene profile showed the potential of this recipe to robustly differentiate the cells in oligodendroglial fate.

Since the expression level of PLP1 was more than 2000, the conditions of optimization of this terminally expressed marker in the model were studied. At optimized conditions, the expression level of PLP1 increased to 3600, with NT-3 and Insulin as its only two positive regulators. Insulin had the highest factor contribution, at 13, and NT-3 was at 7 (FIG. 48). AICAR, Albumax and Purmorphamine had the highest negative impact, with factor contributions of 12, 11 and 10, respectively. Within the specifications of attaining 80% maximal expression of PLP1, this complex media composition had a Cpk value (process capability index) of 0.77, corresponding to a 1.2% risk of failure.

Figure 49:
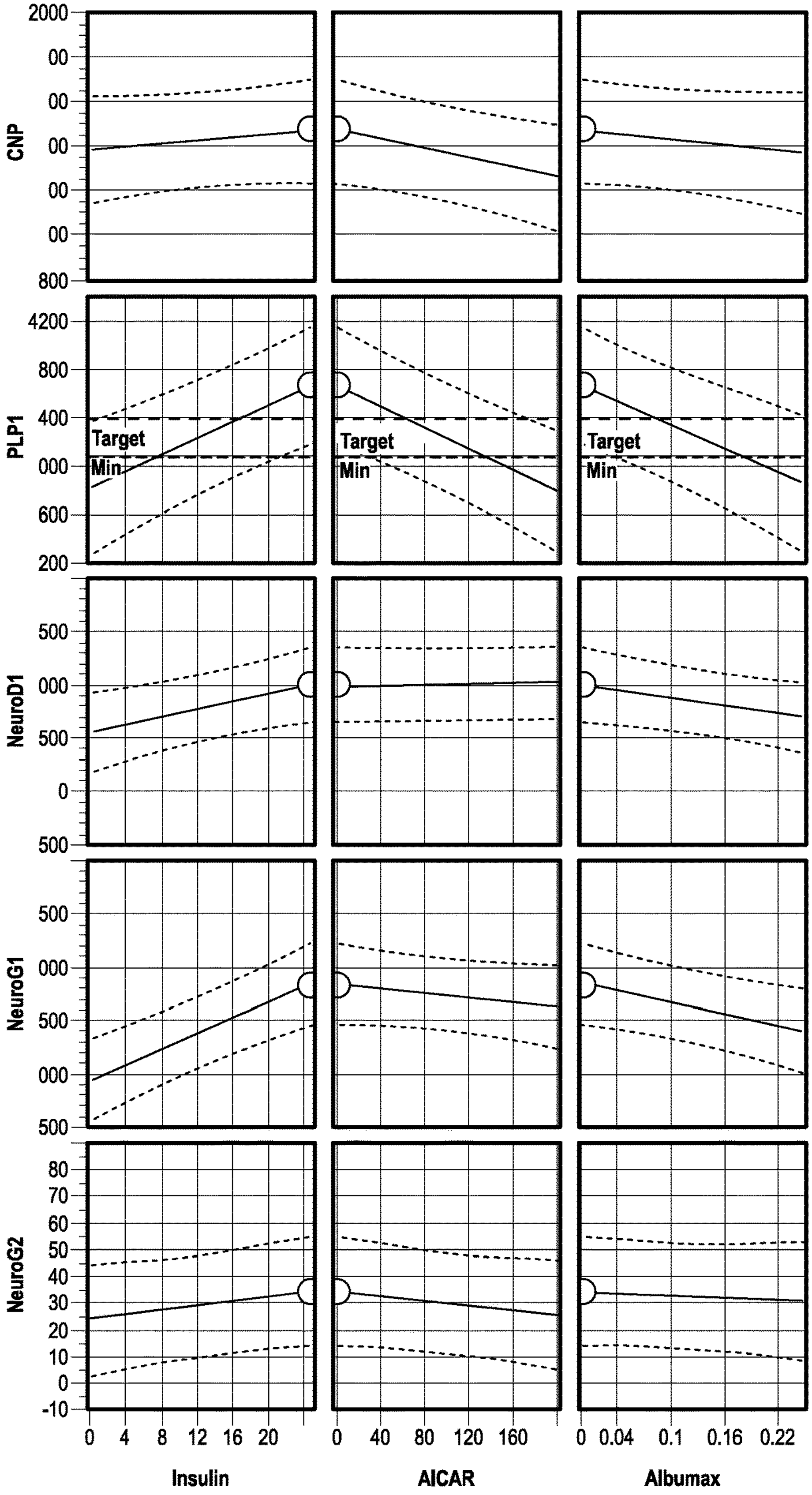
FIG. 49 shows the dynamic profile analysis of expression levels of CNP, PLP1, NeuroD1, NeuroG1 and NeuroG2, relative to the concentration of 12 effectors, when PLP1 is maximally expressed. The positive impact of GSI-XX on expression of neuronal genes and their factor contributions are shown by slope of the plots for each effector.
Figure 49:
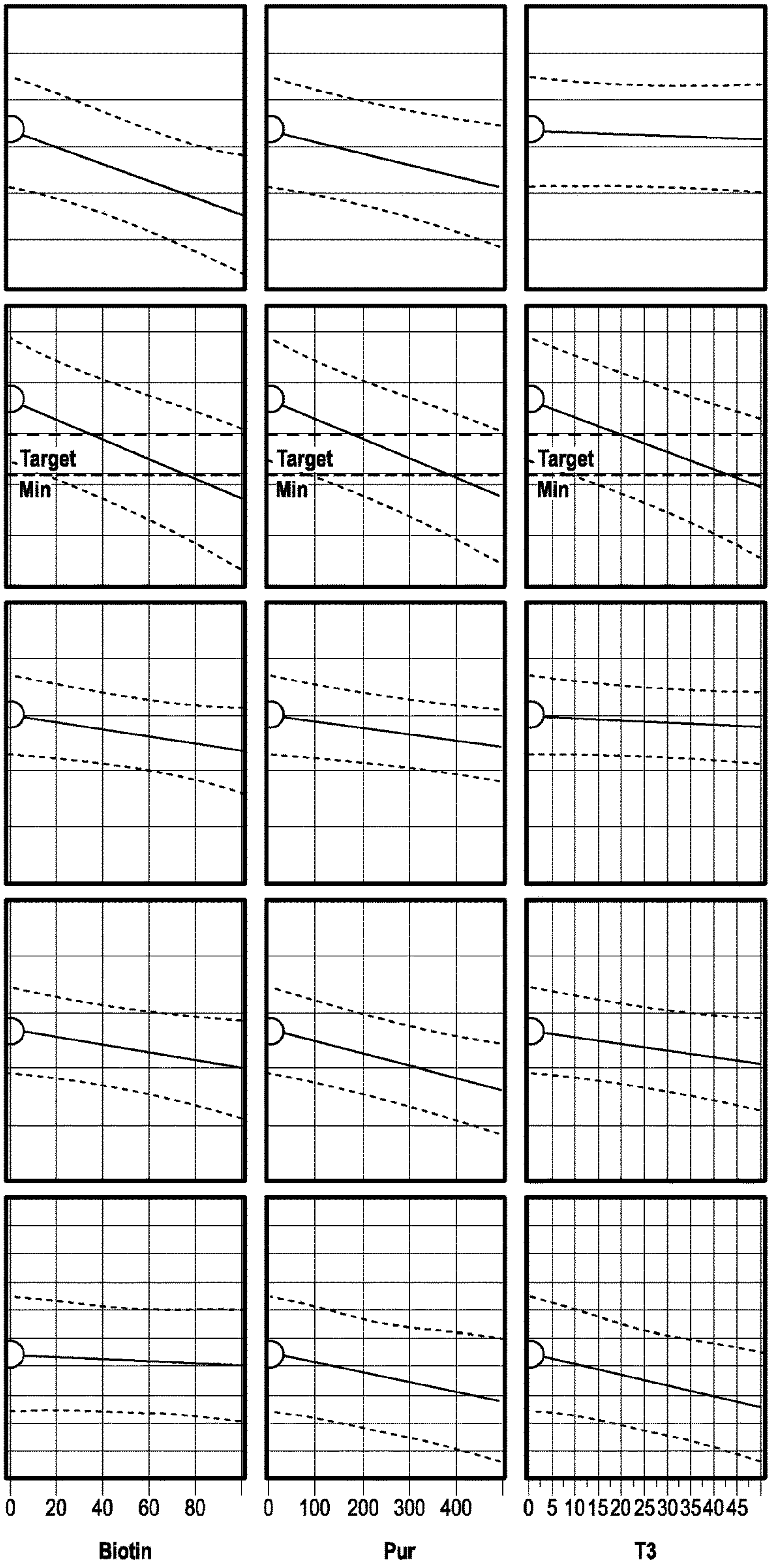
Figure 49:
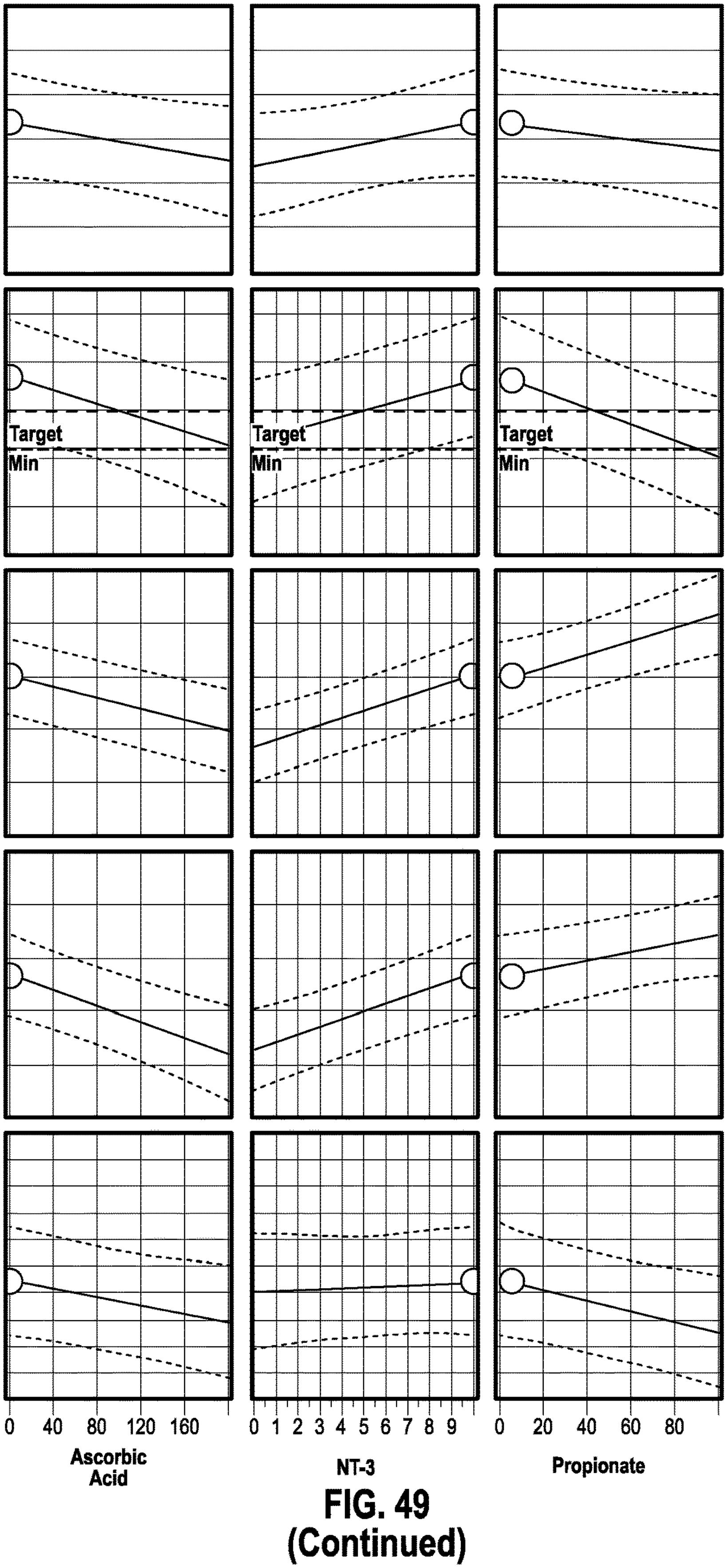
Figure 49:
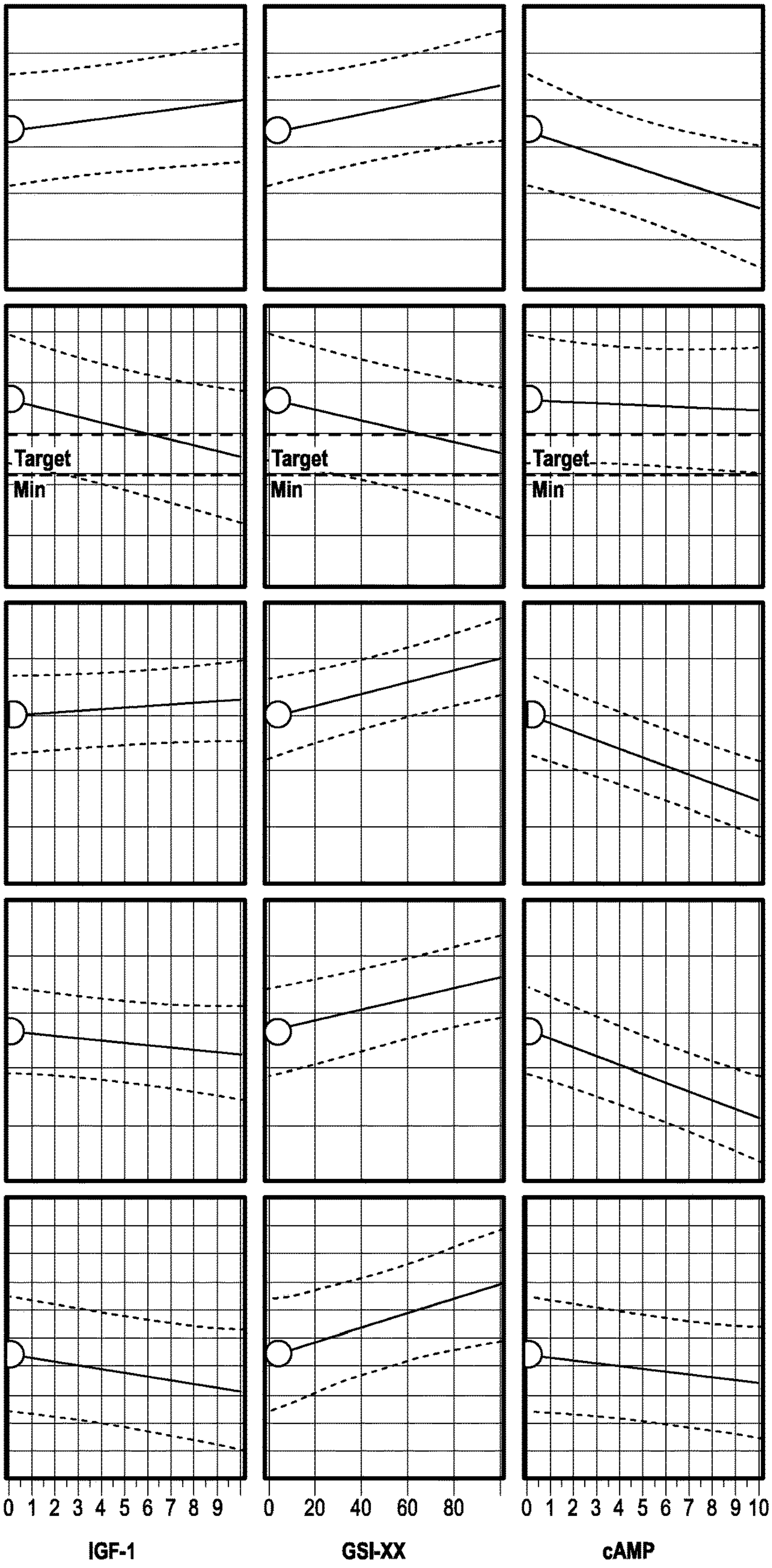

Since GSI-XX and IGF-1 had opposing effect on CNP and PLP1, dynamic profile analysis was used to further investigate their impact on additional genes in the model (FIG. 49). It was observed that GSI-XX positively regulates the expression of neuronal genes such as NeuroG1, NeuroG2 and NeuroD1, as well as CNP. Therefore, it was decided to eliminate it from the final recipe to minimize the heterogeneity in the culture. Since both HD-DoE experiments showed IGF-1 had a positive regulatory impact on CNP, it was decided to add it to the final recipe.

Figure 50:
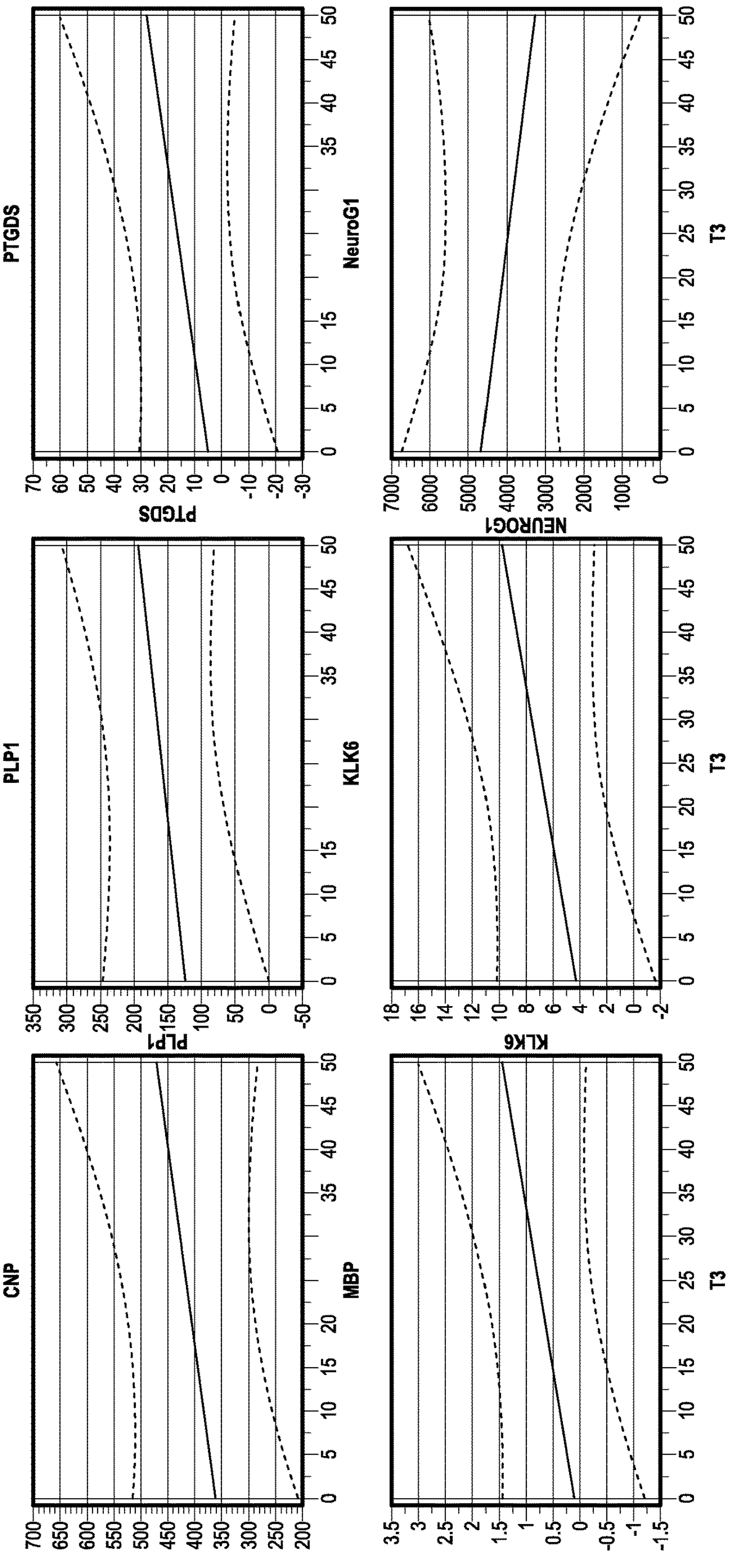
FIG. 50 shows the factor effect plots showing expression levels of CNP, PLP1, PTGDS, MBP, KLK6 and NeuroG1 relative to the concentration of T3 in a 12-factor model. The positive impact of T3 on oligodendrocyte and its negative effect on neuronal gene is shown by the slope of the plots.

Previous HD-DoE experiment results showed that T3 had a high positive regulatory impact on expression of CNP, with a factor contribution of 18. Therefore, the effect of T3 on other genes in the model was further studied. The model showed T3 can upregulate other OL genes such as PLP1, PTGDS, KLK6 and MBP while downregulating neuronal gene NeuroG1 (FIG. 50). This observation led to inclusion of T3 in the final stage 4 recipe.

Finally, PDGF-AA has been established in the literature to promote oligodendrocyte differentiation and thus was added to the final stage 4 recipe without doing an additional HD-DoE model.

Accordingly, a recipe for stage 4 differentiation was made having the components as shown above in Table 5. This recipe is able to maximize differentiation of cells for robust and elevated expression of CNP and O4 and initial expression of PLP1 and MBP. This recipe was validated by immunocytochemistry assay, as described in Example 11.

Example 11: Immunocytochemistry Validation of Culture Protocol for Stem Cell-Derived Pre-Myelinating Oligodendrocytes Expressing CNP and O4

To validate the stage 4 recipe described in Example 10, cells were treated with stage 1, stage 2, and stage 3 differentiation media for a total of 12 days and then were cultured in the stage 4 recipe for 6 days. At that point, immunocytochemistry assays were used to assess the expression of biomarkers of late oligodendrocyte progenitors and early oligodendrocytes in the differentiated cells. Biomarkers included OPC specific markers, such as OLIG2, NKX2-2, PDGFR, and A2B5, oligodendrocyte markers, including CNP, O4, MBP and PLP1, as well as the pan neuronal marker TUBB3 to determine the homogeneity of the culture.

Figure 51:
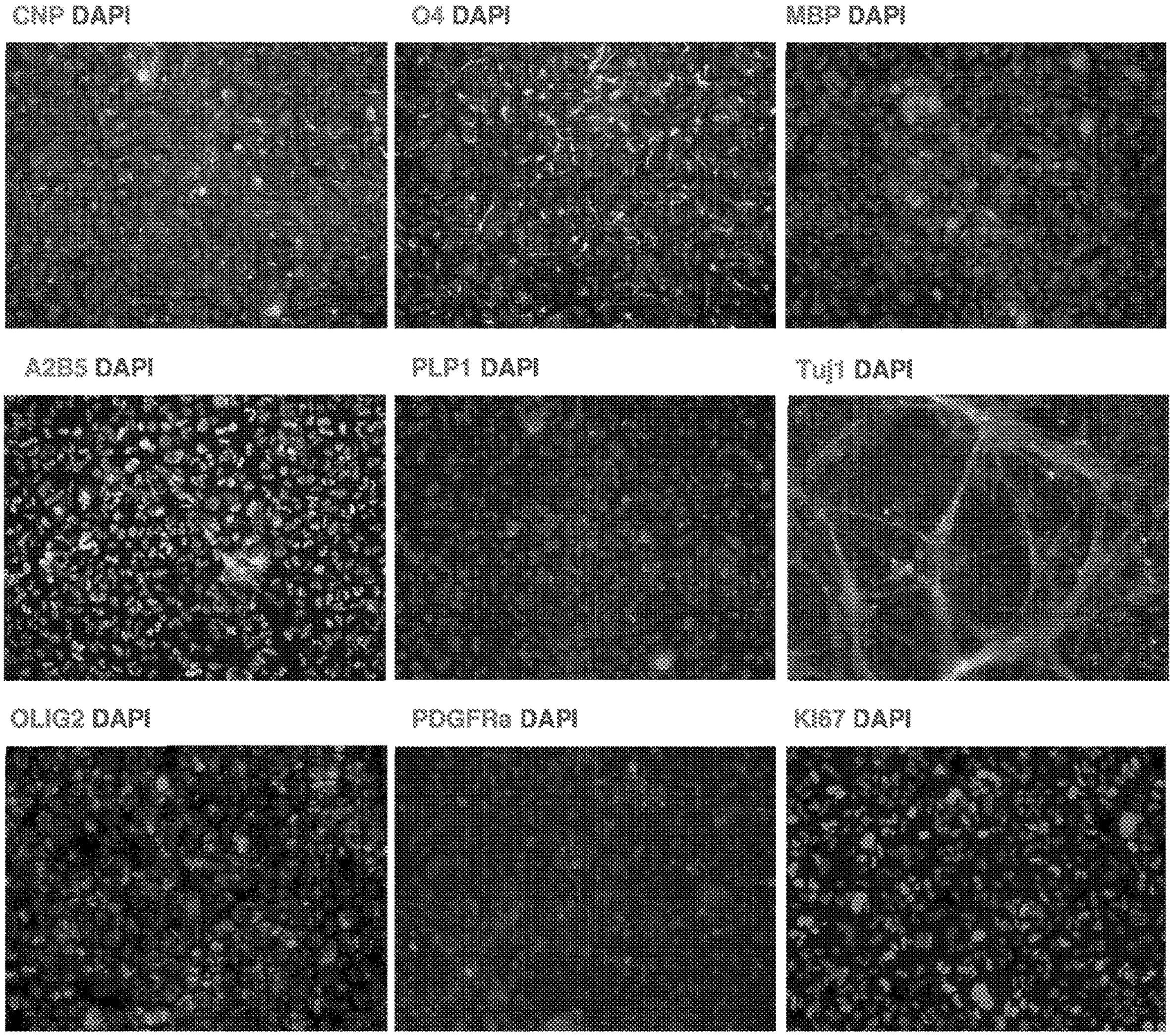
FIG. 51 are photographs showing fluorescence images of hiPSC-derived pre-myelinating oligodendrocytes at the end of stage 4. The cells were stained with OL biomarkers, including A2B5, CNP, O4, PLP1, MBP, OLIG2 and PDGFRa, the pan neuronal biomarker TUBB3 and the proliferation marker KI67. A small population of cells expressed myelinating markers MBP and PLP1 while most cells expressed CNP, O4 and A2B5. PDGFRa and KI67 were detected at some cells, which shows that there are some oligodenedrocyte progenitors present in the culture.

Immunocytochemistry images of cells at the end of stage 4 (Day 18 in culture) confirmed the expression of OLIG2, NKX2-2, CNP and O4 and initial expression of MBP and PLP1 in the differentiated cells (FIG. 51). Expression of KI67 and PDGFRa in a subset of cells showed that some cells were still proliferating. TUBB3 was detected in less than 50% of the cells, which showed that the culture is not 100% glial.

Figure 52:
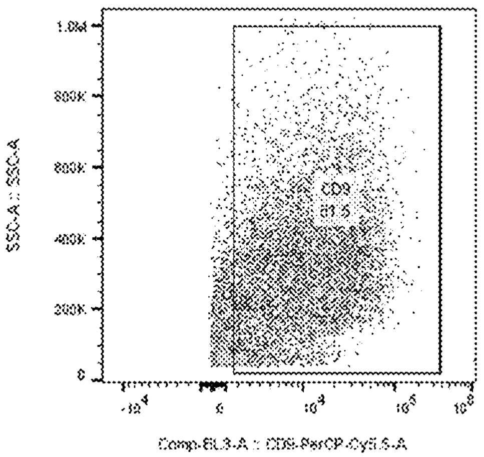
FIG. 52 shows flow cytometry-based detection of CD9+ cells in hiPSC-derived pre-myelinating cells at day 18 of differentiation. CD9+ cells comprise 81.5% of the total number of cell population.

Expression levels of CD9 were also measured at the end of stage 4 using flow cytometry. CD9 is a surface marker expressed in committed oligodendrocyte progenitors and pre-myelinating oligodendrocytes (Goldman and Kuypers (2015) *Development* 142:3983-95). As shown in FIG. 52, 81.5% of cells were CD9 positive, which showed that the majority of the culture is moving forward toward an oligodendrocyte fate.

Detection of CNP, CD9 and O4 in the differentiated cells by the end of stage 4 of differentiation confirmed the robustness and high conversion ability of the 4 stage-wise recipes described in the Examples for differentiation of human induced pluripotent stem cells to pre-myelinating oligodendrocytes after 18 days in vitro.

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. A method of generating CD9+A2B5+O4+CNPase+ pre-myelinating oligodendrocytes (preOLs) comprising culturing SOX10+ OLIG2+ NKX2-2+ oligodendrocyte progenitor cells (OPCs) OPCs in a culture medium media comprising an insulin-like growth factor 1 receptor (IGF1R) pathway agonist, a tropomyosin-related kinase C (TrkC) pathway agonist, a platelet-derived growth factor receptor (PDGFR) pathway agonist, a thyroid hormone receptor agonist, and an insulin receptor agonist such that CD9+A2B5+O4+CNPase+ preOLs are generated.

2. The method of claim 1, wherein the OPCs are cultured in the culture medium for six days.

3. The method of claim 1, wherein the IGF1R pathway agonist is selected from the group consisting of IGF-1, IGF-2, insulin, Rg5, IGF-1 30-41, Demethylasterriquinone B1, IGF1-Ado, X10, mecasermin, and combinations thereof.

4. The method of claim 1, wherein the TrkC pathway agonist is selected from the group consisting of neurotrophin-3 (NT-3), peptidomimetics based on b-turns of NT-3, LM22B 10, GNF 5837, and combinations thereof.

5. The method of claim 1, wherein the PDGFR pathway agonist is PDGF-AA.

6. The method of claim 1, wherein the thyroid hormone receptor agonist is selected from the group consisting of T3, T4, Resmetirom, TRb agonist 3 (Compound 3), Sobetirome, Tiratricol, and combinations thereof.

7. The method of claim 1, wherein the insulin receptor agonist is selected from the group consisting of insulin, IGF-1, IGF-2, Demethylasterriquinone B1, MK-5160, MK-1092, and combinations thereof.

8. A method of generating CD9+A2B5+O4+CNPase+ preOLs comprising:

(a) culturing human OLIG2+ pre-oligodendrocyte progenitor cells (pre-OPCs) in a culture medium comprising a fibroblast growth factor receptor (FGFR) pathway agonist, a mammalian target of rapamycin (mTOR)

pathway antagonist, a sonic hedgehog (SHH) pathway agonist, an Akt pathway antagonist, and an Akt pathway agonist on days 0-3 to obtain a population of cells;

(b) culturing the population of cells from step (a) in a culture medium comprising an FGFR pathway agonist, a PDGFR pathway agonist, an Akt pathway antagonist, and a retinoic acid (RA) pathway agonist on days 3-9, such that SOX10+ OLIG2+ NKX2-2+ OPCs are generated; and (c) culturing the population of cells from step (b) in a culture medium comprising an IGF1R pathway agonist, a TrkC pathway agonist, a PDGFR pathway agonist, a thyroid hormone receptor agonist, and an insulin receptor agonist on days 9-15 such that CD9+A2B5+O4+ CNPase+ preOLs are generated.

9. The method of claim 8, wherein the human OLIG2+ pre-OPCs are obtained by culturing human pluripotent stem cells in a culture medium comprising a RA pathway agonist, an Akt pathway agonist, an mTOR pathway agonist, a WNT pathway antagonist, an SHH pathway agonist, a bone morphogenetic protein (BMP) pathway antagonist, and a protein kinase C (PKC) pathway antagonist on days −3-0.

10. The method of claim 8, wherein the FGFR pathway agonist is FGF2, SUN11602, or combinations thereof.

11. The method of claim 8, wherein the mTOR pathway antagonist is selected from the group consisting of AZD 3147, Dactolisib, Rapamycin, Everolimus, AZD 8055, Temsirolimus, PI-103, NU7441, BC-LI-0186, eCF 309, ETP 45658, Niclosamide, Omipalisib, PF 04691502, PF 05212384, Torin1, Torin 2, WYE 687, XL 388, STK16-IN-1, PP 242, Torkinib, Ridaforolimus, Sapanisertib, Voxtalisib, and combinations thereof.

12. The method of claim 8, wherein the SHH pathway agonist is selected from the group consisting of Purmorphamine, GSA 10, SHH, SAG, and combinations thereof.

13. The method of claim 8, wherein the Akt pathway antagonist is selected from the group consisting of MK2206, GSK690693, Perifosine (KRX-0401), Ipatasertib (GDC-0068), Capivasertib (AZD5363), PF-04691502, AT 7867, Triciribine (NSC154020), ARQ751, Miransertib (ab235550), Borussertib, Cerisertib, Akti1/2, CCT128930, A 674563, PHT 427, Miltefosine, AT 13148, ML 9, BAY 1125976, Oridonin, TIC10, Pectolinarin, Akti IV, 10-DEBC, API-1, SC 66, FPA 124, API-2, Urolithin A, and combinations thereof.

14. The method of claim 8, wherein the Akt pathway agonist is selected from the group consisting of Sc79, Demethyl-Coclaurine, LM22B-10, YS-49, YS-49 monohydrate, Demethylasterriquinone B1, Recilisib, N-Oleyol glycine, NSC45586 sodium, Periplocin, CHPG sodium salt, Bilobalide, 6-hydroxyflavone, Musk ketone, SEW2871, 8-Prenylnaringenin, Razuprotafib, and combinations thereof.

15. The method of claim 8, wherein the PDGFR pathway agonist is PDGF-AA.

16. The method of claim 8, wherein the RA pathway agonist is selected from the group consisting of TTNPB, AM 580, CD 1530, CD 2314, CD 437, Ch 55, BMS 753, BMS 961, Tazarotene, Isotretinoin, Tretinoin, Tamibarotene, ATRA, AC 261066, AC 55649, retinoic acid (RA), Sr11237, adapalene, EC23, 9-cis retinoic acid, 13-cis retinoic acid, 4-oxo retinoic acid, and All-trans Retinoic Acid (ATRA), and combinations thereof.

17. The method of claim 8, wherein the culture medium in step (b) further comprises:

(a) a Wnt pathway antagonist; and (b) a Notch pathway inhibitor.

18. The method of claim 17, wherein:

(a) the Wnt pathway antagonist is selected from the group consisting of XAV939, ICG001, Capmatinib, endo-IWR-1, IWP-2, IWP-4, MSAB, CCT251545, KY02111, NCB-0846, FH535, LF3, WIKI4, Triptonide, KYA1797K, JW55, JW 67, JW74, Cardionogen 1, NLS-StAx-h, TAK715, PNU 74654, iCRT3, WIF-1, DKK1, and combinations thereof; and/or (b) the Notch pathway inhibitor is gamma secretase inhibitor-XX.

19. A method of generating human CD9+A2B5+O4+ CNPase+ preOLs comprising:

(a) culturing human OLIG2+ pre-OPCs in a culture medium comprising an FGFR pathway agonist, an mTOR pathway antagonist, an SHH pathway agonist, and a WNT pathway agonist on days 0-6 to obtain a population of cells; and (b) culturing the population of cells from step (a) in a culture medium comprising an FGFR pathway agonist, an IGF-1 pathway agonist, and an RA pathway agonist on days 6-9, such that SOX10+ OLIG2+ NKX2-2+ OPCs are generated; and (c) culturing the population of cells from step (b) in a culture medium comprising an IGF1R pathway agonist, a TrkC pathway agonist, a PDGFR pathway agonist, a thyroid hormone receptor agonist, and an insulin receptor agonist on days 9-15 such that CD9+A2B5+O4+ CNPase+ preOLs are generated.

20. The method of claim 19, wherein the human OLIG2+ pre-OPCs are obtained by culturing human pluripotent stem cells in a culture medium comprising a RA pathway agonist, an Akt pathway agonist, an mTOR pathway agonist, a WNT pathway antagonist, an SHH pathway agonist, a BMP pathway antagonist, and a PKC pathway antagonist on days −3-0.

21. The method of claim 19, wherein the FGFR pathway agonist is FGF2, SUN11602, or combinations thereof.

22. The method of claim 19, wherein the mTOR pathway antagonist is selected from the group consisting of AZD 3147, Dactolisib, Rapamycin, Everolimus, AZD 8055, Temsirolimus, PI-103, NU7441, BC-LI-0186, eCF 309, ETP 45658, Niclosamide, Omipalisib, PF 04691502, PF 05212384, Torin1, Torin 2, WYE 687, XL 388, STK16-IN-1, PP 242, Torkinib, Ridaforolimus, Sapanisertib, Voxtalisib, and combinations thereof.

23. The method of claim 19, wherein the SHH pathway agonist is selected from the group consisting of Purmorphamine, GSA 10, SHH, SAG, and combinations thereof.

24. The method of claim 19, wherein the WNT pathway agonist is selected from the group consisting of CHIR99021, CHIR98014, SB 216763, SB 415286, LY2090314, 3F8, A 1070722, AR-A 014418, BIO, BIO-acetoxime, AZD1080, WNT3A, alsterpaullone, indirubin-3-oxime, 1-azakenpaullone, kenpaullone, TC-G 24, TDZD 8, TWS 119, NP 031112, AT 7519, KY 19382, AZD2858, and combinations thereof.

25. The method of claim 19, wherein the IGF-1 pathway agonist is selected from the group consisting of IGF-1, IGF-2, insulin, Rg5, IGF-1 30-41, Demethylasterriquinone B1, IGF1-Ado, X10, mecasermin, and combinations thereof.

26. The method of claim 19, wherein the RA pathway antagonist is selected from the group consisting of AGN193109, BMS 195614, CD 2665, ER 50891, LE 135, LY 2955303, MM11253, and combinations thereof.

* * * * *